(12) United States Patent
Omura et al.

(10) Patent No.: US 6,864,073 B1
(45) Date of Patent: Mar. 8, 2005

(54) AVERMECTIN AGLYCON SYNTHASE GENES

(75) Inventors: Satoshi Omura, Tokyo (JP); Haruo Ikeda, Kanagawa (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 09/914,286

(22) PCT Filed: Feb. 23, 2000

(86) PCT No.: PCT/JP00/01041

§ 371 (c)(1),
(2), (4) Date: Aug. 24, 2001

(87) PCT Pub. No.: WO00/50605

PCT Pub. Date: Aug. 31, 2000

(30) Foreign Application Priority Data

Feb. 24, 1999 (JP) .......................................... 11-046961

(51) Int. Cl.[7] .............................. C12N 9/00; C12N 1/20; C12N 15/00; C07H 21/04
(52) U.S. Cl. ............. 435/183; 435/252.35; 435/252.33; 435/252.3; 435/320.1; 536/23.2; 536/23.1; 536/23.7
(58) Field of Search .............................. 435/183, 252.3, 435/252.33, 252.35, 320.1, 252.31; 536/23.2, 23.1, 23.7

(56) References Cited

U.S. PATENT DOCUMENTS 5,252,474 A * 10/1993 Gewain et al. .......... 435/172.3

FOREIGN PATENT DOCUMENTS

| EP | 391594 | 10/1990 |
|---|---|---|
| EP | 0445460 | 9/1991 |
| EP | 791655 | 8/1997 |
| EP | 791656 | 8/1997 |
| WO | WO 00/01827 | 1/2000 |
| WO | WO 01/09155 | 2/2001 |

OTHER PUBLICATIONS

MacNeil, D. J. "Avermectins" Biotechnology 28, 421–442 (1995).*
Bevitt et al. "6–deoxyerythronolide–B synthase 2 from Saccharopolyspora erythraea" XP–001005944 Eur. J. Biochem. 204:39–49 (1992).
Cortes et al. "An unusually large multifunctional polypeptide in the erythromycin–producing polyketide synthase of Saccharopolyspora erythraea" XP–002035889 Nature 348:176–178 (1990).
Database Accession No. AB032367 XP–0022769974 (1999).
Database Accession No. L09654 XP–002276973 (1993).
Database Accession No. AF079138 XP–002276971 (1998).
Database Accession No. AF082100 XP–002276972 (1998).

Donadio et al. "Modular organization of genes required for complex polyketide biosynthesis" XP–002035890 Science 252:675–679 (1991).
Ikeda "Genetic analysis of biosynthesis of polyketide anthelmintic macrolide avermectin in Streptomyces avermitilis" XP–001180664 Actinomycetol. 13:94–112 (1999).
Ikeda et al. "Control of avermectin biosynthesis in Streptomyces avermitilis" XP–009029162 J. Antibiotics 48:549–562 (1995).
Motamedi et al. "The biosynthetic gene cluster for the macrolactone ring of the immunosuppressant FK506" XP–000906738 Eur. J. Biochem. 256:528–534 (1998).
Omura et al. "Selective production of specific components of avermectins in Sterptomyces avermitilis" XP–009029161 J. Antibiotics 44:560–563 (1991).
Pang et al. "Production of 6,8a–seco–6,8a–deoxy derivatives of avermectins by a mutant strain of Streptomyces avermitilis" XP–009029187 J. Antibiotics 48:59–66 (1995).
Swan et al. "Characterisation of a Streptomyces antibioticus gene encoding a type 1 polyketide synthase which has an unusual coding sequence" XP–002087278 Mol. Gen. Genet. 242:358–362 (1994).
Search Report dated May 14, 2004 for European Appln. No. 00905297.8.
Ikeda et al. "Cloning of the gene encoding avermectin B 5–O–methyltransferase in avermectin–producing streptomyces avermitilis" Gene 206:175–180 (1998).
Ikeda et al. "Avermectin Biosynthesis" XP002941702 Chem. Rev. 97:2591–2609 (1997).
MacNeil et al. "Deletion analysis of the avermectin biosynthetic genes of streptomyces avermitilis by gene cluster displacement" XP009008304 J. Bacteriol. 175:2552–2563 (1993).
Supplementary Partial European Search Report dated Apr. 15, 2003.
Ikeda, Haruo et al., "Organization of the biosynthetic gene cluster for the polyketide anthelmintic macrolide avermectin in Streptornyces avernitilis", Proceedings of the National Academy of Sciences of the USA, Aug. 17, 1999, vol. 96, No. 17, pp. 9509–9514.

(List continued on next page.)

Primary Examiner—Nashaat T. Nashed
(74) Attorney, Agent, or Firm—Nixon & Vanderhye P.C.

(57) ABSTRACT

The present invention relates to an isolated DNA which comprises a DNA sequence encoding avermectin aglycon synthase domains that corresponds to multifunctional enzyme proteins involved in the biosynthesis of a polyketide compound, or its mutants having avermectin aglycon synthase activity, particularly functional modules and submodules in the DNA sequence derived from Streptomyces avermitilis, a polypeptide or mutants thereof encoded by the DNA or the mutants, a vector containing the DNA or the mutants, a host cell transformed with the DNA, the mutants thereof, or the vector, and a method for producing avermectin.

12 Claims, 3 Drawing Sheets

OTHER PUBLICATIONS

Marsden, Andrew F.A. et al., "Engineering Broader Specific- ity into an Antibiotic–Producing Polyketide Synthase", Science, Jan. 9, 1998, vol. 279, pp. 199–202.

Xue, Yongquan et al., "A gene cluster for macrolide antibiotic biosynthesis in *Streptomyces venezuelac*: Architecture of metabolic diversity", Proceedings of the National Academy of Sciences of the USA, Oct. 13, 1998, vol. 95, No. 21, pp. 12111–12116.

MacNeil, Douglas J. et al., "Correlation of the Avermectin Polyketide Synthase Genes to the Avermectin Structure", Annals of the New York Academy of Sciences, 1994, vol. 721, pp. 123–132.

MacNeil, Douglas J. et al., "Complex organization of the *Streptomyces avernitilis* genes encoding the avermectin polyketide synthase", Gene, Jun. 15, 1992, vol. 115, No. 1–2, pp. 119–125.

* cited by examiner

SEQUENCE LISTING

<160> NUMBER OF SEQ ID NOS: 16

<210> SEQ ID NO 1
<211> LENGTH: 30690
<212> TYPE: DNA
<213> ORGANISM: Streptomyces avermitilis
<220> FEATURE:
<221> NAME/KEY: CDS
<222> LOCATION: (1)..(11916)
<221> NAME/KEY: CDS
<222> LOCATION: (11971)..(30687)

<400> SEQUENCE: 1

| | | | | | | | | | | | | | | | | |
|---|---|---|---|---|---|---|---|---|---|---|---|---|---|---|---|---|
| gtg | cag | agg | atg | gac | ggc | ggg | gaa | gaa | ccc | cgc | cct | gcg | gca | ggg | gag | 48 |
| Val | Gln | Arg | Met | Asp | Gly | Gly | Glu | Glu | Pro | Arg | Pro | Ala | Ala | Gly | Glu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gtc | ctc | gga | gtg | gcc | gac | gag | gcg | gac | ggc | ggc | gtc | gtc | ttc | gtt | ttt | 96 |
| Val | Leu | Gly | Val | Ala | Asp | Glu | Ala | Asp | Gly | Gly | Val | Val | Phe | Val | Phe | |
| | | | 20 | | | | | 25 | | | | | 30 | | | |

| | | | | | | | | | | | | | | | | |
|---|---|---|---|---|---|---|---|---|---|---|---|---|---|---|---|---|
| ccc | ggg | cag | ggc | ccg | caa | tgg | ccg | ggc | atg | gga | agg | gaa | ctt | ctc | gac | 144 |
| Pro | Gly | Gln | Gly | Pro | Gln | Trp | Pro | Gly | Met | Gly | Arg | Glu | Leu | Leu | Asp | |
| | | 35 | | | | | 40 | | | | | 45 | | | | |

| | | | | | | | | | | | | | | | | |
|---|---|---|---|---|---|---|---|---|---|---|---|---|---|---|---|---|
| gct | tcc | gac | gtc | ttc | cgg | gag | agc | gtc | cgc | gcc | tgc | gaa | gcc | gcg | ttc | 192 |
| Ala | Ser | Asp | Val | Phe | Arg | Glu | Ser | Val | Arg | Ala | Cys | Glu | Ala | Ala | Phe | |
| | 50 | | | | | 55 | | | | | 60 | | | | | |

| | | | | | | | | | | | | | | | | |
|---|---|---|---|---|---|---|---|---|---|---|---|---|---|---|---|---|
| gcg | ccc | tac | gtc | gac | tgg | tcg | gtg | gag | cag | gtg | ttg | cgg | gac | tcg | ccg | 240 |
| Ala | Pro | Tyr | Val | Asp | Trp | Ser | Val | Glu | Gln | Val | Leu | Arg | Asp | Ser | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gac | gct | ccc | ggg | ctg | gac | cgg | gtg | gac | gtc | gtc | cag | ccg | acc | ctg | ttc | 288 |
| Asp | Ala | Pro | Gly | Leu | Asp | Arg | Val | Asp | Val | Val | Gln | Pro | Thr | Leu | Phe | |
| | | | | 85 | | | | | 90 | | | | | 95 | | |

| | | | | | | | | | | | | | | | | |
|---|---|---|---|---|---|---|---|---|---|---|---|---|---|---|---|---|
| gcc | gtc | atg | atc | tcc | ctg | gcc | gcc | ctc | tgg | cgc | tcg | caa | ggg | gtc | gag | 336 |
| Ala | Val | Met | Ile | Ser | Leu | Ala | Ala | Leu | Trp | Arg | Ser | Gln | Gly | Val | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| ccg | tgc | gcg | gtg | ctg | gga | cac | agc | ctg | ggc | gag | atc | gcg | gca | gcc | cac | 384 |
| Pro | Cys | Ala | Val | Leu | Gly | His | Ser | Leu | Gly | Glu | Ile | Ala | Ala | Ala | His | |
| | | 115 | | | | | 120 | | | | | 125 | | | | |

| | | | | | | | | | | | | | | | | |
|---|---|---|---|---|---|---|---|---|---|---|---|---|---|---|---|---|
| gtc | tcg | gga | ggc | ctg | tcc | ctg | gcc | gac | gcc | gca | cgc | gtg | gtg | acg | ctt | 432 |
| Val | Ser | Gly | Gly | Leu | Ser | Leu | Ala | Asp | Ala | Ala | Arg | Val | Val | Thr | Leu | |
| | 130 | | | | | 135 | | | | | 140 | | | | | |

| | | | | | | | | | | | | | | | | |
|---|---|---|---|---|---|---|---|---|---|---|---|---|---|---|---|---|
| tgg | agc | cag | gca | cag | acc | acc | ctt | gcc | ggg | acc | ggc | gcg | ctc | gtc | tcc | 480 |
| Trp | Ser | Gln | Ala | Gln | Thr | Thr | Leu | Ala | Gly | Thr | Gly | Ala | Leu | Val | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtc | gcc | gcc | acg | ccg | gat | gag | ctc | ctg | ccc | cga | atc | gct | ccg | tgg | acc | 528 |
| Val | Ala | Ala | Thr | Pro | Asp | Glu | Leu | Leu | Pro | Arg | Ile | Ala | Pro | Trp | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| gag | gac | aac | ccg | gcg | cgg | ctc | gcc | gtc | gca | gcc | gtc | aac | gga | ccc | cgg | 576 |
| Glu | Asp | Asn | Pro | Ala | Arg | Leu | Ala | Val | Ala | Ala | Val | Asn | Gly | Pro | Arg | |
| | | | 180 | | | | | 185 | | | | | 190 | | | |

| | | | | | | | | | | | | | | | | |
|---|---|---|---|---|---|---|---|---|---|---|---|---|---|---|---|---|
| agc | aca | gtc | gtt | tcc | ggt | gcc | cgc | gag | gcc | gtc | gcg | gac | ctg | gtg | gcc | 624 |
| Ser | Thr | Val | Val | Ser | Gly | Ala | Arg | Glu | Ala | Val | Ala | Asp | Leu | Val | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| gac | ctc | acc | gcc | gcg | cag | gtg | cgc | acg | cgc | atg | atc | ccg | gtg | gac | gtt | 672 |
| Asp | Leu | Thr | Ala | Ala | Gln | Val | Arg | Thr | Arg | Met | Ile | Pro | Val | Asp | Val | |
| | 210 | | | | | 215 | | | | | 220 | | | | | |

| | | | | | | | | | | | | | | | | |
|---|---|---|---|---|---|---|---|---|---|---|---|---|---|---|---|---|
| ccc | gcc | cac | tcc | ccc | ctg | atg | tac | gcc | atc | gag | gaa | cgg | gtc | gtc | agc | 720 |
| Pro | Ala | His | Ser | Pro | Leu | Met | Tyr | Ala | Ile | Glu | Glu | Arg | Val | Val | Ser | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ggc | ctg | ctg | ccc | atc | acc | cca | cgc | ccc | tcc | cgc | atc | ccc | ttc | cac | tcc | 768 |
| Gly | Leu | Leu | Pro | Ile | Thr | Pro | Arg | Pro | Ser | Arg | Ile | Pro | Phe | His | Ser | |

-continued

| | | | | | | | | | | | | | | | | |
|---|---|---|---|---|---|---|---|---|---|---|---|---|---|---|---|---|
| | | 245 | | | | | 250 | | | | | 255 | | | | |
| tcg | gtg | acc | ggc | ggc | cgc | ctc | gac | acc | cgc | gag | cta | gac | gcg | gcg | tac | 816 |
| Ser | Val | Thr | Gly | Gly | Arg | Leu | Asp | Thr | Arg | Glu | Leu | Asp | Ala | Ala | Tyr | |
| | | 260 | | | | | 265 | | | | | 270 | | | | |
| tgg | tac | cgc | aac | atg | tcg | agc | acg | gtc | cgg | ttc | gag | ccc | gcc | gcc | cgg | 864 |
| Trp | Tyr | Arg | Asn | Met | Ser | Ser | Thr | Val | Arg | Phe | Glu | Pro | Ala | Ala | Arg | |
| | | | 275 | | | | | 280 | | | | | 285 | | | |
| ctg | ctt | ctg | cag | cag | ggg | ccc | aag | acg | ttc | gtc | gag | atg | agc | ccg | cac | 912 |
| Leu | Leu | Leu | Gln | Gln | Gly | Pro | Lys | Thr | Phe | Val | Glu | Met | Ser | Pro | His | |
| | | 290 | | | | | 295 | | | | | 300 | | | | |
| ccg | gtg | ctg | acc | atg | ggc | ctc | cag | gag | ctc | gcc | ccg | gac | ctg | ggc | gac | 960 |
| Pro | Val | Leu | Thr | Met | Gly | Leu | Gln | Glu | Leu | Ala | Pro | Asp | Leu | Gly | Asp | |
| 305 | | | | | 310 | | | | | 315 | | | | | 320 | |
| acc | acc | ggc | acc | gcc | gac | acc | gtg | atc | atg | ggc | acg | ctg | cgc | cgc | ggc | 1008 |
| Thr | Thr | Gly | Thr | Ala | Asp | Thr | Val | Ile | Met | Gly | Thr | Leu | Arg | Arg | Gly | |
| | | | | 325 | | | | | 330 | | | | | 335 | | |
| cag | ggc | acc | ctg | gac | cac | ttc | ctg | acg | tct | ctc | gcc | caa | cta | cgg | ggg | 1056 |
| Gln | Gly | Thr | Leu | Asp | His | Phe | Leu | Thr | Ser | Leu | Ala | Gln | Leu | Arg | Gly | |
| | | | 340 | | | | | 345 | | | | | 350 | | | |
| cat | ggt | gag | acg | tcg | gcg | acc | acc | gtc | ctc | tcg | gca | cgc | ctg | acc | gcg | 1104 |
| His | Gly | Glu | Thr | Ser | Ala | Thr | Thr | Val | Leu | Ser | Ala | Arg | Leu | Thr | Ala | |
| | | 355 | | | | | 360 | | | | | 365 | | | | |
| ctg | tcc | ccc | acg | cag | cag | cag | tcg | ctg | ctc | ctg | gac | ctg | gtg | cgc | gcc | 1152 |
| Leu | Ser | Pro | Thr | Gln | Gln | Gln | Ser | Leu | Leu | Leu | Asp | Leu | Val | Arg | Ala | |
| 370 | | | | | 375 | | | | | 380 | | | | | | |
| cac | acc | atg | gcg | gtg | ctg | aac | gac | gac | gga | aac | gag | cgc | acc | gcg | tcg | 1200 |
| His | Thr | Met | Ala | Val | Leu | Asn | Asp | Asp | Gly | Asn | Glu | Arg | Thr | Ala | Ser | |
| 385 | | | | | 390 | | | | | 395 | | | | | 400 | |
| gat | gcc | ggc | cca | tcg | gcg | agt | ttc | gcc | cac | ctc | ggc | ttc | gac | tcc | gtc | 1248 |
| Asp | Ala | Gly | Pro | Ser | Ala | Ser | Phe | Ala | His | Leu | Gly | Phe | Asp | Ser | Val | |
| | | | | 405 | | | | | 410 | | | | | 415 | | |
| atg | ggt | gtc | gaa | ctg | cgc | aac | cgc | ctc | agc | aag | gcc | acg | ggc | ctg | cgg | 1296 |
| Met | Gly | Val | Glu | Leu | Arg | Asn | Arg | Leu | Ser | Lys | Ala | Thr | Gly | Leu | Arg | |
| | | | 420 | | | | | 425 | | | | | 430 | | | |
| ttg | ccc | gtg | acg | ctc | atc | ttc | gac | cac | acc | acg | ccg | gcc | gcg | gtc | gcc | 1344 |
| Leu | Pro | Val | Thr | Leu | Ile | Phe | Asp | His | Thr | Thr | Pro | Ala | Ala | Val | Ala | |
| | | 435 | | | | | 440 | | | | | 445 | | | | |
| gcg | cgc | ctt | cgg | acc | gcg | gcg | ctc | ggc | cac | ctc | gac | gag | gac | acc | gcg | 1392 |
| Ala | Arg | Leu | Arg | Thr | Ala | Ala | Leu | Gly | His | Leu | Asp | Glu | Asp | Thr | Ala | |
| 450 | | | | | 455 | | | | | 460 | | | | | | |
| ccc | gta | ccg | gac | tca | ccc | agc | ggc | cac | gga | ggc | acg | gca | gcg | gcg | gac | 1440 |
| Pro | Val | Pro | Asp | Ser | Pro | Ser | Gly | His | Gly | Gly | Thr | Ala | Ala | Ala | Asp | |
| 465 | | | | | 470 | | | | | 475 | | | | | 480 | |
| gac | ccg | atc | gcc | atc | atc | ggc | atg | gca | tgc | cgt | ttc | ccg | ggc | gga | gtc | 1488 |
| Asp | Pro | Ile | Ala | Ile | Ile | Gly | Met | Ala | Cys | Arg | Phe | Pro | Gly | Gly | Val | |
| | | | | 485 | | | | | 490 | | | | | 495 | | |
| cgg | tcc | ccg | aag | gac | ctg | tgg | gag | ctg | gcc | gcc | tcg | ggc | gga | gac | gcc | 1536 |
| Arg | Ser | Pro | Lys | Asp | Leu | Trp | Glu | Leu | Ala | Ala | Ser | Gly | Gly | Asp | Ala | |
| | | | 500 | | | | | 505 | | | | | 510 | | | |
| atc | ggg | ccg | ttc | ccc | acc | gac | cgc | gga | tgg | ccc | acg | gaa | cag | cgt | cac | 1584 |
| Ile | Gly | Pro | Phe | Pro | Thr | Asp | Arg | Gly | Trp | Pro | Thr | Glu | Gln | Arg | His | |
| | | 515 | | | | | 520 | | | | | 525 | | | | |
| gcc | cag | gac | ccc | acg | cag | ccc | ggc | acg | ttc | tat | ccg | cag | gga | ggc | ggg | 1632 |
| Ala | Gln | Asp | Pro | Thr | Gln | Pro | Gly | Thr | Phe | Tyr | Pro | Gln | Gly | Gly | Gly | |
| | | 530 | | | | | 535 | | | | | 540 | | | | |
| ttc | ctt | cac | gac | gcg | gcg | cac | ttc | gac | gcc | ggc | ttc | ttc | gga | atc | agt | 1680 |
| Phe | Leu | His | Asp | Ala | Ala | His | Phe | Asp | Ala | Gly | Phe | Phe | Gly | Ile | Ser | |
| 545 | | | | | 550 | | | | | 555 | | | | | 560 | |
| cca | cgt | gag | gca | ctg | gcg | atg | gat | ccg | cag | cag | cgg | ctg | ctg | ctg | gag | 1728 |

-continued

```
                    Pro Arg Glu Ala Leu Ala Met Asp Pro Gln Gln Arg Leu Leu Leu Glu
                                    565                 570                 575 acg tcc tgg gag gcg ttc gag cgg gcg gga atc gat ccg ctg tcg gta          1776
Thr Ser Trp Glu Ala Phe Glu Arg Ala Gly Ile Asp Pro Leu Ser Val
            580                 585                 590 cgc ggg tcc cgt acg ggc gtc ttc gcg ggc gcc ctc tcc ttc gac tac          1824
Arg Gly Ser Arg Thr Gly Val Phe Ala Gly Ala Leu Ser Phe Asp Tyr
        595                 600                 605 ggc ccg cgt atg gac acc gcg tcg tcg gag ggc gcc gcg gac gtg gag          1872
Gly Pro Arg Met Asp Thr Ala Ser Ser Glu Gly Ala Ala Asp Val Glu
    610                 615                 620 ggc cac atc ctc acc ggt acc acg ggc agc gtc ctg tcg ggc cgt atc          1920
Gly His Ile Leu Thr Gly Thr Thr Gly Ser Val Leu Ser Gly Arg Ile
625                 630                 635                 640 gcc tac agc ttc ggg ctg gaa ggg ccg gcg atc acc gtg gac acg ggg          1968
Ala Tyr Ser Phe Gly Leu Glu Gly Pro Ala Ile Thr Val Asp Thr Gly
            645                 650                 655 tgc tcg gca tcg ctc gtg acg ctg cat ctg gcg tgc cag tcg ctg cgg          2016
Cys Ser Ala Ser Leu Val Thr Leu His Leu Ala Cys Gln Ser Leu Arg
        660                 665                 670 tcg ggt gag tgc acg ctc gcg ctg gcc ggc ggc gtc tcg gtc atg tcc          2064
Ser Gly Glu Cys Thr Leu Ala Leu Ala Gly Gly Val Ser Val Met Ser
    675                 680                 685 acc ctc ggc atg ttc atc gag ttc tcc cgg cag cgc ggg ctg tcg gtg          2112
Thr Leu Gly Met Phe Ile Glu Phe Ser Arg Gln Arg Gly Leu Ser Val
690                 695                 700 gac ggc agg tgc aag gcg tac tcg gct gca gcc gac ggc acc ggc tgg          2160
Asp Gly Arg Cys Lys Ala Tyr Ser Ala Ala Ala Asp Gly Thr Gly Trp
705                 710                 715                 720 ggc gag ggc gtc ggg atg ctg ttg gtg gag cgg ttg tcg gat gcg gtg          2208
Gly Glu Gly Val Gly Met Leu Leu Val Glu Arg Leu Ser Asp Ala Val
            725                 730                 735 cgg ctg ggg cat cgg gtg ctg gcg gtg gta cgc ggc agt gcg gtc aac          2256
Arg Leu Gly His Arg Val Leu Ala Val Val Arg Gly Ser Ala Val Asn
        740                 745                 750 cag gac ggt gcg tcg aat ggg ctg acg gcg ccg aac ggt ccg gct cag          2304
Gln Asp Gly Ala Ser Asn Gly Leu Thr Ala Pro Asn Gly Pro Ala Gln
    755                 760                 765 gag cgg gtg atc cgg cag gcg ttg gcg aac gcg ggg ttg tcc gtg gcg          2352
Glu Arg Val Ile Arg Gln Ala Leu Ala Asn Ala Gly Leu Ser Val Ala
770                 775                 780 gat gtg gat gtg gtg gag ggg cac ggg acg ggc acg acg ctg ggt gat          2400
Asp Val Asp Val Val Glu Gly His Gly Thr Gly Thr Thr Leu Gly Asp
785                 790                 795                 800 ccg atc gag gca cag gcg ttg ctc gcc acg tac ggg cag cgg gcc ggt          2448
Pro Ile Glu Ala Gln Ala Leu Leu Ala Thr Tyr Gly Gln Arg Ala Gly
            805                 810                 815 gac agg ccg ctg tgg ctg ggg tct ctg aag tcc aac atc ggg cac acc          2496
Asp Arg Pro Leu Trp Leu Gly Ser Leu Lys Ser Asn Ile Gly His Thr
        820                 825                 830 atg gct gcc gcg ggt gtg ggt ggg gtc atc aag atg gtg atg gcg ttg          2544
Met Ala Ala Ala Gly Val Gly Gly Val Ile Lys Met Val Met Ala Leu
    835                 840                 845 cgg gag ggg gtg ttg ccg cgg acg ttg cat gtg gat aag ccg tcg ccg          2592
Arg Glu Gly Val Leu Pro Arg Thr Leu His Val Asp Lys Pro Ser Pro
850                 855                 860 cag gtg gac tgg tcc gcg ggg gcg gtg cgg ctg ctg acg gag gcg gtg          2640
Gln Val Asp Trp Ser Ala Gly Ala Val Arg Leu Leu Thr Glu Ala Val
865                 870                 875                 880
```

-continued

| | |
|---|---|
| ccg tgg ccg ggg gac gcg gca ggg cgg ttg cgg cgg gcg gga gtg tcg<br>Pro Trp Pro Gly Asp Ala Ala Gly Arg Leu Arg Arg Ala Gly Val Ser<br>885               890               895 | 2688 |
| tcg ttc ggg atc ggc ggc acg aat gcg cat gtg att ttg gag gag gcg<br>Ser Phe Gly Ile Gly Gly Thr Asn Ala His Val Ile Leu Glu Glu Ala<br>    900               905               910 | 2736 |
| ccg gcg gcg ggg ggc tgt gtt gcc ggg ggt ggg gtg ttg gag ggt gct<br>Pro Ala Ala Gly Gly Cys Val Ala Gly Gly Gly Val Leu Glu Gly Ala<br>915               920               925 | 2784 |
| ccg ggt ctt gcc att tcg gtg gct gag tcg gtg gcc gct cca gtg gct<br>Pro Gly Leu Ala Ile Ser Val Ala Glu Ser Val Ala Ala Pro Val Ala<br>    930               935               940 | 2832 |
| gtg tct gcg ccg gtg gct gag tcg gtg ccg gtg ccg gtg ccg gtg ccg<br>Val Ser Ala Pro Val Ala Glu Ser Val Pro Val Pro Val Pro Val Pro<br>945               950               955               960 | 2880 |
| gtt cct gtg ccg gtg tcg gct agg tct gag gct ggg ttg cgg gcg cag<br>Val Pro Val Pro Val Ser Ala Arg Ser Glu Ala Gly Leu Arg Ala Gln<br>    965               970               975 | 2928 |
| gcg gag gcg ttg cgt cag tac gtg gca gtc cgg ccg gac gtt tcg ctt<br>Ala Glu Ala Leu Arg Gln Tyr Val Ala Val Arg Pro Asp Val Ser Leu<br>980               985               990 | 2976 |
| gcc gat gtg ggt gcg ggt ctg gcc tgt ggg cgg gct gtg ctg gag cat<br>Ala Asp Val Gly Ala Gly Leu Ala Cys Gly Arg Ala Val Leu Glu His<br>    995             1000             1005 | 3024 |
| cgt gcg gtc gtc ctg gcc gcg gac cgt gag gag ctg gtg caa ggg ttg<br>Arg Ala Val Val Leu Ala Ala Asp Arg Glu Glu Leu Val Gln Gly Leu<br>1010             1015             1020 | 3072 |
| ggg gcg ctg gcg gcg ggt gag ccg gat cgg cgg gtg acc acg ggt cat<br>Gly Ala Leu Ala Ala Gly Glu Pro Asp Arg Arg Val Thr Thr Gly His<br>1025             1030             1035             1040 | 3120 |
| gcg ccg ggt ggt gac cgg ggc ggt gtc gtc ttc gtg ttt ccc gga cag<br>Ala Pro Gly Gly Asp Arg Gly Gly Val Val Phe Val Phe Pro Gly Gln<br>    1045             1050             1055 | 3168 |
| ggt ggg cag tgg gcc ggg atg ggt gtg cgt ctg ctc gcc tcc tct ccg<br>Gly Gly Gln Trp Ala Gly Met Gly Val Arg Leu Leu Ala Ser Ser Pro<br>1060             1065             1070 | 3216 |
| gtg ttc gcc cgg cgg atg cag gcg tgc gag gag gct ctg gcg ccg tgg<br>Val Phe Ala Arg Arg Met Gln Ala Cys Glu Glu Ala Leu Ala Pro Trp<br>1075             1080             1085 | 3264 |
| gtg gac tgg tct gtg gtg gac atc ctg cgc cgg gac gcg ggg gat gcg<br>Val Asp Trp Ser Val Val Asp Ile Leu Arg Arg Asp Ala Gly Asp Ala<br>1090             1095             1100 | 3312 |
| gtg tgg gag cgg gcc gat gtg gtc cag cct gtg ctg ttc agc gtc atg<br>Val Trp Glu Arg Ala Asp Val Val Gln Pro Val Leu Phe Ser Val Met<br>1105             1110             1115             1120 | 3360 |
| gtg tct ttg gct gct ctg tgg cgt tcc tac ggt atc gaa ccc gac gcg<br>Val Ser Leu Ala Ala Leu Trp Arg Ser Tyr Gly Ile Glu Pro Asp Ala<br>    1125             1130             1135 | 3408 |
| gtc ctt ggc cat tcc cag ggc gag atc gcg gcc gcg cat gtg tgt ggg<br>Val Leu Gly His Ser Gln Gly Glu Ile Ala Ala Ala His Val Cys Gly<br>             1140             1145             1150 | 3456 |
| gcg ctg agc ctg aag gac gcg gcg aag act gtt gcg ctg cgc agc cgg<br>Ala Leu Ser Leu Lys Asp Ala Ala Lys Thr Val Ala Leu Arg Ser Arg<br>1155             1160             1165 | 3504 |
| gcg ctg gcc gct gtg cgg ggc cgg ggc ggc atg gcc tca gtg ccg ctg<br>Ala Leu Ala Ala Val Arg Gly Arg Gly Gly Met Ala Ser Val Pro Leu<br>1170             1175             1180 | 3552 |
| cct gcc cag gag gtg gag cag ctc att ggt gag cgg tgg gcg ggg cgg<br>Pro Ala Gln Glu Val Glu Gln Leu Ile Gly Glu Arg Trp Ala Gly Arg<br>1185             1190             1195             1200 | 3600 |

-continued

| | |
|---|---|
| ttg tgg gtg gcg gcg gtc aac ggc ccc cgc tcc acc gcc gtc tcg ggg<br>Leu Trp Val Ala Ala Val Asn Gly Pro Arg Ser Thr Ala Val Ser Gly<br>          1205                      1210                      1215 | 3648 |
| gat gcc gag gcg gtg gac gag gtg ctg gcg tac tgt gcc ggc acc ggg<br>Asp Ala Glu Ala Val Asp Glu Val Leu Ala Tyr Cys Ala Gly Thr Gly<br>        1220                      1225                      1230 | 3696 |
| gtg cgg gcc cgg cgg atc ccg gtc gac tat gcc tcg cac tgc ccc cat<br>Val Arg Ala Arg Arg Ile Pro Val Asp Tyr Ala Ser His Cys Pro His<br>           1235                      1240                      1245 | 3744 |
| gtg cag ccc ctg cgg gag gag ttg ctg gag ctg ctg ggg gac atc agc<br>Val Gln Pro Leu Arg Glu Glu Leu Leu Glu Leu Leu Gly Asp Ile Ser<br>    1250                      1255                      1260 | 3792 |
| ccg cag ccg tcc ggc gtg ccg ttc ttc tcc acg gtg gag ggc acc tgg<br>Pro Gln Pro Ser Gly Val Pro Phe Phe Ser Thr Val Glu Gly Thr Trp<br>1265                      1270                      1275                      1280 | 3840 |
| ctg gac acc aca acc ctg gac gcc gcc tac tgg tac cgc aac ctg cac<br>Leu Asp Thr Thr Thr Leu Asp Ala Ala Tyr Trp Tyr Arg Asn Leu His<br>           1285                      1290                      1295 | 3888 |
| cag ccg gtc cgt ttc agc gat gcc gtc cag gcc ctg gcg gat gac gga<br>Gln Pro Val Arg Phe Ser Asp Ala Val Gln Ala Leu Ala Asp Asp Gly<br>        1300                      1305                      1310 | 3936 |
| cac cgc gtc ttc gtc gaa gtc agc ccc cac ccc acc ctc gtc ccc gcc<br>His Arg Val Phe Val Glu Val Ser Pro His Pro Thr Leu Val Pro Ala<br>           1315                      1320                      1325 | 3984 |
| atc gaa gac acc acc gaa gac acc gcc gaa gac gtc acc gcg atc ggc<br>Ile Glu Asp Thr Thr Glu Asp Thr Ala Glu Asp Val Thr Ala Ile Gly<br>        1330                      1335                      1340 | 4032 |
| agc ctc cgc cgc ggc gac aac gac acc cgc cgc ttc ctc acc gcc ctc<br>Ser Leu Arg Arg Gly Asp Asn Asp Thr Arg Arg Phe Leu Thr Ala Leu<br>1345                      1350                      1355                      1360 | 4080 |
| gcc cac acc cat acc acc ggc atc ggc aca ccc acc acc tgg cac cac<br>Ala His Thr His Thr Thr Gly Ile Gly Thr Pro Thr Thr Trp His His<br>           1365                      1370                      1375 | 4128 |
| cac tac acc cac cac cac acc cac ccc cac ccc cac acg cac ctc gac<br>His Tyr Thr His His His Thr His Pro His Pro His Thr His Leu Asp<br>        1380                      1385                      1390 | 4176 |
| ctg ccc acc tac ccc ttc caa cac cag cac tac tgg ctc gag agc tca<br>Leu Pro Thr Tyr Pro Phe Gln His Gln His Tyr Trp Leu Glu Ser Ser<br>           1395                      1400                      1405 | 4224 |
| cag ccg ggt gcc gga tcc ggt tcg ggt gcc ggt gcc ggt tcg ggt gcc<br>Gln Pro Gly Ala Gly Ser Gly Ser Gly Ala Gly Ala Gly Ser Gly Ala<br>        1410                      1415                      1420 | 4272 |
| ggt tcc ggg cgg gca ggg act gcg ggc ggg acg gca gag gtg gag tcg<br>Gly Ser Gly Arg Ala Gly Thr Ala Gly Gly Thr Ala Glu Val Glu Ser<br>1425                      1430                      1435                      1440 | 4320 |
| cgg ttc tgg gac gcg gtg gcc cgc cag gac ctg gaa acg gtc gcg acc<br>Arg Phe Trp Asp Ala Val Ala Arg Gln Asp Leu Glu Thr Val Ala Thr<br>           1445                      1450                      1455 | 4368 |
| aca ctc gcc gtg ccc ccc tcc gcc ggc ctg gac acg gtg gtg ccc gca<br>Thr Leu Ala Val Pro Pro Ser Ala Gly Leu Asp Thr Val Val Pro Ala<br>        1460                      1465                      1470 | 4416 |
| ctc tcc gcc tgg cac cgc cac caa cac gac caa gcc cgc atc aac acc<br>Leu Ser Ala Trp His Arg His Gln His Asp Gln Ala Arg Ile Asn Thr<br>           1475                      1480                      1485 | 4464 |
| tgg acc tac cag gaa acc tgg aaa ccc ctc acc ctc acc acc cac<br>Trp Thr Tyr Gln Glu Thr Trp Lys Pro Leu Thr Leu Thr Thr His<br>        1490                      1495                      1500 | 4512 |
| caa ccc cac caa acc tgg ctc atc gcc atc ccc gaa acc cag acc cac<br>Gln Pro His Gln Thr Trp Leu Ile Ala Ile Pro Glu Thr Gln Thr His | 4560 |

-continued

```
                1505                1510                1515                1520
cac ccc cac atc acc aac atc ctc acc aac ctc cac cac ggc atc                    4608
His Pro His Ile Thr Asn Ile Leu Thr Asn Leu His His His Gly Ile
            1525                1530                1535 acc ccc atc ccc ctc acc ctc aac cac acc cac acc aac ccc caa cac                4656
Thr Pro Ile Pro Leu Thr Leu Asn His Thr His Thr Asn Pro Gln His
        1540                1545                1550 ctc cac cac acc ctc cac cac acc cga caa caa gcc caa aac cac acc                4704
Leu His His Thr Leu His His Thr Arg Gln Gln Ala Gln Asn His Thr
    1555                1560                1565 acc gga gcc atc acc ggc ctg ctc tcc ctc ctc gcc ctc gac gaa aca                4752
Thr Gly Ala Ile Thr Gly Leu Leu Ser Leu Leu Ala Leu Asp Glu Thr
1570                1575                1580 ccc cac ccc cac cac ccc cac aca ccc acc ggc acc ctc ctc aac ctc                4800
Pro His Pro His His Pro His Thr Pro Thr Gly Thr Leu Leu Asn Leu
1585                1590                1595                1600 acc ctc acc caa acc cac acc caa acc cac cca cca acc ccc ctc tgg                4848
Thr Leu Thr Gln Thr His Thr Gln Thr His Pro Pro Thr Pro Leu Trp
                1605                1610                1615 tac gcc acc acc aac gcc acc acc acc cac ccc aac gac ccc ctc aca                4896
Tyr Ala Thr Thr Asn Ala Thr Thr Thr His Pro Asn Asp Pro Leu Thr
            1620                1625                1630 cac ccc acc caa gcc caa acc tgg gga ctc gcc cgc acc acc ctc ctc                4944
His Pro Thr Gln Ala Gln Thr Trp Gly Leu Ala Arg Thr Thr Leu Leu
        1635                1640                1645 gaa cac ccc acc cac acc gcc gga atc atc gac ctc ccc acc acc ccc                4992
Glu His Pro Thr His Thr Ala Gly Ile Ile Asp Leu Pro Thr Thr Pro
    1650                1655                1660 acc ccc cac acc ctc cag cac ctc acc caa acc ctc acc caa ccc cac                5040
Thr Pro His Thr Leu Gln His Leu Thr Gln Thr Leu Thr Gln Pro His
1665                1670                1675                1680 cac caa acc caa ctc gcc atc cgc acc acc ggc acc cac acc cgc cgc                5088
His Gln Thr Gln Leu Ala Ile Arg Thr Thr Gly Thr His Thr Arg Arg
                1685                1690                1695 ctc acc ccc acc acc ctc acc ccc aca cac caa cca ccc acc ccc acc                5136
Leu Thr Pro Thr Thr Leu Thr Pro Thr His Gln Pro Pro Thr Pro Thr
            1700                1705                1710 ccc cac gga acc acc ctc atc acc ggc gga acc ggc gcc ctc gcc acc                5184
Pro His Gly Thr Thr Leu Ile Thr Gly Gly Thr Gly Ala Leu Ala Thr
        1715                1720                1725 cac ctc acc cac cac ctc acc acc cac caa ccc acc caa cac ctc ctc                5232
His Leu Thr His His Leu Thr Thr His Gln Pro Thr Gln His Leu Leu
    1730                1735                1740 ctc acc agc cga acc ggc ccc cac acc ccc cac gca caa cac ctc acc                5280
Leu Thr Ser Arg Thr Gly Pro His Thr Pro His Ala Gln His Leu Thr
1745                1750                1755                1760 acc caa ctc caa caa aaa ggc atc cac ctc acc atc acc acc tgc gac                5328
Thr Gln Leu Gln Gln Lys Gly Ile His Leu Thr Ile Thr Thr Cys Asp
                1765                1770                1775 acc agc aac cca gac caa ctc caa caa ctc ctc aac acc atc ccc cca                5376
Thr Ser Asn Pro Asp Gln Leu Gln Gln Leu Leu Asn Thr Ile Pro Pro
            1780                1785                1790 caa cac ccc ctc acc acc gtc atc cac acc gca ggc atc ctc gac gac                5424
Gln His Pro Leu Thr Thr Val Ile His Thr Ala Gly Ile Leu Asp Asp
        1795                1800                1805 gcc acc ctc acc aac ctc acc ccc acc caa ctc aac aac gtc ctc cgc                5472
Ala Thr Leu Thr Asn Leu Thr Pro Thr Gln Leu Asn Asn Val Leu Arg
    1810                1815                1820 gcc aaa gcc cac agc gcc cac ctc ctc cac caa ctc acc caa cac acc                5520
```

-continued

```
                 Ala Lys Ala His Ser Ala His Leu Leu His Gln Leu Thr Gln His Thr
                 1825                1830                1835                1840 ccc ctc acc gcc ttc gtc ctc tac tcc tcc gcc gcc gcc acc ttc ggc               5568
Pro Leu Thr Ala Phe Val Leu Tyr Ser Ser Ala Ala Ala Thr Phe Gly
            1845                1850                1855 gca ccc ggc caa gcc aac tac gcc gca gcc aac gcc tac ctc gac gcc               5616
Ala Pro Gly Gln Ala Asn Tyr Ala Ala Ala Asn Ala Tyr Leu Asp Ala
    1860                1865                1870 ctc gcc cac cac cgc cac acc cac cac ctc ccc gcc acc agc atc gcc               5664
Leu Ala His His Arg His Thr His His Leu Pro Ala Thr Ser Ile Ala
1875                1880                1885 tgg ggc acc tgg caa gga aac gga ctc gct gat tcg gac aag gcc cgc               5712
Trp Gly Thr Trp Gln Gly Asn Gly Leu Ala Asp Ser Asp Lys Ala Arg
        1890                1895                1900 gca tat ctc gac cgc cgc ggg ttt cga ccc atg tca ccc gag ttg gcc               5760
Ala Tyr Leu Asp Arg Arg Gly Phe Arg Pro Met Ser Pro Glu Leu Ala
1905                1910                1915                1920 acg gca gcg gtc acg cag gcg atc gcg gac acc gaa cgg ccg tat gtc               5808
Thr Ala Ala Val Thr Gln Ala Ile Ala Asp Thr Glu Arg Pro Tyr Val
            1925                1930                1935 gtc atc gcc gac atc gac tgg agc aag atc gaa cac acc tct cag acc               5856
Val Ile Ala Asp Ile Asp Trp Ser Lys Ile Glu His Thr Ser Gln Thr
        1940                1945                1950 agc gac ctg gtg agc gcg gcc cgg gaa agg gag cca gct gtc cag cgc               5904
Ser Asp Leu Val Ser Ala Ala Arg Glu Arg Glu Pro Ala Val Gln Arg
    1955                1960                1965 ccc act cca ccg gcg gag ttg cac aaa acg ctg gcc cat cag acg tcg               5952
Pro Thr Pro Pro Ala Glu Leu His Lys Thr Leu Ala His Gln Thr Ser
1970                1975                1980 gcc gac caa cgg gcc gca ttg ctc gag ctc gta cga gac cat gtg gcg               6000
Ala Asp Gln Arg Ala Ala Leu Leu Glu Leu Val Arg Asp His Val Ala
1985                1990                1995                2000 gca gtg ctc cgg cac gcg gac ccg aaa gcc atc gcg ccc gac cag tcg               6048
Ala Val Leu Arg His Ala Asp Pro Lys Ala Ile Ala Pro Asp Gln Ser
            2005                2010                2015 ttc cgt gca ctc ggc ttc gat tca ctc acg gcc gtc gag ttc cga aac               6096
Phe Arg Ala Leu Gly Phe Asp Ser Leu Thr Ala Val Glu Phe Arg Asn
        2020                2025                2030 ctg ctg atc aag gca aca gga ctc cgc ctt cct gtc tcg ctg gtc ttc               6144
Leu Leu Ile Lys Ala Thr Gly Leu Arg Leu Pro Val Ser Leu Val Phe
    2035                2040                2045 gac cac ccg acc cct gcc aaa ctc gcc gta cac ctg cag aac caa ctg               6192
Asp His Pro Thr Pro Ala Lys Leu Ala Val His Leu Gln Asn Gln Leu
2050                2055                2060 cgg ggc aca gca gcg gag tcg gct cct tca gcg gca gcc gtt acc gcc               6240
Arg Gly Thr Ala Ala Glu Ser Ala Pro Ser Ala Ala Ala Val Thr Ala
2065                2070                2075                2080 gag gct tct gtc acc gag ccg atc gcc atc gtt ggc atg gcc tgt cgt               6288
Glu Ala Ser Val Thr Glu Pro Ile Ala Ile Val Gly Met Ala Cys Arg
            2085                2090                2095 ttc ccc ggc gga gtg acc tcg gcg gac gac ttc tgg gat ctg atc tcc               6336
Phe Pro Gly Gly Val Thr Ser Ala Asp Asp Phe Trp Asp Leu Ile Ser
        2100                2105                2110 tcc gag cag gac gcg atc ggc gga ttc ccc acc gac cgc ggc tgg gac               6384
Ser Glu Gln Asp Ala Ile Gly Gly Phe Pro Thr Asp Arg Gly Trp Asp
    2115                2120                2125 ctg gac acg ctc tac gac ccc gac ccc gac cac ccc ggc acc tgc tac               6432
Leu Asp Thr Leu Tyr Asp Pro Asp Pro Asp His Pro Gly Thr Cys Tyr
2130                2135                2140
```

-continued

| | |
|---|---|
| acc cga aac ggc gga ttc ctc tac gac gca ggc cac ttc gac gcc gaa<br>Thr Arg Asn Gly Gly Phe Leu Tyr Asp Ala Gly His Phe Asp Ala Glu<br>2145                2150              2155              2160 | 6480 |
| ttc ttc ggc atc agc ccc cgc gaa gcc ctc gcc atg gac ccc cag caa<br>Phe Phe Gly Ile Ser Pro Arg Glu Ala Leu Ala Met Asp Pro Gln Gln<br>              2165              2170              2175 | 6528 |
| cga ctc ctc ctc gaa acc gcc tgg gaa acc atc gaa cac gcc ggc atc<br>Arg Leu Leu Leu Glu Thr Ala Trp Glu Thr Ile Glu His Ala Gly Ile<br>              2180              2185              2190 | 6576 |
| aac ccc cac acc ctc cac ggc acc ccc acc gga gtc ttc acc ggc acc<br>Asn Pro His Thr Leu His Gly Thr Pro Thr Gly Val Phe Thr Gly Thr<br>              2195              2200              2205 | 6624 |
| aac gga cag gac tac gca ctt cgc gtg cac aac gcg ggc cag tca acc<br>Asn Gly Gln Asp Tyr Ala Leu Arg Val His Asn Ala Gly Gln Ser Thr<br>              2210              2215              2220 | 6672 |
| gat ggt ttc gca ctg acc gga acc gcc ggc agc gtc atc tcc ggt cgt<br>Asp Gly Phe Ala Leu Thr Gly Thr Ala Gly Ser Val Ile Ser Gly Arg<br>2225                2230              2235              2240 | 6720 |
| atc tcg tac acg ttt ggt ttt gag ggt cct gcg gtg tcg gtg gac acg<br>Ile Ser Tyr Thr Phe Gly Phe Glu Gly Pro Ala Val Ser Val Asp Thr<br>              2245              2250              2255 | 6768 |
| gct tgt tcc tcg tcg ttg gtg gct ttg cat ctg gcc tgt cag gcg ttg<br>Ala Cys Ser Ser Ser Leu Val Ala Leu His Leu Ala Cys Gln Ala Leu<br>              2260              2265              2270 | 6816 |
| cgt gcg ggt gag tgc tcg atg gcg ctt gcc ggg ggt gtg acg gtg atg<br>Arg Ala Gly Glu Cys Ser Met Ala Leu Ala Gly Gly Val Thr Val Met<br>              2275              2280              2285 | 6864 |
| tcg tct ccg ggt gcc ttc gtg gag ttt tcg cgg cag cgg ggt ctg gcc<br>Ser Ser Pro Gly Ala Phe Val Glu Phe Ser Arg Gln Arg Gly Leu Ala<br>              2290              2295              2300 | 6912 |
| gcg gac ggg cat tgc aag gcg ttc tcg gcg gcg gcg gac ggg acc ggc<br>Ala Asp Gly His Cys Lys Ala Phe Ser Ala Ala Ala Asp Gly Thr Gly<br>2305                2310              2315              2320 | 6960 |
| tgg ggt gag ggt gtg ggg atg ctg ctg gtg gag cgg ctc tcc gac gcc<br>Trp Gly Glu Gly Val Gly Met Leu Leu Val Glu Arg Leu Ser Asp Ala<br>              2325              2330              2335 | 7008 |
| cat cgc aac ggt cac cgt gtc ctg gcc gtg gtg cgt ggc agt gcg gtc<br>His Arg Asn Gly His Arg Val Leu Ala Val Val Arg Gly Ser Ala Val<br>              2340              2345              2350 | 7056 |
| aac cag gac ggt gcg agc aac ggt ctg acc gcg ccc aac ggg ccg tcc<br>Asn Gln Asp Gly Ala Ser Asn Gly Leu Thr Ala Pro Asn Gly Pro Ser<br>              2355              2360              2365 | 7104 |
| cag cag cgt gtc atc cgc cag gcc ctc gcc aac gcc ggc ttg tcg gcc<br>Gln Gln Arg Val Ile Arg Gln Ala Leu Ala Asn Ala Gly Leu Ser Ala<br>              2370              2375              2380 | 7152 |
| ggt gat gtc gac gcg gtg gag gcc cac ggc acc ggc acc act ttg ggc<br>Gly Asp Val Asp Ala Val Glu Ala His Gly Thr Gly Thr Thr Leu Gly<br>2385                2390              2395              2400 | 7200 |
| gac ccg atc gag gcc cag gcc ctc ctc gcg acc tac gga cag gac cgt<br>Asp Pro Ile Glu Ala Gln Ala Leu Leu Ala Thr Tyr Gly Gln Asp Arg<br>              2405              2410              2415 | 7248 |
| gcc ggc gag ggg ccg ctg tgg ctg ggc tcg gtc aag tcc aat gtc ggt<br>Ala Gly Glu Gly Pro Leu Trp Leu Gly Ser Val Lys Ser Asn Val Gly<br>              2420              2425              2430 | 7296 |
| cac aca cag gct gcc gcg ggc gtc gcc ggg gtg atc aag atg gtg atg<br>His Thr Gln Ala Ala Ala Gly Val Ala Gly Val Ile Lys Met Val Met<br>              2435              2440              2445 | 7344 |
| gcg ctg cgg cat ggt ctg ctg ccg cgg acg ttg cat gtg gat gag ccg<br>Ala Leu Arg His Gly Leu Leu Pro Arg Thr Leu His Val Asp Glu Pro<br>2450                2455              2460 | 7392 |

```
tcg ccg cat gtg gac tgg tcc gcg ggt gcg gtg cag ctg ctg acg gag    7440
Ser Pro His Val Asp Trp Ser Ala Gly Ala Val Gln Leu Leu Thr Glu
2465                2470                2475                2480 acg gtg ccc tgg ccc ggc ggg gag ggg cgg cta cgg cgg gca gga gtg    7488
Thr Val Pro Trp Pro Gly Gly Glu Gly Arg Leu Arg Arg Ala Gly Val
            2485                2490                2495 tca tca ttc ggc gtc agc ggc acc aac gcc cac gtc atc ctc gaa gaa    7536
Ser Ser Phe Gly Val Ser Gly Thr Asn Ala His Val Ile Leu Glu Glu
2500                2505                2510 gca ccc gcc gac gac gtt ccg ggg gga cca ccc gcc ggc gag ggt gac    7584
Ala Pro Ala Asp Asp Val Pro Gly Gly Pro Pro Ala Gly Glu Gly Asp
        2515                2520                2525 gcg ggc agc gac gat gag gct gct gcc ggc agt cct ggg gtg tgg ccg    7632
Ala Gly Ser Asp Asp Glu Ala Ala Ala Gly Ser Pro Gly Val Trp Pro
    2530                2535                2540 tgg ctg gtg tcg gcc aag tcg cag ccg gcc ctg cgc gcc cag gcc cag    7680
Trp Leu Val Ser Ala Lys Ser Gln Pro Ala Leu Arg Ala Gln Ala Gln
2545                2550                2555                2560 gcc ctg cac gcc cac ctc acc gac cac ccc ggc ctc gac ctc gcg gat    7728
Ala Leu His Ala His Leu Thr Asp His Pro Gly Leu Asp Leu Ala Asp
            2565                2570                2575 gtc gga tac acc ctc gcc cac gcc cgc gcc gtg ttc gac cac cgc gcc    7776
Val Gly Tyr Thr Leu Ala His Ala Arg Ala Val Phe Asp His Arg Ala
        2580                2585                2590 acc ctc atc gcc gcg gac cgc gac acg ttc ctg caa gca ctc cag gca    7824
Thr Leu Ile Ala Ala Asp Arg Asp Thr Phe Leu Gln Ala Leu Gln Ala
    2595                2600                2605 ctc gcc gca ggc gag ccc cac ccc gcc gtc atc cac agc agc gcc ccg    7872
Leu Ala Ala Gly Glu Pro His Pro Ala Val Ile His Ser Ser Ala Pro
2610                2615                2620 ggc ggg acc ggg acc ggg gag gcc gca gga aag acc gca ttc atc tgc    7920
Gly Gly Thr Gly Thr Gly Glu Ala Ala Gly Lys Thr Ala Phe Ile Cys
2625                2630                2635                2640 tcc gga cag ggc acc caa cgc ccc ggc atg gcc cac ggc ctc tac cac    7968
Ser Gly Gln Gly Thr Gln Arg Pro Gly Met Ala His Gly Leu Tyr His
            2645                2650                2655 acc cac ccc gtc ttc gcc gcc gca ctc aac gac atc tgc acc cac ctc    8016
Thr His Pro Val Phe Ala Ala Ala Leu Asn Asp Ile Cys Thr His Leu
        2660                2665                2670 gac ccc cac ctc gac cac ccc ctc ctc ccc ctc ctc acc caa aac gac    8064
Asp Pro His Leu Asp His Pro Leu Leu Pro Leu Leu Thr Gln Asn Asp
    2675                2680                2685 aac gac aac gag gac gcg gcc gca ctg ctc cag cag acc cgc tac gcc    8112
Asn Asp Asn Glu Asp Ala Ala Ala Leu Leu Gln Gln Thr Arg Tyr Ala
2690                2695                2700 cag ccc gcc ctc ttc gcc ttc cag gtc gcc ctc cac cgc ctc ctc acc    8160
Gln Pro Ala Leu Phe Ala Phe Gln Val Ala Leu His Arg Leu Leu Thr
2705                2710                2715                2720 gac ggc tac cac atc acc ccc cac tac tac gcc gga cac tcc ctc ggc    8208
Asp Gly Tyr His Ile Thr Pro His Tyr Tyr Ala Gly His Ser Leu Gly
            2725                2730                2735 gaa atc acc gcc gcc cac ctc gcc ggc atc ctc acc ctc acc gac gcc    8256
Glu Ile Thr Ala Ala His Leu Ala Gly Ile Leu Thr Leu Thr Asp Ala
        2740                2745                2750 acc acc ctc atc acc caa cgc gcc acc ctc atg caa acc atg ccc ccc    8304
Thr Thr Leu Ile Thr Gln Arg Ala Thr Leu Met Gln Thr Met Pro Pro
    2755                2760                2765 ggc acc atg acc acc ctc cac acc acc ccc cac cac atc acc cac cac    8352
Gly Thr Met Thr Thr Leu His Thr Thr Pro His His Ile Thr His His
```

-continued

| | | |
|---|---|---|
| 2770 | 2775 | 2780 | ctc acc gcc cac gaa aac gac ctc gcc atc gcc gcc atc aac acc ccc    8400
Leu Thr Ala His Glu Asn Asp Leu Ala Ile Ala Ala Ile Asn Thr Pro
2785            2790            2795            2800 acc tcc ctc gtc atc agc ggc acc ccc cac acc gtc caa cac atc acc    8448
Thr Ser Leu Val Ile Ser Gly Thr Pro His Thr Val Gln His Ile Thr
        2805            2810            2815 acc ctc tgc caa caa caa ggc atc aaa acc aaa acc ctc ccc acc aac    8496
Thr Leu Cys Gln Gln Gln Gly Ile Lys Thr Lys Thr Leu Pro Thr Asn
    2820            2825            2830 cac gcc ttc cac tcc ccc cac acc aac ccc atc ctc aac caa ctc cac    8544
His Ala Phe His Ser Pro His Thr Asn Pro Ile Leu Asn Gln Leu His
2835            2840            2845 cag cac acc caa acc ctc acc tac cac cca ccc cac acc ccc ctc atc    8592
Gln His Thr Gln Thr Leu Thr Tyr His Pro Pro His Thr Pro Leu Ile
    2850            2855            2860 acc gcc aac acc cca ccc gac caa ctc ctc acc ccc cac tac tgg acc    8640
Thr Ala Asn Thr Pro Pro Asp Gln Leu Leu Thr Pro His Tyr Trp Thr
2865            2870            2875            2880 caa caa gcc cgc aac acc gtc gac tac gcc acc acc acc caa acc ctc    8688
Gln Gln Ala Arg Asn Thr Val Asp Tyr Ala Thr Thr Thr Gln Thr Leu
        2885            2890            2895 cac caa cac ggc gtc acc acc tac atc gaa ctc gga ccc gac aac acc    8736
His Gln His Gly Val Thr Thr Tyr Ile Glu Leu Gly Pro Asp Asn Thr
    2900            2905            2910 ctc acc acc ctc acc cac cac aac ctc ccc aac ccc ccc acc acc acc    8784
Leu Thr Thr Leu Thr His His Asn Leu Pro Asn Pro Pro Thr Thr Thr
2915            2920            2925 ctc acc ctc acc cac ccc cac cac cac ccc caa acc cac ctc ctc acc    8832
Leu Thr Leu Thr His Pro His His His Pro Gln Thr His Leu Leu Thr
    2930            2935            2940 aac ctc gcc aaa acc acc acc acc tgg cac ccc cac cac tac acc cac    8880
Asn Leu Ala Lys Thr Thr Thr Thr Trp His Pro His His Tyr Thr His
2945            2950            2955            2960 cac gac aac caa ccc cac acc cac acc cac ctc gac ctc ccc acc tac    8928
His Asp Asn Gln Pro His Thr His Thr His Leu Asp Leu Pro Thr Tyr
        2965            2970            2975 ccc ttc caa cac cac cac tac tgg ctc gaa agc aca cag ccc ggt gcc    8976
Pro Phe Gln His His His Tyr Trp Leu Glu Ser Thr Gln Pro Gly Ala
    2980            2985            2990 ggc aac gtg tca gca gcc gga ctc gac ccc acc gaa cac ccc cta ctc    9024
Gly Asn Val Ser Ala Ala Gly Leu Asp Pro Thr Glu His Pro Leu Leu
2995            3000            3005 ggc gcc aca ttg gaa ctg gcg act gac ggt gga gcg ctt ctt gca ggg    9072
Gly Ala Thr Leu Glu Leu Ala Thr Asp Gly Gly Ala Leu Leu Ala Gly
    3010            3015            3020 cgc ttg tct ttg agg tcg cat ccg tgg ctg gct gac cat gcc gtc ggc    9120
Arg Leu Ser Leu Arg Ser His Pro Trp Leu Ala Asp His Ala Val Gly
3025            3030            3035            3040 ggc acg gtg ctg ctg tcg ggc gcc acc ttc ctc gaa ctc gcc ctt cat    9168
Gly Thr Val Leu Leu Ser Gly Ala Thr Phe Leu Glu Leu Ala Leu His
        3045            3050            3055 gcg ggc aca tac gtg ggc tgc gac cga gtg gat gag ctg acg ctg cat    9216
Ala Gly Thr Tyr Val Gly Cys Asp Arg Val Asp Glu Leu Thr Leu His
    3060            3065            3070 gcg ccg ctg gtg gtt cct gtg gat ggg ggt gtg agt gtg cag gtt ggg    9264
Ala Pro Leu Val Val Pro Val Asp Gly Gly Val Ser Val Gln Val Gly
3075            3080            3085 gtt gcg gct gcg gat ggg gag ggg cgg cgt ttg gtg agt gtg tat gcg    9312

| | | |
|---|---|---|
| Val Ala Ala Asp Gly Glu Gly Arg Arg Leu Val Ser Val Tyr Ala<br>3090    3095    3100 | | |
| cgg ggt ggg agt gct tgt ggt ggg ggt ggt gcg tcg ggt ggg gtg tgg<br>Arg Gly Gly Ser Ala Cys Gly Gly Gly Gly Ala Ser Gly Gly Val Trp<br>3105    3110    3115    3120 | | 9360 |
| acg tgt cat gcc tcg ggg gtg ctg gtt gag gct gct gct ggt ggt gtg<br>Thr Cys His Ala Ser Gly Val Leu Val Glu Ala Ala Ala Gly Gly Val<br>    3125    3130    3135 | | 9408 |
| gtg gtg gat ggt ctg gcg ggg gtg tgg ccg ccg cgg ggt gcg gtg gcg<br>Val Val Asp Gly Leu Ala Gly Val Trp Pro Pro Arg Gly Ala Val Ala<br>   3140    3145    3150 | | 9456 |
| gtg gat gtc gat ggt gtc cgt gac cgt ttg gct ggg gct ggt tgt gtt<br>Val Asp Val Asp Gly Val Arg Asp Arg Leu Ala Gly Ala Gly Cys Val<br>  3155    3160    3165 | | 9504 |
| ttg ggg ccg gtg ttt tcg ggg ctg cgt gcg gtg tgg cgt gat ggg ggg<br>Leu Gly Pro Val Phe Ser Gly Leu Arg Ala Val Trp Arg Asp Gly Gly<br>3170    3175    3180 | | 9552 |
| gat ttg ctg gct gag gtg tgt ctg ccg gag gag gcg tgg ggt gat gcg<br>Asp Leu Leu Ala Glu Val Cys Leu Pro Glu Glu Ala Trp Gly Asp Ala<br>3185    3190    3195    3200 | | 9600 |
| gct ggt ttt ggg ctg cat ccg gcg ttg ctg gat ggt gtg gtc cag ccg<br>Ala Gly Phe Gly Leu His Pro Ala Leu Leu Asp Gly Val Val Gln Pro<br>3205    3210    3215 | | 9648 |
| ttg tcg gtg ttg ctt ccg ggt ggg acg ggg ttt ggg gag ggg gcg ggg<br>Leu Ser Val Leu Leu Pro Gly Gly Thr Gly Phe Gly Glu Gly Ala Gly<br>    3220    3225    3230 | | 9696 |
| ttc ggg gag ggt gtt cgg gtg ccg gct gtg tgg ggt ggt gtg tcg ctt<br>Phe Gly Glu Gly Val Arg Val Pro Ala Val Trp Gly Gly Val Ser Leu<br>   3235    3240    3245 | | 9744 |
| cac cgg gcg ggt gtg acc ggt gtg cgg gtg cgt gtg tcg gct gtc ggg<br>His Arg Ala Gly Val Thr Gly Val Arg Val Arg Val Ser Ala Val Gly<br>  3250    3255    3260 | | 9792 |
| cgg ggc ggc ggg cgt gag gcg gtg tcg gtc gtg gtc ggg gat gag gcg<br>Arg Gly Gly Gly Arg Glu Ala Val Ser Val Val Gly Asp Glu Ala<br>3265    3270    3275    3280 | | 9840 |
| ggt gtg ccg gtg gcg tcg gtc gat cgt ctt gag ttg cgg cct gtg gat<br>Gly Val Pro Val Ala Ser Val Asp Arg Leu Glu Leu Arg Pro Val Asp<br>3285    3290    3295 | | 9888 |
| atg ggt cag ttg cgt gct gtc tcg gtt tcg gcg ggg cgg cgg ggt tcg<br>Met Gly Gln Leu Arg Ala Val Ser Val Ser Ala Gly Arg Arg Gly Ser<br>    3300    3305    3310 | | 9936 |
| ctg tat gcg gtg cag tgg gct gag gtg ggt cct gtg ccg gtg tgt ggg<br>Leu Tyr Ala Val Gln Trp Ala Glu Val Gly Pro Val Pro Val Cys Gly<br>   3315    3320    3325 | | 9984 |
| cag gcg tgg gcg tgg cac gag gac gtg ggt gag agc ggt ggt ggg cct<br>Gln Ala Trp Ala Trp His Glu Asp Val Gly Glu Ser Gly Gly Gly Pro<br>  3330    3335    3340 | | 10032 |
| gtg ccg ggg gtg gtg gtg ttg cgg tgc ccg gat gcc ggt gcc ggt ggc<br>Val Pro Gly Val Val Leu Arg Cys Pro Asp Ala Gly Ala Gly Gly<br>3345    3350    3355    3360 | | 10080 |
| ggt ggc ggt ggc ggt ggt ggc ggt ggt gtg ggt gag gtt gtt ggt ggg<br>Gly Gly Gly Gly Gly Gly Gly Gly Val Gly Glu Val Val Gly Gly<br>    3365    3370    3375 | | 10128 |
| gtg ttg ggt gtg gtg cag ggg tgg ctg ggg ctg gag cgg ttt gcg ggt<br>Val Leu Gly Val Val Gln Gly Trp Leu Gly Leu Glu Arg Phe Ala Gly<br>   3380    3385    3390 | | 10176 |
| tcg cgg ctg gtg gtg gtg acc cgg ggt gcg gtg gtg gcc ggc ccg gag<br>Ser Arg Leu Val Val Val Thr Arg Gly Ala Val Val Ala Gly Pro Glu<br>  3395    3400    3405 | | 10224 |

-continued

| | |
|---|---|
| gac ggc ccg gtg gat gtg gtg ggt gcg tcg gtg tgg ggg ctg gtg cgt<br>Asp Gly Pro Val Asp Val Val Gly Ala Ser Val Trp Gly Leu Val Arg<br>3410      3415      3420 | 10272 |
| tcg gcg cag gct gag cat ccg gac cgg ttt gtc ctc ctc gac ctc gac<br>Ser Ala Gln Ala Glu His Pro Asp Arg Phe Val Leu Leu Asp Leu Asp<br>3425      3430      3435      3440 | 10320 |
| acc gac acc ggc acc gac ctc gac acc ggt gct ggt gct ggt tgg ggc<br>Thr Asp Thr Gly Thr Asp Leu Asp Thr Gly Ala Gly Ala Gly Trp Gly<br>3445      3450      3455 | 10368 |
| gtg gat ggt ggg cgt gtg gcg gcg gtg gtg gcg tgt ggt gag ccg cag<br>Val Asp Gly Gly Arg Val Ala Ala Val Val Ala Cys Gly Glu Pro Gln<br>3460      3465      3470 | 10416 |
| ttg gcg gtg cgt ggg gag cgg ttg ctg gcc gca cgc ctg aaa cga ctt<br>Leu Ala Val Arg Gly Glu Arg Leu Leu Ala Ala Arg Leu Lys Arg Leu<br>3475      3480      3485 | 10464 |
| gag tca tcc ggt gat gtt cca gcc cag cgg tcc ggt gac aca cga gcc<br>Glu Ser Ser Gly Asp Val Pro Ala Gln Arg Ser Gly Asp Thr Arg Ala<br>3490      3495      3500 | 10512 |
| cgg cgg tcc gac gtg cct gcc cag cgc tcc ggt ggc gtg cct gct cgg<br>Arg Arg Ser Asp Val Pro Ala Gln Arg Ser Gly Gly Val Pro Ala Arg<br>3505      3510      3515      3520 | 10560 |
| cgg tcg gtt gat gta tcg ggt cgg gag gtg ttg ccg tgg ttg tcg ggt<br>Arg Ser Val Asp Val Ser Gly Arg Glu Val Leu Pro Trp Leu Ser Gly<br>3525      3530      3535 | 10608 |
| ggg tcg gtg ttg gtg acg ggt ggg acg ggt gtg ctg ggt gcg gcg gtg<br>Gly Ser Val Leu Val Thr Gly Gly Thr Gly Val Leu Gly Ala Ala Val<br>3540      3545      3550 | 10656 |
| gcg cgg cat ctg gct ggt gtg tgt ggg gtg cgg gat ctg ctg ttg gtg<br>Ala Arg His Leu Ala Gly Val Cys Gly Val Arg Asp Leu Leu Leu Val<br>3555      3560      3565 | 10704 |
| agc cgg cgt ggt ccg gat gct ccg ggt gcg gag ggt ctg cgg gcg gag<br>Ser Arg Arg Gly Pro Asp Ala Pro Gly Ala Glu Gly Leu Arg Ala Glu<br>3570      3575      3580 | 10752 |
| ctg gcc gcg ttg ggg gcg gag gtg cgg att gtt gcg tgt gat gtg ggg<br>Leu Ala Ala Leu Gly Ala Glu Val Arg Ile Val Ala Cys Asp Val Gly<br>3585      3590      3595      3600 | 10800 |
| gag cgg cgg gag gtg gtc cgg ctg ctg gag ggt gtt cct gcc ggg tgt<br>Glu Arg Arg Glu Val Val Arg Leu Leu Glu Gly Val Pro Ala Gly Cys<br>3605      3610      3615 | 10848 |
| ccg ctg acg ggt gtc gtg cat gcg gct ggt gtg ctg gac gat gcg acg<br>Pro Leu Thr Gly Val Val His Ala Ala Gly Val Leu Asp Asp Ala Thr<br>3620      3625      3630 | 10896 |
| atc gcc tct ctc acg ccc gag cgg ctg ggc acg gtg ttc gcg gcc aag<br>Ile Ala Ser Leu Thr Pro Glu Arg Leu Gly Thr Val Phe Ala Ala Lys<br>3635      3640      3645 | 10944 |
| gtg gat gcc gct ctt ttg ctg gat gag ctg acg cgg ggt atg gag ctg<br>Val Asp Ala Ala Leu Leu Leu Asp Glu Leu Thr Arg Gly Met Glu Leu<br>3650      3655      3660 | 10992 |
| tcg gcg ttc gtg ctg ttc tcc tcg gcc gcg ggg atc ctg ggg tcg gcc<br>Ser Ala Phe Val Leu Phe Ser Ser Ala Ala Gly Ile Leu Gly Ser Ala<br>3665      3670      3675      3680 | 11040 |
| ggg cag ggc aac tac gcc gcg gcc aat gcc gct ctg gac gcg ctg gcg<br>Gly Gln Gly Asn Tyr Ala Ala Ala Asn Ala Ala Leu Asp Ala Leu Ala<br>3685      3690      3695 | 11088 |
| tac cgg cgg cgg gcg gcg ggt ctg ccg ggg gtg tcg ctg gcg tgg ggg<br>Tyr Arg Arg Arg Ala Ala Gly Leu Pro Gly Val Ser Leu Ala Trp Gly<br>3700      3705      3710 | 11136 |
| ctg tgg gaa gag gcc agc ggg atg acc ggg cac ctg gcc ggc acc gac<br>Leu Trp Glu Glu Ala Ser Gly Met Thr Gly His Leu Ala Gly Thr Asp<br>3715      3720      3725 | 11184 |

-continued

| | |
|---|---|
| cac cgg cgc atc atc cgt tcc ggt ctg cat ccc atg tcg acc ccg gac<br>His Arg Arg Ile Ile Arg Ser Gly Leu His Pro Met Ser Thr Pro Asp<br>3730     3735     3740 | 11232 |
| gca ctg gcc ctc ttc gat gcg gcc ctg gct ctg gac cgg ccg gtc ctg<br>Ala Leu Ala Leu Phe Asp Ala Ala Leu Ala Leu Asp Arg Pro Val Leu<br>3745     3750     3755     3760 | 11280 |
| ctg ccc gcc gac ctg cgt ccc gcc ccg ccc ctg ccg ccc ctg cag<br>Leu Pro Ala Asp Leu Arg Pro Ala Pro Pro Leu Pro Pro Leu Leu Gln<br>3765     3770     3775 | 11328 |
| gac ctc ctg ccc gcc acc cgc cgc acc acc cgc acc act acc<br>Asp Leu Leu Pro Ala Thr Arg Arg Thr Thr Arg Thr Thr Thr Thr<br>3780     3785     3790 | 11376 |
| ggt ggt gcg gac aac ggc gcc cag ctg cac gcc cgg ctg gcc ggc cag<br>Gly Gly Ala Asp Asn Gly Ala Gln Leu His Ala Arg Leu Ala Gly Gln<br>3795     3800     3805 | 11424 |
| aca cac gaa caa cag cac acc acc ctc ctc gcc ctg gtc cgc tcc cac<br>Thr His Glu Gln Gln His Thr Thr Leu Leu Ala Leu Val Arg Ser His<br>3810     3815     3820 | 11472 |
| atc gcc acc gtc ctg ggc cac acc acc ccc gac acc atc ccc ccc gac<br>Ile Ala Thr Val Leu Gly His Thr Thr Pro Asp Thr Ile Pro Pro Asp<br>3825     3830     3835     3840 | 11520 |
| cgc gcg ttc cgc gac ctc ggc ttc gac tcc ctc acc gcc gtc gaa cta<br>Arg Ala Phe Arg Asp Leu Gly Phe Asp Ser Leu Thr Ala Val Glu Leu<br>3845     3850     3855 | 11568 |
| cgc aac cgg ctc tcc cgc acc acc gga ctc cgc ctc ccc acc acc ctc<br>Arg Asn Arg Leu Ser Arg Thr Thr Gly Leu Arg Leu Pro Thr Thr Leu<br>3860     3865     3870 | 11616 |
| gcc ttc gac cac ccc aac ccc acc acc ctc acc cac cac ctc cac aca<br>Ala Phe Asp His Pro Asn Pro Thr Thr Leu Thr His His Leu His Thr<br>3875     3880     3885 | 11664 |
| caa ctc cag cca caa ccg gac aac gct gtc gcc ccc gtg ttg gcg gag<br>Gln Leu Gln Pro Gln Pro Asp Asn Ala Val Ala Pro Val Leu Ala Glu<br>3890     3895     3900 | 11712 |
| ctc gac aaa ctc gaa tcc gcc ctc tcc gcc ctc gac aaa acc gac agc<br>Leu Asp Lys Leu Glu Ser Ala Leu Ser Ala Leu Asp Lys Thr Asp Ser<br>3905     3910     3915     3920 | 11760 |
| gcc agc gaa aga gtc acc ctg cgg ctg aag tca ctc atg ttg agg tgg<br>Ala Ser Glu Arg Val Thr Leu Arg Leu Lys Ser Leu Met Leu Arg Trp<br>3925     3930     3935 | 11808 |
| aac gca ccc cag cat ccg aca gcc gaa agc gct gat gac gac gag aag<br>Asn Ala Pro Gln His Pro Thr Ala Glu Ser Ala Asp Asp Asp Glu Lys<br>3940     3945     3950 | 11856 |
| ttc aca tcg gca aca gag gct gag att ttc aaa ttc att gac aac gac<br>Phe Thr Ser Ala Thr Glu Ala Glu Ile Phe Lys Phe Ile Asp Asn Asp<br>3955     3960     3965 | 11904 |
| ctc ggc ctg tcc tgaaccggac gcctgccact ccgcccgtat ccgctgggcc<br>Leu Gly Leu Ser<br>3970 | 11956 |
| ctgctaggac gtga atg caa ttg gcg aat gaa gcg aag ctc ctg gaa tac<br>       Met Gln Leu Ala Asn Glu Ala Lys Leu Leu Glu Tyr<br>            3975     3980 | 12006 |
| ctc aag cgc gtc act gcg gac ctg gac cgc act cgc cgt cgc ctg tac<br>Leu Lys Arg Val Thr Ala Asp Leu Asp Arg Thr Arg Arg Leu Tyr<br>3985     3990     3995     4000 | 12054 |
| gag gtg gtc gag cgt gag cag gag ccg atc gcg att gtg ggg atg gcg<br>Glu Val Val Glu Arg Glu Gln Glu Pro Ile Ala Ile Val Gly Met Ala<br>4005     4010     4015 | 12102 |
| tgt cgt tac cca ggc ggg gcg acg tca ccc acg cga ctg tgg cat ctc<br>Cys Arg Tyr Pro Gly Gly Ala Thr Ser Pro Thr Arg Leu Trp His Leu | 12150 |

-continued

```
                4020              4025              4030
gtc aag tcc cag acg gac gct atc ggg gag ttc ccg acc gac cgt gga        12198
Val Lys Ser Gln Thr Asp Ala Ile Gly Glu Phe Pro Thr Asp Arg Gly
        4035              4040              4045 tgg aac ctg gag cag ctc tac gac ccg gac ccc gac cgc tca gga acc        12246
Trp Asn Leu Glu Gln Leu Tyr Asp Pro Asp Pro Asp Arg Ser Gly Thr
        4050              4055              4060 agt tac acg cgc agc gga ggg ttt ctc tat gac gcg ggc gac ttc gac        12294
Ser Tyr Thr Arg Ser Gly Gly Phe Leu Tyr Asp Ala Gly Asp Phe Asp
4065              4070              4075              4080 gcc gcg ttc ttc gag ttg tca ccg cgt gag gcg ctg gca atg gac ccg        12342
Ala Ala Phe Phe Glu Leu Ser Pro Arg Glu Ala Leu Ala Met Asp Pro
        4085              4090              4095 cag cag cgc ctg ctg ctc gaa acc act tgg gaa acg ttc gaa cag ggc        12390
Gln Gln Arg Leu Leu Leu Glu Thr Thr Trp Glu Thr Phe Glu Gln Gly
        4100              4105              4110 gga atc gac ccg agg tcc atg cgc gga agc cgg acc ggg gtt ttc gtg        12438
Gly Ile Asp Pro Arg Ser Met Arg Gly Ser Arg Thr Gly Val Phe Val
        4115              4120              4125 ggg atc aat ccg gag gac tac acc acc gga tac aca cat cag ccc tca        12486
Gly Ile Asn Pro Glu Asp Tyr Thr Thr Gly Tyr Thr His Gln Pro Ser
        4130              4135              4140 aac gca gtc gag ggc tac ctg ctc act ggc agc gcg gca agc att gcg        12534
Asn Ala Val Glu Gly Tyr Leu Leu Thr Gly Ser Ala Ala Ser Ile Ala
4145              4150              4155              4160 tca ggc cgt atc tcc tac aac ttc ggg ctc gaa ggc cct gcg atc act        12582
Ser Gly Arg Ile Ser Tyr Asn Phe Gly Leu Glu Gly Pro Ala Ile Thr
        4165              4170              4175 atc gac acc gcg tgt tcc tcc tcg ctc gtc gcc ctg cat ctg gcc tgc        12630
Ile Asp Thr Ala Cys Ser Ser Ser Leu Val Ala Leu His Leu Ala Cys
        4180              4185              4190 caa gcg ctc cgg tcc ggt gaa tgc acc atg gcg ctc gca ggc ggc gcc        12678
Gln Ala Leu Arg Ser Gly Glu Cys Thr Met Ala Leu Ala Gly Gly Ala
        4195              4200              4205 tcc gtc atg gcc act ccc ttc gtc ttc acc gag ttc tct cgc cag cgg        12726
Ser Val Met Ala Thr Pro Phe Val Phe Thr Glu Phe Ser Arg Gln Arg
        4210              4215              4220 ggc ctg gcc gca gac ggc cgg tgc aag gcg ttt tcg gcg gcg gcg gac        12774
Gly Leu Ala Ala Asp Gly Arg Cys Lys Ala Phe Ser Ala Ala Ala Asp
4225              4230              4235              4240 ggg acc ggc tgg tcc gag ggt gtg ggg atg ctg ctg gtg gag cgg ctc        12822
Gly Thr Gly Trp Ser Glu Gly Val Gly Met Leu Leu Val Glu Arg Leu
        4245              4250              4255 tcc gac gcc cgc cgc aac ggt cac cgt gtc ctg gcc gtc gtc cgc ggc        12870
Ser Asp Ala Arg Arg Asn Gly His Arg Val Leu Ala Val Val Arg Gly
        4260              4265              4270 agc gcc gtc aac cag gac ggc gca agc aac ggc ctg acc gca ccc aac        12918
Ser Ala Val Asn Gln Asp Gly Ala Ser Asn Gly Leu Thr Ala Pro Asn
        4275              4280              4285 ggt cgt tca caa gtc aag gtc atc cgc cag gct ttg gcc aac gca cac        12966
Gly Arg Ser Gln Val Lys Val Ile Arg Gln Ala Leu Ala Asn Ala His
        4290              4295              4300 ctc tcc cct gcc gat gtc gat gcg gtg gag gcc cac ggc acg ggg acc        13014
Leu Ser Pro Ala Asp Val Asp Ala Val Glu Ala His Gly Thr Gly Thr
4305              4310              4315              4320 acc ctg ggc gac ccg atc gag gct caa gcc ctc gtc gaa gcc tac ggt        13062
Thr Leu Gly Asp Pro Ile Glu Ala Gln Ala Leu Val Glu Ala Tyr Gly
        4325              4330              4335 cag gac cgc ccc aac ggc cgc ccc ctc tgg ctc gga acc ctc aag tcc        13110
```

```
                                                              -continued

Gln Asp Arg Pro Asn Gly Arg Pro Leu Trp Leu Gly Thr Leu Lys Ser
        4340            4345                4350 aac atc ggg cac tcc atg gcc gct gcg ggt gtg ggc ggg gtc atc aag     13158
Asn Ile Gly His Ser Met Ala Ala Ala Gly Val Gly Gly Val Ile Lys
            4355            4360                4365 atg gtg atg gcg ctg cgg aat ggt ctg ctg ccg cgg acg ttg cat gtg     13206
Met Val Met Ala Leu Arg Asn Gly Leu Leu Pro Arg Thr Leu His Val
    4370            4375                4380 gat gag ccg tcg ccg cat gtg gac tgg tcc gcg ggt gcg gtg cag ctg     13254
Asp Glu Pro Ser Pro His Val Asp Trp Ser Ala Gly Ala Val Gln Leu
4385            4390                4395                4400 ctg acg gag acg gtg ccc tgg ccc ggc ggg gag ggg cgg cta cgg cgg     13302
Leu Thr Glu Thr Val Pro Trp Pro Gly Gly Glu Gly Arg Leu Arg Arg
            4405            4410                4415 gca gga gtg tca tca ttc ggc gtc agc ggc acc aac gcc cac gtc atc     13350
Ala Gly Val Ser Ser Phe Gly Val Ser Gly Thr Asn Ala His Val Ile
        4420            4425                4430 ctc gag gaa gca ccc gcc cac aac atc ccg tca gac aca ccc gcc gac     13398
Leu Glu Glu Ala Pro Ala His Asn Ile Pro Ser Asp Thr Pro Ala Asp
            4435            4440                4445 gac gtc ccg gga gaa tca gcc gcc gac gag gat gcc ggt agt ggc gat     13446
Asp Val Pro Gly Glu Ser Ala Ala Asp Glu Asp Ala Gly Ser Gly Asp
    4450            4455                4460 gag gct gct gcc ggc agt cca ggg gtg tgg ccg tgg ctg gtg tcg gcc     13494
Glu Ala Ala Ala Gly Ser Pro Gly Val Trp Pro Trp Leu Val Ser Ala
4465            4470                4475                4480 aag tcg cag ccg gcc ctg cgc gcc cag gcc cag gcc ctg cac gcc cac     13542
Lys Ser Gln Pro Ala Leu Arg Ala Gln Ala Gln Ala Leu His Ala His
            4485            4490                4495 ctc acc gac cac ccc ggc ctc gac ctc gcc gac gtc ggg tac acc ctc     13590
Leu Thr Asp His Pro Gly Leu Asp Leu Ala Asp Val Gly Tyr Thr Leu
        4500            4505                4510 gcc cac gcc cgc gcc gtg ttc gac cac cgc gcc acc ctc atc gcc gcc     13638
Ala His Ala Arg Ala Val Phe Asp His Arg Ala Thr Leu Ile Ala Ala
            4515            4520                4525 gac cgc gac acc ttc ctg caa gca ctc cag gca ctc gcc gca ggc gaa     13686
Asp Arg Asp Thr Phe Leu Gln Ala Leu Gln Ala Leu Ala Ala Gly Glu
    4530            4535                4540 ccc cac ccc gcc gtc atc cac agc agc gcc cca ggc ggg acc ggg acc     13734
Pro His Pro Ala Val Ile His Ser Ser Ala Pro Gly Gly Thr Gly Thr
4545            4550                4555                4560 ggg gag gcc gca gga aag acc gca ttc atc tgc tcc gga cag ggc acc     13782
Gly Glu Ala Ala Gly Lys Thr Ala Phe Ile Cys Ser Gly Gln Gly Thr
            4565            4570                4575 caa cgc ccc ggc atg gcc cac ggc ctc tac cac acc cac ccc gtc ttc     13830
Gln Arg Pro Gly Met Ala His Gly Leu Tyr His Thr His Pro Val Phe
        4580            4585                4590 gcc gcc gca ctc aac gac atc tgc acc cac ctc gac ccc cac ctc gac     13878
Ala Ala Ala Leu Asn Asp Ile Cys Thr His Leu Asp Pro His Leu Asp
            4595            4600                4605 cac ccc ctc ctc ccc ctc ctc acc cag gac ccc aac acc cag gac acc     13926
His Pro Leu Leu Pro Leu Leu Thr Gln Asp Pro Asn Thr Gln Asp Thr
    4610            4615                4620 acc acc ctc gaa gaa gcg gcc gca ctg ctc cag cag acc cgc tac gcc     13974
Thr Thr Leu Glu Glu Ala Ala Ala Leu Leu Gln Gln Thr Arg Tyr Ala
4625            4630                4635                4640 cag ccc gcc ctc ttc gcc ttc cag gtc gcc ctc cac cgc ctc ctc acc     14022
Gln Pro Ala Leu Phe Ala Phe Gln Val Ala Leu His Arg Leu Leu Thr
            4645            4650                4655
```

```
gac ggc tac cac atc acc ccc cac tac tac gcc gga cac tcc ctc ggc      14070
Asp Gly Tyr His Ile Thr Pro His Tyr Tyr Ala Gly His Ser Leu Gly
            4660                4665                4670 gaa atc acc gcc gcc cac ctc gcc ggc atc ctc acc ctc acc gac gcc      14118
Glu Ile Thr Ala Ala His Leu Ala Gly Ile Leu Thr Leu Thr Asp Ala
        4675                4680                4685 acc acc ctc atc acc caa cgc gcc acc ctc atg caa acc atg ccc ccc      14166
Thr Thr Leu Ile Thr Gln Arg Ala Thr Leu Met Gln Thr Met Pro Pro
    4690                4695                4700 ggc acc atg acc acc ctc cac acc acc ccc cac cac atc acc cac cac      14214
Gly Thr Met Thr Thr Leu His Thr Thr Pro His His Ile Thr His His
4705                4710                4715                4720 ctc acc gcc cac gaa aac gac ctc gcc atc gcc gcc atc aac acc ccc      14262
Leu Thr Ala His Glu Asn Asp Leu Ala Ile Ala Ala Ile Asn Thr Pro
            4725                4730                4735 acc tcc ctc gtc atc agc ggc acc ccc cac acc gtc caa cac atc acc      14310
Thr Ser Leu Val Ile Ser Gly Thr Pro His Thr Val Gln His Ile Thr
        4740                4745                4750 acc ctc tgc caa caa caa ggc atc aaa acc aaa acc ctc ccc acc aac      14358
Thr Leu Cys Gln Gln Gln Gly Ile Lys Thr Lys Thr Leu Pro Thr Asn
    4755                4760                4765 cac gcc ttc cac tcc ccc cac acc aac ccc atc ctc aac caa ctc cac      14406
His Ala Phe His Ser Pro His Thr Asn Pro Ile Leu Asn Gln Leu His
    4770                4775                4780 cag cac acc caa acc ctc acc tac cac cca ccc cac acc ccc ctc atc      14454
Gln His Thr Gln Thr Leu Thr Tyr His Pro Pro His Thr Pro Leu Ile
4785                4790                4795                4800 acc gcc aac acc cca ccc gac caa ctc ctc acc ccc cac tac tgg acc      14502
Thr Ala Asn Thr Pro Pro Asp Gln Leu Leu Thr Pro His Tyr Trp Thr
            4805                4810                4815 caa caa gcc cgc aac acc gtc gac tac gcc acc acc acc caa acc ctc      14550
Gln Gln Ala Arg Asn Thr Val Asp Tyr Ala Thr Thr Thr Gln Thr Leu
        4820                4825                4830 cac caa cac ggc gtc acc acc tac atc gaa ctc gga ccc gac aac acc      14598
His Gln His Gly Val Thr Thr Tyr Ile Glu Leu Gly Pro Asp Asn Thr
    4835                4840                4845 ctc acc acc ctc acc cac gac aac ctc ccc aac acc ccc acc acc acc      14646
Leu Thr Thr Leu Thr His Asp Asn Leu Pro Asn Thr Pro Thr Thr Thr
    4850                4855                4860 ctc acc ctc acc cac ccc cac cac cac ccc caa acc cac ctc ctc acc      14694
Leu Thr Leu Thr His Pro His His His Pro Gln Thr His Leu Leu Thr
4865                4870                4875                4880 aac ctc gcc aaa acc acc acc acc tgg cac ccc cac cac tac acc cac      14742
Asn Leu Ala Lys Thr Thr Thr Thr Trp His Pro His His Tyr Thr His
            4885                4890                4895 cac cac aac caa ccc cac acc cac acc cac ctc gac ctc ccc acc tac      14790
His His Asn Gln Pro His Thr His Thr His Leu Asp Leu Pro Thr Tyr
        4900                4905                4910 ccc ttc caa cac cac cac tac tgg ctc caa cca ccc ggc aag ccg agc      14838
Pro Phe Gln His His His Tyr Trp Leu Gln Pro Pro Gly Lys Pro Ser
    4915                4920                4925 gac ccg tca ccg agc gaa ggc cgt gag caa gcc acg acc cca tca acc      14886
Asp Pro Ser Pro Ser Glu Gly Arg Glu Gln Ala Thr Thr Pro Ser Thr
    4930                4935                4940 ccg ctg cgt gat gtc ctc gtg ggc aag tct ccg cag gag cga gac gaa      14934
Pro Leu Arg Asp Val Leu Val Gly Lys Ser Pro Gln Glu Arg Asp Glu
4945                4950                4955                4960 gag ctg ttg cgc ctg gtg cgc acc cat gcg gcc gct gtg ctg ggc cat      14982
Glu Leu Leu Arg Leu Val Arg Thr His Ala Ala Ala Val Leu Gly His
            4965                4970                4975
```

-continued

```
gcc act ccc gaa gtg atc gtt ccg aac aag gcc ttc aaa gag ctg ggt        15030
Ala Thr Pro Glu Val Ile Val Pro Asn Lys Ala Phe Lys Glu Leu Gly
        4980            4985                4990 ttt gat tct ctc gcc gca att cag ctt cgt aat cga ctg ctt gct gac        15078
Phe Asp Ser Leu Ala Ala Ile Gln Leu Arg Asn Arg Leu Leu Ala Asp
    4995                5000                5005 gtt gac ctg ccg ctt ccg gcc acg ctg atc ttc gat tac ccc act ccg        15126
Val Asp Leu Pro Leu Pro Ala Thr Leu Ile Phe Asp Tyr Pro Thr Pro
    5010                5015                5020 atg gcg ctt tgc cag ttc ctc cgg gcg gcg atc gtc gga gcg gac aca        15174
Met Ala Leu Cys Gln Phe Leu Arg Ala Ala Ile Val Gly Ala Asp Thr
5025                5030                5035                5040 ggc acg acc act cgt ctg ccg cta act gcg gtc ccc gcc gac gag ccg        15222
Gly Thr Thr Thr Arg Leu Pro Leu Thr Ala Val Pro Ala Asp Glu Pro
        5045                5050                5055 atc gcc atc gtc ggc atg gcc tgt cgg tac ccc ggt gat gta cgg acg        15270
Ile Ala Ile Val Gly Met Ala Cys Arg Tyr Pro Gly Asp Val Arg Thr
        5060                5065                5070 gtc gat gat ctc tgg cag gtg gtc agt ggt ggc cat gac gcg atc ggc        15318
Val Asp Asp Leu Trp Gln Val Val Ser Gly Gly His Asp Ala Ile Gly
        5075                5080                5085 gga ttc ccg acg aac cgt ggg tgg gac ctc gac acg ctg tac aac ccg        15366
Gly Phe Pro Thr Asn Arg Gly Trp Asp Leu Asp Thr Leu Tyr Asn Pro
        5090                5095                5100 gac ccg gac cac cac gga acc agc tac acc cgg agc ggc gga ttc ctt        15414
Asp Pro Asp His His Gly Thr Ser Tyr Thr Arg Ser Gly Gly Phe Leu
5105                5110                5115                5120 tac gac gca ggc aat ttc gat ccc gac ttc ttc ggt atc agt ccg cgt        15462
Tyr Asp Ala Gly Asn Phe Asp Pro Asp Phe Phe Gly Ile Ser Pro Arg
        5125                5130                5135 gag gca ctg gcg atg gac ccg cag cag cgg ctg ctg ctg gaa aca gcg        15510
Glu Ala Leu Ala Met Asp Pro Gln Gln Arg Leu Leu Leu Glu Thr Ala
        5140                5145                5150 tgg gag agc atc gaa cac gcc tgc atc aac ccc gac agc ctc cgt ggc        15558
Trp Glu Ser Ile Glu His Ala Cys Ile Asn Pro Asp Ser Leu Arg Gly
        5155                5160                5165 aca cca acc ggc gtc ttc gcc ggg ctg acc tac cac gac tac gcc gcg        15606
Thr Pro Thr Gly Val Phe Ala Gly Leu Thr Tyr His Asp Tyr Ala Ala
        5170                5175                5180 cgc ttt ccc aca gct ccg gca ggg ttc gag ggg tat ctc ggg cac gga        15654
Arg Phe Pro Thr Ala Pro Ala Gly Phe Glu Gly Tyr Leu Gly His Gly
5185                5190                5195                5200 agc gca ggc agt atc gcc tcg ggt cgt gtc gcc tac gct ctc ggc ctg        15702
Ser Ala Gly Ser Ile Ala Ser Gly Arg Val Ala Tyr Ala Leu Gly Leu
        5205                5210                5215 gaa ggt ccg gcc ctc aca gtc gac act gcc tgc tct tcg tcc ctg gtc        15750
Glu Gly Pro Ala Leu Thr Val Asp Thr Ala Cys Ser Ser Ser Leu Val
        5220                5225                5230 gct ctg cac ctg gcc tgt cag gcg ctg cgg tcc ggc gag tgt tcc atg        15798
Ala Leu His Leu Ala Cys Gln Ala Leu Arg Ser Gly Glu Cys Ser Met
        5235                5240                5245 gcc ctc gcg ggt ggc gtc acg gtg atg tca acc ccg gcc ggg ttc gtg        15846
Ala Leu Ala Gly Gly Val Thr Val Met Ser Thr Pro Ala Gly Phe Val
        5250                5255                5260 gag ttt tcg cgg cag cgg ggc ctg gcc gtg gac ggg cgg tgc aag gcg        15894
Glu Phe Ser Arg Gln Arg Gly Leu Ala Val Asp Gly Arg Cys Lys Ala
5265                5270                5275                5280 ttc tcg gca gcg gct gac ggc acc ggc tgg ggt gag ggt gtc gga atg        15942
Phe Ser Ala Ala Ala Asp Gly Thr Gly Trp Gly Glu Gly Val Gly Met
```

|  |  |
|---|---|
| ctg ctg gtg gag cgg ctg tcg gac gcg cgg cgg ctc ggt cac cga atc<br>Leu Leu Val Glu Arg Leu Ser Asp Ala Arg Arg Leu Gly His Arg Ile<br>         5300                  5305                5310 | 15990 |
| ctc gcg gtg gtg cgt ggc agt gcg gtc aat cag gac ggt gcg agc aac<br>Leu Ala Val Val Arg Gly Ser Ala Val Asn Gln Asp Gly Ala Ser Asn<br>         5315                  5320                5325 | 16038 |
| ggg ctg acg gcg ccc aac ggg ccg tcc cag gag cgt gtc atc cgc ctg<br>Gly Leu Thr Ala Pro Asn Gly Pro Ser Gln Glu Arg Val Ile Arg Leu<br>         5330                  5335                5340 | 16086 |
| gcc ctg gcc aac gcg gac ctg acc ccc gcc gac gtc gat gcg gtg gag<br>Ala Leu Ala Asn Ala Asp Leu Thr Pro Ala Asp Val Asp Ala Val Glu<br>5345                5350              5355                5360 | 16134 |
| gcc cac ggc acc ggc acc act ttg ggc gac ccg atc gag gcc cag gcc<br>Ala His Gly Thr Gly Thr Thr Leu Gly Asp Pro Ile Glu Ala Gln Ala<br>         5365                  5370                5375 | 16182 |
| ctc ctc gcc acc tac gga cag gac cgc ccc ggc aac gaa ccg ctg tgg<br>Leu Leu Ala Thr Tyr Gly Gln Asp Arg Pro Gly Asn Glu Pro Leu Trp<br>         5380                  5385                5390 | 16230 |
| ctg ggc tcg atg aag tcg aac atc ggc cac gcg cag gct gcc gca ggt<br>Leu Gly Ser Met Lys Ser Asn Ile Gly His Ala Gln Ala Ala Ala Gly<br>         5395                  5400                5405 | 16278 |
| gtg ggc ggg gtc atc aag atg gtg atg gcg ctg cgg aat ggt ctg ctg<br>Val Gly Gly Val Ile Lys Met Val Met Ala Leu Arg Asn Gly Leu Leu<br>         5410                  5415                5420 | 16326 |
| ccg cgg acg ttg cat gtg gat gag ccg tcg ccg cat gtg gac tgg tcc<br>Pro Arg Thr Leu His Val Asp Glu Pro Ser Pro His Val Asp Trp Ser<br>5425                5430              5435                5440 | 16374 |
| gcg ggg gcg gtg cag ctg ctg acg gag acg gtg ccc tgg ccc ggc ggg<br>Ala Gly Ala Val Gln Leu Leu Thr Glu Thr Val Pro Trp Pro Gly Gly<br>         5445                  5450                5455 | 16422 |
| gag ggg cgg ctg cgg cgg gca gga gtg tca tcg ttc ggc gtc agc ggc<br>Glu Gly Arg Leu Arg Arg Ala Gly Val Ser Ser Phe Gly Val Ser Gly<br>         5460                  5465                5470 | 16470 |
| acc aac gcc cac gtc atc ctc gaa gaa gca ccc gcc cac aac atc ccg<br>Thr Asn Ala His Val Ile Leu Glu Glu Ala Pro Ala His Asn Ile Pro<br>         5475                  5480                5485 | 16518 |
| tca gac aca ccc gcc gac gac gcc ccg gga gaa gca gcc gcc gac gat<br>Ser Asp Thr Pro Ala Asp Asp Ala Pro Gly Glu Ala Ala Ala Asp Asp<br>         5490                  5495                5500 | 16566 |
| gtt ccg ggg gaa gcg gcc ggc gac gac gcc ggt acc ggc ggg gaa gcg<br>Val Pro Gly Glu Ala Ala Gly Asp Asp Ala Gly Thr Gly Gly Glu Ala<br>5505                5510              5515                5520 | 16614 |
| act ggt cct gct gcc ggc agt cca ggg gtg tgg ccg tgg ctg gtg tcg<br>Thr Gly Pro Ala Ala Gly Ser Pro Gly Val Trp Pro Trp Leu Val Ser<br>         5525                  5530                5535 | 16662 |
| gcc aag tcg cag ccg gcc ctg cgc gcc cag gcc cag gcc ctg cac gcc<br>Ala Lys Ser Gln Pro Ala Leu Arg Ala Gln Ala Gln Ala Leu His Ala<br>         5540                  5545                5550 | 16710 |
| cac ctc acc gac cac ccc ggc ctc gac ctc gcc gac gtc ggg tac acc<br>His Leu Thr Asp His Pro Gly Leu Asp Leu Ala Asp Val Gly Tyr Thr<br>         5555                  5560                5565 | 16758 |
| ctc gcc cac gcc cgc gcc gtg ttc gac cac cgc gcc acc ctc atc gcc<br>Leu Ala His Ala Arg Ala Val Phe Asp His Arg Ala Thr Leu Ile Ala<br>         5570                  5575                5580 | 16806 |
| gcc gac cgc gac acc ttc ctg caa gca ctc cag gca ctc gcc gca ggc<br>Ala Asp Arg Asp Thr Phe Leu Gln Ala Leu Gln Ala Leu Ala Ala Gly<br>5585                5590              5595                5600 | 16854 |
| gaa ccc cac ccc gcc gtc atc cac agc agc gcc cca ggc ggg acc ggg | 16902 |

```
Glu Pro His Pro Ala Val Ile His Ser Ser Ala Pro Gly Gly Thr Gly
        5605                5610                5615 acc ggg gag gcc gca gga aag acc gca ttc atc tgc tcc gga cag ggc      16950
Thr Gly Glu Ala Ala Gly Lys Thr Ala Phe Ile Cys Ser Gly Gln Gly
        5620                5625                5630 acc caa cgc ccc ggc atg gcc cac ggc ctc tac cac acc cac ccc gtc      16998
Thr Gln Arg Pro Gly Met Ala His Gly Leu Tyr His Thr His Pro Val
        5635                5640                5645 ttc gcc gcc gca ctc aac gac atc tgc acc cac ctc gac ccc cac ctc      17046
Phe Ala Ala Ala Leu Asn Asp Ile Cys Thr His Leu Asp Pro His Leu
    5650                5655                5660 gac cac ccc ctc ctc ccc ctc ctc acc cag gac ccc aac acc cag gac      17094
Asp His Pro Leu Leu Pro Leu Leu Thr Gln Asp Pro Asn Thr Gln Asp
5665                5670                5675                5680 acc acc acc ctc gaa gaa gcg gcc gca ctg ctc cag cag acc ccg tac      17142
Thr Thr Thr Leu Glu Glu Ala Ala Ala Leu Leu Gln Gln Thr Pro Tyr
        5685                5690                5695 gcc cag ccc gcc ctc ttc gcc ttc cag gtc gcc ctc cac cgc ctc ctc      17190
Ala Gln Pro Ala Leu Phe Ala Phe Gln Val Ala Leu His Arg Leu Leu
        5700                5705                5710 acc gac ggc tac cac atc acc ccc cac tac tac gcc gga cac tcc ctc      17238
Thr Asp Gly Tyr His Ile Thr Pro His Tyr Tyr Ala Gly His Ser Leu
        5715                5720                5725 ggc gaa atc acc gcc gcc cac ctc gcc ggc atc ctc acc ctc acc gac      17286
Gly Glu Ile Thr Ala Ala His Leu Ala Gly Ile Leu Thr Leu Thr Asp
        5730                5735                5740 gcc acc acc ctc atc acc caa cgc gcc acc ctc atg caa acc atg ccc      17334
Ala Thr Thr Leu Ile Thr Gln Arg Ala Thr Leu Met Gln Thr Met Pro
5745                5750                5755                5760 ccc ggc acc atg acc acc ctc cac acc acc ccc cac cac atc acc cac      17382
Pro Gly Thr Met Thr Thr Leu His Thr Thr Pro His His Ile Thr His
        5765                5770                5775 cac ctc acc gcc cac gaa aac gac ctc gcc atc gcc gcc atc aac acc      17430
His Leu Thr Ala His Glu Asn Asp Leu Ala Ile Ala Ala Ile Asn Thr
        5780                5785                5790 ccc acc tcc ctc gtc atc agc ggc acc ccc cac acc gtc caa cac atc      17478
Pro Thr Ser Leu Val Ile Ser Gly Thr Pro His Thr Val Gln His Ile
        5795                5800                5805 acc acc ctc tgc caa caa caa ggc atc aaa acc aaa acc ctc ccc acc      17526
Thr Thr Leu Cys Gln Gln Gln Gly Ile Lys Thr Lys Thr Leu Pro Thr
        5810                5815                5820 aaa aac gcc ttc cac tcc ccc cac acc aac ccc atc ctc aac caa ctc      17574
Lys Asn Ala Phe His Ser Pro His Thr Asn Pro Ile Leu Asn Gln Leu
5825                5830                5835                5840 cac cag cac acc caa acc ctc acc tac cac cca ccc cac acc ccc ctc      17622
His Gln His Thr Gln Thr Leu Thr Tyr His Pro Pro His Thr Pro Leu
        5845                5850                5855 atc acc gcc aac acc cca ccc gac caa ctc ctc acc ccc cac tac tgg      17670
Ile Thr Ala Asn Thr Pro Pro Asp Gln Leu Leu Thr Pro His Tyr Trp
        5860                5865                5870 acc caa caa gcc cgc aac acc gtc gac tac gcc acc acc acc caa acc      17718
Thr Gln Gln Ala Arg Asn Thr Val Asp Tyr Ala Thr Thr Thr Gln Thr
        5875                5880                5885 ctc cac caa cac ggc gtc acc acc tac atc gaa ctc gga ccc gac aac      17766
Leu His Gln His Gly Val Thr Thr Tyr Ile Glu Leu Gly Pro Asp Asn
        5890                5895                5900 acc ctc acc acc ctc acc cac cac aac ctc ccc aac acc ccc acc acc      17814
Thr Leu Thr Thr Leu Thr His His Asn Leu Pro Asn Thr Pro Thr Thr
5905                5910                5915                5920
```

-continued

```
acc ctc acc ctc acc cac ccc cac cac cac ccc caa acc cac ctc ctc         17862
Thr Leu Thr Leu Thr His Pro His His His Pro Gln Thr His Leu Leu
        5925                5930                5935 acc aac ctc gcc aaa acc acc acc acc tgg cac ccc cac cac tac acc         17910
Thr Asn Leu Ala Lys Thr Thr Thr Thr Trp His Pro His His Tyr Thr
        5940                5945                5950 cac cac cac aac caa ccc cac acc cac acc cac ctc gac ctc ccc acc         17958
His His His Asn Gln Pro His Thr His Thr His Leu Asp Leu Pro Thr
        5955                5960                5965 tac ccc ttc caa cac cag cac tac tgg ctc gaa agc aca cag ccg ggt         18006
Tyr Pro Phe Gln His Gln His Tyr Trp Leu Glu Ser Thr Gln Pro Gly
        5970                5975                5980 gcc gga tcc ggt tcg ggt tcc ggt tcc ggg cgg gca ggg act gcg ggc         18054
Ala Gly Ser Gly Ser Gly Ser Gly Ser Gly Arg Ala Gly Thr Ala Gly
5985                5990                5995                6000 ggg acg gca gag gtg gag tcg cgg ttc tgg gac gcg gtg gcc cgc cag         18102
Gly Thr Ala Glu Val Glu Ser Arg Phe Trp Asp Ala Val Ala Arg Gln
        6005                6010                6015 gac ctg gaa acg gtc gcg acc acg ctc gcc gtg ccc ccc tcc gcc ggc         18150
Asp Leu Glu Thr Val Ala Thr Thr Leu Ala Val Pro Pro Ser Ala Gly
        6020                6025                6030 ctg gac acg gtg gtg ccc gca ctc tcc gcc tgg cac cgc cac caa cac         18198
Leu Asp Thr Val Val Pro Ala Leu Ser Ala Trp His Arg His Gln His
        6035                6040                6045 gac caa gcc cgc atc aac acc tgg acc tac cag gaa acc tgg aaa ccc         18246
Asp Gln Ala Arg Ile Asn Thr Trp Thr Tyr Gln Glu Thr Trp Lys Pro
        6050                6055                6060 ctc acc ctc ccc acc acc cac caa ccc cac caa acc tgg ctc atc gcc         18294
Leu Thr Leu Pro Thr Thr His Gln Pro His Gln Thr Trp Leu Ile Ala
6065                6070                6075                6080 atc ccc gaa acc cag acc cac cac ccc cac atc acc aac atc ctc acc         18342
Ile Pro Glu Thr Gln Thr His His Pro His Ile Thr Asn Ile Leu Thr
        6085                6090                6095 aac ctc cac cac cac ggc atc acc ccc atc ccc ctc acc ctc aac cac         18390
Asn Leu His His His Gly Ile Thr Pro Ile Pro Leu Thr Leu Asn His
        6100                6105                6110 acc cac acc aac ccc caa cac ctc cac cac acc cga caa caa gcc caa         18438
Thr His Thr Asn Pro Gln His Leu His His Thr Arg Gln Gln Ala Gln
        6115                6120                6125 aac cac acc acc gga ccc atc acc ggc ctg ctc tcc ctc ctc gcc ctc         18486
Asn His Thr Thr Gly Pro Ile Thr Gly Leu Leu Ser Leu Leu Ala Leu
        6130                6135                6140 gac gaa aca ccc cac ccc cac cac ccc cac aca ccc acc ggc acc ctc         18534
Asp Glu Thr Pro His Pro His His Pro His Thr Pro Thr Gly Thr Leu
6145                6150                6155                6160 ctc aac ctc acc ctc acc caa acc cac acc caa acc cac cca cca acc         18582
Leu Asn Leu Thr Leu Thr Gln Thr His Thr Gln Thr His Pro Pro Thr
        6165                6170                6175 ccc ctc tgg tac gcc acc acc aac gcc acc acc acc cac ccc aac gac         18630
Pro Leu Trp Tyr Ala Thr Thr Asn Ala Thr Thr Thr His Pro Asn Asp
        6180                6185                6190 ccc ctc aca cac ccc acc caa gcc caa acc tgg gga ctc gcc cgc acc         18678
Pro Leu Thr His Pro Thr Gln Ala Gln Thr Trp Gly Leu Ala Arg Thr
        6195                6200                6205 acc ctc ctc gaa cac ccc acc cac acc gcc gga atc atc gac ctc ccc         18726
Thr Leu Leu Glu His Pro Thr His Thr Ala Gly Ile Ile Asp Leu Pro
        6210                6215                6220 acc acc ccc acc ccc cac acc ctc cac cac ctc acc caa acc ctc acc         18774
Thr Thr Pro Thr Pro His Thr Leu His His Leu Thr Gln Thr Leu Thr
6225                6230                6235                6240
```

-continued

| | |
|---|---|
| caa ccc cac cac caa acc caa ctc gcc atc cgc acc acc ggc acc cac<br>Gln Pro His His Gln Thr Gln Leu Ala Ile Arg Thr Thr Gly Thr His<br>          6245                        6250                        6255 | 18822 |
| acc cgc cgc ctc acc ccc acc acc ctc acc ccc aca cac caa cca ccc<br>Thr Arg Arg Leu Thr Pro Thr Thr Leu Thr Pro Thr His Gln Pro Pro<br>          6260                        6265                        6270 | 18870 |
| acc ccc acc ccc cac gga acc acc ctc atc acc ggc gga acc ggc gcc<br>Thr Pro Thr Pro His Gly Thr Thr Leu Ile Thr Gly Gly Thr Gly Ala<br>          6275                        6280                        6285 | 18918 |
| ctc gcc acc cac ctc acc cac cac ctc acc acc cac caa ccc acc caa<br>Leu Ala Thr His Leu Thr His His Leu Thr Thr His Gln Pro Thr Gln<br>          6290                        6295                        6300 | 18966 |
| cac ctc ctc ctc acc agc cga acc ggc ccc cac acc ccc cac gca caa<br>His Leu Leu Leu Thr Ser Arg Thr Gly Pro His Thr Pro His Ala Gln<br>6305                        6310                        6315                        6320 | 19014 |
| cac ctc acc acc caa ctc caa caa aaa ggc atc cac ctc acc atc acc<br>His Leu Thr Thr Gln Leu Gln Gln Lys Gly Ile His Leu Thr Ile Thr<br>          6325                        6330                        6335 | 19062 |
| acc tgc gac acc agc aac cca gac caa ctc caa caa ctc ctc aac acc<br>Thr Cys Asp Thr Ser Asn Pro Asp Gln Leu Gln Gln Leu Leu Asn Thr<br>          6340                        6345                        6350 | 19110 |
| atc ccc cca caa cac ccc ctc acc acc gtc atc cac acc gca ggc atc<br>Ile Pro Pro Gln His Pro Leu Thr Thr Val Ile His Thr Ala Gly Ile<br>          6355                        6360                        6365 | 19158 |
| ctc gac gac gcc acc ctc acc aac ctc acc ccc acc caa ctc aac aac<br>Leu Asp Asp Ala Thr Leu Thr Asn Leu Thr Pro Thr Gln Leu Asn Asn<br>          6370                        6375                        6380 | 19206 |
| gtc ctc cgc gcc aaa gcc cac agc gcc cac ctc ctc cac caa ctc acc<br>Val Leu Arg Ala Lys Ala His Ser Ala His Leu Leu His Gln Leu Thr<br>6385                        6390                        6395                        6400 | 19254 |
| caa cac acc ccc ctc aac gcc ttc gtc ctc tac tcc tcc gcc gcc gcc<br>Gln His Thr Pro Leu Asn Ala Phe Val Leu Tyr Ser Ser Ala Ala Ala<br>          6405                        6410                        6415 | 19302 |
| acc ttc ggc gca ccc ggc caa gcc aac tac gcc gca gcc aac gcc tac<br>Thr Phe Gly Ala Pro Gly Gln Ala Asn Tyr Ala Ala Ala Asn Ala Tyr<br>          6420                        6425                        6430 | 19350 |
| ctc gac gcc ctc gcc cac cac cgc cac acc cac cac ctc ccc gcc acc<br>Leu Asp Ala Leu Ala His His Arg His Thr His His Leu Pro Ala Thr<br>          6435                        6440                        6445 | 19398 |
| agc atc gcc tgg ggc acc tgg caa gga aac gga ctg gcg act ggt caa<br>Ser Ile Ala Trp Gly Thr Trp Gln Gly Asn Gly Leu Ala Thr Gly Gln<br>          6450                        6455                        6460 | 19446 |
| gtc agc gaa cat ctc cgc cgc cgc ggg atg ttc gcc atg ccg ccc gag<br>Val Ser Glu His Leu Arg Arg Arg Gly Met Phe Ala Met Pro Pro Glu<br>6465                        6470                        6475                        6480 | 19494 |
| ttg gcg gtc aca gct gtt gac ggc gcg atc gcg agc ggg cgc ccg agt<br>Leu Ala Val Thr Ala Val Asp Gly Ala Ile Ala Ser Gly Arg Pro Ser<br>          6485                        6490                        6495 | 19542 |
| ctc ctc gtc gcc gat atc gac tgg aag aaa ttg gga ccg gtt ctc tcc<br>Leu Leu Val Ala Asp Ile Asp Trp Lys Lys Leu Gly Pro Val Leu Ser<br>          6500                        6505                        6510 | 19590 |
| agc aag tcg tcg gtc ttg ctc gag gac ctt ccc cag gca cag gga act<br>Ser Lys Ser Ser Val Leu Leu Glu Asp Leu Pro Gln Ala Gln Gly Thr<br>          6515                        6520                        6525 | 19638 |
| gag gag gcg cgc agt acc gtt gag cag acg gag agc aca aac ctc cgg<br>Glu Glu Ala Arg Ser Thr Val Glu Gln Thr Glu Ser Thr Asn Leu Arg<br>          6530                        6535                        6540 | 19686 |
| caa ctc ctc atg ggt cgg tca cgt tcc gag cag gaa gaa gag ctg ctc<br>Gln Leu Leu Met Gly Arg Ser Arg Ser Glu Gln Glu Glu Glu Leu Leu | 19734 |

-continued

| | |
|---|---|
| agc ctc gtc cgc atc cac tcc gcg gca gtg ctc ggg cgc gac gac tcc<br>Ser Leu Val Arg Ile His Ser Ala Ala Val Leu Gly Arg Asp Asp Ser<br>6565            6570            6575 | 19782 |
| gag gcc atc ccg ccc ggt cgg ctg ttc agg gat cta ggg ttc gac tcg<br>Glu Ala Ile Pro Pro Gly Arg Leu Phe Arg Asp Leu Gly Phe Asp Ser<br>6580            6585            6590 | 19830 |
| ctt gcg gcg gtg gag ctt cgc aac cac ctc gca gca cag acg gag ctg<br>Leu Ala Ala Val Glu Leu Arg Asn His Leu Ala Ala Gln Thr Glu Leu<br>6595            6600            6605 | 19878 |
| gct ctg ccg acg act ctc gtc ttc gat tac ccc agc ccc acc aag ctc<br>Ala Leu Pro Thr Thr Leu Val Phe Asp Tyr Pro Ser Pro Thr Lys Leu<br>6610            6615            6620 | 19926 |
| gcc caa ttt ctg ctc tcc gag atc gcg gag ttc cag ccc gac aac tca<br>Ala Gln Phe Leu Leu Ser Glu Ile Ala Glu Phe Gln Pro Asp Asn Ser<br>6625            6630            6635            6640 | 19974 |
| act ccg ctt ccg cga ccc cgg gca gag ctc gat gag ccg atc gcc atc<br>Thr Pro Leu Pro Arg Pro Arg Ala Glu Leu Asp Glu Pro Ile Ala Ile<br>6645            6650            6655 | 20022 |
| gtt ggc atg gcc tgt cgc ttc ccc ggc gga gtg acc tcg gcg gac gac<br>Val Gly Met Ala Cys Arg Phe Pro Gly Gly Val Thr Ser Ala Asp Asp<br>6660            6665            6670 | 20070 |
| ttc tgg gat ctg atc tcc tcc gag cag gac gcg atc ggc gga ttc ccc<br>Phe Trp Asp Leu Ile Ser Ser Glu Gln Asp Ala Ile Gly Gly Phe Pro<br>6675            6680            6685 | 20118 |
| acc gac cgc ggc tgg gac ctg gac acg ctc tac gac ccc gac ccc gac<br>Thr Asp Arg Gly Trp Asp Leu Asp Thr Leu Tyr Asp Pro Asp Pro Asp<br>6690            6695            6700 | 20166 |
| cac ccc ggc acc tgc tac acc cga aac ggc gga ttc ctc tac gac gca<br>His Pro Gly Thr Cys Tyr Thr Arg Asn Gly Gly Phe Leu Tyr Asp Ala<br>6705            6710            6715            6720 | 20214 |
| ggc cac ttc gac gcc gaa ttc ttc ggc atc agc ccc cgc gaa gcc ctc<br>Gly His Phe Asp Ala Glu Phe Phe Gly Ile Ser Pro Arg Glu Ala Leu<br>6725            6730            6735 | 20262 |
| gcc atg gac ccc cag caa cga ctc ctc ctc gaa acc gcc tgg gaa acc<br>Ala Met Asp Pro Gln Gln Arg Leu Leu Leu Glu Thr Ala Trp Glu Thr<br>6740            6745            6750 | 20310 |
| atc gaa cac gcc ggc atc aac ccc cac acc ctc cac ggc acc ccc acc<br>Ile Glu His Ala Gly Ile Asn Pro His Thr Leu His Gly Thr Pro Thr<br>6755            6760            6765 | 20358 |
| gga gtc ttc acc ggc acc aac gga cag gac cac gcg gca cac atc cgt<br>Gly Val Phe Thr Gly Thr Asn Gly Gln Asp His Ala Ala His Ile Arg<br>6770            6775            6780 | 20406 |
| cag gcc ccg agc ggt acc gag gga ttc gtc ctg acc ggg gca gcc acc<br>Gln Ala Pro Ser Gly Thr Glu Gly Phe Val Leu Thr Gly Ala Ala Thr<br>6785            6790            6795            6800 | 20454 |
| agc atc gcc tcc ggc cga atc tcc tac atc ctc ggg ttg gaa ggg cct<br>Ser Ile Ala Ser Gly Arg Ile Ser Tyr Ile Leu Gly Leu Glu Gly Pro<br>6805            6810            6815 | 20502 |
| gcg gtc acc ctc gac aca gcg tgt tcc tcc tcg ctc gtc gcc ctg cac<br>Ala Val Thr Leu Asp Thr Ala Cys Ser Ser Ser Leu Val Ala Leu His<br>6820            6825            6830 | 20550 |
| ctc gcc tgc cag tcc ctc agg tcc ggt gaa tgc acc atg gcc ttg gcc<br>Leu Ala Cys Gln Ser Leu Arg Ser Gly Glu Cys Thr Met Ala Leu Ala<br>6835            6840            6845 | 20598 |
| ggc ggg gcc acg gtc atg acc acc ccg atc acc ttc acc gaa ttc gcc<br>Gly Gly Ala Thr Val Met Thr Thr Pro Ile Thr Phe Thr Glu Phe Ala<br>6850            6855            6860 | 20646 |
| cgc caa cgc gga ctc gcc ccc gac ggg cgt tgc aag gcg ttc tcg gcg | 20694 |

-continued

```
Arg Gln Arg Gly Leu Ala Pro Asp Gly Arg Cys Lys Ala Phe Ser Ala
6865                6870                6875                6880 gcg gct gac ggt acc ggc tgg ggt gag ggt gtg ggg atg ctg ctg gtg      20742
Ala Ala Asp Gly Thr Gly Trp Gly Glu Gly Val Gly Met Leu Leu Val
            6885                6890                6895 gag cgg ctc tcc gac gcc cgc cgc aac ggt cac cgt gtc ctg gcc gtg      20790
Glu Arg Leu Ser Asp Ala Arg Arg Asn Gly His Arg Val Leu Ala Val
        6900                6905                6910 gtg cgt ggc agt gcg gtc aac cag gac ggt gcg agc aac ggt ctg acc      20838
Val Arg Gly Ser Ala Val Asn Gln Asp Gly Ala Ser Asn Gly Leu Thr
    6915                6920                6925 gcg ccc aac ggg ccc tcc cag cag cgc gtc atc cgc cag gcc ctc gcc      20886
Ala Pro Asn Gly Pro Ser Gln Gln Arg Val Ile Arg Gln Ala Leu Ala
 6930                6935                6940 aac gcg gac ctg acc ccc gcc gac gtc gat gcg gtg gag gcc cac ggc      20934
Asn Ala Asp Leu Thr Pro Ala Asp Val Asp Ala Val Glu Ala His Gly
6945                6950                6955                6960 acc ggc acc act ttg ggc gac ccg atc gag gcc cag gcc atc ctc gcg      20982
Thr Gly Thr Thr Leu Gly Asp Pro Ile Glu Ala Gln Ala Ile Leu Ala
            6965                6970                6975 acc tac gga cag gac cgt ccc ggc aac ggg ccg ttg tgg ctg ggc tcc      21030
Thr Tyr Gly Gln Asp Arg Pro Gly Asn Gly Pro Leu Trp Leu Gly Ser
        6980                6985                6990 gtc aag tcc aac gtc gga cac aca cag gcc gcg gcg ggc gtg gcc gga      21078
Val Lys Ser Asn Val Gly His Thr Gln Ala Ala Ala Gly Val Ala Gly
    6995                7000                7005 gtg atc aag atg gtg atg gcc ctc cgc cac cgg aca ctc cca ccg act      21126
Val Ile Lys Met Val Met Ala Leu Arg His Arg Thr Leu Pro Pro Thr
 7010                7015                7020 ctc cac gcg gat gag ccg tcg ccg cat gtg gac tgg tcc gcg ggt gcg      21174
Leu His Ala Asp Glu Pro Ser Pro His Val Asp Trp Ser Ala Gly Ala
7025                7030                7035                7040 gtg cag ctg ctg acg gag acg gtg ccc tgg ccc ggc ggg gag ggg cgg      21222
Val Gln Leu Leu Thr Glu Thr Val Pro Trp Pro Gly Gly Glu Gly Arg
            7045                7050                7055 ccg cgg cgg gca gga gtg tca tca ttc ggc gtc agc ggc acc aac gcc      21270
Pro Arg Arg Ala Gly Val Ser Ser Phe Gly Val Ser Gly Thr Asn Ala
        7060                7065                7070 cac gtc atc ctc gaa gaa gca ccc gcc gac gac gtt ccg ggg gga cca      21318
His Val Ile Leu Glu Glu Ala Pro Ala Asp Asp Val Pro Gly Gly Pro
    7075                7080                7085 ccc gcc gac gag gat gcc ggt agt ggc gag gag gct gct gcc ggc agt      21366
Pro Ala Asp Glu Asp Ala Gly Ser Gly Glu Glu Ala Ala Ala Gly Ser
 7090                7095                7100 cct ggg gtg tgg ccg tgg ctg gtg tcg gcc aag tcg cag ccg gcc ctg      21414
Pro Gly Val Trp Pro Trp Leu Val Ser Ala Lys Ser Gln Pro Ala Leu
7105                7110                7115                7120 cgc gcc cag gcc cag gcc ctg cac gcc cac ctc acc gac cac ccc ggc      21462
Arg Ala Gln Ala Gln Ala Leu His Ala His Leu Thr Asp His Pro Gly
            7125                7130                7135 ctc gac ctc gcc gac gtc gga tac acc ctc gcc cac gcc cgc gcc gtg      21510
Leu Asp Leu Ala Asp Val Gly Tyr Thr Leu Ala His Ala Arg Ala Val
        7140                7145                7150 ttc gac cac cgc gcc acc ctc atc gcc gcc gac cgc gac acc ttc ctg      21558
Phe Asp His Arg Ala Thr Leu Ile Ala Ala Asp Arg Asp Thr Phe Leu
    7155                7160                7165 caa gca ctc cag gca ctc gcc gca ggc gaa ccc cac ccc gcc gtc atc      21606
Gln Ala Leu Gln Ala Leu Ala Ala Gly Glu Pro His Pro Ala Val Ile
 7170                7175                7180
```

-continued

| | |
|---|---|
| cac agc agc gcc cca ggc ggg acc ggg acc ggg gag gcc gca gga aag<br>His Ser Ser Ala Pro Gly Gly Thr Gly Thr Gly Glu Ala Ala Gly Lys<br>7185                    7190                    7195                    7200 | 21654 |
| acc gca ttc atc tgc tcc gga cag ggc acc caa cgc ccc ggc atg gcc<br>Thr Ala Phe Ile Cys Ser Gly Gln Gly Thr Gln Arg Pro Gly Met Ala<br>                    7205                    7210                    7215 | 21702 |
| cac ggc ctc tac cac acc cac ccc gtc ttc gcc gcc gca ctc aac gac<br>His Gly Leu Tyr His Thr His Pro Val Phe Ala Ala Ala Leu Asn Asp<br>                    7220                    7225                    7230 | 21750 |
| atc tgc acc cac ctc gac ccc cac ctc gac cac ccc ctc ctc ccc ctc<br>Ile Cys Thr His Leu Asp Pro His Leu Asp His Pro Leu Leu Pro Leu<br>                    7235                    7240                    7245 | 21798 |
| ctc acc caa aac gac aac gac aac gac aac gag gac gcg gcc gca ctg<br>Leu Thr Gln Asn Asp Asn Asp Asn Asp Asn Glu Asp Ala Ala Ala Leu<br>7250                    7255                    7260 | 21846 |
| ctc cag cag acc ccg tac gcc cag ccc gcc ctc ttc gcc ttc cag gtc<br>Leu Gln Gln Thr Pro Tyr Ala Gln Pro Ala Leu Phe Ala Phe Gln Val<br>7265                    7270                    7275                    7280 | 21894 |
| gcc ctc cac cgc ctc ctc acc gac ggc tac cac atc acc ccc cac tac<br>Ala Leu His Arg Leu Leu Thr Asp Gly Tyr His Ile Thr Pro His Tyr<br>                    7285                    7290                    7295 | 21942 |
| tac gcc gga cac tcc ctc ggc gaa atc acc gcc gcc cac ctc gcc ggc<br>Tyr Ala Gly His Ser Leu Gly Glu Ile Thr Ala Ala His Leu Ala Gly<br>                    7300                    7305                    7310 | 21990 |
| atc ctc acc ctc acc gac gcc acc acc ctc atc acc caa cgc gcc acc<br>Ile Leu Thr Leu Thr Asp Ala Thr Thr Leu Ile Thr Gln Arg Ala Thr<br>                    7315                    7320                    7325 | 22038 |
| ctc atg caa acc atg ccc ccc ggc acc atg acc acc ctc cac acc acc<br>Leu Met Gln Thr Met Pro Pro Gly Thr Met Thr Thr Leu His Thr Thr<br>                    7330                    7335                    7340 | 22086 |
| cca cac cac atc acc cac cac ctc acc gcc cac gaa aac gac ctc gcc<br>Pro His His Ile Thr His His Leu Thr Ala His Glu Asn Asp Leu Ala<br>7345                    7350                    7355                    7360 | 22134 |
| atc gcc gcc atc aac acc ccc acc tcc ctc gtc atc agc ggc acc ccc<br>Ile Ala Ala Ile Asn Thr Pro Thr Ser Leu Val Ile Ser Gly Thr Pro<br>                    7365                    7370                    7375 | 22182 |
| cac acc gtc caa cac atc acc acc ctc tgc caa caa caa ggc atc aaa<br>His Thr Val Gln His Ile Thr Thr Leu Cys Gln Gln Gln Gly Ile Lys<br>                    7380                    7385                    7390 | 22230 |
| acc aaa acc ctc ccc acc aac cac gcc ttc cac tcc ccc cac acc aac<br>Thr Lys Thr Leu Pro Thr Asn His Ala Phe His Ser Pro His Thr Asn<br>                    7395                    7400                    7405 | 22278 |
| ccc atc ctc aac caa ctc cac cag cac acc caa acc ctc acc tac cac<br>Pro Ile Leu Asn Gln Leu His Gln His Thr Gln Thr Leu Thr Tyr His<br>7410                    7415                    7420 | 22326 |
| cca ccc cac acc ccc ctc atc acc gcc aac acc cca ccc gac caa ctc<br>Pro Pro His Thr Pro Leu Ile Thr Ala Asn Thr Pro Pro Asp Gln Leu<br>7425                    7430                    7435                    7440 | 22374 |
| ctc acc ccc cac tac tgg acc caa caa gcc cgc aac acc gtc gac tac<br>Leu Thr Pro His Tyr Trp Thr Gln Gln Ala Arg Asn Thr Val Asp Tyr<br>                    7445                    7450                    7455 | 22422 |
| gcc acc acc acc caa acc ctc cac caa cac ggc gtc acc acc tac atc<br>Ala Thr Thr Thr Gln Thr Leu His Gln His Gly Val Thr Thr Tyr Ile<br>                    7460                    7465                    7470 | 22470 |
| gaa ctc gga ccc gac aac acc ctc acc acc ctc acc cac cac aac ctc<br>Glu Leu Gly Pro Asp Asn Thr Leu Thr Thr Leu Thr His His Asn Leu<br>                    7475                    7480                    7485 | 22518 |
| ccc aac acc ccc acc acc acc ctc acc ctc acc cac ccc cac cac cac<br>Pro Asn Thr Pro Thr Thr Thr Leu Thr Leu Thr His Pro His His His<br>                    7490                    7495                    7500 | 22566 |

```
ccc caa acc cac ctc ctc acc aac ctc gcc aaa acc acc acc acc tgg    22614
Pro Gln Thr His Leu Leu Thr Asn Leu Ala Lys Thr Thr Thr Thr Trp
7505                7510                7515                7520 cac ccc cac cac tac acc cac cac aac caa ccc cac acc cac acc        22662
His Pro His His Tyr Thr His His Asn Gln Pro His Thr His Thr
            7525                7530                7535 cac ctc gac ctc ccc acc tac ccc ttc caa cac cac cac tac tgg ctc    22710
His Leu Asp Leu Pro Thr Tyr Pro Phe Gln His His His Tyr Trp Leu
        7540                7545                7550 gaa cta ccc agc gcc caa acc agc ccc ggt caa agg cgt tct cgc cgc    22758
Glu Leu Pro Ser Ala Gln Thr Ser Pro Gly Gln Arg Arg Ser Arg Arg
    7555                7560                7565 tcg gct cca gac acc gcc gag tcg gag ttc tgg gac gcg gtg aac gag    22806
Ser Ala Pro Asp Thr Ala Glu Ser Glu Phe Trp Asp Ala Val Asn Glu
7570                7575                7580 gaa gac ctc cag agc ctc gcc gaa acc ctc gac atc gac gcc tct gct    22854
Glu Asp Leu Gln Ser Leu Ala Glu Thr Leu Asp Ile Asp Ala Ser Ala
7585                7590                7595                7600 ctg gac acg gtg gtg ccc gca ctc tcc gcc tgg cac cgc cac caa cac    22902
Leu Asp Thr Val Val Pro Ala Leu Ser Ala Trp His Arg His Gln His
            7605                7610                7615 gac caa gcc cgc atc aac acc tgg acc tac cag gaa acc tgg aaa ccc    22950
Asp Gln Ala Arg Ile Asn Thr Trp Thr Tyr Gln Glu Thr Trp Lys Pro
        7620                7625                7630 ctc acc ctc ccc acc acc cac caa ccc cac caa acc tgg ctc atc gcc    22998
Leu Thr Leu Pro Thr Thr His Gln Pro His Gln Thr Trp Leu Ile Ala
    7635                7640                7645 atc ccc gaa acc cag acc cac cac ccc cac atc acc aac atc ctc acc    23046
Ile Pro Glu Thr Gln Thr His His Pro His Ile Thr Asn Ile Leu Thr
7650                7655                7660 aac ctc cac cac cac ggc atc acc ccc atc ccc ctc act gtc aac cac    23094
Asn Leu His His His Gly Ile Thr Pro Ile Pro Leu Thr Val Asn His
            7665                7670                7675                7680 acc cac acc aac ccc caa cac ctc cac cac acc ctc cac cac acc cga    23142
Thr His Thr Asn Pro Gln His Leu His His Thr Leu His His Thr Arg
        7685                7690                7695 caa caa gcc caa aac cac acc acc gga ccc atc acc ggc ctg ctc tcc    23190
Gln Gln Ala Gln Asn His Thr Thr Gly Pro Ile Thr Gly Leu Leu Ser
    7700                7705                7710 ctc ctc gcc ctc gac gaa aca ccc cac ccc cac cac ccc cac aca ccc    23238
Leu Leu Ala Leu Asp Glu Thr Pro His Pro His His Pro His Thr Pro
7715                7720                7725 acc ggc acc ctc ctc aac ctc acc ctc ccc caa acc cac acc caa acc    23286
Thr Gly Thr Leu Leu Asn Leu Thr Leu Pro Gln Thr His Thr Gln Thr
            7730                7735                7740 cac cca cca acc ccc ctc tgg tac gcc acc acc aac gcc acc acc acc    23334
His Pro Pro Thr Pro Leu Trp Tyr Ala Thr Thr Asn Ala Thr Thr Thr
        7745                7750                7755                7760 cac ccc aac gac ccc ctc aca cac ccc acc caa gcc caa acc tgg gga    23382
His Pro Asn Asp Pro Leu Thr His Pro Thr Gln Ala Gln Thr Trp Gly
    7765                7770                7775 ctc gcc cgc acc acc ctc ctc gaa cac ccc acc cac acc gcc gga atc    23430
Leu Ala Arg Thr Thr Leu Leu Glu His Pro Thr His Thr Ala Gly Ile
7780                7785                7790 atc gac ctc ccc acc acc ccc acc ccc cac acc ctc cac cac ctc acc    23478
Ile Asp Leu Pro Thr Thr Pro Thr Pro His Thr Leu His His Leu Thr
            7795                7800                7805 caa acc ctc acc caa ccc cac cac caa acc caa ctc gcc atc cgc acc    23526
Gln Thr Leu Thr Gln Pro His His Gln Thr Gln Leu Ala Ile Arg Thr
```

-continued

```
       7810                7815                7820
acc ggc acc cac acc cgc cgc ctc acc ccc acc acc ctc acc ccc aca    23574
Thr Gly Thr His Thr Arg Arg Leu Thr Pro Thr Thr Leu Thr Pro Thr
    7825                7830                7835                7840 cac caa cca ccc acc ccc acc ccc cac gga acc acc ctc atc acc ggc    23622
His Gln Pro Pro Thr Pro Thr Pro His Gly Thr Thr Leu Ile Thr Gly
            7845                7850                7855 gga acc ggc gcc ctc gcc acc cac ctc acc cac cac ctc acc acc cac    23670
Gly Thr Gly Ala Leu Ala Thr His Leu Thr His His Leu Thr Thr His
                7860                7865                7870 caa ccc acc caa cac ctc ctc ctc acc agc cga acc ggc ccc cac acc    23718
Gln Pro Thr Gln His Leu Leu Leu Thr Ser Arg Thr Gly Pro His Thr
    7875                7880                7885 ccc cac gca caa cac ctc acc acc caa ctc caa caa aaa ggc atc cac    23766
Pro His Ala Gln His Leu Thr Thr Gln Leu Gln Gln Lys Gly Ile His
            7890                7895                7900 ctc acc atc acc acc tgc gac acc agc aac cca gac caa ctc caa caa    23814
Leu Thr Ile Thr Thr Cys Asp Thr Ser Asn Pro Asp Gln Leu Gln Gln
7905                7910                7915                7920 ctc ctc aac acc atc ccc cca caa cac ccc ctc acc acc gtc atc cac    23862
Leu Leu Asn Thr Ile Pro Pro Gln His Pro Leu Thr Thr Val Ile His
                7925                7930                7935 acc gca ggc gtc aat ctc ttc gcc ccc gtg tcg gaa acc gat gcc gaa    23910
Thr Ala Gly Val Asn Leu Phe Ala Pro Val Ser Glu Thr Asp Ala Glu
        7940                7945                7950 tcc ttc tct tcc gtt acg gca gcg aag gca acg ggc gcg gcg att ctg    23958
Ser Phe Ser Ser Val Thr Ala Ala Lys Ala Thr Gly Ala Ala Ile Leu
    7955                7960                7965 cat gag ttg ctg ctg gac cat gaa acg ctt gaa cac ttc att ctc ttc    24006
His Glu Leu Leu Leu Asp His Glu Thr Leu Glu His Phe Ile Leu Phe
    7970                7975                7980 tcg tcg ggc gcc ggc gct tgg ggc agc ggg aat cag tgc gca tac tcg    24054
Ser Ser Gly Ala Gly Ala Trp Gly Ser Gly Asn Gln Cys Ala Tyr Ser
7985                7990                7995                8000 gcg gcc aac gca tac ctg gac gcg ctc gcg acg cat cgt cag aca cat    24102
Ala Ala Asn Ala Tyr Leu Asp Ala Leu Ala Thr His Arg Gln Thr His
            8005                8010                8015 gga ctt ccc ggg gca tcg atc gcc tgg ggc ccc tgg gcc gga aag ggc    24150
Gly Leu Pro Gly Ala Ser Ile Ala Trp Gly Pro Trp Ala Gly Lys Gly
                8020                8025                8030 atg tcg gcc ggt gat gcg gct cat ggt tac ctg gaa aag cgc ggc att    24198
Met Ser Ala Gly Asp Ala Ala His Gly Tyr Leu Glu Lys Arg Gly Ile
    8035                8040                8045 ctg ccg atg gag cca cgc atg gcg ctc gcg gca ttc cat cgt gcg cgg    24246
Leu Pro Met Glu Pro Arg Met Ala Leu Ala Ala Phe His Arg Ala Arg
    8050                8055                8060 gcg cag cgg ccg aat tcc aac ctg atc atc gcg gac atc gac tgg gag    24294
Ala Gln Arg Pro Asn Ser Asn Leu Ile Ile Ala Asp Ile Asp Trp Glu
8065                8070                8075                8080 cgc ttc gtc ccc gcc ttc acc gct cga cgc cac agc ccg ctc atc gag    24342
Arg Phe Val Pro Ala Phe Thr Ala Arg Arg His Ser Pro Leu Ile Glu
        8085                8090                8095 gac att ccg gag gtt cgg caa gcg gct cag gag ctg gaa gca gct gcg    24390
Asp Ile Pro Glu Val Arg Gln Ala Ala Gln Glu Leu Glu Ala Ala Ala
            8100                8105                8110 tcg acg gca aag acg acc aca gct cag ccg att gcg acg tct ctc cgt    24438
Ser Thr Ala Lys Thr Thr Thr Ala Gln Pro Ile Ala Thr Ser Leu Arg
    8115                8120                8125 gag cga ttg gcc cga ctg acg tcc tca aag cag aac cag gtg ctg ctc    24486
```

-continued

```
                Glu Arg Leu Ala Arg Leu Thr Ser Ser Lys Gln Asn Gln Val Leu Leu
                    8130                8135                8140 ggc ctg att cgg aca ggc atc tgc acc gtt ctc ggc ctt cgt aat ccg          24534
Gly Leu Ile Arg Thr Gly Ile Cys Thr Val Leu Gly Leu Arg Asn Pro
8145                8150                8155                8160 gaa ggc atc gag gac caa cga gcc ttc cgc gac ctc ggc ttc gac tcg          24582
Glu Gly Ile Glu Asp Gln Arg Ala Phe Arg Asp Leu Gly Phe Asp Ser
            8165                8170                8175 ctg acg tcg gct cag ttc agc aag gaa ctc gcc aag gaa acc gga ctg          24630
Leu Thr Ser Ala Gln Phe Ser Lys Glu Leu Ala Lys Glu Thr Gly Leu
        8180                8185                8190 cca ctc ccc ccg tcc ctg gtc ttc gac tat ccc acc ccg cag gaa tgt          24678
Pro Leu Pro Pro Ser Leu Val Phe Asp Tyr Pro Thr Pro Gln Glu Cys
    8195                8200                8205 gct gcc cat ctg cgc aca caa ctc gtc gac cta gac gac gaa gag gac          24726
Ala Ala His Leu Arg Thr Gln Leu Val Asp Leu Asp Asp Glu Glu Asp
8210                8215                8220 gcg gca ctg tcg aat gct ctc ccg caa gtg gcc cat cgg cgt acc gtc          24774
Ala Ala Leu Ser Asn Ala Leu Pro Gln Val Ala His Arg Arg Thr Val
8225                8230                8235                8240 gag gac gaa ccg atc gcc atc atc ggt atg gca tgt cgc ttc ccc ggc          24822
Glu Asp Glu Pro Ile Ala Ile Ile Gly Met Ala Cys Arg Phe Pro Gly
            8245                8250                8255 ggc gta cgt tct gcc gac gac ctg tgg gaa ttg ctc gct tcg ggt aag          24870
Gly Val Arg Ser Ala Asp Asp Leu Trp Glu Leu Leu Ala Ser Gly Lys
        8260                8265                8270 gac gct atc ggc gtc ttc ccg acc gac cgc ggc tgg gac ctg gac acg          24918
Asp Ala Ile Gly Val Phe Pro Thr Asp Arg Gly Trp Asp Leu Asp Thr
    8275                8280                8285 ctc tac gac ccc gac ccc gac cac ccc ggc acc tgc tac acc cga aac          24966
Leu Tyr Asp Pro Asp Pro Asp His Pro Gly Thr Cys Tyr Thr Arg Asn
8290                8295                8300 ggc gga ttc ctc tac ggc gca ggc cac ttc gac gcc gaa ttc ttc ggc          25014
Gly Gly Phe Leu Tyr Gly Ala Gly His Phe Asp Ala Glu Phe Phe Gly
8305                8310                8315                8320 atc agc ccc cgc gaa gcc ctc gcc atg gac ccc cag caa cga ctc ctc          25062
Ile Ser Pro Arg Glu Ala Leu Ala Met Asp Pro Gln Gln Arg Leu Leu
            8325                8330                8335 ctc gaa acc gcc tgg gaa acc atc gaa cac gcc ggc atc aac ccc cac          25110
Leu Glu Thr Ala Trp Glu Thr Ile Glu His Ala Gly Ile Asn Pro His
        8340                8345                8350 acc ctc cac ggc acc ccc acc gga gtc ttc gcc gga atc aac gct caa          25158
Thr Leu His Gly Thr Pro Thr Gly Val Phe Ala Gly Ile Asn Ala Gln
    8355                8360                8365 gac cac gcc gcg cat atc cgc caa agc cgt gat gtg gag acc atc gag          25206
Asp His Ala Ala His Ile Arg Gln Ser Arg Asp Val Glu Thr Ile Glu
8370                8375                8380 ggc tac gcc ctg acc ggc agt tcg gga agt gtg gcg tcc ggc cgg gtg          25254
Gly Tyr Ala Leu Thr Gly Ser Ser Gly Ser Val Ala Ser Gly Arg Val
8385                8390                8395                8400 gcc tac acg ctc ggg ctc gaa ggc ccc gcg gtg tcg gtg gat acg gcg          25302
Ala Tyr Thr Leu Gly Leu Glu Gly Pro Ala Val Ser Val Asp Thr Ala
            8405                8410                8415 tgt tcg tcg tcg ttg gtg gcg ttg cat tgg gcg gcg cag gcg ttg cgt          25350
Cys Ser Ser Ser Leu Val Ala Leu His Trp Ala Ala Gln Ala Leu Arg
        8420                8425                8430 gcg ggt gag tgt tcg atg gcg ctt gcc ggg ggt gtg acg gtg atg tcg          25398
Ala Gly Glu Cys Ser Met Ala Leu Ala Gly Gly Val Thr Val Met Ser
    8435                8440                8445
```

-continued

| | |
|---|---|
| tct ccg ggt acg ttt gtg gag ttc tca cgt cag cgg ggt ctg gcc gcg<br>Ser Pro Gly Thr Phe Val Glu Phe Ser Arg Gln Arg Gly Leu Ala Ala<br>    8450                      8455                          8460 | 25446 |
| gac ggg cgg tgc aag gcc tat tcg gcg gct gct gac ggt acc ggc tgg<br>Asp Gly Arg Cys Lys Ala Tyr Ser Ala Ala Ala Asp Gly Thr Gly Trp<br>8465                      8470                        8475                        8480 | 25494 |
| gcc gag ggt gtg ggg atg ctg ctg gtg gag cgg ctc tcc gac gcc cgt<br>Ala Glu Gly Val Gly Met Leu Leu Val Glu Arg Leu Ser Asp Ala Arg<br>                8485                        8490                        8495 | 25542 |
| cgc aac ggt cac cgt gtc ctg gcc gtg gtg cgt ggc agt gcg gtc aac<br>Arg Asn Gly His Arg Val Leu Ala Val Val Arg Gly Ser Ala Val Asn<br>    8500                      8505                          8510 | 25590 |
| cag gac ggt gcg agc aac ggt ctg acc gcg ccc aac ggg ccc tcc cag<br>Gln Asp Gly Ala Ser Asn Gly Leu Thr Ala Pro Asn Gly Pro Ser Gln<br>                8515                        8520                        8525 | 25638 |
| cag cgt gtc atc cgt cag gcc ctg gcc aat gcg gga ctg acc ccg gcc<br>Gln Arg Val Ile Arg Gln Ala Leu Ala Asn Ala Gly Leu Thr Pro Ala<br>    8530                      8535                          8540 | 25686 |
| gat gtc gac gca gtg gag ggc cac ggc acc ggg acc act ctg ggg gac<br>Asp Val Asp Ala Val Glu Gly His Gly Thr Gly Thr Thr Leu Gly Asp<br>8545                      8550                        8555                        8560 | 25734 |
| ccg atc gag gcc cag gca ctc ctg gcc gcc tac gga caa cac cgc ccc<br>Pro Ile Glu Ala Gln Ala Leu Leu Ala Ala Tyr Gly Gln His Arg Pro<br>                8565                        8570                        8575 | 25782 |
| cac cac cgc ccc ttg tgg ctg gga tcc ctc aaa tcc aac atc ggg cac<br>His His Arg Pro Leu Trp Leu Gly Ser Leu Lys Ser Asn Ile Gly His<br>                8580                        8585                        8590 | 25830 |
| gca cag gcc gcc gcg ggc gtg ggc gga gtc atc aag atg gtg atg gcc<br>Ala Gln Ala Ala Ala Gly Val Gly Gly Val Ile Lys Met Val Met Ala<br>    8595                      8600                          8605 | 25878 |
| ctg cgc aac ggg ctg ctg cca cag acc ctc cac gtg gac gag ccc acc<br>Leu Arg Asn Gly Leu Leu Pro Gln Thr Leu His Val Asp Glu Pro Thr<br>                8610                        8615                        8620 | 25926 |
| ccc cag gtc gac tgg tcc aca ggc gca gta caa ctc ctg aca caa ccg<br>Pro Gln Val Asp Trp Ser Thr Gly Ala Val Gln Leu Leu Thr Gln Pro<br>8625                      8630                        8635                        8640 | 25974 |
| gtg ccc tgg ccc gcc gac ccg gcc ggc cgg cca cgc cac gcc ggc gtg<br>Val Pro Trp Pro Ala Asp Pro Ala Gly Arg Pro Arg His Ala Gly Val<br>                8645                        8650                        8655 | 26022 |
| tca tca ttc ggc gtc agc ggc acc aac gcc cac atc atc ctc gaa gaa<br>Ser Ser Phe Gly Val Ser Gly Thr Asn Ala His Ile Ile Leu Glu Glu<br>    8660                      8665                          8670 | 26070 |
| gca ccc act ccc cag gac agc gat acc gac gac gaa ccg cct gcc aac<br>Ala Pro Thr Pro Gln Asp Ser Asp Thr Asp Asp Glu Pro Pro Ala Asn<br>                8675                        8680                        8685 | 26118 |
| gca cca gcc ctg ccc cat ccc ctc cct ctt ccc gtg ccg gtg tcg gcg<br>Ala Pro Ala Leu Pro His Pro Leu Pro Leu Pro Val Pro Val Ser Ala<br>    8690                      8695                          8700 | 26166 |
| agg tct gag gcc ggg ttg cgg gcg cag gca cag gcg ttg cgc cag tac<br>Arg Ser Glu Ala Gly Leu Arg Ala Gln Ala Gln Ala Leu Arg Gln Tyr<br>8705                      8710                        8715                        8720 | 26214 |
| gtg gca gcc cgc ccg gac atg tca cct gcc gac att ggt gcg ggt ctg<br>Val Ala Ala Arg Pro Asp Met Ser Pro Ala Asp Ile Gly Ala Gly Leu<br>                8725                        8730                        8735 | 26262 |
| gcc cgc ggc cgg gcc gta ctg gaa cac cgc gcc gtc atc ctg gcc gcg<br>Ala Arg Gly Arg Ala Val Leu Glu His Arg Ala Val Ile Leu Ala Ala<br>                8740                        8745                        8750 | 26310 |
| gac cgc gag gaa ctg gcg cag gca ctg aca gcc ctg gca gcc ggc gaa<br>Asp Arg Glu Glu Leu Ala Gln Ala Leu Thr Ala Leu Ala Ala Gly Glu<br>    8755                      8760                          8765 | 26358 |

```
ccc cac ccc cac atc acc aca ggc cac acc cgg ggc ggt gac cgc ggc    26406
Pro His Pro His Ile Thr Thr Gly His Thr Arg Gly Gly Asp Arg Gly
    8770            8775                8780 ggc gtc gtc ttc gtc ttc ccc gga cag ggc ggc cag tgg gcc ggg atg    26454
Gly Val Val Phe Val Phe Pro Gly Gln Gly Gly Gln Trp Ala Gly Met
8785            8790                8795                8800 ggc ctg acc ctg ctc acc tcc tca ccc gtg ttc gcc gaa cac atc gac    26502
Gly Leu Thr Leu Leu Thr Ser Ser Pro Val Phe Ala Glu His Ile Asp
            8805                8810                8815 gca tgc gag aaa gcc ctc acc ccc tgg gtg ccc tgg tcc ctg acc gac    26550
Ala Cys Glu Lys Ala Leu Thr Pro Trp Val Pro Trp Ser Leu Thr Asp
                8820                8825                8830 atc ctg cac cgc gac ccc gac gac ccc gca tgg caa caa gcc gac gtg    26598
Ile Leu His Arg Asp Pro Asp Asp Pro Ala Trp Gln Gln Ala Asp Val
    8835                8840                8845 gtc cag ccc gtg ctc ttc agc atc atg gtc tcc ctc gcc gcc ctg tgg    26646
Val Gln Pro Val Leu Phe Ser Ile Met Val Ser Leu Ala Ala Leu Trp
        8850                8855                8860 cgc tcc tac ggc atc gaa ccc gac gcg gtc ctc ggc cac tcc cag gga    26694
Arg Ser Tyr Gly Ile Glu Pro Asp Ala Val Leu Gly His Ser Gln Gly
8865                8870                8875                8880 gaa atc gcc gcc gcc cac atc tgc ggc gca ctc agc ctg aaa gac gcc    26742
Glu Ile Ala Ala Ala His Ile Cys Gly Ala Leu Ser Leu Lys Asp Ala
            8885                8890                8895 gcc aaa acc gtt gca ctg cgc agc cgc gca ctg gcc gcc gta cga ggc    26790
Ala Lys Thr Val Ala Leu Arg Ser Arg Ala Leu Ala Ala Val Arg Gly
                8900                8905                8910 cgg ggc gcc atg gcc tca ctg ccc ctg ccc gcc cag gac gtg cag cag    26838
Arg Gly Ala Met Ala Ser Leu Pro Leu Pro Ala Gln Asp Val Gln Gln
    8915                8920                8925 ctc att tcc gaa cgg tgg gaa ggg cag ttg tgg gtg gca gcc ctc aac    26886
Leu Ile Ser Glu Arg Trp Glu Gly Gln Leu Trp Val Ala Ala Leu Asn
        8930                8935                8940 ggc ccc cac tcc acc acc gtc tcc ggc gac acc aag gcg gtg gat gag    26934
Gly Pro His Ser Thr Thr Val Ser Gly Asp Thr Lys Ala Val Asp Glu
8945                8950                8955                8960 gtg ctg gcg cac tgc acc gac acc ggc cta cgg gcc aaa cgc atc ccc    26982
Val Leu Ala His Cys Thr Asp Thr Gly Leu Arg Ala Lys Arg Ile Pro
            8965                8970                8975 gtc gac tac gcc tcc cac tgc ccc cac gtc caa ccc ctc cac gac gaa    27030
Val Asp Tyr Ala Ser His Cys Pro His Val Gln Pro Leu His Asp Glu
                8980                8985                8990 ctc ctg cac ctg ctg gga gac atc acc ccc cag ccg tcc acc gtg ccg    27078
Leu Leu His Leu Leu Gly Asp Ile Thr Pro Gln Pro Ser Thr Val Pro
    8995                9000                9005 ttc ttc tcc acc gtg gaa ggc acc tgg ctg gac acc aca acc ctg gac    27126
Phe Phe Ser Thr Val Glu Gly Thr Trp Leu Asp Thr Thr Thr Leu Asp
        9010                9015                9020 gcc gcc tac tgg tac cgc aac ctc cac cag ccc gtc cgc ttc agc cac    27174
Ala Ala Tyr Trp Tyr Arg Asn Leu His Gln Pro Val Arg Phe Ser His
9025                9030                9035                9040 gcc atc cag acc ctg acc gac gac gga cac cgc gcc ttc atc gaa atc    27222
Ala Ile Gln Thr Leu Thr Asp Asp Gly His Arg Ala Phe Ile Glu Ile
            9045                9050                9055 agc ccc cac ccc acc ctc gtc ccc gcc atc gaa gac acc acc gaa aac    27270
Ser Pro His Pro Thr Leu Val Pro Ala Ile Glu Asp Thr Thr Glu Asn
                9060                9065                9070 acc acc gaa aac atc acc gcg acc ggc agc ctc cgc cgc ggc gac aac    27318
Thr Thr Glu Asn Ile Thr Ala Thr Gly Ser Leu Arg Arg Gly Asp Asn
```

```
                     9075                9080                9085
gac acc cac cgc ttc ctc acc gcc ctc gcc cac acc cac acc acc ggc    27366
Asp Thr His Arg Phe Leu Thr Ala Leu Ala His Thr His Thr Thr Gly
    9090                9095                9100 atc ggc aca ccc acc acc tgg cac cac cac tac acc caa acc cac ccc    27414
Ile Gly Thr Pro Thr Thr Trp His His His Tyr Thr Gln Thr His Pro
9105                9110                9115                9120 cac ccc aac ccc cac acc cac ctc gac ctg ccc acc tac ccc ttc caa    27462
His Pro Asn Pro His Thr His Leu Asp Leu Pro Thr Tyr Pro Phe Gln
            9125                9130                9135 cac cag cac tac tgg ctc caa cca ccc acc aca aca acc gac ctc acc    27510
His Gln His Tyr Trp Leu Gln Pro Pro Thr Thr Thr Thr Asp Leu Thr
                9140                9145                9150 acc acc ggc ctc acc ccc acc cac cac ccc ctc ctc acc gcc aca ctc    27558
Thr Thr Gly Leu Thr Pro Thr His His Pro Leu Leu Thr Ala Thr Leu
    9155                9160                9165 acc ctc gcc gac aac aac aca caa cta ctc acc ggc cgc ctc tcc cta    27606
Thr Leu Ala Asp Asn Asn Thr Gln Leu Leu Thr Gly Arg Leu Ser Leu
9170                9175                9180 cgc acc cac ccc tgg ctc acc gac cac acc gtc gcc ggc atg gtc ctc    27654
Arg Thr His Pro Trp Leu Thr Asp His Thr Val Ala Gly Met Val Leu
9185                9190                9195                9200 ctg ccg ggc acc gcg ctc ctc gaa ctc gcc ctc caa gcc ggc gaa cgg    27702
Leu Pro Gly Thr Ala Leu Leu Glu Leu Ala Leu Gln Ala Gly Glu Arg
                9205                9210                9215 gtg gac tgc cct cgg gtg gag gaa ctg acc ctg cac gca ccg ttg gtg    27750
Val Asp Cys Pro Arg Val Glu Glu Leu Thr Leu His Ala Pro Leu Val
    9220                9225                9230 atc ccg cac acc gag gac gtg acg ttg cag gtc acc gtt cgg gca gcc    27798
Ile Pro His Thr Glu Asp Val Thr Leu Gln Val Thr Val Arg Ala Ala
9235                9240                9245 gat gag agt ggc cat cgc gcc ctc gcg atc cac tcg tac tcc ggc acc    27846
Asp Glu Ser Gly His Arg Ala Leu Ala Ile His Ser Tyr Ser Gly Thr
    9250                9255                9260 gcg tcg tcg gcg gac cgg gag tgg acc cgt cac gcc acg ggc ctc ctc    27894
Ala Ser Ser Ala Asp Arg Glu Trp Thr Arg His Ala Thr Gly Leu Leu
9265                9270                9275                9280 aca cac cac gcc gac acc gat cac cgt gcc gac acg cac acg gac gcg    27942
Thr His His Ala Asp Thr Asp His Arg Ala Asp Thr His Thr Asp Ala
        9285                9290                9295 tgc ctt ggc ggg agc tgg ccc ccg ccc ggc gcg cag ccc atc gaa ctg    27990
Cys Leu Gly Gly Ser Trp Pro Pro Pro Gly Ala Gln Pro Ile Glu Leu
    9300                9305                9310 ggc gac gtc tac ggt cgt atg gcg gcg gac tcg gac atc gcc tac ggg    28038
Gly Asp Val Tyr Gly Arg Met Ala Ala Asp Ser Asp Ile Ala Tyr Gly
9315                9320                9325 ccg gtc ttc cag ggg ctg cac gcc gcc tgg agg ttc ggc gac gat gtc    28086
Pro Val Phe Gln Gly Leu His Ala Ala Trp Arg Phe Gly Asp Asp Val
    9330                9335                9340 ctg gcc gag gtg cgt ctg ccg gaa gag gct ctg cgc gat gct ccg gcg    28134
Leu Ala Glu Val Arg Leu Pro Glu Glu Ala Leu Arg Asp Ala Pro Ala
9345                9350                9355                9360 gcg gcc ttc ggt gtt cac ccg gcc ttg ctc gac gcg gcc ctg cac gcc    28182
Ala Ala Phe Gly Val His Pro Ala Leu Leu Asp Ala Ala Leu His Ala
        9365                9370                9375 acg gcg ctc acc ccc cag aac ggg gac ggc tcg acg gag aac gtc gcc    28230
Thr Ala Leu Thr Pro Gln Asn Gly Asp Gly Ser Thr Glu Asn Val Ala
    9380                9385                9390 cag gag agc atg cct gac cgc gca gcc cac cag gcg cga ctg ccg ttc    28278
```

```
                    Gln Glu Ser Met Pro Asp Arg Ala Ala His Gln Ala Arg Leu Pro Phe
                        9395                9400                9405 agc tgg agc ggc gtg tcc ctg cac acg gcg ggc agt tcc gtg ttg cgc              28326
Ser Trp Ser Gly Val Ser Leu His Thr Ala Gly Ser Ser Val Leu Arg
    9410                9415                9420 gta cgg ctg tcg cgc agt ccg cag cac ggt aat gcc gtg gcc ctc acc              28374
Val Arg Leu Ser Arg Ser Pro Gln His Gly Asn Ala Val Ala Leu Thr
9425                9430                9435                9440 gcg gcc gac gag gac ggt cgg ccg gtg gtg acg atc gag tcg ctc gcg              28422
Ala Ala Asp Glu Asp Gly Arg Pro Val Val Thr Ile Glu Ser Leu Ala
            9445                9450                9455 ctg cgg ccg gtg tcc acc gag gag ctg cgc gcg gcc gcg gat cgt acg              28470
Leu Arg Pro Val Ser Thr Glu Glu Leu Arg Ala Ala Ala Asp Arg Thr
                9460                9465                9470 ccc gag cac gag tcg ctc ttc cga ctg gac tgg gtt tcc gta cca gtg              28518
Pro Glu His Glu Ser Leu Phe Arg Leu Asp Trp Val Ser Val Pro Val
        9475                9480                9485 ccc gcc aac gcc cct tcg ccc acc gcg gac cgg ccc tgg gcg gtc atc              28566
Pro Ala Asn Ala Pro Ser Pro Thr Ala Asp Arg Pro Trp Ala Val Ile
    9490                9495                9500 ggc gcg ggc ctt ccc cac ctg ccc ggc ctg acg gag cac gag cac gtg              28614
Gly Ala Gly Leu Pro His Leu Pro Gly Leu Thr Glu His Glu His Val
9505                9510                9515                9520 acc gcg tat gac gag ccg gcg gac ctg ctt ctg gct ctg gac cgc ggt              28662
Thr Ala Tyr Asp Glu Pro Ala Asp Leu Leu Leu Ala Leu Asp Arg Gly
            9525                9530                9535 gct ccg ccg ccc ggt gtg ctg gtc gta ggt ggt gtc gcc cac acc gaa              28710
Ala Pro Pro Pro Gly Val Leu Val Val Gly Gly Val Ala His Thr Glu
                9540                9545                9550 gcc cgg gag tat tcc gcc gaa gcc ccc ggg gag cgc ggg acc gag gcc              28758
Ala Arg Glu Tyr Ser Ala Glu Ala Pro Gly Glu Arg Gly Thr Glu Ala
        9555                9560                9565 tgc gag gcc cgg ccg gac gtc gtg cac gtg ggc gtc gtg cac acg gct              28806
Cys Glu Ala Arg Pro Asp Val Val His Val Gly Val Val His Thr Ala
    9570                9575                9580 gcc gtg cac gcg gct gcc gcg cag atg ttg gcc agg ctc cag gcc tgg              28854
Ala Val His Ala Ala Ala Ala Gln Met Leu Ala Arg Leu Gln Ala Trp
9585                9590                9595                9600 ctg ggc gac gag cgc ctc gca gac agc cgg ctg ctc gtc ctg acg tgc              28902
Leu Gly Asp Glu Arg Leu Ala Asp Ser Arg Leu Leu Val Leu Thr Cys
            9605                9610                9615 ggc gcg gtc gcc cgc gcc tcc ggc gac gat gcg acg gac ctg ccc ggg              28950
Gly Ala Val Ala Arg Ala Ser Gly Asp Asp Ala Thr Asp Leu Pro Gly
                9620                9625                9630 gcc gcc gtg tgg ggg ctg gtg cgt tcg gcg cag tcc gag cac ccg gac              28998
Ala Ala Val Trp Gly Leu Val Arg Ser Ala Gln Ser Glu His Pro Asp
        9635                9640                9645 cgc atc acg ctg ctg gac ttc gag cgg ggc aca gag gcg gag ccc ggt              29046
Arg Ile Thr Leu Leu Asp Phe Glu Arg Gly Thr Glu Ala Glu Pro Gly
    9650                9655                9660 cag ctg gcg acg gcg ctg aac tgc ggg gag cgg cag ctt gcc gtc cgc              29094
Gln Leu Ala Thr Ala Leu Asn Cys Gly Glu Arg Gln Leu Ala Val Arg
9665                9670                9675                9680 ccc gga ggg ctg ttc acg cca cgg ctg gtg cgc gcg cca cgt gtc gcc              29142
Pro Gly Gly Leu Phe Thr Pro Arg Leu Val Arg Ala Pro Arg Val Ala
            9685                9690                9695 gac gcc gta ccc gcc gta ccc gcc gtg gcc gta ccg tca gcg ggt cac              29190
Asp Ala Val Pro Ala Val Pro Ala Val Ala Val Pro Ser Ala Gly His
                9700                9705                9710
```

```
gca gcc gta ccg gca gcg ggt ccc ttc ctt ccg ggc gga acg gtg ctg      29238
Ala Ala Val Pro Ala Ala Gly Pro Phe Leu Pro Gly Gly Thr Val Leu
        9715                9720                9725 atc acc ggc gga acc ggt gtc ctg ggc cgg ctc gtg gcc cgg cat ctg      29286
Ile Thr Gly Gly Thr Gly Val Leu Gly Arg Leu Val Ala Arg His Leu
        9730                9735                9740 gtg gag gcg cac ggc gta cgg cat ctg ttg ctg gcg ggt cgg cgc gga      29334
Val Glu Ala His Gly Val Arg His Leu Leu Leu Ala Gly Arg Arg Gly
9745                9750                9755                9760 ccg gac gcc gag ggt gcg ccg gag ttg cgg gcg gag ctc ggt ggg ctc      29382
Pro Asp Ala Glu Gly Ala Pro Glu Leu Arg Ala Glu Leu Gly Gly Leu
        9765                9770                9775 ggc gcg acg gtg gag gtc gtc gcc tgc gac gcg gcg gac cgg cag cag      29430
Gly Ala Thr Val Glu Val Val Ala Cys Asp Ala Ala Asp Arg Gln Gln
        9780                9785                9790 ctg gcc gac ctg ctg aca cgg atc ccc gac gat cgg ccg ctg acc ggt      29478
Leu Ala Asp Leu Leu Thr Arg Ile Pro Asp Asp Arg Pro Leu Thr Gly
        9795                9800                9805 gtc gtg cac agt gcg ggc atc ctg gac gac ggc gtg atc acg tcg ctg      29526
Val Val His Ser Ala Gly Ile Leu Asp Asp Gly Val Ile Thr Ser Leu
        9810                9815                9820 tcg ccg gag cgg ctc ggg gcc gtc ctc cgg gcc aag gcg gac gct gcg      29574
Ser Pro Glu Arg Leu Gly Ala Val Leu Arg Ala Lys Ala Asp Ala Ala
9825                9830                9835                9840 ctg ctt ctc gac gag ctg acg cgc ggg gca gag ctg tcg gct ttc gtc      29622
Leu Leu Leu Asp Glu Leu Thr Arg Gly Ala Glu Leu Ser Ala Phe Val
        9845                9850                9855 atg ttc tcc tcc gcg tcg gcg gtg gtc ggc tcg ccc ggg cag ggc aac      29670
Met Phe Ser Ser Ala Ser Ala Val Val Gly Ser Pro Gly Gln Gly Asn
        9860                9865                9870 tac gcc gcc gcc aac gcc gtc ctc gac ttc ctt gct cat cgc cgc cgc      29718
Tyr Ala Ala Ala Asn Ala Val Leu Asp Phe Leu Ala His Arg Arg Arg
        9875                9880                9885 gcc gag ggg ctg ccc gcc gtc tct ctc gcc tgg ggc ctg tgg gaa gag      29766
Ala Glu Gly Leu Pro Ala Val Ser Leu Ala Trp Gly Leu Trp Glu Glu
        9890                9895                9900 ggc aca ggg atg acg ggc cac ctc gac gtc gac gac cat gcg cgg atc      29814
Gly Thr Gly Met Thr Gly His Leu Asp Val Asp Asp His Ala Arg Ile
9905                9910                9915                9920 agc cgc gcg gga atg cgg ccg ctg ccg act gcc gag gct ctg gcg ctg      29862
Ser Arg Ala Gly Met Arg Pro Leu Pro Thr Ala Glu Ala Leu Ala Leu
        9925                9930                9935 ttc gac gcg gcc ttg gcc gac ggc gag ccg ttc ctg atg ccg gct cgg      29910
Phe Asp Ala Ala Leu Ala Asp Gly Glu Pro Phe Leu Met Pro Ala Arg
        9940                9945                9950 ctc gac ctc acg gcc gta cgg tct ggt gcc gcg tcc gca ccg gtg ccg      29958
Leu Asp Leu Thr Ala Val Arg Ser Gly Ala Ala Ser Ala Pro Val Pro
        9955                9960                9965 ccg ctg ctg caa ggt ctg ctt cag ctg cct cgg tcc cgc tcg gcc gcc      30006
Pro Leu Leu Gln Gly Leu Leu Gln Leu Pro Arg Ser Arg Ser Ala Ala
        9970                9975                9980 gcg gcc ccc ggc cat ggg gcc ccg gcg gcg gac gag gcg gcg gcc tgg      30054
Ala Ala Pro Gly His Gly Ala Pro Ala Ala Asp Glu Ala Ala Ala Trp
9985                9990                9995                10000 cgt gag cgt ctg gcc cgg cag agt gcc ggt gag cgc agg cag gcg ctg      30102
Arg Glu Arg Leu Ala Arg Gln Ser Ala Gly Glu Arg Arg Gln Ala Leu
        10005               10010               10015 ctg cgc ctg gtg cgg tcg cat gtc gcg gcg gtg ctc ggc cat agc ggt      30150
Leu Arg Leu Val Arg Ser His Val Ala Ala Val Leu Gly His Ser Gly
        10020               10025               10030
```

-continued

| | |
|---|---|
| gcc gac gga atc gac gca tcg cgg gcg ttc cgc gag ctg ggg ttc gac<br>Ala Asp Gly Ile Asp Ala Ser Arg Ala Phe Arg Glu Leu Gly Phe Asp<br>     10035                    10040                   10045 | 30198 |
| tcg ctc acg gcg gtc gag ctg cgc aac cgt ctc acg gcc gcg acg ggc<br>Ser Leu Thr Ala Val Glu Leu Arg Asn Arg Leu Thr Ala Ala Thr Gly<br>10050                    10055                   10060 | 30246 |
| ctg cgg ctg cgg gcc acg ctg gcc ttc gat ttc ccg acc ccg gca gcg<br>Leu Arg Leu Arg Ala Thr Leu Ala Phe Asp Phe Pro Thr Pro Ala Ala<br>10065                    10070                   10075                   10080 | 30294 |
| ctg gcc gag cac ttg ggc gag cgt ctg ctt ccc gac cag gag gcc acg<br>Leu Ala Glu His Leu Gly Glu Arg Leu Leu Pro Asp Gln Glu Ala Thr<br>                 10085                   10090                   10095 | 30342 |
| ggc gag caa gcc ggc gat cag ctc tcc ggc ggc agc gag gag gac gta<br>Gly Glu Gln Ala Gly Asp Gln Leu Ser Gly Gly Ser Glu Glu Asp Val<br>10100                    10105                   10110 | 30390 |
| cgc agc ctc ctg acg tcc att ccg atc ggc agg ctg cgg gac gcg ggg<br>Arg Ser Leu Leu Thr Ser Ile Pro Ile Gly Arg Leu Arg Asp Ala Gly<br>     10115                    10120                   10125 | 30438 |
| ctc ctc ggg ccc ctg ctc acg ctc gcg gac acg ggc cgc ggc gcc tcg<br>Leu Leu Gly Pro Leu Leu Thr Leu Ala Asp Thr Gly Arg Gly Ala Ser<br>10130                    10135                   10140 | 30486 |
| ggc gcc gcc gca ggt ccg gag gac gcg ccg ccc tcc ggc cag gac aca<br>Gly Ala Ala Ala Gly Pro Glu Asp Ala Pro Pro Ser Gly Gln Asp Thr<br>10145                    10150                   10155                   10160 | 30534 |
| ccg gct ccc gtc tcg atc gac gag atg gac atc gac gac ctg atg gat<br>Pro Ala Pro Val Ser Ile Asp Glu Met Asp Ile Asp Asp Leu Met Asp<br>                 10165                   10170                   10175 | 30582 |
| ctg gcg cac ggg cat ggc acc gca ccc gcc cgt gag ccc gcc gac gca<br>Leu Ala His Gly His Gly Thr Ala Pro Ala Arg Glu Pro Ala Asp Ala<br>10180                    10185                   10190 | 30630 |
| gag gac tcg tcg tca tca cga aac cgg aca cac cac aca cac gaa ggt<br>Glu Asp Ser Ser Ser Ser Arg Asn Arg Thr His His Thr His Glu Gly<br>     10195                    10200                   10205 | 30678 |
| gag aca gcg tga<br>Glu Thr Ala<br>  10210 | 30690 |

```
<210> SEQ ID NO 2
<211> LENGTH: 31422
<212> TYPE: DNA
<213> ORGANISM: Streptomyces avermitilis
<220> FEATURE:
<221> NAME/KEY: CDS
<222> LOCATION: (1)..(14643)
<221> NAME/KEY: CDS
<222> LOCATION: (14824)..(31419)

<400> SEQUENCE: 2
```

| | |
|---|---|
| atg gct aac gag gaa aag ctc cgc gac tat ctc aag cgc gtt act gcc<br>Met Ala Asn Glu Glu Lys Leu Arg Asp Tyr Leu Lys Arg Val Thr Ala<br>1                  5                      10                     15 | 48 |
| gat ctc ctc aat gtg cgg cgt cga ctt cag cag att gaa tcg ggc gag<br>Asp Leu Leu Asn Val Arg Arg Arg Leu Gln Gln Ile Glu Ser Gly Glu<br>                  20                     25                     30 | 96 |
| cag gag ccg att gca att gtg ggg atg gcg tgc cgt ttt ccg ggg ggt<br>Gln Glu Pro Ile Ala Ile Val Gly Met Ala Cys Arg Phe Pro Gly Gly<br>            35                     40                     45 | 144 |
| gtg gag tcg gcg gag gat ttc tgg gag ttg att gcg tcg ggt cgg gat<br>Val Glu Ser Ala Glu Asp Phe Trp Glu Leu Ile Ala Ser Gly Arg Asp<br>50                    55                     60 | 192 |
| gcg gtg ggg gag ttt ccg gtc gac cgg ggt tgg gac gtg gag gct ttc | 240 |

```
                Ala Val Gly Glu Phe Pro Val Asp Arg Gly Trp Asp Val Glu Ala Phe
                 65                  70                  75                  80 tat gat ccg gag ccg ggg cgg gcg ggt tcg tcg tat acg cgc cgg ggc         288
Tyr Asp Pro Glu Pro Gly Arg Ala Gly Ser Ser Tyr Thr Arg Arg Gly
                    85                  90                  95 ggt ttc ctg gag ggt gcg gcg gag ttc gat gcg ggg ttt ttc ggg atc         336
Gly Phe Leu Glu Gly Ala Ala Glu Phe Asp Ala Gly Phe Phe Gly Ile
                100                 105                 110 agt ccg cgt gag gcg ttg gcg atg gat ccg cag cag cgg ttg atg ctg         384
Ser Pro Arg Glu Ala Leu Ala Met Asp Pro Gln Gln Arg Leu Met Leu
            115                 120                 125 gag gtg tcc tgg gag gcg ttg gag cgg gcg ggc atc gac ccc gcc acg         432
Glu Val Ser Trp Glu Ala Leu Glu Arg Ala Gly Ile Asp Pro Ala Thr
        130                 135                 140 ttg cgc ggc agc cgg acg ggc gtc ttc gcc ggc ctc atg tcc cag gac         480
Leu Arg Gly Ser Arg Thr Gly Val Phe Ala Gly Leu Met Ser Gln Asp
145                 150                 155                 160 tac gcg acc cgt ctc ctc tcg gtc ccc gac gac ctg gcc ggc tac ctg         528
Tyr Ala Thr Arg Leu Leu Ser Val Pro Asp Asp Leu Ala Gly Tyr Leu
                165                 170                 175 ggc aac ggc aac gcg gga agc atc ctg tcc gga cgc gtc gcc tac acc         576
Gly Asn Gly Asn Ala Gly Ser Ile Leu Ser Gly Arg Val Ala Tyr Thr
                180                 185                 190 ttc ggc ttc gag ggc ccc gcg gtg acg gtc gac acg gcg tgc tcg tcg         624
Phe Gly Phe Glu Gly Pro Ala Val Thr Val Asp Thr Ala Cys Ser Ser
            195                 200                 205 tcg ctg gtg gca ctg cac ctc gcc tgc cag tca ctg cgc acc ggt gag         672
Ser Leu Val Ala Leu His Leu Ala Cys Gln Ser Leu Arg Thr Gly Glu
        210                 215                 220 tcc tcc ttc gcc ctc gcc gga ggc gtg acg gtc atg tcc acc ccg ggc         720
Ser Ser Phe Ala Leu Ala Gly Gly Val Thr Val Met Ser Thr Pro Gly
225                 230                 235                 240 atg ttc gtg gag ttc tcg cgg cag cgg ggt ctg tcg ccg gac ggc cgg         768
Met Phe Val Glu Phe Ser Arg Gln Arg Gly Leu Ser Pro Asp Gly Arg
                245                 250                 255 tgc aag gcg tac gcg tcg gct gcc gac ggc acc ggc atg tcc gag ggc         816
Cys Lys Ala Tyr Ala Ser Ala Ala Asp Gly Thr Gly Met Ser Glu Gly
                260                 265                 270 gtg ggg att ttg ctg ctg gag cgg ctg tcc gag gct gaa cgt cgt ggt         864
Val Gly Ile Leu Leu Leu Glu Arg Leu Ser Glu Ala Glu Arg Arg Gly
            275                 280                 285 cat cgg gtt ttg gcg gtg gtg cgg ggg agt gcg gtg aat cag gac ggt         912
His Arg Val Leu Ala Val Val Arg Gly Ser Ala Val Asn Gln Asp Gly
        290                 295                 300 gcg tcg aat ggg ttg acg gcg ccg aat ggt ccg tcg cag cag cgg gtg         960
Ala Ser Asn Gly Leu Thr Ala Pro Asn Gly Pro Ser Gln Gln Arg Val
305                 310                 315                 320 att cgg cag gcg ttg gcg tgt gcg ggg ttg tct gtg gcg gat gtg gat         1008
Ile Arg Gln Ala Leu Ala Cys Ala Gly Leu Ser Val Ala Asp Val Asp
                325                 330                 335 gtg gtg gag ggg cac ggg acg ggc acg acg ctg ggt gat ccg atc gag         1056
Val Val Glu Gly His Gly Thr Gly Thr Thr Leu Gly Asp Pro Ile Glu
                340                 345                 350 gcg cag gcg ttg ctc gcc acg tac ggg cag cgg gcc ggt gac acg ccg         1104
Ala Gln Ala Leu Leu Ala Thr Tyr Gly Gln Arg Ala Gly Asp Thr Pro
            355                 360                 365 gtg tgg ttg ggg tcg gtg aag tcg aac atc ggg cat gcg cag gct gct         1152
Val Trp Leu Gly Ser Val Lys Ser Asn Ile Gly His Ala Gln Ala Ala
        370                 375                 380
```

```
gcg ggt gtg gcg ggt gtg atc aag atg gtg atg gcg ttg cgg gcg ggg     1200
Ala Gly Val Ala Gly Val Ile Lys Met Val Met Ala Leu Arg Ala Gly
385                 390                 395                 400 gtg ttg ccg cgg acg ttg cat gtg gat gag ccg tcg tcg cag gtg gat     1248
Val Leu Pro Arg Thr Leu His Val Asp Glu Pro Ser Ser Gln Val Asp
            405                 410                 415 tgg tcg agt ggg tcg gtt cgt gtg ttg gcg gat gag gtg gag tgg ccg     1296
Trp Ser Ser Gly Ser Val Arg Val Leu Ala Asp Glu Val Glu Trp Pro
        420                 425                 430 ggg gtg gag ggt cgg ctg cgg cgt gcg ggg gtg tct gcg ttc ggg gtg     1344
Gly Val Glu Gly Arg Leu Arg Arg Ala Gly Val Ser Ala Phe Gly Val
    435                 440                 445 agt ggg acg aat gcg cat gtg att ttg gag gag gcg tcg ggg ggc gcg     1392
Ser Gly Thr Asn Ala His Val Ile Leu Glu Glu Ala Ser Gly Gly Ala
450                 455                 460 ggt ggg ggt gcg ggc cgg ctg cag gag ttg ggt ccg ggg gtg gtg tcg     1440
Gly Gly Gly Ala Gly Arg Leu Gln Glu Leu Gly Pro Gly Val Val Ser
465                 470                 475                 480 ggt tcg ggg gtg gtg ccg tgg gtg gtg tcg gcg cgg tcg gag ttg gcg     1488
Gly Ser Gly Val Val Pro Trp Val Val Ser Ala Arg Ser Glu Leu Ala
            485                 490                 495 ttg cgg ggg cag gcg cgt cgg ttg cgt ggg gtt gtg gcg gtt ggt ggg     1536
Leu Arg Gly Gln Ala Arg Arg Leu Arg Gly Val Val Ala Val Gly Gly
        500                 505                 510 ggt gcg gat ggt gtg ggg gtg agt ccg gct ggg gtc ggg cgg gct ttg     1584
Gly Ala Asp Gly Val Gly Val Ser Pro Ala Gly Val Gly Arg Ala Leu
    515                 520                 525 gtg tcg gag cgg tcg gtg ttc gag cat cgt gcg gtg gtc gtg gcc gag     1632
Val Ser Glu Arg Ser Val Phe Glu His Arg Ala Val Val Val Ala Glu
530                 535                 540 gac cgc gac gag ttc ctg cac gca ctc gac gca ctg gcc ggc ggc cgc     1680
Asp Arg Asp Glu Phe Leu His Ala Leu Asp Ala Leu Ala Gly Gly Arg
545                 550                 555                 560 ccc gtg ccc ggc gtc gtc gag gga cga acc acc tcg ggc gaa ctc gcc     1728
Pro Val Pro Gly Val Val Glu Gly Arg Thr Thr Ser Gly Glu Leu Ala
            565                 570                 575 gta ctc ttc gcc ggg cag gga acc cag cgc gca ggc atg ggc cgc gaa     1776
Val Leu Phe Ala Gly Gln Gly Thr Gln Arg Ala Gly Met Gly Arg Glu
        580                 585                 590 ctg tac gag gcg tac ccc gtc ttc gcc cag gcc atc gac gag atc tgc     1824
Leu Tyr Glu Ala Tyr Pro Val Phe Ala Gln Ala Ile Asp Glu Ile Cys
    595                 600                 605 gcg gag gcc gac acc gcc cgc acc gac ccc ggt gcc cct ggg ctg cgg     1872
Ala Glu Ala Asp Thr Ala Arg Thr Asp Pro Gly Ala Pro Gly Leu Arg
610                 615                 620 gac gta ctc ttc gca ccg cag gac tct ccc gaa ggc cgg ctg atc gag     1920
Asp Val Leu Phe Ala Pro Gln Asp Ser Pro Glu Gly Arg Leu Ile Glu
625                 630                 635                 640 gac acg ggt ttc gcc cag ccc gcc ctg ttc gcc ttc gag gtg gcg ctg     1968
Asp Thr Gly Phe Ala Gln Pro Ala Leu Phe Ala Phe Glu Val Ala Leu
            645                 650                 655 ttc cgg ctg ctg gag acc tgg ggt ctg acg ccc gac tac gtc ctc ggc     2016
Phe Arg Leu Leu Glu Thr Trp Gly Leu Thr Pro Asp Tyr Val Leu Gly
        660                 665                 670 cat tcc gtc ggt gaa ctg gcg gcc gcc cat gtc gcc ggg atg ctc tgc     2064
His Ser Val Gly Glu Leu Ala Ala Ala His Val Ala Gly Met Leu Cys
    675                 680                 685 ctt gcc gac gcg gtg gca ctg gtg gtc gca cga ggc cgc ctg atg caa     2112
Leu Ala Asp Ala Val Ala Leu Val Val Ala Arg Gly Arg Leu Met Gln
690                 695                 700
```

-continued

| | | |
|---|---|---|
| ggg ctc ccg tcc ggc gga gcc atg gtg gcc atc gag gcg tcc gag gac<br>Gly Leu Pro Ser Gly Gly Ala Met Val Ala Ile Glu Ala Ser Glu Asp<br>705                      710                  715                  720 | 2160 |
| gag atc ctc ccg ctg ccc gac gaa tac gca tcc cgg gtc gcg cac gcc<br>Glu Ile Leu Pro Leu Pro Asp Glu Tyr Ala Ser Arg Val Ala His Ala<br>                  725                  730                  735 | 2208 |
| gcg gtg aac ggg ccg cgg tcg atc gtc ctc tcc ggg gac gag gac gcg<br>Ala Val Asn Gly Pro Arg Ser Ile Val Leu Ser Gly Asp Glu Asp Ala<br>        740                  745                  750 | 2256 |
| gtc ctg gac ctc gcg cag caa tgg gcg gca cga ggc cgc cgc acc cgg<br>Val Leu Asp Leu Ala Gln Gln Trp Ala Ala Arg Gly Arg Arg Thr Arg<br>755                      760                  765 | 2304 |
| cgg ctg cgg acc agc cac gcc ttc cac tcg ccg cac atg gac gcc atg<br>Arg Leu Arg Thr Ser His Ala Phe His Ser Pro His Met Asp Ala Met<br>770                      775                  780 | 2352 |
| ttg ggc gac ttc cgc cgc gcg gcc gag cag gtc acc ttc agc gcc ccg<br>Leu Gly Asp Phe Arg Arg Ala Ala Glu Gln Val Thr Phe Ser Ala Pro<br>785                      790                  795                  800 | 2400 |
| cgg att ccc gtc gtc tcc aac gtc acc ggc gcg ccc ctc ccc gcc gag<br>Arg Ile Pro Val Val Ser Asn Val Thr Gly Ala Pro Leu Pro Ala Glu<br>                  805                  810                  815 | 2448 |
| acc atg tgc acc ccg gac tac tgg gtc gaa cac gcc cgc agc acg gtc<br>Thr Met Cys Thr Pro Asp Tyr Trp Val Glu His Ala Arg Ser Thr Val<br>                  820                  825                  830 | 2496 |
| cgt ttc gcg gac ggc atc tca tgg ctt cag gaa cag ggc gtc acc acc<br>Arg Phe Ala Asp Gly Ile Ser Trp Leu Gln Glu Gln Gly Val Thr Thr<br>                  835                  840                  845 | 2544 |
| tgc ctc gaa atc ggc ccc gac ggc acg ctg tcg gcc ctc gca cag gac<br>Cys Leu Glu Ile Gly Pro Asp Gly Thr Leu Ser Ala Leu Ala Gln Asp<br>850                      855                  860 | 2592 |
| tcg ctc agt gca ccg gcc cgc gcc atc ccc gcc ctg cgg ccg gac cag<br>Ser Leu Ser Ala Pro Ala Arg Ala Ile Pro Ala Leu Arg Pro Asp Gln<br>865                      870                  875                  880 | 2640 |
| ccg gag gca cgg tcg gtc atg acc gcc ctg gcg gag ttg ttc gtg gct<br>Pro Glu Ala Arg Ser Val Met Thr Ala Leu Ala Glu Leu Phe Val Ala<br>                  885                  890                  895 | 2688 |
| ggg acg gcg gtt gag tgg gcc ggt gtg ttc gag ggg act gct cgc gag<br>Gly Thr Ala Val Glu Trp Ala Gly Val Phe Glu Gly Thr Ala Arg Glu<br>                      900                  905                  910 | 2736 |
| gtc ggt gat gga tgc ggg gtg gag ctg ccg acg tat gcg ttt gag cgg<br>Val Gly Asp Gly Cys Gly Val Glu Leu Pro Thr Tyr Ala Phe Glu Arg<br>        915                  920                  925 | 2784 |
| gag cga ttt tgg ctg gac gtg gag gag gga tct gcg gga ggt tcc ggg<br>Glu Arg Phe Trp Leu Asp Val Glu Glu Gly Ser Ala Gly Gly Ser Gly<br>930                      935                  940 | 2832 |
| gtt tcc ggg atg tgg ggt ggt ccg ttg tgg gag gcg gtc gag tgt ggt<br>Val Ser Gly Met Trp Gly Gly Pro Leu Trp Glu Ala Val Glu Cys Gly<br>945                      950                  955                  960 | 2880 |
| gat gcg ggg gtg gtg gca tcg ctc ctt ggg gtg gat gag ggg gcg tcg<br>Asp Ala Gly Val Val Ala Ser Leu Leu Gly Val Asp Glu Gly Ala Ser<br>                  965                  970                  975 | 2928 |
| ctg ggt gcg gtg gtg tcg gcg ttg ggg gaa tgg ggg cgg gta cgg cac<br>Leu Gly Ala Val Val Ser Ala Leu Gly Glu Trp Gly Arg Val Arg His<br>                  980                  985                  990 | 2976 |
| gag cgt gaa gtg gtg gac ggg tgg cgc tat cgg gag gtg tgg cga ccc<br>Glu Arg Glu Val Val Asp Gly Trp Arg Tyr Arg Glu Val Trp Arg Pro<br>995                      1000                  1005 | 3024 |
| gtt tcg ggc ggt ggt gta ggg ggg ctg tcg ggc gcg tgg ctg gtg gtg<br>Val Ser Gly Gly Gly Val Gly Gly Leu Ser Gly Ala Trp Leu Val Val | 3072 |

```
                                    -continued
     1010                1015                1020
tcc gag ggc gag gcg ggc ccg gtt gat gtg gtg gcg gag ggg ttg gag    3120
Ser Glu Gly Glu Ala Gly Pro Val Asp Val Val Ala Glu Gly Leu Glu
1025                1030                1035                1040 cgg tgt ggg gcg cga gtg gtt cgg gtg gag gtg gaa gcg ggg tgt gtg    3168
Arg Cys Gly Ala Arg Val Val Arg Val Glu Val Glu Ala Gly Cys Val
                1045                1050                1055 agc agg gaa gtg ttg gcc ggc cac ctg cgt gag gcg gtc gat ggt gag    3216
Ser Arg Glu Val Leu Ala Gly His Leu Arg Glu Ala Val Asp Gly Glu
         1060                1065                1070 gct gtc ggc ggt gtc gtc tcc ctt gtg ggc tgg ggg agt ggc gtc gtg    3264
Ala Val Gly Gly Val Val Ser Leu Val Gly Trp Gly Ser Gly Val Val
    1075                1080                1085 cag gcg gga gtg gcg tct gtg ggg ttg gtg cag gcg ctg ggt gat gtg    3312
Gln Ala Gly Val Ala Ser Val Gly Leu Val Gln Ala Leu Gly Asp Val
1090                1095                1100 ggc gtg ggg gcg cgg ctg tgg tgt gtg acg ggc ggg gcc gtg tcg gtg    3360
Gly Val Gly Ala Arg Leu Trp Cys Val Thr Gly Gly Ala Val Ser Val
1105                1110                1115                1120 ggg ggc cgg gat gct gtg tgg ggg ccg gcc tcg ggt gtg gtg tgg ggg    3408
Gly Gly Arg Asp Ala Val Trp Gly Pro Ala Ser Gly Val Val Trp Gly
                1125                1130                1135 ctg ggc cgt gtg gtg ggg gcg gag gca ccg gac cgc tgg ggt ggg ctg    3456
Leu Gly Arg Val Val Gly Ala Glu Ala Pro Asp Arg Trp Gly Gly Leu
         1140                1145                1150 gtt gat gtg ccg gag ctc gtg gat gag cgg gtg gtc gat ggg ttg gta    3504
Val Asp Val Pro Glu Leu Val Asp Glu Arg Val Val Asp Gly Leu Val
    1155                1160                1165 ggt gtg ctg gcg ggt gtg ggg gga ggg ggt gag agt gag ttt gcc gtg    3552
Gly Val Leu Ala Gly Val Gly Gly Gly Glu Ser Glu Phe Ala Val
1170                1175                1180 cgg tct tcg ggg gcg ttt gtg cgg cgg ttg gtg cgg gcg ccg ttg gag    3600
Arg Ser Ser Gly Ala Phe Val Arg Arg Leu Val Arg Ala Pro Leu Glu
1185                1190                1195                1200 gag gcc gtc gcg gag cgg gag tgg cgg ccc cgc ggc acc gta ctc gtc    3648
Glu Ala Val Ala Glu Arg Glu Trp Arg Pro Arg Gly Thr Val Leu Val
                1205                1210                1215 acc gga ggc acc ggc gag ttg ggt gcg cac gtc gcc cgg tgg atg gcc    3696
Thr Gly Gly Thr Gly Glu Leu Gly Ala His Val Ala Arg Trp Met Ala
         1220                1225                1230 cgg cgt ggc gcc gaa cac ctg ctg ctg gtg agc cga cgc ggg gag agc    3744
Arg Arg Gly Ala Glu His Leu Leu Leu Val Ser Arg Arg Gly Glu Ser
    1235                1240                1245 gcc cag gga gtc gaa gaa ctc cga gcg gac ttg atg ggc ttg ggc gcg    3792
Ala Gln Gly Val Glu Glu Leu Arg Ala Asp Leu Met Gly Leu Gly Ala
1250                1255                1260 cgg gtg tcg gtg gtg gcg tgt gat gcg gcg gac cgt gag gcg ttg gcg    3840
Arg Val Ser Val Val Ala Cys Asp Ala Ala Asp Arg Glu Ala Leu Ala
1265                1270                1275                1280 gag gtg ttg cgg tcg gcc gtt ccg gcg gag tgc ccg ctg ggt gtg gtg    3888
Glu Val Leu Arg Ser Ala Val Pro Ala Glu Cys Pro Leu Gly Val Val
                1285                1290                1295 gtg cat gcc gcg gga gtt gtg gat gac ggg gtg ttg gag ggg ttg tcg    3936
Val His Ala Ala Gly Val Val Asp Asp Gly Val Leu Glu Gly Leu Ser
         1300                1305                1310 tcc gag cgt gtc acg ggg gtg ctg cgg gcg aag gcg ctg gcg gcc tgg    3984
Ser Glu Arg Val Thr Gly Val Leu Arg Ala Lys Ala Leu Ala Ala Trp
    1315                1320                1325 aat ctg cat gag ttg acg cgg ggg gcg gat ctt tcg ggg ttc gtg gtg    4032
```

```
               Asn Leu His Glu Leu Thr Arg Gly Ala Asp Leu Ser Gly Phe Val Val
                   1330                1335                1340 ttc tcg tcg gct gcg gcg acg ttc ggg ccg gcg gga cag ggg agt tac        4080
Phe Ser Ser Ala Ala Ala Thr Phe Gly Pro Ala Gly Gln Gly Ser Tyr
1345                1350                1355                1360 gcg gcg gcg aac gcg tat gtg gag gca atc gtt cgg cac cgg cgt ggt        4128
Ala Ala Ala Asn Ala Tyr Val Glu Ala Ile Val Arg His Arg Arg Gly
                1365                1370                1375 gag ggc ctg ccg ggg ttg gcg gtg gcg tgg ggt ccg tgg gct ggt ggg        4176
Glu Gly Leu Pro Gly Leu Ala Val Ala Trp Gly Pro Trp Ala Gly Gly
            1380                1385                1390 ggg atg gcg gag ggg gcc gtg ggg cag atg cgg cgt cgg ggt ctg gcg        4224
Gly Met Ala Glu Gly Ala Val Gly Gln Met Arg Arg Arg Gly Leu Ala
        1395                1400                1405 gcg atg acg ccg gag acg gcg ctg gtg gca ctg ggc cag gcg ttg gac        4272
Ala Met Thr Pro Glu Thr Ala Leu Val Ala Leu Gly Gln Ala Leu Asp
    1410                1415                1420 cat gac gag acc tgt gtg acg gtc gcc gac atc gac tgg gac cga ttc        4320
His Asp Glu Thr Cys Val Thr Val Ala Asp Ile Asp Trp Asp Arg Phe
1425                1430                1435                1440 acc gcc aac tcc ctc ccc ggc tcc cga ctc tcg ccc ctc atc agc gac        4368
Thr Ala Asn Ser Leu Pro Gly Ser Arg Leu Ser Pro Leu Ile Ser Asp
                1445                1450                1455 atc ccc gaa gca cgc ctc gcc cgg gaa acc acc gga ctc gac acc gcc        4416
Ile Pro Glu Ala Arg Leu Ala Arg Glu Thr Thr Gly Leu Asp Thr Ala
            1460                1465                1470 acc gca tcc ccc gac tcg ttc tcc gca cgg ctc aag gcc atg gac acc        4464
Thr Ala Ser Pro Asp Ser Phe Ser Ala Arg Leu Lys Ala Met Asp Thr
        1475                1480                1485 gcc gag cag gaa cgt gcg ctt ctc gac ctg gtc cgt acg tac gcg gcg        4512
Ala Glu Gln Glu Arg Ala Leu Leu Asp Leu Val Arg Thr Tyr Ala Ala
    1490                1495                1500 acc gtg ctc gga cac agc acc ccc acc gcc gta cgc cct gag cga gcc        4560
Thr Val Leu Gly His Ser Thr Pro Thr Ala Val Arg Pro Glu Arg Ala
1505                1510                1515                1520 ttc cgc gac ctg ggc ttc gtc tcc gtg agc gcc gtc gaa ctg cgc aac        4608
Phe Arg Asp Leu Gly Phe Val Ser Val Ser Ala Val Glu Leu Arg Asn
                1525                1530                1535 cgc ctc aac gcc gtc acc ggg ctc ctc ctg ccc acc acg ctg atc ttc        4656
Arg Leu Asn Ala Val Thr Gly Leu Leu Leu Pro Thr Thr Leu Ile Phe
            1540                1545                1550 gac tac ccc act ccc tcc gcg ctg gcc gga tac ctc aag gaa cag ctg        4704
Asp Tyr Pro Thr Pro Ser Ala Leu Ala Gly Tyr Leu Lys Glu Gln Leu
        1555                1560                1565 gag gag ggc gcg ggc ggc cag cgt gac att gct cct ccg gtc ccg gcg        4752
Glu Glu Gly Ala Gly Gly Gln Arg Asp Ile Ala Pro Pro Val Pro Ala
    1570                1575                1580 tcg cgt gtc gac gtt gac gag ccg att gcg att gtg ggg atg gcg tgc        4800
Ser Arg Val Asp Val Asp Glu Pro Ile Ala Ile Val Gly Met Ala Cys
1585                1590                1595                1600 cgt ttt ccg ggg ggt gtg gag tcg gcg gag gac ttg tgg gaa ctg gtc        4848
Arg Phe Pro Gly Gly Val Glu Ser Ala Glu Asp Leu Trp Glu Leu Val
                1605                1610                1615 gcg tcg ggt cgg gat gcg gtg gga gag ttt ccg gtc gac cgg ggt tgg        4896
Ala Ser Gly Arg Asp Ala Val Gly Glu Phe Pro Val Asp Arg Gly Trp
            1620                1625                1630 gac gtg gag gct ttc tat gat ccg gag ccg ggg cgg gcg ggt tcg tcg        4944
Asp Val Glu Ala Phe Tyr Asp Pro Glu Pro Gly Arg Ala Gly Ser Ser
        1635                1640                1645
```

```
tat acg cgc cgg ggc ggt ttc ctg gag ggt gcg gcg gag ttc gat gcg      4992
Tyr Thr Arg Arg Gly Gly Phe Leu Glu Gly Ala Ala Glu Phe Asp Ala
    1650                1655                1660 ggg ttt ttc ggg atc agt ccg cgt gag gcg ttg gcg atg gat ccg cag      5040
Gly Phe Phe Gly Ile Ser Pro Arg Glu Ala Leu Ala Met Asp Pro Gln
1665                1670                1675                1680 cag cgg ttg atg ctg gag gtg tcc tgg gag gcg ttg gag cgg gcg ggc      5088
Gln Arg Leu Met Leu Glu Val Ser Trp Glu Ala Leu Glu Arg Ala Gly
            1685                1690                1695 atc gac ccc gcc acg ttg cgc ggg tcc acg acc ggt gtc ttc gcc ggc      5136
Ile Asp Pro Ala Thr Leu Arg Gly Ser Thr Thr Gly Val Phe Ala Gly
        1700                1705                1710 atg tgc agt cag gac tac gcc gac ctc gtg cgc cgg gcc acc gag gac      5184
Met Cys Ser Gln Asp Tyr Ala Asp Leu Val Arg Arg Ala Thr Glu Asp
    1715                1720                1725 ctc gag ggc tac gcc atg acg ggc ctg tcc agc agc gtc aca tcc gga      5232
Leu Glu Gly Tyr Ala Met Thr Gly Leu Ser Ser Ser Val Thr Ser Gly
1730                1735                1740 cgc gtc gcc tac acc ctg ggg ctc gag ggt ccg gcg gtg acg gtg gat      5280
Arg Val Ala Tyr Thr Leu Gly Leu Glu Gly Pro Ala Val Thr Val Asp
1745                1750                1755                1760 acg gcg tgt tcg tcg tcg ttg gtg gcg ctg cat ctg gcg tgt cag gcg      5328
Thr Ala Cys Ser Ser Ser Leu Val Ala Leu His Leu Ala Cys Gln Ala
            1765                1770                1775 ttg agg tcg ggg gag tgt tcg ctg gcg ttg gcg ggg ggt gtg acg gtg      5376
Leu Arg Ser Gly Glu Cys Ser Leu Ala Leu Ala Gly Gly Val Thr Val
        1780                1785                1790 atg tcg acg ccg ggt gcg ttt gtg gag ttc tcg cgg cag cgg ggt ctg      5424
Met Ser Thr Pro Gly Ala Phe Val Glu Phe Ser Arg Gln Arg Gly Leu
    1795                1800                1805 tcg ccg gac ggc cgg tgc aag gcg tac ggg tcg ggg gcc gat ggg gtc      5472
Ser Pro Asp Gly Arg Cys Lys Ala Tyr Gly Ser Gly Ala Asp Gly Val
1810                1815                1820 ggc tgg gcc gag ggt gtg ggt gtg ctg ttg gtg gag cgg ctg tcc gag      5520
Gly Trp Ala Glu Gly Val Gly Val Leu Leu Val Glu Arg Leu Ser Glu
1825                1830                1835                1840 gct gaa cgt cgt ggt cat cgg gtt ttg gcg gtg gtg cgg ggg agt gcg      5568
Ala Glu Arg Arg Gly His Arg Val Leu Ala Val Val Arg Gly Ser Ala
            1845                1850                1855 gtg aat cag gac ggt gcg tcg aat ggg ttg acg gcg ccg aat ggt ccg      5616
Val Asn Gln Asp Gly Ala Ser Asn Gly Leu Thr Ala Pro Asn Gly Pro
        1860                1865                1870 tcg cag cag cgg gtg att cgg cag gcg ttg gcg tgt gcg ggg ttg tcc      5664
Ser Gln Gln Arg Val Ile Arg Gln Ala Leu Ala Cys Ala Gly Leu Ser
    1875                1880                1885 gtg gcg gat gtg gat gtg gtg gag ggg cac ggg acg ggt acg acg ttg      5712
Val Ala Asp Val Asp Val Val Glu Gly His Gly Thr Gly Thr Thr Leu
1890                1895                1900 ggt gat ccg atc gag gcg cag gcg ttg ctc gcc act tat ggg cag ggt      5760
Gly Asp Pro Ile Glu Ala Gln Ala Leu Leu Ala Thr Tyr Gly Gln Gly
1905                1910                1915                1920 cgt tcg ggg gag cgg ccg gtg tgg ttg ggg tcg gtg aag tcg aac atc      5808
Arg Ser Gly Glu Arg Pro Val Trp Leu Gly Ser Val Lys Ser Asn Ile
            1925                1930                1935 ggg cat gcg cag gct gct gcg ggt gtg gcg ggt gtg atc aag atg gtg      5856
Gly His Ala Gln Ala Ala Ala Gly Val Ala Gly Val Ile Lys Met Val
        1940                1945                1950 atg gcg ttg cgg gcg ggg gtg ttg ccg cgg acg ttg cat gtg gat gag      5904
Met Ala Leu Arg Ala Gly Val Leu Pro Arg Thr Leu His Val Asp Glu
    1955                1960                1965
```

-continued

| | |
|---|---|
| ccg tcg tcg cag gtg gat tgg tcg agt ggg tcg gtt cgt gtg ttg gcg<br>Pro Ser Ser Gln Val Asp Trp Ser Ser Gly Ser Val Arg Val Leu Ala<br>    1970                    1975                    1980 | 5952 |
| gat gag gtg gag tgg ccg ggg gtg gag ggt cgg ctg cgg cgt gcg ggg<br>Asp Glu Val Glu Trp Pro Gly Val Glu Gly Arg Leu Arg Arg Ala Gly<br>1985                  1990                  1995                  2000 | 6000 |
| gtg tct gcg ttc ggg gtg agt ggg acg aat gcg cat gtg att ttg gag<br>Val Ser Ala Phe Gly Val Ser Gly Thr Asn Ala His Val Ile Leu Glu<br>              2005                  2010                  2015 | 6048 |
| gag gcg tcc ggg ggc gcg gat ggg ggt gcg ggc cgg ctg cag gag ttg<br>Glu Ala Ser Gly Gly Ala Asp Gly Gly Ala Gly Arg Leu Gln Glu Leu<br>        2020                  2025                  2030 | 6096 |
| ggt ccg ggg gtg gtg tcg ggt tcg ggg gtg gtg ccg tgg gtg gtg tcg<br>Gly Pro Gly Val Val Ser Gly Ser Gly Val Val Pro Trp Val Val Ser<br>              2035                  2040                  2045 | 6144 |
| gcg cgg tcg gag ttg gcg ttg cgg ggg cag gcg cgt cgg ttg cgt ggg<br>Ala Arg Ser Glu Leu Ala Leu Arg Gly Gln Ala Arg Arg Leu Arg Gly<br>    2050                    2055                  2060 | 6192 |
| gtt gtg gcg gtt ggt ggg ggt gcg gat ggt gtg ggg gtg agt ccg gct<br>Val Val Ala Val Gly Gly Gly Ala Asp Gly Val Gly Val Ser Pro Ala<br>2065                  2070                  2075                  2080 | 6240 |
| ggg gtc ggg cgg gct ttg gtg tcg gag cgg tcg gtg ttc gag cat cgt<br>Gly Val Gly Arg Ala Leu Val Ser Glu Arg Ser Val Phe Glu His Arg<br>              2085                  2090                  2095 | 6288 |
| gcg gtg gtc gtg gcc gag gac cgc gac gag ttc ctg cac gca ctc gac<br>Ala Val Val Val Ala Glu Asp Arg Asp Glu Phe Leu His Ala Leu Asp<br>        2100                  2105                  2110 | 6336 |
| gca ctg gcc gag ggg gca ccc acc gcg ggg gtg gta cag ggt gtg gcc<br>Ala Leu Ala Glu Gly Ala Pro Thr Ala Gly Val Val Gln Gly Val Ala<br>              2115                  2120                  2125 | 6384 |
| gga ccg gcg gcc gac gga aag atc gcc atg ctg ttc gga gga cag ggc<br>Gly Pro Ala Ala Asp Gly Lys Ile Ala Met Leu Phe Gly Gly Gln Gly<br>2130                  2135                  2140 | 6432 |
| acc cac tgg gaa ggc atg gcg cag gaa ctc ctc ggc tca ccg gtc<br>Thr His Trp Glu Gly Met Ala Gln Glu Leu Leu Gly Ser Ser Pro Val<br>2145                  2150                  2155                  2160 | 6480 |
| ttc gcc cag cag atg tcc gac tgc gcc caa gcc ctc gaa ccg tac ctg<br>Phe Ala Gln Gln Met Ser Asp Cys Ala Gln Ala Leu Glu Pro Tyr Leu<br>              2165                  2170                  2175 | 6528 |
| gac tgg tct ctc ctc gac gtc ctg cgc ggc gca ccg gac gca ccc cct<br>Asp Trp Ser Leu Leu Asp Val Leu Arg Gly Ala Pro Asp Ala Pro Pro<br>            2180                  2185                  2190 | 6576 |
| ctg caa cgc gtc gat gtc gtc cag ccc gtc ctc ttc gcg gtg atg gtc<br>Leu Gln Arg Val Asp Val Val Gln Pro Val Leu Phe Ala Val Met Val<br>        2195                  2200                  2205 | 6624 |
| tcg ctg gcg gcg ctc tgg cgc tcg tac ggt gta cac ccg gac gcg gtg<br>Ser Leu Ala Ala Leu Trp Arg Ser Tyr Gly Val His Pro Asp Ala Val<br>    2210                    2215                  2220 | 6672 |
| gcc ggg cac tcg cag ggc gag atc gca gcg gcc tac gtc gcc ggt gca<br>Ala Gly His Ser Gln Gly Glu Ile Ala Ala Ala Tyr Val Ala Gly Ala<br>2225                  2230                  2235                  2240 | 6720 |
| ctc tcc ctc gac gac gcc gcc cgg gtc acc gcc ctg cgc agc cag gcg<br>Leu Ser Leu Asp Asp Ala Ala Arg Val Thr Ala Leu Arg Ser Gln Ala<br>              2245                  2250                  2255 | 6768 |
| ctg gcc gca ctg gcc ggg cag ggg gcg atg gca tcg gtc ggt ctg ccg<br>Leu Ala Ala Leu Ala Gly Gln Gly Ala Met Ala Ser Val Gly Leu Pro<br>        2260                  2265                  2270 | 6816 |
| gtc gag aag ctg gag ccg cgt ctt gcg aca tgg ggc gac cgt ctg gtc<br>Val Glu Lys Leu Glu Pro Arg Leu Ala Thr Trp Gly Asp Arg Leu Val | 6864 |

-continued

| | | |
|---|---|---|
| atc gcc gcc gtg aac ggg gcg cgt tcg gcc gtg gtc tcc ggg gag ccg<br>Ile Ala Ala Val Asn Gly Ala Arg Ser Ala Val Val Ser Gly Glu Pro<br>2290                 2295               2300 | 6912 |
| gaa gcg gtc gac gcc ctg gtg gag gag ctg tca cac gaa gac gta ccg<br>Glu Ala Val Asp Ala Leu Val Glu Glu Leu Ser His Glu Asp Val Pro<br>2305             2310             2315             2320 | 6960 |
| gcc cgc agg ctc atg gtc gac tgg gcg tcg cac tcc ccg cag gtc gag<br>Ala Arg Arg Leu Met Val Asp Trp Ala Ser His Ser Pro Gln Val Glu<br>2325             2330             2335 | 7008 |
| gcg atc cag ggg cgg ctg ctc gaa ctc ctc gcc ccc atc cgc gcg agg<br>Ala Ile Gln Gly Arg Leu Leu Glu Leu Leu Ala Pro Ile Arg Ala Arg<br>2340             2345             2350 | 7056 |
| acc ggc gac gtg ccc ttc tac tcc acc gtc acc ggc gaa cgc atc gac<br>Thr Gly Asp Val Pro Phe Tyr Ser Thr Val Thr Gly Glu Arg Ile Asp<br>2355             2360             2365 | 7104 |
| ggc acc gaa ctc gac gcc gac tac tgg tac cgc aac ctg cgc cag gtc<br>Gly Thr Glu Leu Asp Ala Asp Tyr Trp Tyr Arg Asn Leu Arg Gln Val<br>2370             2375             2380 | 7152 |
| gtc cgc ttc cgg gac gcg aca cag gcg ctg gtc cgc gcc ggc cac acc<br>Val Arg Phe Arg Asp Ala Thr Gln Ala Leu Val Arg Ala Gly His Thr<br>2385             2390             2395             2400 | 7200 |
| gtc ttc atc gag gcg tgc ccg cat ccg gcc gtc gcg gtc ggt gtg cag<br>Val Phe Ile Glu Ala Cys Pro His Pro Ala Val Ala Val Gly Val Gln<br>2405             2410             2415 | 7248 |
| gaa acc ctg gac gag atg ggt gac ttg gac agc ctg gtc gtc gga tct<br>Glu Thr Leu Asp Glu Met Gly Asp Leu Asp Ser Leu Val Val Gly Ser<br>2420             2425             2430 | 7296 |
| ctg cgc cgg ggc gaa ggc ggc ttg cga cgc ttc ctg atg tcc gtg gcc<br>Leu Arg Arg Gly Glu Gly Gly Leu Arg Arg Phe Leu Met Ser Val Ala<br>2435             2440             2445 | 7344 |
| gag ttg ttc gtg ggt ggg gtg gcg gtt gag tgg tcc ggt gtg ttc ggg<br>Glu Leu Phe Val Gly Gly Val Ala Val Glu Trp Ser Gly Val Phe Gly<br>2450             2455             2460 | 7392 |
| agt gtt ggt cgc ggg gtc gct ggt ggt tgc ggg gtg gag ctg ccg acg<br>Ser Val Gly Arg Gly Val Ala Gly Gly Cys Gly Val Glu Leu Pro Thr<br>2465             2470             2475             2480 | 7440 |
| tat gcg ttc gag cga gag cgc ttt tgg ctg gat gtg gag ggg gcg ccg<br>Tyr Ala Phe Glu Arg Glu Arg Phe Trp Leu Asp Val Glu Gly Ala Pro<br>2485             2490             2495 | 7488 |
| cgg ggt tcc ggg gtc tct ggg cag tgg ggt ggt cag ttg tcg gag gcg<br>Arg Gly Ser Gly Val Ser Gly Gln Trp Gly Gly Gln Leu Ser Glu Ala<br>2500             2505             2510 | 7536 |
| gtg gac acc gtg cgc ggc ggc atg ctg cgc gac tgc ctc gcc gga ctc<br>Val Asp Thr Val Arg Gly Gly Met Leu Arg Asp Cys Leu Ala Gly Leu<br>2515             2520             2525 | 7584 |
| gac ccc gcc gca cag gcc gag acc gtg ctg gac ctg gtc ctt acc cat<br>Asp Pro Ala Ala Gln Ala Glu Thr Val Leu Asp Leu Val Leu Thr His<br>2530             2535             2540 | 7632 |
| gcc gcg gcc gtc ctt gga cac ggc acc gcc gat gcg gtg gtg ccc gag<br>Ala Ala Ala Val Leu Gly His Gly Thr Ala Asp Ala Val Val Pro Glu<br>2545             2550             2555             2560 | 7680 |
| cgc gcc ttc cgc gac ctc ggt ttc gac tcc ctc acc gcc gtc gaa cta<br>Arg Ala Phe Arg Asp Leu Gly Phe Asp Ser Leu Thr Ala Val Glu Leu<br>2565             2570             2575 | 7728 |
| cgc aac cgc ctc aac acc gcc acg ggc ctg cgc ttc ccg agg acc ctg<br>Arg Asn Arg Leu Asn Thr Ala Thr Gly Leu Arg Phe Pro Arg Thr Leu<br>2580             2585             2590 | 7776 |
| gtg ttc gac cat ccc cgc ccg gtg gca ctc gcg gca cac atc cac gag | 7824 |

```
Val Phe Asp His Pro Arg Pro Val Ala Leu Ala Ala His Ile His Glu
    2595                2600                2605 cag ctg agc ggc gga agc ccg acc acc ggc act gcc ctt gcc ctt gcc      7872
Gln Leu Ser Gly Gly Ser Pro Thr Thr Gly Thr Ala Leu Ala Leu Ala
       2610                2615                2620 ctt cgg gcc ccg gca ccg cgt gtg gat gtc gac gag ccg att gcc att      7920
Leu Arg Ala Pro Ala Pro Arg Val Asp Val Asp Glu Pro Ile Ala Ile
2625                2630                2635                2640 gtg ggg atg gcg tgc cgt ttt ccg ggg ggt gtg gag tcg gcg gag gat      7968
Val Gly Met Ala Cys Arg Phe Pro Gly Gly Val Glu Ser Ala Glu Asp
              2645                2650                2655 ttc tgg gag ttg atc gcg tcg ggt cgg gat gcg gtg ggg gag ttt ccg      8016
Phe Trp Glu Leu Ile Ala Ser Gly Arg Asp Ala Val Gly Glu Phe Pro
          2660                2665                2670 gtc gac cgg ggt tgg gac gtg gag gct ttc tat gat ccg gag ccg ggg      8064
Val Asp Arg Gly Trp Asp Val Glu Ala Phe Tyr Asp Pro Glu Pro Gly
      2675                2680                2685 cgg gcg ggt acg tcc tac acg cgg tgt ggt ggg ttt ttg cag ggt gcg      8112
Arg Ala Gly Thr Ser Tyr Thr Arg Cys Gly Gly Phe Leu Gln Gly Ala
  2690                2695                2700 gcg gag ttc gat gcg ggg ttt ttc ggg atc agt ccg cgt gag gcg ttg      8160
Ala Glu Phe Asp Ala Gly Phe Phe Gly Ile Ser Pro Arg Glu Ala Leu
2705                2710                2715                2720 gcg atg gat ccg cag cag cgg ttg atg ctg gag gtg tcc tgg gag gcg      8208
Ala Met Asp Pro Gln Gln Arg Leu Met Leu Glu Val Ser Trp Glu Ala
              2725                2730                2735 ttg gag cgg gcg ggc atc gac ccc gcc acg ctg cac ggg tcc acg acc      8256
Leu Glu Arg Ala Gly Ile Asp Pro Ala Thr Leu His Gly Ser Thr Thr
          2740                2745                2750 ggt gtc ttc gcc ggc gtc tcg cag cag gac tac gcc gag ctc ctg cgc      8304
Gly Val Phe Ala Gly Val Ser Gln Gln Asp Tyr Ala Glu Leu Leu Arg
      2755                2760                2765 cgc ggc acc cag gac cac gag ggg tac gcg ctc acc ggc gtc tcc aac      8352
Arg Gly Thr Gln Asp His Glu Gly Tyr Ala Leu Thr Gly Val Ser Asn
  2770                2775                2780 agc gtc gtc tcc ggg cgg ctt tcc tac acc ttc ggc ttc gag ggt ccg      8400
Ser Val Val Ser Gly Arg Leu Ser Tyr Thr Phe Gly Phe Glu Gly Pro
2785                2790                2795                2800 gcg gtg acg gtg gat acg gcg tgt tcg tcg tcg ttg gtg gcg ctg cat      8448
Ala Val Thr Val Asp Thr Ala Cys Ser Ser Ser Leu Val Ala Leu His
              2805                2810                2815 ctg gcg tgt cag gcg ttg agg tcg ggg gag tgt tcg ctg gcg ttg gcg      8496
Leu Ala Cys Gln Ala Leu Arg Ser Gly Glu Cys Ser Leu Ala Leu Ala
          2820                2825                2830 ggg ggt gtg acg gtg atg tcg acg ccg ggt gcg ttt gtg gag ttc tcg      8544
Gly Gly Val Thr Val Met Ser Thr Pro Gly Ala Phe Val Glu Phe Ser
      2835                2840                2845 cgg cag cgg ggt ctg tcg ccg gac ggc cgg tgc aag gcg tac ggg tcg      8592
Arg Gln Arg Gly Leu Ser Pro Asp Gly Arg Cys Lys Ala Tyr Gly Ser
  2850                2855                2860 ggg gcc gat ggg gtc ggc tgg gcc gag ggt gtg ggt gtg ctg ttg gtg      8640
Gly Ala Asp Gly Val Gly Trp Ala Glu Gly Val Gly Val Leu Leu Val
2865                2870                2875                2880 gag cgg ctg tcc gag gct gaa cgt cgt ggt cat cgg gtt ttg gcg gtg      8688
Glu Arg Leu Ser Glu Ala Glu Arg Arg Gly His Arg Val Leu Ala Val
              2885                2890                2895 gtg cgg ggg agt gcg gtg aat cag gac ggt gcg tcg aat ggg ttg acg      8736
Val Arg Gly Ser Ala Val Asn Gln Asp Gly Ala Ser Asn Gly Leu Thr
          2900                2905                2910
```

```
                                                         -continued gcg ccg aat ggt ccg tcg cag cag cgg gtg att cgg cag gcg ttg gcg        8784
Ala Pro Asn Gly Pro Ser Gln Gln Arg Val Ile Arg Gln Ala Leu Ala
            2915                2920                2925 tgt gcg ggg ttg tcc gtg gcg gat gtg gat gtg gtg gag ggg cac ggg        8832
Cys Ala Gly Leu Ser Val Ala Asp Val Asp Val Val Glu Gly His Gly
        2930                2935                2940 acg ggt acg acg ttg ggt gat ccg atc gag gcg cag gcg ttg ctc gcc        8880
Thr Gly Thr Thr Leu Gly Asp Pro Ile Glu Ala Gln Ala Leu Leu Ala
2945                2950                2955                2960 acg tac ggg cag ggt cgt tcg ggg gag cgg ccg gtg tgg ttg ggg tcg        8928
Thr Tyr Gly Gln Gly Arg Ser Gly Glu Arg Pro Val Trp Leu Gly Ser
            2965                2970                2975 gtg aag tcg aac atc ggg cat gcg cag gct gcc gcg ggt gtg gcc ggt        8976
Val Lys Ser Asn Ile Gly His Ala Gln Ala Ala Ala Gly Val Ala Gly
        2980                2985                2990 gtg atc aag atg gtc atg gcc ctg aac cac gaa ctg ttg ccg acc agc        9024
Val Ile Lys Met Val Met Ala Leu Asn His Glu Leu Leu Pro Thr Ser
    2995                3000                3005 ctg cac atc gac gaa ccc tcc ccc cac atc gac tgg tcg agc ggc ggc        9072
Leu His Ile Asp Glu Pro Ser Pro His Ile Asp Trp Ser Ser Gly Gly
    3010                3015                3020 gtc cgg ctt ctc acc gag ccc gta ccg tgg cag cag aac ggc cgg ccc        9120
Val Arg Leu Leu Thr Glu Pro Val Pro Trp Gln Gln Asn Gly Arg Pro
3025                3030                3035                3040 agg cgc gcg ggc gtc tcc gcg ttc gga gtc agc ggg acc aac gcc cac        9168
Arg Arg Ala Gly Val Ser Ala Phe Gly Val Ser Gly Thr Asn Ala His
            3045                3050                3055 gtc atc atc gag cag gcg ccg gtc gag gcg cac gtc atc agt gag ccg        9216
Val Ile Ile Glu Gln Ala Pro Val Glu Ala His Val Ile Ser Glu Pro
        3060                3065                3070 gta ccg gct gag gcg cac gtc atc gtc gag cag gcg ccg gtc gag gcg        9264
Val Pro Ala Glu Ala His Val Ile Val Glu Gln Ala Pro Val Glu Ala
3075                3080                3085 ccc cac gtg gtc gac gcc acc gga ccg gcg gac ctc acc gag ccg caa        9312
Pro His Val Val Asp Ala Thr Gly Pro Ala Asp Leu Thr Glu Pro Gln
    3090                3095                3100 gag gag gcg gct gaa ccg gag tgc gtc gct gac gcc gtg acc gag atg        9360
Glu Glu Ala Ala Glu Pro Glu Cys Val Ala Asp Ala Val Thr Glu Met
3105                3110                3115                3120 tcg gct gaa ccg gag tgc gtc gcc gac gcc atg tcc gag atg tcg gct        9408
Ser Ala Glu Pro Glu Cys Val Ala Asp Ala Met Ser Glu Met Ser Ala
            3125                3130                3135 gag tgc gtc gcc gag gcc gtg tcc gac aag tcg gct gaa ccg gag tgc        9456
Glu Cys Val Ala Glu Ala Val Ser Asp Lys Ser Ala Glu Pro Glu Cys
        3140                3145                3150 gtc gcc gac gcc atg tcc gac aag ccg gcc ctc ctg ccc atc ccg tgg        9504
Val Ala Asp Ala Met Ser Asp Lys Pro Ala Leu Leu Pro Ile Pro Trp
    3155                3160                3165 ctg ctc tcc gcc aag tcc gag cga gcg ctg cgg ggc cag gcg cga cgg        9552
Leu Leu Ser Ala Lys Ser Glu Arg Ala Leu Arg Gly Gln Ala Arg Arg
    3170                3175                3180 ttg cgg cag ttc gct gcc agg gca tcc gat gcc cgg ccg gcc gac gtg        9600
Leu Arg Gln Phe Ala Ala Arg Ala Ser Asp Ala Arg Pro Ala Asp Val
3185                3190                3195                3200 gcg cac gcc ctg gcg gca cag cgg tcc gtg ttc gat cac cgg gcc gtc        9648
Ala His Ala Leu Ala Ala Gln Arg Ser Val Phe Asp His Arg Ala Val
            3205                3210                3215 gtc gtg gcc gag gac cgc gac ggc ttc ctt cag gcc ctc gac gcg ctg        9696
Val Val Ala Glu Asp Arg Asp Gly Phe Leu Gln Ala Leu Asp Ala Leu
        3220                3225                3230
```

```
                                                                -continued gcc gag ggc cgg tcg gcg gac ggc ctg atc gaa ggg tcg gtc ggc ccg     9744
Ala Glu Gly Arg Ser Ala Asp Gly Leu Ile Glu Gly Ser Val Gly Pro
        3235                3240                3245 cgt ggc ggc cac tca ggc cgc cgg cgc gga aag acc gcc atg ctg ttc     9792
Arg Gly Gly His Ser Gly Arg Arg Arg Gly Lys Thr Ala Met Leu Phe
        3250                3255                3260 gcc gga cag ggc acg caa cgc gtg gga atg ggc cgt cag ctg tat gcg     9840
Ala Gly Gln Gly Thr Gln Arg Val Gly Met Gly Arg Gln Leu Tyr Ala
3265                3270                3275                3280 gct cac ccg gcc tac gcg gac gcg ctg gac cag gta ctg gcg gaa ctg     9888
Ala His Pro Ala Tyr Ala Asp Ala Leu Asp Gln Val Leu Ala Glu Leu
            3285                3290                3295 gac ggt cac ctg gac cag ccc ctg cgc ccg ctg atc cac gcc agt gcg     9936
Asp Gly His Leu Asp Gln Pro Leu Arg Pro Leu Ile His Ala Ser Ala
        3300                3305                3310 gat ctt gcg gat gtc gcg gat gcc gcg gat gtt ctg gac cgt acg cgg     9984
Asp Leu Ala Asp Val Ala Asp Ala Ala Asp Val Leu Asp Arg Thr Arg
        3315                3320                3325 tac gcc cag ccg gcg ctg ttc gcc gtc cag gtc gcg ctc ttc cgg cac    10032
Tyr Ala Gln Pro Ala Leu Phe Ala Val Gln Val Ala Leu Phe Arg His
    3330                3335                3340 ctg gaa cgt ctc ggc gtg cgc gcg gac ttc gtg gcc ggg cac tcg atc    10080
Leu Glu Arg Leu Gly Val Arg Ala Asp Phe Val Ala Gly His Ser Ile
3345                3350                3355                3360 ggc gag ctc gcg gcc gcc cac gtc gcc ggg gtg ctt ccc ctg gca gca    10128
Gly Glu Leu Ala Ala Ala His Val Ala Gly Val Leu Pro Leu Ala Ala
            3365                3370                3375 gcc tgc cgc ctg gtg gcg gcc cgc ggg cgc ctg atg gag cag ctc gca    10176
Ala Cys Arg Leu Val Ala Ala Arg Gly Arg Leu Met Glu Gln Leu Ala
        3380                3385                3390 cca ggc ggc gcc atg gtc gcc gta cgg gcg agc gaa gcc gag gcg cga    10224
Pro Gly Gly Ala Met Val Ala Val Arg Ala Ser Glu Ala Glu Ala Arg
        3395                3400                3405 cag gcg ctc gac ggc cgg gaa gcc cgg gtg tcg gtc gcg gcc gtg aac    10272
Gln Ala Leu Asp Gly Arg Glu Ala Arg Val Ser Val Ala Ala Val Asn
3410                3415                3420 gga ccc gcc tcg gtg gtg ttc tcc ggc gcc gag gac gag gtg ggg aac    10320
Gly Pro Ala Ser Val Val Phe Ser Gly Ala Glu Asp Glu Val Gly Asn
        3425                3430                3435                3440 atg gcg gac tgg ttc gcc gag cgc ggg cgg aga gtc aag cgc ctg cga    10368
Met Ala Asp Trp Phe Ala Glu Arg Gly Arg Arg Val Lys Arg Leu Arg
                3445                3450                3455 acc ggg cat gcc ttc cac tca ccg ctg atg gac ccg atg ctg gag gag    10416
Thr Gly His Ala Phe His Ser Pro Leu Met Asp Pro Met Leu Glu Glu
            3460                3465                3470 ttc cag cag gtc gcg gcc tcg ctg acc tac agc gaa cca gcc att ccc    10464
Phe Gln Gln Val Ala Ala Ser Leu Thr Tyr Ser Glu Pro Ala Ile Pro
        3475                3480                3485 atg gtg tcg acg ctc acc ggc gac atc gtg gcg gcg gga gaa ctg agc    10512
Met Val Ser Thr Leu Thr Gly Asp Ile Val Ala Ala Gly Glu Leu Ser
    3490                3495                3500 gac ccc gag tac tgg gtc cgg cag gta cgg cgg acc gtg cgc ttc ggc    10560
Asp Pro Glu Tyr Trp Val Arg Gln Val Arg Arg Thr Val Arg Phe Gly
3505                3510                3515                3520 gac gcg atc agc cgc ctg cac acc gac gga gtc cgc acc ttc atg gaa    10608
Asp Ala Ile Ser Arg Leu His Thr Asp Gly Val Arg Thr Phe Met Glu
            3525                3530                3535 ctg ggc cca gac ggg acc ctg tcg gca ctg gcc gag gaa tgc cta gag    10656
Leu Gly Pro Asp Gly Thr Leu Ser Ala Leu Ala Glu Glu Cys Leu Glu
```

```
                                    -continued
          3540              3545              3550
gcc acc gcc gac agc cac ccc gcc gac gac acc ggc acc ccg caa    10704
Ala Thr Ala Asp Ser His Pro Ala Asp Asp Thr Gly Thr Pro Gln
         3555              3560              3565 gag aac ctg ctc atc ccg ctc cta cgg ccg gac agc ccg gaa ccc ggc 10752
Glu Asn Leu Leu Ile Pro Leu Leu Arg Pro Asp Ser Pro Glu Pro Gly
    3570              3575              3580 acc ctg ctc acc ggc ttg gcc cgg ctg cat acg cac gga gcg gcg gcg 10800
Thr Leu Leu Thr Gly Leu Ala Arg Leu His Thr His Gly Ala Ala Ala
3585              3590              3595              3600 gtc aac tgg ccc gcc gcc ctg ccc gaa cgc gat cga gcc cgc cac ctc 10848
Val Asn Trp Pro Ala Ala Leu Pro Glu Arg Asp Arg Ala Arg His Leu
         3605              3610              3615 gac ctg ccg acc tac gcc ttc gat cac cac cgc tac tgg gtc gac acc 10896
Asp Leu Pro Thr Tyr Ala Phe Asp His His Arg Tyr Trp Val Asp Thr
              3620              3625              3630 tcg gcc ggc cac ccg ggg gac ctg tcg gca gcg ggc ctc ggc acc gcc 10944
Ser Ala Gly His Pro Gly Asp Leu Ser Ala Ala Gly Leu Gly Thr Ala
    3635              3640              3645 ggg cat ccc ctg ctc ggt tcc gcg gtg gca ctg gcc gag tcg cag gaa 10992
Gly His Pro Leu Leu Gly Ser Ala Val Ala Leu Ala Glu Ser Gln Glu
         3650              3655              3660 ctc ctc ttc acc ggc cgt ctc tcc ctg cgc aca cac ccg tgg ctg gcc 11040
Leu Leu Phe Thr Gly Arg Leu Ser Leu Arg Thr His Pro Trp Leu Ala
3665              3670              3675              3680 gac cac gcc atc ttc ggt acc gtc ctg ctg ccc ggc acg gcc atc ctg 11088
Asp His Ala Ile Phe Gly Thr Val Leu Leu Pro Gly Thr Ala Ile Leu
              3685              3690              3695 gaa ctg gcc gtg cgc gca ggc gac gag gtc gac tgc ggc acc gtc gag 11136
Glu Leu Ala Val Arg Ala Gly Asp Glu Val Asp Cys Gly Thr Val Glu
    3700              3705              3710 gaa ctc acc ctg cgg aca ccg ctc gtc ctt ccc gaa cag ggc tcg gtg 11184
Glu Leu Thr Leu Arg Thr Pro Leu Val Leu Pro Glu Gln Gly Ser Val
         3715              3720              3725 atc ctg caa ctc tcc gtc ggg gca ccc cag ggc ccc cag acg ccc gag 11232
Ile Leu Gln Leu Ser Val Gly Ala Pro Gln Gly Pro Gln Thr Pro Glu
              3730              3735              3740 gag ccc gaa cgg cgc acc ttc gcc ctg tac gcc cgc gaa gac gac gga 11280
Glu Pro Glu Arg Arg Thr Phe Ala Leu Tyr Ala Arg Glu Asp Asp Gly
3745              3750              3755              3760 ctg tcg tcc tcg tcc gcg gcg gcg acc ggc acc gag tgg acc tgc cac 11328
Leu Ser Ser Ser Ser Ala Ala Ala Thr Gly Thr Glu Trp Thr Cys His
         3765              3770              3775 gcc acc ggc gtc ctg acc ggc acc gcc cgg ccc gcg gag gag cac aca 11376
Ala Thr Gly Val Leu Thr Gly Thr Ala Arg Pro Ala Glu Glu His Thr
    3780              3785              3790 cag gaa ccg tgg ccg ccc gcc gac gca gca ccg gtg gac ctg gac ggc 11424
Gln Glu Pro Trp Pro Pro Ala Asp Ala Ala Pro Val Asp Leu Asp Gly
         3795              3800              3805 tgg tac gag cag ctg gcc ggc gcc ggc ctg gga tac ggg ccg gtg ttc 11472
Trp Tyr Glu Gln Leu Ala Gly Ala Gly Leu Gly Tyr Gly Pro Val Phe
              3810              3815              3820 cag ggg ctg cgc gag gtc tgg cgg cgc ggg gac gag gtg ttc gcc gtc 11520
Gln Gly Leu Arg Glu Val Trp Arg Arg Gly Asp Glu Val Phe Ala Val
3825              3830              3835              3840 gtc acc ctg ccc gag agc acg gag gga cag gcg gcc gac gcc gcc cgg 11568
Val Thr Leu Pro Glu Ser Thr Glu Gly Gln Ala Ala Asp Ala Ala Arg
         3845              3850              3855 tac gcc ctg cac ccg gcc ctg ctg gac gcg gca ctg cac ccg gtc gtt 11616
```

-continued

```
Tyr Ala Leu His Pro Ala Leu Leu Asp Ala Ala Leu His Pro Val Val
        3860             3865             3870 ctg cgc cac gag ggc gat gcc gcc gcc gac gga cac ggc tgg ctg ccg      11664
Leu Arg His Glu Gly Asp Ala Ala Ala Asp Gly His Gly Trp Leu Pro
    3875             3880             3885 ttc tcc tgg acc ggc gtc acg gtc gcc gcc tcc ggc gcc tcc acc ctg      11712
Phe Ser Trp Thr Gly Val Thr Val Ala Ala Ser Gly Ala Ser Thr Leu
        3890             3895             3900 cac gtc cgt ctc acc gtc cgc acg gac gag gac gcg gtc gga ctg ctg      11760
His Val Arg Leu Thr Val Arg Thr Asp Glu Asp Ala Val Gly Leu Leu
3905             3910             3915             3920 gcc acc gac gca tcg gga cgc atc gtc atc tcc gcg ggg tcc ctc gcc      11808
Ala Thr Asp Ala Ser Gly Arg Ile Va-
l Ile Ser Ala Gly Ser Leu Ala                    3925         3930         3935 ttc cgg ccc gtc tcc gcc gag cag ctc cag gcc gcg cgc acc ggc tac      11856
Phe Arg Pro Val Ser Ala Glu Gln Leu Gln Ala Ala Arg Thr Gly Tyr
        3940             3945             3950 cac gac cac ctc ttc cgc atc gaa tgg cgg ccg ctg cac ctc ccc acc      11904
His Asp His Leu Phe Arg Ile Glu Trp Arg Pro Leu His Leu Pro Thr
        3955             3960             3965 aca ccg gca cgg aca gcc gac tgg gcc cta atc ggc ccc ggt gcc cgg      11952
Thr Pro Ala Arg Thr Ala Asp Trp Ala Leu Ile Gly Pro Gly Ala Arg
    3970             3975             3980 cgg acg gcc gcc gtc ctg gag cgc aac ggc gcc tcc tgg cag gcc tac      12000
Arg Thr Ala Ala Val Leu Glu Arg Asn Gly Ala Ser Trp Gln Ala Tyr
3985             3990             3995             4000 ccg gac ccg gcg gct ctc gca gaa gcc ctg gcg gcc ggc gcc ccg gca      12048
Pro Asp Pro Ala Ala Leu Ala Glu Ala Leu Ala Ala Gly Ala Pro Ala
        4005             4010             4015 ccg ggc atg gtc gtc atc tcg tgc gag ccg gac ggc gca tcc gcc ccc      12096
Pro Gly Met Val Val Ile Ser Cys Glu Pro Asp Gly Ala Ser Ala Pro
        4020             4025             4030 acc gat tcc gcc ctc acc gat tcc gcc ctc acc gat tcc gcc ccg gcc      12144
Thr Asp Ser Ala Leu Thr Asp Ser Ala Leu Thr Asp Ser Ala Pro Ala
        4035             4040             4045 ggc tcg gcc ccg gcc gac tcc acc gcc ctc gcc gac gcc acc cgg caa      12192
Gly Ser Ala Pro Ala Asp Ser Thr Ala Leu Ala Asp Ala Thr Arg Gln
    4050             4055             4060 gcc acc acc cgc gtc ctc gcc ctg ctc cag gaa tgg gtc gcc gac gaa      12240
Ala Thr Thr Arg Val Leu Ala Leu Leu Gln Glu Trp Val Ala Asp Glu
4065             4070             4075             4080 cgg ctc gcg gcc tgc cgc ctg gcc ctc ctc acg cac ggc tcg gtc acc      12288
Arg Leu Ala Ala Cys Arg Leu Ala Leu Leu Thr His Gly Ser Val Thr
        4085             4090             4095 gcg acc ccc gac gag ccc gtg tcc gac ctc gca cac gcc gcc gtc tgg      12336
Ala Thr Pro Asp Glu Pro Val Ser Asp Leu Ala His Ala Ala Val Trp
        4100             4105             4110 gga ctg gtc cgc tcc gtg cag acc gag aac ccc gac cgg ttc ctg ctg      12384
Gly Leu Val Arg Ser Val Gln Thr Glu Asn Pro Asp Arg Phe Leu Leu
    4115             4120             4125 gcc gac acc gac gac acc gac gcc tcc cgc aac gcc ctt ccc ctg ctg      12432
Ala Asp Thr Asp Asp Thr Asp Ala Ser Arg Asn Ala Leu Pro Leu Leu
    4130             4135             4140 gcc ggg gaa ccg cag atc gcc ctg cga aat ggt gcc gtc cgc atc ccg      12480
Ala Gly Glu Pro Gln Ile Ala Leu Arg Asn Gly Ala Val Arg Ile Pro
4145             4150             4155             4160 cgg atg aca cga gtg ccc gtc cgg cag cca cag ccg agc acc acc gac      12528
Arg Met Thr Arg Val Pro Val Arg Gln Pro Gln Pro Ser Thr Thr Asp
        4165             4170             4175
```

```
gcc gac tgg gac ccg gag gcc acg gtc ctc atc acg ggc ggt acc ggc      12576
Ala Asp Trp Asp Pro Glu Ala Thr Val Leu Ile Thr Gly Gly Thr Gly
        4180              4185              4190 gtc ctc ggc cgg ctc gtc gcc cgt cat ctc gcc acg gcc cac ggg gta      12624
Val Leu Gly Arg Leu Val Ala Arg His Leu Ala Thr Ala His Gly Val
    4195              4200              4205 cgg cac ctg ctg ctg gcc acc cgc cgc ggc acg gcc gcg gac ggc gcc      12672
Arg His Leu Leu Leu Ala Thr Arg Arg Gly Thr Ala Ala Asp Gly Ala
4210              4215              4220 gcc gac ctg gtc gcc gaa ctc gcc ggc ctc ggc gcc gag gcc acg gtc      12720
Ala Asp Leu Val Ala Glu Leu Ala Gly Leu Gly Ala Glu Ala Thr Val
4225              4230              4235              4240 gcg gcc tgc gac atc ggg gac cgg gcg gcc gtc gcc gcg ctc ctc gac      12768
Ala Ala Cys Asp Ile Gly Asp Arg Ala Ala Val Ala Ala Leu Leu Asp
        4245              4250              4255 caa gtg ccc gcg cag cac ccc ctg aaa gcc gtg atc cac acg gcc ggt      12816
Gln Val Pro Ala Gln His Pro Leu Lys Ala Val Ile His Thr Ala Gly
        4260              4265              4270 gtg gtc gac gac ggc atc ctc acc tcg ctc act ccg gag cgc atg gag      12864
Val Val Asp Asp Gly Ile Leu Thr Ser Leu Thr Pro Glu Arg Met Glu
    4275              4280              4285 gcc gtc ctg cac gcg aag gcg ttc ggc gcc gcg cac ctg cac gac ctg      12912
Ala Val Leu His Ala Lys Ala Phe Gly Ala Ala His Leu His Asp Leu
    4290              4295              4300 acc cgc gac gcc ggc ctc acc acc ttc acc gtc ttc tcc tcg gcc gcc      12960
Thr Arg Asp Ala Gly Leu Thr Thr Phe Thr Val Phe Ser Ser Ala Ala
4305              4310              4315              4320 gcc tcc ttc ggc agt ccc gga cag ggc aac tac acc gcg gcg aac gcc      13008
Ala Ser Phe Gly Ser Pro Gly Gln Gly Asn Tyr Thr Ala Ala Asn Ala
        4325              4330              4335 ttt ctg gac gcc ctg atg cag cac cgc cac acc cag gca ctg ccg ggc      13056
Phe Leu Asp Ala Leu Met Gln His Arg His Thr Gln Ala Leu Pro Gly
        4340              4345              4350 cgg tcg ctc gcc tgg ggc ctt tgg ggc gag gcc gac ggc atg acc cgc      13104
Arg Ser Leu Ala Trp Gly Leu Trp Gly Glu Ala Asp Gly Met Thr Arg
        4355              4360              4365 aac ctc gcc ggc acc gac ttc gcg cgc atg gcc cgc ggc ggc ctg ctc      13152
Asn Leu Ala Gly Thr Asp Phe Ala Arg Met Ala Arg Gly Gly Leu Leu
    4370              4375              4380 ccc ctg tcc aac gca cag gga ctc gcg ctc ctc gac aca gcg gat cgc      13200
Pro Leu Ser Asn Ala Gln Gly Leu Ala Leu Leu Asp Thr Ala Asp Arg
4385              4390              4395              4400 ctc ggc cct ttc ggt gac ggg ctg ctc ctc gcc acc cgg ctc gac gcg      13248
Leu Gly Pro Phe Gly Asp Gly Leu Leu Leu Ala Thr Arg Leu Asp Ala
        4405              4410              4415 gcc acc ctc cac gca cag gcc acg gcc ggc gcc ctg ccg cgc atc ctg      13296
Ala Thr Leu His Ala Gln Ala Thr Ala Gly Ala Leu Pro Arg Ile Leu
        4420              4425              4430 cac ggg ctg atc cgc atc ccg gcc cgg cgg tcc gcc gac cac ggc atc      13344
His Gly Leu Ile Arg Ile Pro Ala Arg Arg Ser Ala Asp His Gly Ile
        4435              4440              4445 gcg acc gac acc ccc gcc acg ctg cgc gag cgc ctg gcc gga ctc acc      13392
Ala Thr Asp Thr Pro Ala Thr Leu Arg Glu Arg Leu Ala Gly Leu Thr
    4450              4455              4460 atc ccc gcg cag cgc acc ggt ctc ctc ctg gaa ctc gta cgg acc cat      13440
Ile Pro Ala Gln Arg Thr Gly Leu Leu Leu Glu Leu Val Arg Thr His
4465              4470              4475              4480 gcc gcc gcc gtc ctc ggc cac ccc acc agc gcc gtc aca gcc gcg gac      13488
Ala Ala Ala Val Leu Gly His Pro Thr Ser Ala Val Thr Ala Ala Asp
        4485              4490              4495
```

-continued

| | |
|---|---|
| ggc gca ctc ccg gac gat ctg gtc ccg gcc gac acc gag ttc cgc gac<br>Gly Ala Leu Pro Asp Asp Leu Val Pro Ala Asp Thr Glu Phe Arg Asp<br>        4500                        4505                        4510 | 13536 |
| ctc ggc ttc gac tcg ctg acc gcc gtc gaa ctc cgc aac cgg atc aac<br>Leu Gly Phe Asp Ser Leu Thr Ala Val Glu Leu Arg Asn Arg Ile Asn<br>        4515                        4520                        4525 | 13584 |
| gcc gtc acc ggc ctg cgc ctc ccg gca acg ctc atc ttc gac cag ccc<br>Ala Val Thr Gly Leu Arg Leu Pro Ala Thr Leu Ile Phe Asp Gln Pro<br>        4530                        4535                        4540 | 13632 |
| agc ccc gcg gca ctc gcc gat cac ctc gcg acc cgc ctg acg gcc gag<br>Ser Pro Ala Ala Leu Ala Asp His Leu Ala Thr Arg Leu Thr Ala Glu<br>4545                      4550                        4555                        4560 | 13680 |
| gcg ggc acg ccg gac gag ccg gcc cct gcc gcc gcg gca gcc ggg gcc<br>Ala Gly Thr Pro Asp Glu Pro Ala Pro Ala Ala Ala Ala Ala Gly Ala<br>        4565                        4570                        4575 | 13728 |
| ggg agc gca ggg agt gcc gag acc gga cag cag cgc agt acg ggg agc<br>Gly Ser Ala Gly Ser Ala Glu Thr Gly Gln Gln Arg Ser Thr Gly Ser<br>        4580                        4585                        4590 | 13776 |
| gag aag cag cag acc agg ggc ggc acc tcc acc gaa acc gtc gaa tcc<br>Glu Lys Gln Gln Thr Arg Gly Gly Thr Ser Thr Glu Thr Val Glu Ser<br>        4595                        4600                        4605 | 13824 |
| ctg ttc tgg atc gga cac gac acc cgc cgc atc gag gag tcc atg gcc<br>Leu Phe Trp Ile Gly His Asp Thr Arg Arg Ile Glu Glu Ser Met Ala<br>        4610                        4615                        4620 | 13872 |
| ctg ctc tcg gcg gcc tcc ttc ttc cgg ccc gcc ttc acg gac ccc tcg<br>Leu Leu Ser Ala Ala Ser Phe Phe Arg Pro Ala Phe Thr Asp Pro Ser<br>4625                      4630                        4635                        4640 | 13920 |
| gac atc ccg gag ccg acg ttc gtc cgg ctc gcc cag ggt gaa gcg cgc<br>Asp Ile Pro Glu Pro Thr Phe Val Arg Leu Ala Gln Gly Glu Ala Arg<br>        4645                        4650                        4655 | 13968 |
| gcc caa ggt gaa gca ctc gcc cgg ggc gaa aca cgg ccc gcc ctc atc<br>Ala Gln Gly Glu Ala Leu Ala Arg Gly Glu Thr Arg Pro Ala Leu Ile<br>        4660                        4665                        4670 | 14016 |
| tgc ctg ccc acc gtc gcc gcc gtg tcg agc gtg tac cag tac tca cgt<br>Cys Leu Pro Thr Val Ala Ala Val Ser Ser Val Tyr Gln Tyr Ser Arg<br>        4675                        4680                        4685 | 14064 |
| ttc gcg gcg gga ctg aac gga cac cga gac gtc tgg tac gtt cct gcg<br>Phe Ala Ala Gly Leu Asn Gly His Arg Asp Val Trp Tyr Val Pro Ala<br>        4690                        4695                        4700 | 14112 |
| cca ggg ttc ctg gag ggc gaa ccc ctg ccg tcc gga atc ggc gcg gtg<br>Pro Gly Phe Leu Glu Gly Glu Pro Leu Pro Ser Gly Ile Gly Ala Val<br>4705                      4710                        4715                        4720 | 14160 |
| acc cgc atg ttc gcc gac gcg atc gtc cgg ttc acc gac ggc gcg cct<br>Thr Arg Met Phe Ala Asp Ala Ile Val Arg Phe Thr Asp Gly Ala Pro<br>        4725                        4730                        4735 | 14208 |
| ttt gcg ctc gcc ggg cat tcc gcg ggc gga tgg ttc gtc tac gcg gtg<br>Phe Ala Leu Ala Gly His Ser Ala Gly Gly Trp Phe Val Tyr Ala Val<br>        4740                        4745                        4750 | 14256 |
| acg agt cat ctg gag cgt cta ggc gtc cgt ccg gaa gcg gtg gtg acc<br>Thr Ser His Leu Glu Arg Leu Gly Val Arg Pro Glu Ala Val Val Thr<br>        4755                        4760                        4765 | 14304 |
| atg gac gcc tat ctc ccg gac gac ggc atc gca cct gtc gcg tcc gcg<br>Met Asp Ala Tyr Leu Pro Asp Asp Gly Ile Ala Pro Val Ala Ser Ala<br>        4770                        4775                        4780 | 14352 |
| ctg aca agt gaa atc ttc gac cgc gtc acg cag ttt gtg gac gtg gac<br>Leu Thr Ser Glu Ile Phe Asp Arg Val Thr Gln Phe Val Asp Val Asp<br>4785                      4790                        4795                        4800 | 14400 |
| tac aca cgc ctg gtc gcc atg ggc gga tac ttc cgc atc ttc tcc ggc<br>Tyr Thr Arg Leu Val Ala Met Gly Gly Tyr Phe Arg Ile Phe Ser Gly | 14448 |

-continued

| | |
|---|---|
| tgg agt cct ccg gac atc acc aca ccc gcc ctc ttc ctg cgc ggc cgg<br>Trp Ser Pro Pro Asp Ile Thr Thr Pro Ala Leu Phe Leu Arg Gly Arg<br>            4820                        4825                        4830 | 14496 |
| gac gga gaa cag atg ccg ccg ccg tgg gga gtt ccg cac acc gtt ctg<br>Asp Gly Glu Gln Met Pro Pro Pro Trp Gly Val Pro His Thr Val Leu<br>4835                        4840                        4845 | 14544 |
| gac atc cag ggg aat cac ttc acg atg ctg gaa cag ttt gcg gat tcg<br>Asp Ile Gln Gly Asn His Phe Thr Met Leu Glu Gln Phe Ala Asp Ser<br>            4850                        4855                        4860 | 14592 |
| act gct cgg cat gtc gac gaa tgg ctg aca gaa atc gca tca gtg cgg<br>Thr Ala Arg His Val Asp Glu Trp Leu Thr Glu Ile Ala Ser Val Arg<br>4865                        4870                        4875                        4880 | 14640 |
| cgc tgatcgcgcc tctgatcgcg gtcctgatcg cggccctgat cggcgggtcg<br>Arg | 14693 |
| ggcacagccc ggtcggccgg tcggccagtc ggccagtcgg tggtatccgg tcggctccgg | 14753 |
| catcgatcag tgctttcccc cttacggcca tacgggcctt tctgagactt cttgaatttg | 14813 |
| ggagacagtg atg gac acg tcc agc gaa aag ctc gtc gac gcg ctt agg<br>             Met Asp Thr Ser Ser Glu Lys Leu Val Asp Ala Leu Arg<br>                       4885                        4890 | 14862 |
| gcg tct ctg aag gcg aac cag acc ctg cgg gca cgt aat gag caa ctg<br>Ala Ser Leu Lys Ala Asn Gln Thr Leu Arg Ala Arg Asn Glu Gln Leu<br>4895                        4900                        4905                        4910 | 14910 |
| gca gcc gcc atg gag gcg tcc agc gag ccg att gcg att gtg ggg atg<br>Ala Ala Ala Met Glu Ala Ser Ser Glu Pro Ile Ala Ile Val Gly Met<br>            4915                        4920                        4925 | 14958 |
| gcg tgt cgt ttt ccg ggt ggg gtg tgt tcg ccg gag gag ttg tgg gag<br>Ala Cys Arg Phe Pro Gly Gly Val Cys Ser Pro Glu Glu Leu Trp Glu<br>                 4930                        4935                        4940 | 15006 |
| ctg gtt gcg tcg ggt ggg gat gcg att ggt gaa ttt ccg gcc ggt cgg<br>Leu Val Ala Ser Gly Gly Asp Ala Ile Gly Glu Phe Pro Ala Gly Arg<br>            4945                        4950                        4955 | 15054 |
| ggg tgg gat ctg gag ggg ttg ttt gat tcg gac cct gac cgg tcg ggg<br>Gly Trp Asp Leu Glu Gly Leu Phe Asp Ser Asp Pro Asp Arg Ser Gly<br>            4960                        4965                        4970 | 15102 |
| acg tcg tac gcg cgg tat ggc ggg ttt ttg tat gag gcg ggg gag ttc<br>Thr Ser Tyr Ala Arg Tyr Gly Gly Phe Leu Tyr Glu Ala Gly Glu Phe<br>4975                        4980                        4985                        4990 | 15150 |
| gat gcg gac ttc ttc ggg atc agt ccg cgt gag gcg ttg gcg atg gat<br>Asp Ala Asp Phe Phe Gly Ile Ser Pro Arg Glu Ala Leu Ala Met Asp<br>                 4995                        5000                        5005 | 15198 |
| ccg cag cag cgg ttg ttg ctg gag acg tcg tgg gag gcg ttc gag cgg<br>Pro Gln Gln Arg Leu Leu Leu Glu Thr Ser Trp Glu Ala Phe Glu Arg<br>            5010                        5015                        5020 | 15246 |
| gcg ggt atc gat ccg ctg tcg atg cgt ggc tcc cgt acg ggt gtc ttc<br>Ala Gly Ile Asp Pro Leu Ser Met Arg Gly Ser Arg Thr Gly Val Phe<br>        5025                        5030                        5035 | 15294 |
| gcc ggg gtg atg tac cac gac tac gga tcc cgc ctg ggt acc atc ccc<br>Ala Gly Val Met Tyr His Asp Tyr Gly Ser Arg Leu Gly Thr Ile Pro<br>5040                        5045                        5050 | 15342 |
| gag gga ttc gag ggc tac atc ggc aac ggt agc ggc ggc gcc gtc gcg<br>Glu Gly Phe Glu Gly Tyr Ile Gly Asn Gly Ser Gly Gly Ala Val Ala<br>5055                        5060                        5065                        5070 | 15390 |
| tcg ggc cgc gtc gcc tac acg ctc ggt ctc gag ggc cct gcc gtc tcg<br>Ser Gly Arg Val Ala Tyr Thr Leu Gly Leu Glu Gly Pro Ala Val Ser<br>                 5075                        5080                        5085 | 15438 |
| gtg gac acg gca tgt tcg tcg tcg ttg gtg gcg ctg cat ctg gcg tgc<br>Val Asp Thr Ala Cys Ser Ser Ser Leu Val Ala Leu His Leu Ala Cys | 15486 |

```
                5090             5095              5100
cag tcg ctg cgg tcg ggt gag tgc acg ctc gcg ctg gcc ggc ggt gtg      15534
Gln Ser Leu Arg Ser Gly Glu Cys Thr Leu Ala Leu Ala Gly Gly Val
        5105             5110             5115 acg gtg atg tcg acc ccg cac ctc ttc gtc gag ttc tca cgc cag cgc      15582
Thr Val Met Ser Thr Pro His Leu Phe Val Glu Phe Ser Arg Gln Arg
    5120             5125             5130 gga ctg tcg gtg gac ggc cgc tgc aag tcc ttc gcg ggt gga gcc gac      15630
Gly Leu Ser Val Asp Gly Arg Cys Lys Ser Phe Ala Gly Gly Ala Asp
5135             5140             5145             5150 ggc acc ggc atg ggc gag ggc gtc ggg atg ctg ttg gtg gag cgg ttg      15678
Gly Thr Gly Met Gly Glu Gly Val Gly Met Leu Leu Val Glu Arg Leu
        5155             5160             5165 tcg gat gcg gtg cgg ctg ggg cat cgg gtg ctg gcg gtg ctg cgc ggc      15726
Ser Asp Ala Val Arg Leu Gly His Arg Val Leu Ala Val Leu Arg Gly
        5170             5175             5180 agt gcg gtc aat cag gac ggt gcg tcg aat ggg ttg acg gcg ccg aat      15774
Ser Ala Val Asn Gln Asp Gly Ala Ser Asn Gly Leu Thr Ala Pro Asn
        5185             5190             5195 ggt ccg gct cag gag cgg gtg atc cgg cag gcg ttg gcg aac gcg ggg      15822
Gly Pro Ala Gln Glu Arg Val Ile Arg Gln Ala Leu Ala Asn Ala Gly
    5200             5205             5210 ttg tcc gtg gcg gat gtg gat gtg gtg gag ggg cat ggg acg ggc acg      15870
Leu Ser Val Ala Asp Val Asp Val Val Glu Gly His Gly Thr Gly Thr
5215             5220             5225             5230 acg ctg ggt gat ccg atc gag gcg cag gcg ttg ctc gcc acg tac ggg      15918
Thr Leu Gly Asp Pro Ile Glu Ala Gln Ala Leu Leu Ala Thr Tyr Gly
        5235             5240             5245 cag cgg gcc ggt aac agg ccg ctg tgg ctg gga tcg gtg aag tcg aac      15966
Gln Arg Ala Gly Asn Arg Pro Leu Trp Leu Gly Ser Val Lys Ser Asn
        5250             5255             5260 atc ggc cat gcg cag gct gcc gcg ggt gtg ggt ggg gtc atc aag atg      16014
Ile Gly His Ala Gln Ala Ala Ala Gly Val Gly Gly Val Ile Lys Met
        5265             5270             5275 gtg atg gcg ttg cgg gag ggg gtg ttg ccg cgg acg ttg cat gtg gat      16062
Val Met Ala Leu Arg Glu Gly Val Leu Pro Arg Thr Leu His Val Asp
    5280             5285             5290 gag ccg tcg ccg cag gtg gac tgg tcc gcg ggg gcg gtg cgg ctg ctg      16110
Glu Pro Ser Pro Gln Val Asp Trp Ser Ala Gly Ala Val Arg Leu Leu
5295             5300             5305             5310 acg gag gcg gtg ccg tgg ccg ggg gac gcg gca ggg cgg ttg cgg cgg      16158
Thr Glu Ala Val Pro Trp Pro Gly Asp Ala Ala Gly Arg Leu Arg Arg
        5315             5320             5325 gcg gga gtg tcg tcg ttc ggg gtc agt ggc acg aat gcg cat gtg att      16206
Ala Gly Val Ser Ser Phe Gly Val Ser Gly Thr Asn Ala His Val Ile
        5330             5335             5340 ttg gag gag gcg ccg gcg gcg ggg ggc tgt gtt gcc ggg ggt ggg gtg      16254
Leu Glu Glu Ala Pro Ala Ala Gly Gly Cys Val Ala Gly Gly Gly Val
        5345             5350             5355 ttg gag ggt gct ccg ggt ctt gcc att tcg gtg gct gag tcg gtg gcc      16302
Leu Glu Gly Ala Pro Gly Leu Ala Ile Ser Val Ala Glu Ser Val Ala
        5360             5365             5370 gct cca gtg gct gtg tct gcg ccg gtg gct gag tcg gtg ccg gtg ccg      16350
Ala Pro Val Ala Val Ser Ala Pro Val Ala Glu Ser Val Pro Val Pro
5375             5380             5385             5390 gtg ccg gtg ccg gtt cct gtg ccg gtg tcg gct agg tct gag gct ggg      16398
Val Pro Val Pro Val Pro Val Pro Val Ser Ala Arg Ser Glu Ala Gly
        5395             5400             5405 ttg cgg gcg cag gcg gag gcg ttg cgt cag tac gtg gca gtc cgg ccg      16446
```

-continued

| | |
|---|---|
| Leu Arg Ala Gln Ala Glu Ala Leu Arg Gln Tyr Val Ala Val Arg Pro<br>　　　　5410　　　　　　　　　5415　　　　　　　　　5420 | |
| gac gtt tcg ctt gcc gat gtg ggt gcg ggt ctg gcc tgt ggg cgg gct<br>Asp Val Ser Leu Ala Asp Val Gly Ala Gly Leu Ala Cys Gly Arg Ala<br>　　　　5425　　　　　　　　　5430　　　　　　　　　5435 | 16494 |
| gtg ctg gag cat cgt gcg gtc gtc ctg gcc gcg gac cgt gag gag ctg<br>Val Leu Glu His Arg Ala Val Val Leu Ala Ala Asp Arg Glu Glu Leu<br>5440　　　　　　　　　5445　　　　　　　　　5450 | 16542 |
| gtg caa ggg ttg ggg gcg ctg gcg gcg ggt gag ccg gat cgg cgg gtg<br>Val Gln Gly Leu Gly Ala Leu Ala Ala Gly Glu Pro Asp Arg Arg Val<br>5455　　　　　　　　　5460　　　　　　　　　5465　　　　　　　　　5470 | 16590 |
| acc acg ggt cat gcg ccg ggt ggt gac cgg ggc ggt gtc gtc ttc gtg<br>Thr Thr Gly His Ala Pro Gly Gly Asp Arg Gly Gly Val Val Phe Val<br>　　　　5475　　　　　　　　　5480　　　　　　　　　5485 | 16638 |
| ttt ccc gga cag ggt ggg cag tgg gcc ggg atg ggt gtg cgt ctg ctc<br>Phe Pro Gly Gln Gly Gly Gln Trp Ala Gly Met Gly Val Arg Leu Leu<br>　　　　5490　　　　　　　　　5495　　　　　　　　　5500 | 16686 |
| gcc tcc tct ccg gtg ttc gcc cgg cgg atg cag gcg tgc gag gag gct<br>Ala Ser Ser Pro Val Phe Ala Arg Arg Met Gln Ala Cys Glu Glu Ala<br>　　　　5505　　　　　　　　　5510　　　　　　　　　5515 | 16734 |
| ctg gcg ccg tgg gtg gac tgg tct gtg gtg gac atc ctg cgc cgg gac<br>Leu Ala Pro Trp Val Asp Trp Ser Val Val Asp Ile Leu Arg Arg Asp<br>5520　　　　　　　　　5525　　　　　　　　　5530 | 16782 |
| gcg ggg gat gcg gtg tgg gag cgg gcc gat gtg gtc cag cct gtg ctg<br>Ala Gly Asp Ala Val Trp Glu Arg Ala Asp Val Val Gln Pro Val Leu<br>5535　　　　　　　　　5540　　　　　　　　　5545　　　　　　　　　5550 | 16830 |
| ttc agc gtc atg gtg tct ttg gct gct ctg tgg cgt tcc tac ggt atc<br>Phe Ser Val Met Val Ser Leu Ala Ala Leu Trp Arg Ser Tyr Gly Ile<br>　　　　5555　　　　　　　　　5560　　　　　　　　　5565 | 16878 |
| gaa ccc gac gcg gtc ctt ggc cat tcc cag ggc gag atc gcg gcc gcg<br>Glu Pro Asp Ala Val Leu Gly His Ser Gln Gly Glu Ile Ala Ala Ala<br>　　　　5570　　　　　　　　　5575　　　　　　　　　5580 | 16926 |
| cat gtg tgt ggg gcg ctg agc ctg aag gac gcg gcg aag act gtt gcg<br>His Val Cys Gly Ala Leu Ser Leu Lys Asp Ala Ala Lys Thr Val Ala<br>　　　　5585　　　　　　　　　5590　　　　　　　　　5595 | 16974 |
| ctg cgc agc cgg gcg ctg gcc gct gtg cgg ggc cgg ggc ggc atg gcc<br>Leu Arg Ser Arg Ala Leu Ala Ala Val Arg Gly Arg Gly Gly Met Ala<br>　　　　5600　　　　　　　　　5605　　　　　　　　　5610 | 17022 |
| tca gtg ccg ctg cct gcc cag gag gtg gag cag ctc att ggt gag cgg<br>Ser Val Pro Leu Pro Ala Gln Glu Val Glu Gln Leu Ile Gly Glu Arg<br>5615　　　　　　　　　5620　　　　　　　　　5625　　　　　　　　　5630 | 17070 |
| tgg gcg ggg cgg ttg tgg gtg gcg gcg gtc aac ggc ccc cgc tcc acc<br>Trp Ala Gly Arg Leu Trp Val Ala Ala Val Asn Gly Pro Arg Ser Thr<br>　　　　5635　　　　　　　　　5640　　　　　　　　　5645 | 17118 |
| gcc gtc tcg ggg gat gcc gag gcg gtg gac gag gtg ctg gcg tac tgt<br>Ala Val Ser Gly Asp Ala Glu Ala Val Asp Glu Val Leu Ala Tyr Cys<br>　　　　5650　　　　　　　　　5655　　　　　　　　　5660 | 17166 |
| gcc ggc acc ggg gtg cgg gcc cgg cgg atc ccg gtc gac tat gcc tcg<br>Ala Gly Thr Gly Val Arg Ala Arg Arg Ile Pro Val Asp Tyr Ala Ser<br>　　　　5665　　　　　　　　　5670　　　　　　　　　5675 | 17214 |
| cac tgc ccc cat gtg cag ccc ctg cgg gag gag ttg ctg gag ctg ctg<br>His Cys Pro His Val Gln Pro Leu Arg Glu Glu Leu Leu Glu Leu Leu<br>　　　　5680　　　　　　　　　5685　　　　　　　　　5690 | 17262 |
| ggg gac atc agc ccg cag ccg tcc ggc gtg ccg ttc ttc tcc acg gtg<br>Gly Asp Ile Ser Pro Gln Pro Ser Gly Val Pro Phe Phe Ser Thr Val<br>5695　　　　　　　　　5700　　　　　　　　　5705　　　　　　　　　5710 | 17310 |
| gag ggc acc tgg ctg gac acc aca acc ctg gac gcc gcc tac tgg tac<br>Glu Gly Thr Trp Leu Asp Thr Thr Thr Leu Asp Ala Ala Tyr Trp Tyr<br>　　　　5715　　　　　　　　　5720　　　　　　　　　5725 | 17358 |

```
cgc aac ctg cac cag cct gtc cgt ttc agc gat gcc gtc cag gcc ctg    17406
Arg Asn Leu His Gln Pro Val Arg Phe Ser Asp Ala Val Gln Ala Leu
            5730                5735                5740 gcg gat gac gga cac cgc gtc ttc gtc gaa gtc agc ccc cac ccc acc    17454
Ala Asp Asp Gly His Arg Val Phe Val Glu Val Ser Pro His Pro Thr
        5745                5750                5755 ctc gtc ccc gcc atc gaa gac acc acc gaa gac acc gcc gaa gac gtc    17502
Leu Val Pro Ala Ile Glu Asp Thr Thr Glu Asp Thr Ala Glu Asp Val
    5760                5765                5770 acc gcg atc ggc agc ctc cgc cgc ggc gac aac gac acc cgc cgc ttc    17550
Thr Ala Ile Gly Ser Leu Arg Arg Gly Asp Asn Asp Thr Arg Arg Phe
5775                5780                5785                5790 ctc acc gcc ctc gcc cac acc cac acc acc ggc atc ggc aca ccc acc    17598
Leu Thr Ala Leu Ala His Thr His Thr Thr Gly Ile Gly Thr Pro Thr
            5795                5800                5805 acc tgg cac cac cac tac acc cac cac cac acc cac ccc cac aac cac    17646
Thr Trp His His His Tyr Thr His His His Thr His Pro His Asn His
            5810                5815                5820 cac ctc gac ctc ccc act tat ccc ttc caa cgc cag cac tac tgg ctc    17694
His Leu Asp Leu Pro Thr Tyr Pro Phe Gln Arg Gln His Tyr Trp Leu
        5825                5830                5835 gac gct ccc acg gga gca ggt gac gtc gcc gct gct ggc ttg gag ccg    17742
Asp Ala Pro Thr Gly Ala Gly Asp Val Ala Ala Ala Gly Leu Glu Pro
    5840                5845                5850 gcc gaa cac cct ctg ctc gcg gca aca gtc caa ctc gca gac acg gac    17790
Ala Glu His Pro Leu Leu Ala Ala Thr Val Gln Leu Ala Asp Thr Asp
5855                5860                5865                5870 ggc tgc cta ctg acg ggt cgc ctg tcc ttg cgc tcg cat ccg tgg ctg    17838
Gly Cys Leu Leu Thr Gly Arg Leu Ser Leu Arg Ser His Pro Trp Leu
            5875                5880                5885 ggc gat tac gag gtg ggg ggt gcg gtc ctg ctg tcg ggg tcg gcg ttc    17886
Gly Asp Tyr Glu Val Gly Gly Ala Val Leu Leu Ser Gly Ser Ala Phe
            5890                5895                5900 gtg gag ctg gcg gtc cag gtt ggc gaa cgc gtg ggc tgc acc cga atc    17934
Val Glu Leu Ala Val Gln Val Gly Glu Arg Val Gly Cys Thr Arg Ile
        5905                5910                5915 gag caa ctc act gtg cat gcg ccg ctg gtg gtt cct gtg ggt ggg ggt    17982
Glu Gln Leu Thr Val His Ala Pro Leu Val Val Pro Val Gly Gly Gly
    5920                5925                5930 gtg agt gtg cag gtt ggg gtt gcg gct gcg gat ggg gag ggg cgg cgt    18030
Val Ser Val Gln Val Gly Val Ala Ala Ala Asp Gly Glu Gly Arg Arg
5935                5940                5945                5950 ttg gtg agt gtg tat gcg cgg ggt ggg agt gct tgt ggt ggg ggt ggt    18078
Leu Val Ser Val Tyr Ala Arg Gly Gly Ser Ala Cys Gly Gly Gly Gly
            5955                5960                5965 gcg tcg ggt ggg gtg tgg acg tgt cat gcc tcg ggg gtg ctg gtt gag    18126
Ala Ser Gly Gly Val Trp Thr Cys His Ala Ser Gly Val Leu Val Glu
            5970                5975                5980 gct gct gct ggt ggt ggt gtg gtg gtg gat ggt ctg gcg ggg gtg tgg    18174
Ala Ala Ala Gly Gly Gly Val Val Val Asp Gly Leu Ala Gly Val Trp
        5985                5990                5995 ccg ccg cgg ggt gcg gtg gcg gtg gat gtc gat ggt gtc cgt gac cgt    18222
Pro Pro Arg Gly Ala Val Ala Val Asp Val Asp Gly Val Arg Asp Arg
    6000                6005                6010 ttg gct ggg gct ggt tgt gtt ttg ggg ccg gtg ttt tcg ggg ctg cgt    18270
Leu Ala Gly Ala Gly Cys Val Leu Gly Pro Val Phe Ser Gly Leu Arg
6015                6020                6025                6030 gcg gtg tgg cgt gat ggg ggg gat ttg ctg gct gag gtg tgt ctg ccg    18318
Ala Val Trp Arg Asp Gly Gly Asp Leu Leu Ala Glu Val Cys Leu Pro
            6035                6040                6045
```

```
                                                                -continued gag gag gcg tgg ggt gat gcg gct ggt ttt ggg ctg cat ccg gcg ttg        18366
Glu Glu Ala Trp Gly Asp Ala Ala Gly Phe Gly Leu His Pro Ala Leu
        6050                6055                6060 ctg gat ggt gtg gtc cag ccg ttg tcg gtg ttg ctt ccg ggt ggg acg        18414
Leu Asp Gly Val Val Gln Pro Leu Ser Val Leu Pro Gly Gly Thr
    6065                6070                6075 ggg ttt ggg gag ggg gcg ggg ttc ggg gag ggt gtt cgg gtg ccg gct        18462
Gly Phe Gly Glu Gly Ala Gly Phe Gly Glu Gly Val Arg Val Pro Ala
        6080                6085                6090 gtg tgg ggt ggt gtg tcg ctt cac cgg gcg ggt gtg acc ggt gtg cgg        18510
Val Trp Gly Gly Val Ser Leu His Arg Ala Gly Val Thr Gly Val Arg
6095                6100                6105                6110 gtg cgt gtg tgg gct gta ggg cgg ggc ggc ggg cgt gag gcg gtg tcg        18558
Val Arg Val Trp Ala Val Gly Arg Gly Gly Gly Arg Glu Ala Val Ser
            6115                6120                6125 gtc gtg gtc ggg gat gag gcg ggt gtg ccg gtg gcg tcg gtc gat cgt        18606
Val Val Val Gly Asp Glu Ala Gly Val Pro Val Ala Ser Val Asp Arg
        6130                6135                6140 ctt gag ttg cgg cct gtg gat atg ggt cag ttg cgt gct gtc tcg gtt        18654
Leu Glu Leu Arg Pro Val Asp Met Gly Gln Leu Arg Ala Val Ser Val
    6145                6150                6155 tcg gcg ggg cgg cgg ggt tcg ctg tat gcg gtg cag tgg gct gag gtg        18702
Ser Ala Gly Arg Arg Gly Ser Leu Tyr Ala Val Gln Trp Ala Glu Val
6160                6165                6170 ggt cct gtg ccg gtg tgt ggg cag gcg tgg gcg tgg cac gag gac gtg        18750
Gly Pro Val Pro Val Cys Gly Gln Ala Trp Ala Trp His Glu Asp Val
6175                6180                6185                6190 ggt gag agc ggt ggt ggg cct gtg ccg ggg gtg gtg gtg ttg cgg tgc        18798
Gly Glu Ser Gly Gly Gly Pro Val Pro Gly Val Val Val Leu Arg Cys
        6195                6200                6205 ccg gat gcc ggt gcc ggt ggc ggc ggt ggc ggt ggt gtg ggt gag gtt        18846
Pro Asp Ala Gly Ala Gly Gly Gly Gly Gly Gly Gly Val Gly Glu Val
    6210                6215                6220 gtt ggt ggg gtg ttg ggt gtg gtg cag ggg tgg ctg ggg ctg gag cgg        18894
Val Gly Gly Val Leu Gly Val Val Gln Gly Trp Leu Gly Leu Glu Arg
        6225                6230                6235 ttt gcg ggt tcg cgg ctg gtg gtg gtg acc cgg ggt gcg gtg gtg gcc        18942
Phe Ala Gly Ser Arg Leu Val Val Val Thr Arg Gly Ala Val Val Ala
    6240                6245                6250 ggc caa gaa gac ggc ccg gtg gat gtg gtg ggt gcg gcg gtg tgg ggg        18990
Gly Gln Glu Asp Gly Pro Val Asp Val Val Gly Ala Ala Val Trp Gly
6255                6260                6265                6270 ctg gtg cgg tcg gcg cag gct gag cat ccg gac cgg ttt gtc ctc ctc        19038
Leu Val Arg Ser Ala Gln Ala Glu His Pro Asp Arg Phe Val Leu Leu
        6275                6280                6285 gac ctc gac acc gac acc gac acc ggc acc gac ctc gac acc ggt gct        19086
Asp Leu Asp Thr Asp Thr Asp Thr Gly Thr Asp Leu Asp Thr Gly Ala
    6290                6295                6300 ggt gct ggt gct ggt gct ggt tgg ggc gtg gat ggt ggg cat gtg gcg        19134
Gly Ala Gly Ala Gly Ala Gly Trp Gly Val Asp Gly Gly His Val Ala
        6305                6310                6315 gcg gtg gtg gcg tgt ggt gag ccg cag ttg gcg gtg cgt ggt gag cgg        19182
Ala Val Val Ala Cys Gly Glu Pro Gln Leu Ala Val Arg Gly Glu Arg
    6320                6325                6330 gtg ctg gcc gca cgc ctg acg cga ctt gag tcg tcc gtt gat gta cct        19230
Val Leu Ala Ala Arg Leu Thr Arg Leu Glu Ser Ser Val Asp Val Pro
6335                6340                6345                6350 gct cag cgg tcc ggt gat gtt gct ggt cgg gag gtg ttg ccg tgg ttg        19278
Ala Gln Arg Ser Gly Asp Val Ala Gly Arg Glu Val Leu Pro Trp Leu
```

-continued

| | |
|---|---|
| tcg ggt ggg tcg gtg ttg gtg acg ggt ggg acg ggt gtg ctg ggt gcg<br>Ser Gly Gly Ser Val Leu Val Thr Gly Gly Thr Gly Val Leu Gly Ala<br>        6370                  6375                  6380 | 19326 |
| gcg gtg gcg cgg cat ctg gct ggt gtg tgt ggg gtg cgg gat ctg ctg<br>Ala Val Ala Arg His Leu Ala Gly Val Cys Gly Val Arg Asp Leu Leu<br>6385                  6390                  6395 | 19374 |
| ttg gtg agc cgg cgt ggt ccg gat gct ccg ggt gcg gag ggt ttg cgg<br>Leu Val Ser Arg Arg Gly Pro Asp Ala Pro Gly Ala Glu Gly Leu Arg<br>        6400                  6405                  6410 | 19422 |
| gcg gag ctg gcc gcg ttg ggg gcg gag gtg cgg att gtt gcg tgt gat<br>Ala Glu Leu Ala Ala Leu Gly Ala Glu Val Arg Ile Val Ala Cys Asp<br>6415                  6420                  6425                  6430 | 19470 |
| gtg ggg gag cgg cgg gag gtg gtc cgg ctg ctg gag ggt gtt cct gcc<br>Val Gly Glu Arg Arg Glu Val Val Arg Leu Leu Glu Gly Val Pro Ala<br>        6435                  6440                  6445 | 19518 |
| ggg tgt ccg ctg acg ggt gtc gtg cat gcg gct ggt gtg ctg gac gat<br>Gly Cys Pro Leu Thr Gly Val Val His Ala Ala Gly Val Leu Asp Asp<br>                6450                  6455                  6460 | 19566 |
| gcg acg atc gcc tct ctc acg ccc gag cgg ctg ggc acg gtg ttc gcg<br>Ala Thr Ile Ala Ser Leu Thr Pro Glu Arg Leu Gly Thr Val Phe Ala<br>6465                  6470                  6475 | 19614 |
| gcc aag gtg gat gcc gct ctt ttg ctg gat gag ctg acg cgg ggt atg<br>Ala Lys Val Asp Ala Ala Leu Leu Leu Asp Glu Leu Thr Arg Gly Met<br>        6480                  6485                  6490 | 19662 |
| gag ctg tcg gcg ttc gtg ctg ttc tcc tcg gcc gcg ggg atc ctg ggg<br>Glu Leu Ser Ala Phe Val Leu Phe Ser Ser Ala Ala Gly Ile Leu Gly<br>6495                  6500                  6505                  6510 | 19710 |
| tcg gcc ggg cag ggc aac tac gcc gcg gcc aat gcc gct ctg gac gcg<br>Ser Ala Gly Gln Gly Asn Tyr Ala Ala Ala Asn Ala Ala Leu Asp Ala<br>        6515                  6520                  6525 | 19758 |
| ctg gcg tac cgg cgg cgg gcg gcg ggt ctg ccg ggg gtg tcg ctg gcg<br>Leu Ala Tyr Arg Arg Arg Ala Ala Gly Leu Pro Gly Val Ser Leu Ala<br>                6530                  6535                  6540 | 19806 |
| tgg ggg ctg tgg gaa gag gcc agc ggg atg acc ggg cac ctg gcc ggc<br>Trp Gly Leu Trp Glu Glu Ala Ser Gly Met Thr Gly His Leu Ala Gly<br>6545                  6550                  6555 | 19854 |
| acc gac cac cgg cgc atc atc cgt tcc ggt ctg cat ccc atg tcg acc<br>Thr Asp His Arg Arg Ile Ile Arg Ser Gly Leu His Pro Met Ser Thr<br>        6560                  6565                  6570 | 19902 |
| ccg gac gca ctg gct ctc ttc gat gcg gcc ctg gct ctg gac cgg ccg<br>Pro Asp Ala Leu Ala Leu Phe Asp Ala Ala Leu Ala Leu Asp Arg Pro<br>6575                  6580                  6585                  6590 | 19950 |
| gtc ctg ctg ccc gcc gac ctg cgt ccc gcc ccg ccc ctg ccg ccc ctg<br>Val Leu Leu Pro Ala Asp Leu Arg Pro Ala Pro Pro Leu Pro Pro Leu<br>                6595                  6600                  6605 | 19998 |
| ctg cag gac ctc ctg ccc gcc acc cgc cgc cgc acc acc cgc acc acc<br>Leu Gln Asp Leu Leu Pro Ala Thr Arg Arg Arg Thr Thr Arg Thr Thr<br>6610                  6615                  6620 | 20046 |
| act acc ggt ggt gcg gac aac ggc gcc cag ctg cat gcc cgg ctg gcc<br>Thr Thr Gly Gly Ala Asp Asn Gly Ala Gln Leu His Ala Arg Leu Ala<br>        6625                  6630                  6635 | 20094 |
| ggc cag aca cac gaa caa cag cac acc acc ctc ctc gcc ctg gtc cgc<br>Gly Gln Thr His Glu Gln Gln His Thr Thr Leu Leu Ala Leu Val Arg<br>                6640                  6645                  6650 | 20142 |
| tcc cac atc gcc acc gtc ctc ggc cac acc acc ccc gac acc atc ccc<br>Ser His Ile Ala Thr Val Leu Gly His Thr Thr Pro Asp Thr Ile Pro<br>6655                  6660                  6665                  6670 | 20190 |
| ccc gac cgc gcg ttc cgc gac ctc ggc ttc gac tcc ctc acc gcc gtc | 20238 |

```
                                                        -continued

Pro Asp Arg Ala Phe Arg Asp Leu Gly Phe Asp Ser Leu Thr Ala Val
            6675                6680                6685 gaa cta cgc aac cgg ctc tcc cgc acc acc gga ctc cgc ctc ccc acc       20286
Glu Leu Arg Asn Arg Leu Ser Arg Thr Thr Gly Leu Arg Leu Pro Thr
            6690                6695                6700 acc ctc gcc ttc gac cac ccc aac ccc acc acc ctc acc cac cac ctc       20334
Thr Leu Ala Phe Asp His Pro Asn Pro Thr Thr Leu Thr His His Leu
            6705                6710                6715 cac aca caa ctt ctg ggc tcg gac agc act gcc tcc atc cca gct ccc       20382
His Thr Gln Leu Leu Gly Ser Asp Ser Thr Ala Ser Ile Pro Ala Pro
    6720                6725                6730 cgt gct gcg gct gtg cct gca gac cag gac gag ccc gtc gcg atc att       20430
Arg Ala Ala Ala Val Pro Ala Asp Gln Asp Glu Pro Val Ala Ile Ile
6735                6740                6745                6750 ggc atg gcg tgc cgc tat ccc gga ggc gtc acc tca gcc gag gag ctg       20478
Gly Met Ala Cys Arg Tyr Pro Gly Gly Val Thr Ser Ala Glu Glu Leu
            6755                6760                6765 tgg gaa ctg ctc gca tcg ggg agg gac acg gtc ggc gag ttt ccg acg       20526
Trp Glu Leu Leu Ala Ser Gly Arg Asp Thr Val Gly Glu Phe Pro Thr
            6770                6775                6780 gac cgt ggg tgg gac ctg gaa gca ctg ttc gat ccg gaa ccg ggt cgg       20574
Asp Arg Gly Trp Asp Leu Glu Ala Leu Phe Asp Pro Glu Pro Gly Arg
            6785                6790                6795 ccg ggc acc tcg tac acc cgc tgt ggg agt ttc ctc tac gac gcg ggg       20622
Pro Gly Thr Ser Tyr Thr Arg Cys Gly Ser Phe Leu Tyr Asp Ala Gly
    6800                6805                6810 gag ttc gac gcc ggc ttc ttc ggg atc agt ccg cgt gag gca ctg gcg       20670
Glu Phe Asp Ala Gly Phe Phe Gly Ile Ser Pro Arg Glu Ala Leu Ala
6815                6820                6825                6830 atg gac ccg cag cag cga ttg ctg ctg gag gcc tca tgg gag gcc atg       20718
Met Asp Pro Gln Gln Arg Leu Leu Leu Glu Ala Ser Trp Glu Ala Met
            6835                6840                6845 gag cag gca ggt att gac cct acg acc gta cgc ggg agc cag aca ggc       20766
Glu Gln Ala Gly Ile Asp Pro Thr Thr Val Arg Gly Ser Gln Thr Gly
            6850                6855                6860 gtg ttc gcg ggc ctc att ccg cag gcc tat gga ccc agg ctg cac gaa       20814
Val Phe Ala Gly Leu Ile Pro Gln Ala Tyr Gly Pro Arg Leu His Glu
            6865                6870                6875 aac gcc gca gcc gac acc gag ggc tat gtc ctg acc ggc aca tcc ggg       20862
Asn Ala Ala Ala Asp Thr Glu Gly Tyr Val Leu Thr Gly Thr Ser Gly
            6880                6885                6890 agt gtg gcc tcc ggt cgt atc tcg tac acg ttt ggt ttt gag ggt cct       20910
Ser Val Ala Ser Gly Arg Ile Ser Tyr Thr Phe Gly Phe Glu Gly Pro
6895                6900                6905                6910 gcg gtg tcg gtg gac acg gct tgt tcc tcg tcg ttg gtg gct tta cat       20958
Ala Val Ser Val Asp Thr Ala Cys Ser Ser Ser Leu Val Ala Leu His
            6915                6920                6925 ctg gcc tgt cag gcg ttg cgt gcg ggt gag tgc tcg atg gcg ctt gcc       21006
Leu Ala Cys Gln Ala Leu Arg Ala Gly Glu Cys Ser Met Ala Leu Ala
            6930                6935                6940 ggg ggt gtg acg gtg atg tcg tct ccg ggt gcc ttc gtg gag ttt tcg       21054
Gly Gly Val Thr Val Met Ser Ser Pro Gly Ala Phe Val Glu Phe Ser
            6945                6950                6955 cgg cag cgg ggt ctg gcc gcg gac ggg cat tgc aag gcg ttc tcg gcg       21102
Arg Gln Arg Gly Leu Ala Ala Asp Gly His Cys Lys Ala Phe Ser Ala
            6960                6965                6970 gcg gcg gac ggg acc ggc tgg ggt gag ggt gtg ggg atg ctg ctg gtg       21150
Ala Ala Asp Gly Thr Gly Trp Gly Glu Gly Val Gly Met Leu Leu Val
6975                6980                6985                6990
```

```
gag cgg ctc tcc gac gcc cgt cgc aac ggt cac cgt gtc ctg gcc gtg        21198
Glu Arg Leu Ser Asp Ala Arg Arg Asn Gly His Arg Val Leu Ala Val
            6995                7000                7005 gtg cgt ggc agt gcg gtc aac cag gac ggt gcg agc aac ggg ctg acc        21246
Val Arg Gly Ser Ala Val Asn Gln Asp Gly Ala Ser Asn Gly Leu Thr
        7010                7015                7020 gcg ccc aac ggg ccc tcc cag cag cgt gtc atc cgc cag gcc ctc gcc        21294
Ala Pro Asn Gly Pro Ser Gln Gln Arg Val Ile Arg Gln Ala Leu Ala
    7025                7030                7035 aac gcc ggc ttg tcg gcc ggt gat gtc gat gcg gtg gag gcc cac ggc        21342
Asn Ala Gly Leu Ser Ala Gly Asp Val Asp Ala Val Glu Ala His Gly
7040                7045                7050 acc ggc acc act ttg ggc gac ccg atc gag gcc cag gcc ctc ctt gcg        21390
Thr Gly Thr Thr Leu Gly Asp Pro Ile Glu Ala Gln Ala Leu Leu Ala
            7055                7060                7065                7070 acc tac ggg cag gac cgt gcc ggc gag ggg ccg ctg tgg ctg ggc tcg        21438
Thr Tyr Gly Gln Asp Arg Ala Gly Glu Gly Pro Leu Trp Leu Gly Ser
        7075                7080                7085 gtc aag tcc aat gtc ggt cac aca cag gct gcc gcg ggc gtc gcc ggg        21486
Val Lys Ser Asn Val Gly His Thr Gln Ala Ala Ala Gly Val Ala Gly
    7090                7095                7100 gtg atc aag atg gtg atg gcg ctg cgg aat ggt ctg ctg ccg cgg acg        21534
Val Ile Lys Met Val Met Ala Leu Arg Asn Gly Leu Leu Pro Arg Thr
7105                7110                7115 ttg cat gtg gat gag ccg tcg ccg cat gtg gac tgg tcc gcg ggt gcg        21582
Leu His Val Asp Glu Pro Ser Pro His Val Asp Trp Ser Ala Gly Ala
        7120                7125                7130 gtg cag ctg ctg acg gag acg gtg ccc tgg ccc ggc ggg gag ggg cgg        21630
Val Gln Leu Leu Thr Glu Thr Val Pro Trp Pro Gly Gly Glu Gly Arg
7135                7140                7145                7150 cta cgg cgg gca gga gtg tca tca ttc ggc gtc agc ggc acc aac gcc        21678
Leu Arg Arg Ala Gly Val Ser Ser Phe Gly Val Ser Gly Thr Asn Ala
            7155                7160                7165 cac gtc atc ctc gaa gaa gca ccc gcc cac aac atc ccg tca gac aca        21726
His Val Ile Leu Glu Glu Ala Pro Ala His Asn Ile Pro Ser Asp Thr
        7170                7175                7180 ccc gcc gac gac gtt ccg ggg gga cca ccc gcc ggc gag gat gcc ggt        21774
Pro Ala Asp Asp Val Pro Gly Gly Pro Pro Ala Gly Glu Asp Ala Gly
    7185                7190                7195 agt ggc gag gag gct gct gcc ggc agt cca ggg gtg tgg ccg tgg ctg        21822
Ser Gly Glu Glu Ala Ala Ala Gly Ser Pro Gly Val Trp Pro Trp Leu
7200                7205                7210 gtg tcg gcc aag tcg cag ccg gcc ctg cgc gcc cag gcc cag gcc ctg        21870
Val Ser Ala Lys Ser Gln Pro Ala Leu Arg Ala Gln Ala Gln Ala Leu
7215                7220                7225                7230 cac gcc cac ctc acc gac cac ccc ggc ctc gac ctc gcc gac gtc gga        21918
His Ala His Leu Thr Asp His Pro Gly Leu Asp Leu Ala Asp Val Gly
            7235                7240                7245 tac acc ctc gcc cac gcc cgc gcc gtg ttc gac cac cgc gcc acc ctc        21966
Tyr Thr Leu Ala His Ala Arg Ala Val Phe Asp His Arg Ala Thr Leu
        7250                7255                7260 atc gcc gcc gac cgc gac acc ttc ctg caa gca ctc cag gca ctc gcc        22014
Ile Ala Ala Asp Arg Asp Thr Phe Leu Gln Ala Leu Gln Ala Leu Ala
    7265                7270                7275 gca ggc gaa ccc cac ccc gcc gtc atc cac agc agc gcc cca ggc ggg        22062
Ala Gly Glu Pro His Pro Ala Val Ile His Ser Ser Ala Pro Gly Gly
7280                7285                7290 acc ggg acc ggg gag gcc gca gga aag acc gca ttc atc tgc tcc gga        22110
Thr Gly Thr Gly Glu Ala Ala Gly Lys Thr Ala Phe Ile Cys Ser Gly
7295                7300                7305                7310
```

-continued

| | |
|---|---|
| cag ggc acc caa cgc ccc ggc atg gcc cac ggc ctc tac cac acc cac<br>Gln Gly Thr Gln Arg Pro Gly Met Ala His Gly Leu Tyr His Thr His<br>            7315                    7320                    7325 | 22158 |
| ccc gtc ttc gcc gcc gca ctc aac gac atc tgc acc cac ctc gac ccc<br>Pro Val Phe Ala Ala Ala Leu Asn Asp Ile Cys Thr His Leu Asp Pro<br>            7330                    7335                    7340 | 22206 |
| cac ctc gac cac ccc ctc ctc ccc ctc ctc acc cag gac ccc aac acc<br>His Leu Asp His Pro Leu Leu Pro Leu Leu Thr Gln Asp Pro Asn Thr<br>            7345                    7350                    7355 | 22254 |
| cag gac acc acc acc ctc gaa gaa gcg gcc gca ctg ctc cag cag acc<br>Gln Asp Thr Thr Thr Leu Glu Glu Ala Ala Ala Leu Leu Gln Gln Thr<br>    7360                    7365                    7370 | 22302 |
| ccg tac gcc cag ccc gcc ctc ttc gcc ttc cag gtc gcc ctc cac cgc<br>Pro Tyr Ala Gln Pro Ala Leu Phe Ala Phe Gln Val Ala Leu His Arg<br>7375                    7380                    7385                    7390 | 22350 |
| ctc ctc acc gac ggc tac cac atc acc ccc cac tac tac gcc gga cac<br>Leu Leu Thr Asp Gly Tyr His Ile Thr Pro His Tyr Tyr Ala Gly His<br>            7395                    7400                    7405 | 22398 |
| tcc ctc ggc gaa atc acc gcc gcc cac ctc gcc ggc atc ctc acc ctc<br>Ser Leu Gly Glu Ile Thr Ala Ala His Leu Ala Gly Ile Leu Thr Leu<br>            7410                    7415                    7420 | 22446 |
| acc gac gcc acc acc ctc atc acc caa cgc gcc acc ctc atg caa acc<br>Thr Asp Ala Thr Thr Leu Ile Thr Gln Arg Ala Thr Leu Met Gln Thr<br>    7425                    7430                    7435 | 22494 |
| atg ccc ccc ggc acc atg acc acc ctc cac acc acc ccc cac cac atc<br>Met Pro Pro Gly Thr Met Thr Thr Leu His Thr Thr Pro His His Ile<br>7440                    7445                    7450 | 22542 |
| acc cac cac atc acc gcc cac gaa aac gac ctc gcc atc gcc gcc atc<br>Thr His His Ile Thr Ala His Glu Asn Asp Leu Ala Ile Ala Ala Ile<br>7455                    7460                    7465                    7470 | 22590 |
| aac acc ccc acc tcc ctc gtc atc agc ggc acc ccc cac acc gtc caa<br>Asn Thr Pro Thr Ser Leu Val Ile Ser Gly Thr Pro His Thr Val Gln<br>            7475                    7480                    7485 | 22638 |
| cac atc acc acc ctc tgc caa caa caa ggc atc aaa acc aaa acc ctc<br>His Ile Thr Thr Leu Cys Gln Gln Gln Gly Ile Lys Thr Lys Thr Leu<br>            7490                    7495                    7500 | 22686 |
| ccc acc aac cac gcc ttc cac tcc ccc cac acc aac ccc atc ctc aac<br>Pro Thr Asn His Ala Phe His Ser Pro His Thr Asn Pro Ile Leu Asn<br>    7505                    7510                    7515 | 22734 |
| caa ctc cac cag cac acc caa acc ctc acc tac cac cca ccc cac acc<br>Gln Leu His Gln His Thr Gln Thr Leu Thr Tyr His Pro Pro His Thr<br>7520                    7525                    7530 | 22782 |
| ccc ctc atc acc gcc aac acc cca ccc gac caa ctc ctc acc ccc cac<br>Pro Leu Ile Thr Ala Asn Thr Pro Pro Asp Gln Leu Leu Thr Pro His<br>7535                    7540                    7545                    7550 | 22830 |
| tac tgg acc caa caa gcc cgc aac acc gtc gac ata gcc acc acc acc<br>Tyr Trp Thr Gln Gln Ala Arg Asn Thr Val Asp Ile Ala Thr Thr Thr<br>            7555                    7560                    7565 | 22878 |
| caa acc ctc cac caa cac ggc gtc acc acc tac atc gaa ctc gga ccc<br>Gln Thr Leu His Gln His Gly Val Thr Thr Tyr Ile Glu Leu Gly Pro<br>            7570                    7575                    7580 | 22926 |
| gac aac acc ctc acc acc ctc acc cac cac aac ctc ccc aac acc ccc<br>Asp Asn Thr Leu Thr Thr Leu Thr His His Asn Leu Pro Asn Thr Pro<br>    7585                    7590                    7595 | 22974 |
| acc acc acc ctc acc ctc acc cac ccc cac cac cac ccc caa acc cac<br>Thr Thr Thr Leu Thr Leu Thr His Pro His His His Pro Gln Thr His<br>        7600                    7605                    7610 | 23022 |
| ctc ctc acc aac ctc gcc aaa acc acc acc acc tgg cac ccc cac cac<br>Leu Leu Thr Asn Leu Ala Lys Thr Thr Thr Thr Trp His Pro His His | 23070 |

-continued

```
                7615                7620                7625                7630
tac acc cac cac cac aac caa ccc cac acc cac cac ctc gac ctc                    23118
Tyr Thr His His His Asn Gln Pro His Thr His His Leu Asp Leu
                7635                7640                7645 ccc acc tac ccc ttc caa cac cac cac tac tgg ctc gaa agc aca cag                23166
Pro Thr Tyr Pro Phe Gln His His His Tyr Trp Leu Glu Ser Thr Gln
            7650                7655                7660 ccc ggt gcc gga aac gtg tca gca gcc gga ctc gac ccc acc gaa cac                23214
Pro Gly Ala Gly Asn Val Ser Ala Ala Gly Leu Asp Pro Thr Glu His
                7665                7670                7675 ccc cta ctc ggc gcc aca ttg gaa ctg gcc gaa ggg gac ggc tgc cta                23262
Pro Leu Leu Gly Ala Thr Leu Glu Leu Ala Glu Gly Asp Gly Cys Leu
        7680                7685                7690 ctg acg ggg cgc ctc tcg ttg cgc acg cat ccc tgg ctc gcc ggc cat                23310
Leu Thr Gly Arg Leu Ser Leu Arg Thr His Pro Trp Leu Ala Gly His
7695                7700                7705                7710 gcg gta ggc ggt gtc gtg ctg ctg ccg ggt acg gcc ttc gcg gaa ctg                23358
Ala Val Gly Gly Val Val Leu Leu Pro Gly Thr Ala Phe Ala Glu Leu
                7715                7720                7725 gcc ctt cat gcc gga gaa agt gtg ggt tgc gac cac gtg gac gag ctg                23406
Ala Leu His Ala Gly Glu Ser Val Gly Cys Asp His Val Asp Glu Leu
            7730                7735                7740 acg ctc cac aca ccg ttg gtc att cct gag gtc gga gac gtg acc ctt                23454
Thr Leu His Thr Pro Leu Val Ile Pro Glu Val Gly Asp Val Thr Leu
        7745                7750                7755 cag gtt gcc att gcg gcg ccg gac gag tcg ggt cgc cgc atg atg acc                23502
Gln Val Ala Ile Ala Ala Pro Asp Glu Ser Gly Arg Arg Met Met Thr
    7760                7765                7770 atc cac tca cgc ggt gag ggc ggc agt ggt gga gcc gat gcg tcg gcc                23550
Ile His Ser Arg Gly Glu Gly Gly Ser Gly Gly Ala Asp Ala Ser Ala
7775                7780                7785                7790 agt gcg tgg acg cgt cat gcc gcg ggt gtg ctg agc cct gcc aag gac                23598
Ser Ala Trp Thr Arg His Ala Ala Gly Val Leu Ser Pro Ala Lys Asp
                7795                7800                7805 gat gac act gcc tcg tac gag ctg ctt gcg gga ccc tgg cct ccc gtt                23646
Asp Asp Thr Ala Ser Tyr Glu Leu Leu Ala Gly Pro Trp Pro Pro Val
            7810                7815                7820 gga gct acg cct gtc gac ctg aac acg gct tac gat caa atg gcc gac                23694
Gly Ala Thr Pro Val Asp Leu Asn Thr Ala Tyr Asp Gln Met Ala Asp
        7825                7830                7835 gcc ggc ttt gct tat ggc ctg gca ttc caa ggg ttg cgc gcg gcc tgg                23742
Ala Gly Phe Ala Tyr Gly Leu Ala Phe Gln Gly Leu Arg Ala Ala Trp
    7840                7845                7850 cgc tac ggc gac gac atc ctc gtc gag gca cgt ctt ccc gaa gaa gtg                23790
Arg Tyr Gly Asp Asp Ile Leu Val Glu Ala Arg Leu Pro Glu Glu Val
7855                7860                7865                7870 tcg gga gac gcg gcg gcg tac ggt ctg cac ccg gcc ctg ctc gac gct                23838
Ser Gly Asp Ala Ala Ala Tyr Gly Leu His Pro Ala Leu Leu Asp Ala
                7875                7880                7885 gcc ctt cag ggc acc ggc ctg ctt tct gtg gcg ggt ccg ggg acg ccc                23886
Ala Leu Gln Gly Thr Gly Leu Leu Ser Val Ala Gly Pro Gly Thr Pro
            7890                7895                7900 gtc gtg ccc cat gtg tgg aac ggt ctg cgg ttc cgt acg cat ggt gca                23934
Val Val Pro His Val Trp Asn Gly Leu Arg Phe Arg Thr His Gly Ala
        7905                7910                7915 gtc tcc gtg cgc gcg tgc ctg tcg acg ctt gga gcg aca ggg gcg gcc                23982
Val Ser Val Arg Ala Cys Leu Ser Thr Leu Gly Ala Thr Gly Ala Ala
    7920                7925                7930 gtg tgc gtg cgc atc acc gac gac acc ggg gtg ccg gtg gcg tcg gtc                24030
```

-continued

```
Val Cys Val Arg Ile Thr Asp Asp Thr Gly Val Pro Val Ala Ser Val
7935              7940                7945                7950 gat cgt ctt gag ttg cgg cct gtg gat atg ggt cag ttg cgt gct gtc    24078
Asp Arg Leu Glu Leu Arg Pro Val Asp Met Gly Gln Leu Arg Ala Val
         7955                7960                7965 tcg gtt tcg gcg ggg cgg cgg ggt tcg ctg tat gcg gtg cag tgg gct    24126
Ser Val Ser Ala Gly Arg Arg Gly Ser Leu Tyr Ala Val Gln Trp Ala
             7970                7975                7980 gag gtg ggt cct gtg ccg gtg tgt ggg cag gcg tgg gcg tgg cac gag    24174
Glu Val Gly Pro Val Pro Val Cys Gly Gln Ala Trp Ala Trp His Glu
        7985                7990                7995 gac gtg ggt gag agc ggt ggt ggg cct gtg ccg ggg gtg gtg gtg ttg    24222
Asp Val Gly Glu Ser Gly Gly Gly Pro Val Pro Gly Val Val Val Leu
    8000                8005                8010 cgg tgc ccg gat gcc ggt gcc gat ggc ggt ggc ggt ggt gtg ggt        24270
Arg Cys Pro Asp Ala Gly Ala Asp Gly Gly Gly Gly Gly Gly Val Gly
8015                8020                8025                8030 gag gtt gtt ggt ggg gtg ttg ggt gtg gtg cag ggg tgg ctg ggg ctg    24318
Glu Val Val Gly Gly Val Leu Gly Val Val Gln Gly Trp Leu Gly Leu
             8035                8040                8045 gag cgg ttt gcg ggt tcg cgg ctg gtg gtg gtg acc cgg ggt gcg gtg    24366
Glu Arg Phe Ala Gly Ser Arg Leu Val Val Val Thr Arg Gly Ala Val
         8050                8055                8060 gtg gcc ggc ccg gag gac ggc ccg gtg gat gtg gtg ggt gcg gcg gtg    24414
Val Ala Gly Pro Glu Asp Gly Pro Val Asp Val Val Gly Ala Ala Val
     8065                8070                8075 tgg ggg ctg gtg cgg tcg gcg cag gct gag cat ccg gac cgg ttt gtc    24462
Trp Gly Leu Val Arg Ser Ala Gln Ala Glu His Pro Asp Arg Phe Val
 8080                8085                8090 ctc ctc gac ctg gac acc gac ctc gac agc ggc gct gac gcc gat gcc    24510
Leu Leu Asp Leu Asp Thr Asp Leu Asp Ser Gly Ala Asp Ala Asp Ala
8095                8100                8105                8110 ggc aac gag gcc ggt atg ggg tct ggt ctg gat ggt ggg cgt gtg gct    24558
Gly Asn Glu Ala Gly Met Gly Ser Gly Leu Asp Gly Gly Arg Val Ala
             8115                8120                8125 gcg gtg gtg gcg tgt ggt gag ccg cag ttg gcg gtg cgt ggt gag cgg    24606
Ala Val Val Ala Cys Gly Glu Pro Gln Leu Ala Val Arg Gly Glu Arg
         8130                8135                8140 gtg ctg gcc gca cgc ctg aca cga ctt gag tcg ccg gtt gat gta tcg    24654
Val Leu Ala Ala Arg Leu Thr Arg Leu Glu Ser Pro Val Asp Val Ser
     8145                8150                8155 ggt cgg gag gtg ttg ccg tgg ttg tcg ggt ggg tcg gtg ttg gtg acg    24702
Gly Arg Glu Val Leu Pro Trp Leu Ser Gly Gly Ser Val Leu Val Thr
 8160                8165                8170 ggt ggg acg ggt gtg ctg ggt gcg gcg gtg gcg cgg cat ctg gct ggt    24750
Gly Gly Thr Gly Val Leu Gly Ala Ala Val Ala Arg His Leu Ala Gly
8175                8180                8185                8190 gtg tgt ggg gtg cgg gat ctg ttg ttg gtg agc cgg cgt ggt ccg gat    24798
Val Cys Gly Val Arg Asp Leu Leu Leu Val Ser Arg Arg Gly Pro Asp
             8195                8200                8205 gct ccg ggt gcg gag ggt ttg cgg gcg gag ctg gcc gcg ttg ggg gcg    24846
Ala Pro Gly Ala Glu Gly Leu Arg Ala Glu Leu Ala Ala Leu Gly Ala
         8210                8215                8220 gag gtg cgg att gtt gcg tgt gat gtg ggg gag cgg cgg gag gtg gtc    24894
Glu Val Arg Ile Val Ala Cys Asp Val Gly Glu Arg Arg Glu Val Val
     8225                8230                8235 cgg ctg ctg gag ggt gtt cct gcc ggg tgt ccg ctg acg ggt gtc gtg    24942
Arg Leu Leu Glu Gly Val Pro Ala Gly Cys Pro Leu Thr Gly Val Val
 8240                8245                8250
```

-continued

| | |
|---|---|
| cat gcg gct ggt gtg ctg gac gat gcg acg atc gcc tct ctc acg ccc<br>His Ala Ala Gly Val Leu Asp Asp Ala Thr Ile Ala Ser Leu Thr Pro<br>8255                    8260                    8265                    8270 | 24990 |
| gag cgg ctg ggc acg gtg ttc gcg gcc aag gtg gat gcc gct ctt ttg<br>Glu Arg Leu Gly Thr Val Phe Ala Ala Lys Val Asp Ala Ala Leu Leu<br>                  8275                    8280                    8285 | 25038 |
| ctg gat gag ctg acg cgg ggt atg gag ctg tcg gcg ttc gtg ctg ttc<br>Leu Asp Glu Leu Thr Arg Gly Met Glu Leu Ser Ala Phe Val Leu Phe<br>8290                      8295                    8300 | 25086 |
| tcc tcg gcc gcg ggg atc ctg ggg tcg gcc ggg cag ggc aac tac gcc<br>Ser Ser Ala Ala Gly Ile Leu Gly Ser Ala Gly Gln Gly Asn Tyr Ala<br>                  8305                    8310                    8315 | 25134 |
| gcg gcc aat gcc gct ctg gac gcg ctg gcg tac cgg cgg cgg gcg gcg<br>Ala Ala Asn Ala Ala Leu Asp Ala Leu Ala Tyr Arg Arg Arg Ala Ala<br>8320                      8325                    8330 | 25182 |
| ggt ctg ccg ggg gtg tcg ctg gcg tgg ggg ctg tgg gaa gag gcc agc<br>Gly Leu Pro Gly Val Ser Leu Ala Trp Gly Leu Trp Glu Glu Ala Ser<br>8335                      8340                    8345                    8350 | 25230 |
| ggg atg acc ggg cac ctg gcc ggc acc gac cac cgg cgc atc atc cgt<br>Gly Met Thr Gly His Leu Ala Gly Thr Asp His Arg Arg Ile Ile Arg<br>                  8355                    8360                    8365 | 25278 |
| tcc ggt ctg cat ccc atg tcg acc ccg gac gca ctg gct ctc ttc gat<br>Ser Gly Leu His Pro Met Ser Thr Pro Asp Ala Leu Ala Leu Phe Asp<br>8370                      8375                    8380 | 25326 |
| gcg gcc ctg gct ctg gac cgg ccg gtc ctg ctg ccc gcc gac ctg cgt<br>Ala Ala Leu Ala Leu Asp Arg Pro Val Leu Leu Pro Ala Asp Leu Arg<br>8385                      8390                    8395 | 25374 |
| ccc gcc ccg ccc ctg ccg ccc ctg ctg cag gac ctc ctg ccc gcc acc<br>Pro Ala Pro Pro Leu Pro Pro Leu Leu Gln Asp Leu Leu Pro Ala Thr<br>                  8400                    8405                    8410 | 25422 |
| cgc cgc cgc acc acc cgc acc acc act acc ggt ggt gcg gac aac ggc<br>Arg Arg Arg Thr Thr Arg Thr Thr Thr Gly Gly Ala Asp Asn Gly<br>8415                      8420                    8425                    8430 | 25470 |
| gcc cag ctg cat gcc cgg ctg gcc ggc cag aca cac gaa caa cag cac<br>Ala Gln Leu His Ala Arg Leu Ala Gly Gln Thr His Glu Gln Gln His<br>                  8435                    8440                    8445 | 25518 |
| acc acc ctc ctc gcc ctg gtc cgc tcc cac atc gcc acc gtc ctc ggc<br>Thr Thr Leu Leu Ala Leu Val Arg Ser His Ile Ala Thr Val Leu Gly<br>8450                      8455                    8460 | 25566 |
| cac aac gcg ccg gag atg atc ccc gtt gac tcg gcg ttc cgc gac cta<br>His Asn Ala Pro Glu Met Ile Pro Val Asp Ser Ala Phe Arg Asp Leu<br>8465                      8470                    8475 | 25614 |
| ggc ttc gac tcc ttg aca gcg gtg gaa ctc cgt aac cgc ctg ggt gag<br>Gly Phe Asp Ser Leu Thr Ala Val Glu Leu Arg Asn Arg Leu Gly Glu<br>8480                      8485                    8490 | 25662 |
| gca acg gga ctg cga ctg ccg acc agt ctg gtc ttc gac cag ccg aat<br>Ala Thr Gly Leu Arg Leu Pro Thr Ser Leu Val Phe Asp Gln Pro Asn<br>8495                      8500                    8505                    8510 | 25710 |
| gca gcg acc ctg gcg cgt cac cta cgt cgt gag ctg atg ggc gac gac<br>Ala Ala Thr Leu Ala Arg His Leu Arg Arg Glu Leu Met Gly Asp Asp<br>                  8515                    8520                    8525 | 25758 |
| gcg gaa ggc gag acg cca tcg cag gtc gca ctt cat cag gtt gcc gcg<br>Ala Glu Gly Glu Thr Pro Ser Gln Val Ala Leu His Gln Val Ala Ala<br>8530                      8535                    8540 | 25806 |
| gat gag ccg att gcg att gtg ggg atg gcg tgt cgt ttt ccg ggt ggg<br>Asp Glu Pro Ile Ala Ile Val Gly Met Ala Cys Arg Phe Pro Gly Gly<br>8545                      8550                    8555 | 25854 |
| gtg tgt tcg ccg gag gag ttg tgg gag ctg gtt gcg tcg ggt ggg gat<br>Val Cys Ser Pro Glu Glu Leu Trp Glu Leu Val Ala Ser Gly Gly Asp<br>                  8560                    8565                    8570 | 25902 |

```
                                                  -continued gcg att ggt gaa ttt ccg gcc ggt cgg ggg tgg gat ctg gag ggg ttg     25950
Ala Ile Gly Glu Phe Pro Ala Gly Arg Gly Trp Asp Leu Glu Gly Leu
8575             8580                8585                8590 ttt gat tcg gac cct gac cgg tcg ggg acg tcg tac gcg cgg tat ggc     25998
Phe Asp Ser Asp Pro Asp Arg Ser Gly Thr Ser Tyr Ala Arg Tyr Gly
             8595                8600                8605 ggg ttt ttg tat gag gcg ggg gag ttc gat gcg gac ttc ttc ggg atc     26046
Gly Phe Leu Tyr Glu Ala Gly Glu Phe Asp Ala Asp Phe Phe Gly Ile
         8610                8615                8620 agt ccg cgt gag gcg ttg gcg atg gat ccg cag cag cgg ttg ttg ctg     26094
Ser Pro Arg Glu Ala Leu Ala Met Asp Pro Gln Gln Arg Leu Leu Leu
     8625                8630                8635 gag acg tcg tgg gag gcg ttc gag cgg gcg ggt atc gat ccg ctg tcg     26142
Glu Thr Ser Trp Glu Ala Phe Glu Arg Ala Gly Ile Asp Pro Leu Ser
 8640                8645                8650 atg cgt ggc tcc cgt acg ggt gtc ttc gcc ggg gtg atg tac cac gac     26190
Met Arg Gly Ser Arg Thr Gly Val Phe Ala Gly Val Met Tyr His Asp
8655             8660                8665                8670 tac gcc gcg cgt ctc cac cat gtc ccc gag ggt ttc gaa ggc ctc atc     26238
Tyr Ala Ala Arg Leu His His Val Pro Glu Gly Phe Glu Gly Leu Ile
             8675                8680                8685 gcc aac ggc agc gca ggc agc gtc gcg acc ggc cgg gtg gcc tac agc     26286
Ala Asn Gly Ser Ala Gly Ser Val Ala Thr Gly Arg Val Ala Tyr Ser
         8690                8695                8700 ttt ggc ctt gag ggt ccg gcc gtg acc gtc gat acg gcg tgt tcg tcg     26334
Phe Gly Leu Glu Gly Pro Ala Val Thr Val Asp Thr Ala Cys Ser Ser
     8705                8710                8715 tcg ttg gtg gcg ttg cat tgg gcg gcg cag gcg ttg cgt gcg ggt gag     26382
Ser Leu Val Ala Leu His Trp Ala Ala Gln Ala Leu Arg Ala Gly Glu
 8720                8725                8730 tgt tcg atg gcg ctt gcc ggg ggt gtg acg gtg atg tcg tct ccg ggt     26430
Cys Ser Met Ala Leu Ala Gly Gly Val Thr Val Met Ser Ser Pro Gly
8735             8740                8745                8750 acg ttt gtg gag ttc tca cgt cag cgg ggt ctg gcc gcg gac ggg cgg     26478
Thr Phe Val Glu Phe Ser Arg Gln Arg Gly Leu Ala Ala Asp Gly Arg
             8755                8760                8765 tgc aag gcc tat tcg gcg gct gct gac ggt acc ggc tgg gcc gag ggt     26526
Cys Lys Ala Tyr Ser Ala Ala Ala Asp Gly Thr Gly Trp Ala Glu Gly
         8770                8775                8780 gtg ggg atg ctg ctg gtg gag cgg ctc tcc gac gcc cgt cgc aac ggt     26574
Val Gly Met Leu Leu Val Glu Arg Leu Ser Asp Ala Arg Arg Asn Gly
     8785                8790                8795 cac cgt gtc ctg gcc gtg gtg cgt ggc agt gcg gtc aac cag gac ggt     26622
His Arg Val Leu Ala Val Val Arg Gly Ser Ala Val Asn Gln Asp Gly
 8800                8805                8810 gcg agc aac ggt ctg acc gcg ccc aac ggg ccc tcc cag cag cgt gtc     26670
Ala Ser Asn Gly Leu Thr Ala Pro Asn Gly Pro Ser Gln Gln Arg Val
8815             8820                8825                8830 atc cgt cag gcc ctg gcc aat gcg gga ctg acc ccg gcc gat gtc gac     26718
Ile Arg Gln Ala Leu Ala Asn Ala Gly Leu Thr Pro Ala Asp Val Asp
             8835                8840                8845 gca gtg gag ggc cac ggc acc ggg acc act ctg ggg gac ccg atc gag     26766
Ala Val Glu Gly His Gly Thr Gly Thr Thr Leu Gly Asp Pro Ile Glu
         8850                8855                8860 gcc cag gca ctc ctg gcc gcc tac gga caa cac cgc ccc cac cac cgc     26814
Ala Gln Ala Leu Leu Ala Ala Tyr Gly Gln His Arg Pro His His Arg
     8865                8870                8875 ccc ttg tgg ctg gga tcc ctc aaa tcc aac atc ggg cac gca cag gcc     26862
Pro Leu Trp Leu Gly Ser Leu Lys Ser Asn Ile Gly His Ala Gln Ala
```

```
                                                        -continued
     8880              8885              8890 gcc gcg ggc gtg ggc gga gtc atc aag atg gtg atg gcc ctg cgc aac    26910
Ala Ala Gly Val Gly Gly Val Ile Lys Met Val Met Ala Leu Arg Asn
8895              8900              8905              8910 ggg ctg ctg cca cag acc ctc cac gtg gac gag ccc acc ccc cag gtc    26958
Gly Leu Leu Pro Gln Thr Leu His Val Asp Glu Pro Thr Pro Gln Val
        8915              8920              8925 gac tgg tcc aca ggc gca gta caa ctc ctg aca caa ccg gtc ccc tgg    27006
Asp Trp Ser Thr Gly Ala Val Gln Leu Leu Thr Gln Pro Val Pro Trp
            8930              8935              8940 ccc gcc gac ccg gcc ggc cgg cca cgc cac gcc ggc gtg tca tca ttc    27054
Pro Ala Asp Pro Ala Gly Arg Pro Arg His Ala Gly Val Ser Ser Phe
        8945              8950              8955 ggc gtc agc ggc acc aac gcc cat gtg att ttg gag gag gcg cct gcg    27102
Gly Val Ser Gly Thr Asn Ala His Val Ile Leu Glu Glu Ala Pro Ala
        8960              8965              8970 gcg gcg ggc ggt gct gcc ggt ggt ggg gtg tcg gtg ggt gct ccg aat    27150
Ala Ala Gly Gly Ala Ala Gly Gly Gly Val Ser Val Gly Ala Pro Asn
8975              8980              8985              8990 cca gcc ctt ccg gtg gct gag tct gag ccg gtg ccg gtg ccg gtg ccg    27198
Pro Ala Leu Pro Val Ala Glu Ser Glu Pro Val Pro Val Pro Val Pro
            8995              9000              9005 gtg tcg gcg agg tct gag gcc ggg ttg cgg gcg cag gca cag gcg ttg    27246
Val Ser Ala Arg Ser Glu Ala Gly Leu Arg Ala Gln Ala Gln Ala Leu
                9010              9015              9020 cgc cag tac gtg gca gcc cgc ccg gac atg tca cct gcc gac atc ggt    27294
Arg Gln Tyr Val Ala Ala Arg Pro Asp Met Ser Pro Ala Asp Ile Gly
        9025              9030              9035 gcg ggt ctg gcc cgc ggc cgg gcc gta ctg gaa cac cgc gcc gtc atc    27342
Ala Gly Leu Ala Arg Gly Arg Ala Val Leu Glu His Arg Ala Val Ile
        9040              9045              9050 ctg gcc gcg gac cgc gag gaa ctg gcg cag gca ctg aca gcc ctg gca    27390
Leu Ala Ala Asp Arg Glu Glu Leu Ala Gln Ala Leu Thr Ala Leu Ala
9055              9060              9065              9070 gcc ggc gaa ccc cac ccc cac atc acc aca ggc cac acc cgg ggc agt    27438
Ala Gly Glu Pro His Pro His Ile Thr Thr Gly His Thr Arg Gly Ser
            9075              9080              9085 gac cgc ggc ggc gtc gtc ttc gtc ttc ccc gga cag ggc ggc cag tgg    27486
Asp Arg Gly Gly Val Val Phe Val Phe Pro Gly Gln Gly Gly Gln Trp
        9090              9095              9100 gcc ggg atg ggc ctg acc ctg ctc acc tcc tca ccc gtg ttc gcc gaa    27534
Ala Gly Met Gly Leu Thr Leu Leu Thr Ser Ser Pro Val Phe Ala Glu
        9105              9110              9115 cac atc gac gca tgc gag aaa gcc ctc acc ccc tgg gtg ccc tgg tcc    27582
His Ile Asp Ala Cys Glu Lys Ala Leu Thr Pro Trp Val Pro Trp Ser
9120              9125              9130 ctg acc gac atc ctg cac cgc gac ccc gac gac ccc gca tgg caa caa    27630
Leu Thr Asp Ile Leu His Arg Asp Pro Asp Asp Pro Ala Trp Gln Gln
9135              9140              9145              9150 gcc gac gtg gtc cag ccc gtg ctc ttc agc atc atg gtc tcc ctc gcc    27678
Ala Asp Val Val Gln Pro Val Leu Phe Ser Ile Met Val Ser Leu Ala
            9155              9160              9165 gcc ctg tgg cgc tcc tac ggc atc gaa ccc gac gcg gtc ctc ggc cac    27726
Ala Leu Trp Arg Ser Tyr Gly Ile Glu Pro Asp Ala Val Leu Gly His
        9170              9175              9180 tcc cag gga gaa atc gcc gcc gcc cac atc tgc ggc gca ctc agc ctg    27774
Ser Gln Gly Glu Ile Ala Ala Ala His Ile Cys Gly Ala Leu Ser Leu
        9185              9190              9195 aaa gac gcc gcc aaa acc gtt gca ctg cgc agc cag gca ctg gcc gcc    27822
```

```
                              -continued

Lys Asp Ala Ala Lys Thr Val Ala Leu Arg Ser Gln Ala Leu Ala Ala
    9200                9205                9210 gta cga ggc cgg ggc gcc atg gtc tca ctg ccc ctg ccc gcc cag gac      27870
Val Arg Gly Arg Gly Ala Met Val Ser Leu Pro Leu Pro Ala Gln Asp
9215                9220                9225                9230 gtg cag cag ctc att tcc gaa cgg tgg gaa ggg cag ttg tgg gtg gca      27918
Val Gln Gln Leu Ile Ser Glu Arg Trp Glu Gly Gln Leu Trp Val Ala
        9235                9240                9245 gcc ctc aac ggc ccc cac tcc acc acc gtc tcc ggc gac acc acc gca      27966
Ala Leu Asn Gly Pro His Ser Thr Thr Val Ser Gly Asp Thr Thr Ala
            9250                9255                9260 gta gaa gaa ctc ctc acc cac tgt gcc gac acc ggc cta cgg gcc aaa      28014
Val Glu Glu Leu Leu Thr His Cys Ala Asp Thr Gly Leu Arg Ala Lys
                9265                9270                9275 cgc atc ccc gtc gac tac gcc tcc cac tgc ccc cac gtc caa ccc ctc      28062
Arg Ile Pro Val Asp Tyr Ala Ser His Cys Pro His Val Gln Pro Leu
    9280                9285                9290 cac gac gaa ctc ctg cac ctg ctg gga gac atc acc ccc cag ccg tcc      28110
His Asp Glu Leu Leu His Leu Leu Gly Asp Ile Thr Pro Gln Pro Ser
9295                9300                9305                9310 acc atg ccg ttc ttc tcc acc gtc gta ggg cac ctg gtc tgg tac acc      28158
Thr Met Pro Phe Phe Ser Thr Val Val Gly His Leu Val Trp Tyr Thr
        9315                9320                9325 aca acc ctg gac gcc gcc tac tgg tac cgc aac ctc cac cag ccc gtc      28206
Thr Thr Leu Asp Ala Ala Tyr Trp Tyr Arg Asn Leu His Gln Pro Val
            9330                9335                9340 cgc ttc agc cac gcc atc cag acc ctg acc gac gac gga cac cgc ccc      28254
Arg Phe Ser His Ala Ile Gln Thr Leu Thr Asp Asp Gly His Arg Pro
                9345                9350                9355 ttc atc gaa atc agt ccc cac ccc acc ctc gtc ccc gcc atc gaa gac      28302
Phe Ile Glu Ile Ser Pro His Pro Thr Leu Val Pro Ala Ile Glu Asa
    9360                9365                9370 acc acc gaa aac acc acc gaa aac atc acc gcg acc ggc agc ctc cgc      28350
Thr Thr Glu Asn Thr Thr Glu Asn Ile Thr Ala Thr Gly Ser Leu Arg
9375                9380                9385                9390 cgc ggc gac aac gac acc cac cgc ttc ctc acc gcc ctc gcc cac acc      28398
Arg Gly Asp Asn Asp Thr His Arg Phe Leu Thr Ala Leu Ala His Thr
        9395                9400                9405 cac acc acc ggc att cgg aca ccc acc acc tgg cac cac cac tac acc      28446
His Thr Thr Gly Ile Arg Thr Pro Thr Thr Trp His His His Tyr Thr
            9410                9415                9420 caa acc cac ccc cac ccc cac aac cac cac ctc gac ctg ccc acc tac      28494
Gln Thr His Pro His Pro His Asn His His Leu Asp Leu Pro Thr Tyr
                9425                9430                9435 ccc ttc caa cac cag cac tac tgg ctc caa cca ccc acc acg aca acc      28542
Pro Phe Gln His Gln His Tyr Trp Leu Gln Pro Pro Thr Thr Thr Thr
    9440                9445                9450 gac ctc acc acc acc ggc ctc acc ccc acc cac cac ccc ctc ctc acc      28590
Asp Leu Thr Thr Thr Gly Leu Thr Pro Thr His His Pro Leu Leu Thr
9455                9460                9465                9470 gca aca ctc acc ctc gcc aac aac aac aca caa cta ctc acc ggc cgc      28638
Ala Thr Leu Thr Leu Ala Asn Asn Asn Thr Gln Leu Leu Thr Gly Arg
        9475                9480                9485 ctc tcc cta cgc acc cac ccc tgg ctc acc gac cac acc gtc gtc ggt      28686
Leu Ser Leu Arg Thr His Pro Trp Leu Thr Asp His Thr Val Val Gly
            9490                9495                9500 acc act ctt gtg cca gga acc gcc ctc ctc gaa ctc gcc ctc caa gca      28734
Thr Thr Leu Val Pro Gly Thr Ala Leu Leu Glu Leu Ala Leu Gln Ala
                9505                9510                9515
```

-continued

| | |
|---|---|
| acc acg acc gac cac ctc gaa gaa ctc gcc ctc cac acg cct ctc gtc<br>Thr Thr Thr Asp His Leu Glu Glu Leu Ala Leu His Thr Pro Leu Val<br>              9520                    9525                 9530 | 28782 |
| atc ccc cgt gag ggt gcc gtc gac gtt cag gtg cac atc aat cca ccg<br>Ile Pro Arg Glu Gly Ala Val Asp Val Gln Val His Ile Asn Pro Pro<br>9535                    9540                 9545                 9550 | 28830 |
| gac gac acc gac act cgt tca ctg acg atc tac tcg cga agc gag aac<br>Asp Asp Thr Asp Thr Arg Ser Leu Thr Ile Tyr Ser Arg Ser Glu Asn<br>              9555                    9560                 9565 | 28878 |
| gcc ccc gca gcg gct ccc tgg cgt cat cac gcc acg gcc gtt ctg gga<br>Ala Pro Ala Ala Ala Pro Trp Arg His His Ala Thr Ala Val Leu Gly<br>              9570                    9575                 9580 | 28926 |
| acc aag acc tcg cgc att gag aca ggc cgt agc cac gat gat ctg tcg<br>Thr Lys Thr Ser Arg Ile Glu Thr Gly Arg Ser His Asp Asp Leu Ser<br>9585                    9590                 9595 | 28974 |
| atg tgg ccg cca gcg ggc gca gtt cgc tgt gct gat gag gaa ttg gca<br>Met Trp Pro Pro Ala Gly Ala Val Arg Cys Ala Asp Glu Glu Leu Ala<br>9600                    9605                 9610 | 29022 |
| gcc ttg tat ggc gac tac gag gca aat ggc ttt gtc tat ggc ccc gca<br>Ala Leu Tyr Gly Asp Tyr Glu Ala Asn Gly Phe Val Tyr Gly Pro Ala<br>9615                    9620                 9625                 9630 | 29070 |
| ttc cgg ggg ctg act gct gcc tgg cgt ctg gga gac gag gtg ttt gcc<br>Phe Arg Gly Leu Thr Ala Ala Trp Arg Leu Gly Asp Glu Val Phe Ala<br>              9635                    9640                 9645 | 29118 |
| gag gtt cgc ctt cca gaa cag gtg cac ggc gag gca tcc gcg tac aac<br>Glu Val Arg Leu Pro Glu Gln Val His Gly Glu Ala Ser Ala Tyr Asn<br>              9650                    9655                 9660 | 29166 |
| ctg cac ccg gca ctg ctg gat gct gcc ttg cac gca gcg gcc ttt gcg<br>Leu His Pro Ala Leu Leu Asp Ala Ala Leu His Ala Ala Ala Phe Ala<br>              9665                    9670                 9675 | 29214 |
| ccg tcg ggc agt ctg ccg cag gga tcc gta ccg ttc tcc ttc acc ggt<br>Pro Ser Gly Ser Leu Pro Gln Gly Ser Val Pro Phe Ser Phe Thr Gly<br>9680                    9685                 9690 | 29262 |
| gtg acg ctg cac gcc gcc aat gcg tcg tcg ttg cgc gtg cga ctc tcg<br>Val Thr Leu His Ala Ala Asn Ala Ser Ser Leu Arg Val Arg Leu Ser<br>9695                    9700                 9705                 9710 | 29310 |
| ccg gcc gat ccg aac agc ggc cac gcc gca gtt tcc gtg ctg gtc acg<br>Pro Ala Asp Pro Asn Ser Gly His Ala Ala Val Ser Val Leu Val Thr<br>              9715                    9720                 9725 | 29358 |
| gat gac acc ggt acg ccc gtg gcg tcc gtc gag gcg ttg gcg gtg cgc<br>Asp Asp Thr Gly Thr Pro Val Ala Ser Val Glu Ala Leu Ala Val Arg<br>              9730                    9735                 9740 | 29406 |
| ccg ttg gcg gcg gac gaa ttg cga gct gcc gag cgc gcc gta cag cgc<br>Pro Leu Ala Ala Asp Glu Leu Arg Ala Ala Glu Arg Ala Val Gln Arg<br>9745                    9750                 9755 | 29454 |
| gct gag ctc ttc gac atg aag tgg gtt gag gtg ccc tca gat gta ctg<br>Ala Glu Leu Phe Asp Met Lys Trp Val Glu Val Pro Ser Asp Val Leu<br>              9760                    9765                 9770 | 29502 |
| gtg tcg ggc ggg gca tcg gtg gtg gtg ctg gat ggt gcc gac gac ctc<br>Val Ser Gly Gly Ala Ser Val Val Val Leu Asp Gly Ala Asp Asp Leu<br>9775                    9780                 9785                 9790 | 29550 |
| gtt ggt ctg gcg gct gag gag gat ggt gtg ccg ggg gtg gtg gtg ttg<br>Val Gly Leu Ala Ala Glu Glu Asp Gly Val Pro Gly Val Val Val Leu<br>              9795                    9800                 9805 | 29598 |
| cgg tgc ccg gat gcc ggt gcc gat ggc ggc ggt ggt ggc ggt ggt gtg<br>Arg Cys Pro Asp Ala Gly Ala Asp Gly Gly Gly Gly Gly Gly Gly Val<br>              9810                    9815                 9820 | 29646 |
| ggt gag gtt gtt ggt ggg gtg ttg ggt gtg gtg cag ggg tgg ctg ggg<br>Gly Glu Val Val Gly Gly Val Leu Gly Val Val Gln Gly Trp Leu Gly<br>9825                    9830                 9835 | 29694 |

-continued

```
ctg gag cgg ttt gcg ggt tcg cgg ctg gtg gtg gtg acc cgg ggt gcg        29742
Leu Glu Arg Phe Ala Gly Ser Arg Leu Val Val Val Thr Arg Gly Ala
    9840            9845                9850 gtg gtg gcc ggc ccg gag gac ggc ccg gtg gat ggc ccg gtg gat gtg        29790
Val Val Ala Gly Pro Glu Asp Gly Pro Val Asp Gly Pro Val Asp Val
9855                9860                9865                9870 gtg ggt gcg gcg gtg tgg ggg ctg gtg cgg tcg gcg cag gct gag cat        29838
Val Gly Ala Ala Val Trp Gly Leu Val Arg Ser Ala Gln Ala Glu His
        9875                9880                9885 ccg gac cgg ttt gtc ctc ctc gac ctg gac acc gac ctc gac agc ggc        29886
Pro Asp Arg Phe Val Leu Leu Asp Leu Asp Thr Asp Leu Asp Ser Gly
            9890                9895                9900 gct gac cgc gat gcc ggc aac gag gcc ggt atg ggg tct ggt ctg gat        29934
Ala Asp Arg Asp Ala Gly Asn Glu Ala Gly Met Gly Ser Gly Leu Asp
                9905                9910                9915 ggt ggg cgt gtg gct gcg gtg gtg gcg tgt ggt gag ccg cag ttg gcg        29982
Gly Gly Arg Val Ala Ala Val Val Ala Cys Gly Glu Pro Gln Leu Ala
    9920                9925                9930 gtg cgt ggt gag cgg gtg ctg gcc gca cgc ctg aca cga ctt gag tcg        30030
Val Arg Gly Glu Arg Val Leu Ala Ala Arg Leu Thr Arg Leu Glu Ser
9935                9940                9945                9950 ccg gtt gat gta tcg ggt cgg gag gtg ttg ccg tgg ttg tcg ggt ggg        30078
Pro Val Asp Val Ser Gly Arg Glu Val Leu Pro Trp Leu Ser Gly Gly
        9955                9960                9965 tcg gtg ttg gtg acg ggt ggg acg ggt gtg ctg ggt gcg gcg gtg gcg        30126
Ser Val Leu Val Thr Gly Gly Thr Gly Val Leu Gly Ala Ala Val Ala
            9970                9975                9980 cgg cat ctg gct ggt gtg tgt ggg gtg cgg gat ctg ttg ttg gtg agc        30174
Arg His Leu Ala Gly Val Cys Gly Val Arg Asp Leu Leu Leu Val Ser
                9985                9990                9995 cgg cgt ggt ccg gat gct ccg ggt gcg gag ggt ttg cgg gcg gag ctg        30222
Arg Arg Gly Pro Asp Ala Pro Gly Ala Glu Gly Leu Arg Ala Glu Leu
    10000               10005               10010 gcc gcg ttg ggg gcg gag gtg cgg att gtt gcg tgt gat gtg ggg gag        30270
Ala Ala Leu Gly Ala Glu Val Arg Ile Val Ala Cys Asp Val Gly Glu
10015               10020               10025               10030 cgg cgg gag gtg gtc cgg ctg ctg gag ggt gtt cct gcc ggg tgt ccg        30318
Arg Arg Glu Val Val Arg Leu Leu Glu Gly Val Pro Ala Gly Cys Pro
        10035               10040               10045 ctg acg ggt gtc gtg cat gcg gct ggt gtg ctg gac gat gcg acg atc        30366
Leu Thr Gly Val Val His Ala Ala Gly Val Leu Asp Asp Ala Thr Ile
            10050               10055               10060 gcc tct ctc acg ccc gag cgg ctg ggc acg gtg ttc gcg gcc aag gtg        30414
Ala Ser Leu Thr Pro Glu Arg Leu Gly Thr Val Phe Ala Ala Lys Val
                10065               10070               10075 gat gcc gct ctt ttg ctg gat gag ctg acg cgg ggt atg gag ctg tcg        30462
Asp Ala Ala Leu Leu Leu Asp Glu Leu Thr Arg Gly Met Glu Leu Ser
    10080               10085               10090 gcg ttc gtg ctg ttc tcc tcg gcc gcg ggg atc ctg ggg tcg gcc ggg        30510
Ala Phe Val Leu Phe Ser Ser Ala Ala Gly Ile Leu Gly Ser Ala Gly
10095               10100               10105               10110 cag ggc aac tac gcc gcg gcc aat gcc gct ctg gac gcg ctg gcg tac        30558
Gln Gly Asn Tyr Ala Ala Ala Asn Ala Ala Leu Asp Ala Leu Ala Tyr
        10115               10120               10125 cgg cgg cgg gcg gcg ggt ctg ccg ggg gtg tcg ctg gcg tgg ggg ctg        30606
Arg Arg Arg Ala Ala Gly Leu Pro Gly Val Ser Leu Ala Trp Gly Leu
            10130               10135               10140 tgg gaa gag gcc agc ggg atg acc ggg cat ctg gcc ggc acc gac cac        30654
Trp Glu Glu Ala Ser Gly Met Thr Gly His Leu Ala Gly Thr Asp His
```

```
cgg cgc atc atc cgt tcc ggt ctg cat ccc atg tcg acc ccg gac gca      30702
Arg Arg Ile Ile Arg Ser Gly Leu His Pro Met Ser Thr Pro Asp Ala
    10160           10165               10170 ctg gcc ctc ttc gat gcg gcc ctg gct ctg gac cgg ccg gtc ctg ctg      30750
Leu Ala Leu Phe Asp Ala Ala Leu Ala Leu Asp Arg Pro Val Leu Leu
10175           10180            10185               10190 ccc gcc gac ctg cgt ccc gcc ccg ccc ctg ccg ccc ctg ctg cag gac      30798
Pro Ala Asp Leu Arg Pro Ala Pro Pro Leu Pro Pro Leu Leu Gln Asp
            10195            10200               10205 ctc ctg ccc gcc acc cgc cgc gcc acc acc cgc acc acc act acc ggt      30846
Leu Leu Pro Ala Thr Arg Arg Arg Thr Thr Arg Thr Thr Thr Thr Gly
        10210            10215                10220 ggt gcg gac aac ggc gcc cag ctg cac ggc cgg ctg gcc ggc cag aca      30894
Gly Ala Asp Asn Gly Ala Gln Leu His Gly Arg Leu Ala Gly Gln Thr
    10225            10230               10235 cac gaa caa cag cac acc acc ctc ctc gcc ctg gtc cgc tcc cac atc      30942
His Glu Gln Gln His Thr Thr Leu Leu Ala Leu Val Arg Ser His Ile
    10240            10245               10250 gcc acc gtc ctg ggc cac acc acc ccc gac acc atc ccc ccc gac cgc      30990
Ala Thr Val Leu Gly His Thr Thr Pro Asp Thr Ile Pro Pro Asp Arg
10255           10260            10265                10270 gcg ttc cgc gac ctc ggc ttc gac tcc ctc acc gcc gtc gaa cta cgc      31038
Ala Phe Arg Asp Leu Gly Phe Asp Ser Leu Thr Ala Val Glu Leu Arg
            10275            10280               10285 aac cgg ctc tcc cac acc acc gga ctc cgc ctc ccc acc acc ctc gcc      31086
Asn Arg Leu Ser His Thr Thr Gly Leu Arg Leu Pro Thr Thr Leu Ala
        10290            10295               10300 ttc gac cac ccc aac ccc acc acc ctc acc cac cac ctc cac aca caa      31134
Phe Asp His Pro Asn Pro Thr Thr Leu Thr His His Leu His Thr Gln
    10305            10310               10315 ctc gtc agc aag gga ctc acc gcc gcg gcc gag ccg gac gcc gca acg      31182
Leu Val Ser Lys Gly Leu Thr Ala Ala Ala Glu Pro Asp Ala Ala Thr
    10320            10325               10330 aca ccc ccg ggg ctg ccc tcg ctg ctc tcg gag ctc gag cgg ctg gag      31230
Thr Pro Pro Gly Leu Pro Ser Leu Leu Ser Glu Leu Glu Arg Leu Glu
10335           10340            10345               10350 gcg gta gtg ctc tcc tcc acc aca tcc tcc gct gcc ccg ctg gac gac      31278
Ala Val Val Leu Ser Ser Thr Thr Ser Ser Ala Ala Pro Leu Asp Asp
            10355            10360               10365 ggc gcg cgc acg cgg ctg gcc tcc cga ctg cat tcc ctc gcc cag aag      31326
Gly Ala Arg Thr Arg Leu Ala Ser Arg Leu His Ser Leu Ala Gln Lys
        10370            10375               10380 ttg aac ggc gac gac acc gcc ccc gac ctc gca gag aca tcg gac gag      31374
Leu Asn Gly Asp Asp Thr Ala Pro Asp Leu Ala Glu Thr Ser Asp Glu
    10385            10390               10395 gag atg ttc gct ctc atc gac agg gaa gtc gga ttc gaa tct caa tga      31422
Glu Met Phe Ala Leu Ile Asp Arg Glu Val Gly Phe Glu Ser Gln
    10400            10405               10410

<210> SEQ ID NO 3
<211> LENGTH: 3972
<212> TYPE: PRT
<213> ORGANISM: Streptomyces avermitilis

<400> SEQUENCE: 3

Val Gln Arg Met Asp Gly Gly Glu Pro Arg Pro Ala Ala Gly Glu
1               5                   10                  15

Val Leu Gly Val Ala Asp Glu Ala Asp Gly Gly Val Val Phe Val Phe
            20                  25                  30
```

-continued

```
Pro Gly Gln Gly Pro Gln Trp Pro Gly Met Gly Arg Glu Leu Leu Asp
         35                  40                  45

Ala Ser Asp Val Phe Arg Glu Ser Val Arg Ala Cys Glu Ala Ala Phe
     50                  55                  60

Ala Pro Tyr Val Asp Trp Ser Val Glu Gln Val Leu Arg Asp Ser Pro
 65                  70                  75                  80

Asp Ala Pro Gly Leu Asp Arg Val Asp Val Gln Pro Thr Leu Phe
                 85                  90                  95

Ala Val Met Ile Ser Leu Ala Ala Leu Trp Arg Ser Gln Gly Val Glu
             100                 105                 110

Pro Cys Ala Val Leu Gly His Ser Leu Gly Glu Ile Ala Ala His
             115                 120                 125

Val Ser Gly Gly Leu Ser Leu Ala Asp Ala Ala Arg Val Val Thr Leu
         130                 135                 140

Trp Ser Gln Ala Gln Thr Thr Leu Ala Gly Thr Gly Ala Leu Val Ser
145                 150                 155                 160

Val Ala Ala Thr Pro Asp Glu Leu Leu Pro Arg Ile Ala Pro Trp Thr
                 165                 170                 175

Glu Asp Asn Pro Ala Arg Leu Ala Val Ala Ala Val Asn Gly Pro Arg
                 180                 185                 190

Ser Thr Val Val Ser Gly Ala Arg Glu Ala Val Ala Asp Leu Val Ala
             195                 200                 205

Asp Leu Thr Ala Ala Gln Val Arg Thr Arg Met Ile Pro Val Asp Val
         210                 215                 220

Pro Ala His Ser Pro Leu Met Tyr Ala Ile Glu Glu Arg Val Val Ser
225                 230                 235                 240

Gly Leu Leu Pro Ile Thr Pro Arg Pro Ser Arg Ile Pro Phe His Ser
                 245                 250                 255

Ser Val Thr Gly Gly Arg Leu Asp Thr Arg Glu Leu Asp Ala Ala Tyr
             260                 265                 270

Trp Tyr Arg Asn Met Ser Ser Thr Val Arg Phe Glu Pro Ala Ala Arg
         275                 280                 285

Leu Leu Leu Gln Gln Gly Pro Lys Thr Phe Val Glu Met Ser Pro His
     290                 295                 300

Pro Val Leu Thr Met Gly Leu Gln Glu Leu Ala Pro Asp Leu Gly Asp
305                 310                 315                 320

Thr Thr Gly Thr Ala Asp Thr Val Ile Met Gly Thr Leu Arg Arg Gly
                 325                 330                 335

Gln Gly Thr Leu Asp His Phe Leu Thr Ser Leu Ala Gln Leu Arg Gly
             340                 345                 350

His Gly Glu Thr Ser Ala Thr Thr Val Leu Ser Ala Arg Leu Thr Ala
         355                 360                 365

Leu Ser Pro Thr Gln Gln Gln Ser Leu Leu Asp Leu Val Arg Ala
     370                 375                 380

His Thr Met Ala Val Leu Asn Asp Asp Gly Asn Glu Arg Thr Ala Ser
385                 390                 395                 400

Asp Ala Gly Pro Ser Ala Ser Phe Ala His Leu Gly Phe Asp Ser Val
                 405                 410                 415

Met Gly Val Glu Leu Arg Asn Arg Leu Ser Lys Ala Thr Gly Leu Arg
                 420                 425                 430

Leu Pro Val Thr Leu Ile Phe Asp His Thr Thr Pro Ala Ala Val Ala
             435                 440                 445
```

```
Ala Arg Leu Arg Thr Ala Ala Leu Gly His Leu Asp Glu Asp Thr Ala
    450                 455                 460
Pro Val Pro Asp Ser Pro Ser Gly His Gly Gly Thr Ala Ala Ala Asp
465                 470                 475                 480
Asp Pro Ile Ala Ile Ile Gly Met Ala Cys Arg Phe Pro Gly Gly Val
                485                 490                 495
Arg Ser Pro Lys Asp Leu Trp Glu Leu Ala Ala Ser Gly Gly Asp Ala
            500                 505                 510
Ile Gly Pro Phe Pro Thr Asp Arg Gly Trp Pro Thr Glu Gln Arg His
        515                 520                 525
Ala Gln Asp Pro Thr Gln Pro Gly Thr Phe Tyr Pro Gln Gly Gly Gly
    530                 535                 540
Phe Leu His Asp Ala Ala His Phe Asp Ala Gly Phe Phe Gly Ile Ser
545                 550                 555                 560
Pro Arg Glu Ala Leu Ala Met Asp Pro Gln Gln Arg Leu Leu Leu Glu
                565                 570                 575
Thr Ser Trp Glu Ala Phe Glu Arg Ala Gly Ile Asp Pro Leu Ser Val
            580                 585                 590
Arg Gly Ser Arg Thr Gly Val Phe Ala Gly Ala Leu Ser Phe Asp Tyr
        595                 600                 605
Gly Pro Arg Met Asp Thr Ala Ser Ser Glu Gly Ala Ala Asp Val Glu
    610                 615                 620
Gly His Ile Leu Thr Gly Thr Thr Gly Ser Val Leu Ser Gly Arg Ile
625                 630                 635                 640
Ala Tyr Ser Phe Gly Leu Glu Gly Pro Ala Ile Thr Val Asp Thr Gly
                645                 650                 655
Cys Ser Ala Ser Leu Val Thr Leu His Leu Ala Cys Gln Ser Leu Arg
            660                 665                 670
Ser Gly Glu Cys Thr Leu Ala Leu Ala Gly Gly Val Ser Val Met Ser
        675                 680                 685
Thr Leu Gly Met Phe Ile Glu Phe Ser Arg Gln Arg Gly Leu Ser Val
    690                 695                 700
Asp Gly Arg Cys Lys Ala Tyr Ser Ala Ala Asp Gly Thr Gly Trp
705                 710                 715                 720
Gly Glu Gly Val Gly Met Leu Leu Val Glu Arg Leu Ser Asp Ala Val
                725                 730                 735
Arg Leu Gly His Arg Val Leu Ala Val Val Arg Gly Ser Ala Val Asn
            740                 745                 750
Gln Asp Gly Ala Ser Asn Gly Leu Thr Ala Pro Asn Gly Pro Ala Gln
        755                 760                 765
Glu Arg Val Ile Arg Gln Ala Leu Ala Asn Ala Gly Leu Ser Val Ala
    770                 775                 780
Asp Val Asp Val Val Glu Gly His Gly Thr Gly Thr Thr Leu Gly Asp
785                 790                 795                 800
Pro Ile Glu Ala Gln Ala Leu Leu Ala Thr Tyr Gly Gln Arg Ala Gly
                805                 810                 815
Asp Arg Pro Leu Trp Leu Gly Ser Leu Lys Ser Asn Ile Gly His Thr
            820                 825                 830
Met Ala Ala Ala Gly Val Gly Val Ile Lys Met Val Met Ala Leu
        835                 840                 845
Arg Glu Gly Val Leu Pro Arg Thr Leu His Val Asp Lys Pro Ser Pro
    850                 855                 860
Gln Val Asp Trp Ser Ala Gly Ala Val Arg Leu Leu Thr Glu Ala Val
```

```
                    865                 870                 875                 880
Pro Trp Pro Gly Asp Ala Ala Gly Arg Leu Arg Arg Ala Gly Val Ser
                885                 890                 895
Ser Phe Gly Ile Gly Gly Thr Asn Ala His Val Ile Leu Glu Glu Ala
            900                 905                 910
Pro Ala Ala Gly Gly Cys Val Ala Gly Gly Val Leu Glu Gly Ala
        915                 920                 925
Pro Gly Leu Ala Ile Ser Val Ala Glu Ser Val Ala Ala Pro Val Ala
    930                 935                 940
Val Ser Ala Pro Val Ala Glu Ser Val Pro Val Pro Val Pro Val Pro
945                 950                 955                 960
Val Pro Val Pro Val Ser Ala Arg Ser Glu Ala Gly Leu Arg Ala Gln
                965                 970                 975
Ala Glu Ala Leu Arg Gln Tyr Val Ala Val Arg Pro Asp Val Ser Leu
            980                 985                 990
Ala Asp Val Gly Ala Gly Leu Ala Cys Gly Arg Ala Val Leu Glu His
        995                 1000                1005
Arg Ala Val Val Leu Ala Ala Asp Arg Glu Glu Leu Val Gln Gly Leu
    1010                1015                1020
Gly Ala Leu Ala Ala Gly Glu Pro Asp Arg Arg Val Thr Thr Gly His
1025                1030                1035                1040
Ala Pro Gly Gly Asp Arg Gly Val Val Phe Val Phe Pro Gly Gln
                1045                1050                1055
Gly Gly Gln Trp Ala Gly Met Gly Val Arg Leu Leu Ala Ser Ser Pro
            1060                1065                1070
Val Phe Ala Arg Arg Met Gln Ala Cys Glu Glu Ala Leu Ala Pro Trp
        1075                1080                1085
Val Asp Trp Ser Val Val Asp Ile Leu Arg Arg Asp Ala Gly Asp Ala
    1090                1095                1100
Val Trp Glu Arg Ala Asp Val Val Gln Pro Val Leu Phe Ser Val Met
1105                1110                1115                1120
Val Ser Leu Ala Ala Leu Trp Arg Ser Tyr Gly Ile Glu Pro Asp Ala
                1125                1130                1135
Val Leu Gly His Ser Gln Gly Glu Ile Ala Ala Ala His Val Cys Gly
            1140                1145                1150
Ala Leu Ser Leu Lys Asp Ala Ala Lys Thr Val Ala Leu Arg Ser Arg
        1155                1160                1165
Ala Leu Ala Ala Val Arg Gly Arg Gly Gly Met Ala Ser Val Pro Leu
    1170                1175                1180
Pro Ala Gln Glu Val Glu Gln Leu Ile Gly Glu Arg Trp Ala Gly Arg
1185                1190                1195                1200
Leu Trp Val Ala Ala Val Asn Gly Pro Arg Ser Thr Ala Val Ser Gly
                1205                1210                1215
Asp Ala Glu Ala Val Asp Glu Val Leu Ala Tyr Cys Ala Gly Thr Gly
            1220                1225                1230
Val Arg Ala Arg Arg Ile Pro Val Asp Tyr Ala Ser His Cys Pro His
        1235                1240                1245
Val Gln Pro Leu Arg Glu Glu Leu Leu Glu Leu Leu Gly Asp Ile Ser
    1250                1255                1260
Pro Gln Pro Ser Gly Val Pro Phe Phe Ser Thr Val Glu Gly Thr Trp
1265                1270                1275                1280
Leu Asp Thr Thr Thr Leu Asp Ala Ala Tyr Trp Tyr Arg Asn Leu His
                1285                1290                1295
```

-continued

```
Gln Pro Val Arg Phe Ser Asp Ala Val Gln Ala Leu Ala Asp Asp Gly
        1300                1305                1310
His Arg Val Phe Val Glu Val Ser Pro His Pro Thr Leu Val Pro Ala
    1315                1320                1325
Ile Glu Asp Thr Thr Glu Asp Thr Ala Glu Asp Val Thr Ala Ile Gly
        1330                1335                1340
Ser Leu Arg Arg Gly Asp Asn Asp Thr Arg Arg Phe Leu Thr Ala Leu
1345                1350                1355                1360
Ala His Thr His Thr Thr Gly Ile Gly Thr Pro Thr Thr Trp His His
            1365                1370                1375
His Tyr Thr His His His Thr His Pro His Pro His Thr His Leu Asp
        1380                1385                1390
Leu Pro Thr Tyr Pro Phe Gln His Gln His Tyr Trp Leu Glu Ser Ser
    1395                1400                1405
Gln Pro Gly Ala Gly Ser Gly Ser Gly Ala Gly Ala Gly Ser Gly Ala
        1410                1415                1420
Gly Ser Gly Arg Ala Gly Thr Ala Gly Gly Thr Ala Glu Val Glu Ser
1425                1430                1435                1440
Arg Phe Trp Asp Ala Val Ala Arg Gln Asp Leu Glu Thr Val Ala Thr
            1445                1450                1455
Thr Leu Ala Val Pro Pro Ser Ala Gly Leu Asp Thr Val Val Pro Ala
        1460                1465                1470
Leu Ser Ala Trp His Arg His Gln His Asp Gln Ala Arg Ile Asn Thr
    1475                1480                1485
Trp Thr Tyr Gln Glu Thr Trp Lys Pro Leu Thr Leu Pro Thr Thr His
        1490                1495                1500
Gln Pro His Gln Thr Trp Leu Ile Ala Ile Pro Glu Thr Gln Thr His
1505                1510                1515                1520
His Pro His Ile Thr Asn Ile Leu Thr Asn Leu His His His Gly Ile
            1525                1530                1535
Thr Pro Ile Pro Leu Thr Leu Asn His Thr His Thr Asn Pro Gln His
        1540                1545                1550
Leu His His Thr Leu His His Thr Arg Gln Gln Ala Gln Asn His Thr
    1555                1560                1565
Thr Gly Ala Ile Thr Gly Leu Leu Ser Leu Leu Ala Leu Asp Glu Thr
        1570                1575                1580
Pro His Pro His His Pro His Thr Pro Thr Gly Thr Leu Leu Asn Leu
1585                1590                1595                1600
Thr Leu Thr Gln Thr His Thr Gln Thr His Pro Pro Thr Pro Leu Trp
            1605                1610                1615
Tyr Ala Thr Thr Asn Ala Thr Thr Thr His Pro Asn Asp Pro Leu Thr
        1620                1625                1630
His Pro Thr Gln Ala Gln Thr Trp Gly Leu Ala Arg Thr Thr Leu Leu
    1635                1640                1645
Glu His Pro Thr His Thr Ala Gly Ile Ile Asp Leu Pro Thr Thr Pro
1650                1655                1660
Thr Pro His Thr Leu Gln His Leu Thr Gln Thr Leu Thr Gln Pro His
1665                1670                1675                1680
His Gln Thr Gln Leu Ala Ile Arg Thr Thr Gly Thr His Thr Arg Arg
            1685                1690                1695
Leu Thr Pro Thr Thr Leu Thr Pro Thr His Gln Pro Pro Thr Pro Thr
        1700                1705                1710
```

-continued

```
Pro His Gly Thr Thr Leu Ile Thr Gly Gly Thr Gly Ala Leu Ala Thr
    1715                1720                1725
His Leu Thr His His Leu Thr Thr His Gln Pro Thr Gln His Leu Leu
        1730                1735                1740
Leu Thr Ser Arg Thr Gly Pro His Thr Pro His Ala Gln His Leu Thr
1745                1750                1755                1760
Thr Gln Leu Gln Gln Lys Gly Ile His Leu Thr Ile Thr Thr Cys Asp
            1765                1770                1775
Thr Ser Asn Pro Asp Gln Leu Gln Gln Leu Leu Asn Thr Ile Pro Pro
                1780                1785                1790
Gln His Pro Leu Thr Thr Val Ile His Thr Ala Gly Ile Leu Asp Asp
            1795                1800                1805
Ala Thr Leu Thr Asn Leu Thr Pro Thr Gln Leu Asn Asn Val Leu Arg
    1810                1815                1820
Ala Lys Ala His Ser Ala His Leu Leu His Gln Leu Thr Gln His Thr
1825                1830                1835                1840
Pro Leu Thr Ala Phe Val Leu Tyr Ser Ser Ala Ala Ala Thr Phe Gly
            1845                1850                1855
Ala Pro Gly Gln Ala Asn Tyr Ala Ala Ala Asn Ala Tyr Leu Asp Ala
        1860                1865                1870
Leu Ala His His Arg His Thr His His Leu Pro Ala Thr Ser Ile Ala
    1875                1880                1885
Trp Gly Thr Trp Gln Gly Asn Gly Leu Ala Asp Ser Asp Lys Ala Arg
        1890                1895                1900
Ala Tyr Leu Asp Arg Arg Gly Phe Arg Pro Met Ser Pro Glu Leu Ala
1905                1910                1915                1920
Thr Ala Ala Val Thr Gln Ala Ile Ala Asp Thr Glu Arg Pro Tyr Val
            1925                1930                1935
Val Ile Ala Asp Ile Asp Trp Ser Lys Ile Glu His Thr Ser Gln Thr
        1940                1945                1950
Ser Asp Leu Val Ser Ala Ala Arg Glu Arg Glu Pro Ala Val Gln Arg
    1955                1960                1965
Pro Thr Pro Pro Ala Glu Leu His Lys Thr Leu Ala His Gln Thr Ser
1970                1975                1980
Ala Asp Gln Arg Ala Ala Leu Leu Glu Leu Val Arg Asp His Val Ala
1985                1990                1995                2000
Ala Val Leu Arg His Ala Asp Pro Lys Ala Ile Ala Pro Asp Gln Ser
            2005                2010                2015
Phe Arg Ala Leu Gly Phe Asp Ser Leu Thr Ala Val Glu Phe Arg Asn
        2020                2025                2030
Leu Leu Ile Lys Ala Thr Gly Leu Arg Leu Pro Val Ser Leu Val Phe
    2035                2040                2045
Asp His Pro Thr Pro Ala Lys Leu Ala Val His Leu Gln Asn Gln Leu
2050                2055                2060
Arg Gly Thr Ala Ala Glu Ser Ala Pro Ser Ala Ala Ala Val Thr Ala
2065                2070                2075                2080
Glu Ala Ser Val Thr Glu Pro Ile Ala Ile Val Gly Met Ala Cys Arg
            2085                2090                2095
Phe Pro Gly Gly Val Thr Ser Ala Asp Asp Phe Trp Asp Leu Ile Ser
        2100                2105                2110
Ser Glu Gln Asp Ala Ile Gly Gly Phe Pro Thr Asp Arg Gly Trp Asp
    2115                2120                2125
Leu Asp Thr Leu Tyr Asp Pro Asp Pro Asp His Pro Gly Thr Cys Tyr
```

```
                  2130                2135                2140
Thr Arg Asn Gly Gly Phe Leu Tyr Asp Ala Gly His Phe Asp Ala Glu
2145                2150                2155                2160

Phe Phe Gly Ile Ser Pro Arg Glu Ala Leu Ala Met Asp Pro Gln Gln
                2165                2170                2175

Arg Leu Leu Leu Glu Thr Ala Trp Glu Thr Ile Glu His Ala Gly Ile
        2180                2185                2190

Asn Pro His Thr Leu His Gly Thr Pro Thr Gly Val Phe Thr Gly Thr
            2195                2200                2205

Asn Gly Gln Asp Tyr Ala Leu Arg Val His Asn Ala Gly Gln Ser Thr
    2210                2215                2220

Asp Gly Phe Ala Leu Thr Gly Thr Ala Gly Ser Val Ile Ser Gly Arg
2225                2230                2235                2240

Ile Ser Tyr Thr Phe Gly Phe Glu Gly Pro Ala Val Ser Val Asp Thr
                2245                2250                2255

Ala Cys Ser Ser Ser Leu Val Ala Leu His Leu Ala Cys Gln Ala Leu
            2260                2265                2270

Arg Ala Gly Glu Cys Ser Met Ala Leu Ala Gly Gly Val Thr Val Met
    2275                2280                2285

Ser Ser Pro Gly Ala Phe Val Glu Phe Ser Arg Gln Arg Gly Leu Ala
    2290                2295                2300

Ala Asp Gly His Cys Lys Ala Phe Ser Ala Ala Ala Asp Gly Thr Gly
2305                2310                2315                2320

Trp Gly Glu Gly Val Gly Met Leu Leu Val Glu Arg Leu Ser Asp Ala
            2325                2330                2335

His Arg Asn Gly His Arg Val Leu Ala Val Val Arg Gly Ser Ala Val
        2340                2345                2350

Asn Gln Asp Gly Ala Ser Asn Gly Leu Thr Ala Pro Asn Gly Pro Ser
    2355                2360                2365

Gln Gln Arg Val Ile Arg Gln Ala Leu Ala Asn Ala Gly Leu Ser Ala
        2370                2375                2380

Gly Asp Val Asp Ala Val Glu Ala His Gly Thr Gly Thr Thr Leu Gly
2385                2390                2395                2400

Asp Pro Ile Glu Ala Gln Ala Leu Leu Ala Thr Tyr Gly Gln Asp Arg
            2405                2410                2415

Ala Gly Glu Gly Pro Leu Trp Leu Gly Ser Val Lys Ser Asn Val Gly
        2420                2425                2430

His Thr Gln Ala Ala Ala Gly Val Ala Gly Val Ile Lys Met Val Met
    2435                2440                2445

Ala Leu Arg His Gly Leu Leu Pro Arg Thr Leu His Val Asp Glu Pro
2450                2455                2460

Ser Pro His Val Asp Trp Ser Ala Gly Ala Val Gln Leu Leu Thr Glu
2465                2470                2475                2480

Thr Val Pro Trp Pro Gly Gly Glu Gly Arg Leu Arg Arg Ala Gly Val
            2485                2490                2495

Ser Ser Phe Gly Val Ser Gly Thr Asn Ala His Val Ile Leu Glu Glu
        2500                2505                2510

Ala Pro Ala Asp Asp Val Pro Gly Gly Pro Ala Gly Glu Gly Asp
        2515                2520                2525

Ala Gly Ser Asp Asp Glu Ala Ala Ala Gly Ser Pro Gly Val Trp Pro
    2530                2535                2540

Trp Leu Val Ser Ala Lys Ser Gln Pro Ala Leu Arg Ala Gln Ala Gln
2545                2550                2555                2560
```

```
Ala Leu His Ala His Leu Thr Asp His Pro Gly Leu Asp Leu Ala Asp
            2565                2570                2575

Val Gly Tyr Thr Leu Ala His Ala Arg Ala Val Phe Asp His Arg Ala
        2580                2585                2590

Thr Leu Ile Ala Ala Asp Arg Asp Thr Phe Leu Gln Ala Leu Gln Ala
        2595                2600                2605

Leu Ala Ala Gly Glu Pro His Pro Ala Val Ile His Ser Ser Ala Pro
    2610                2615                2620

Gly Gly Thr Gly Thr Gly Glu Ala Ala Gly Lys Thr Ala Phe Ile Cys
2625                2630                2635                2640

Ser Gly Gln Gly Thr Gln Arg Pro Gly Met Ala His Gly Leu Tyr His
            2645                2650                2655

Thr His Pro Val Phe Ala Ala Ala Leu Asn Asp Ile Cys Thr His Leu
        2660                2665                2670

Asp Pro His Leu Asp His Pro Leu Leu Pro Leu Leu Thr Gln Asn Asp
    2675                2680                2685

Asn Asp Asn Glu Asp Ala Ala Ala Leu Leu Gln Gln Thr Arg Tyr Ala
2690                2695                2700

Gln Pro Ala Leu Phe Ala Phe Gln Val Ala Leu His Arg Leu Leu Thr
2705                2710                2715                2720

Asp Gly Tyr His Ile Thr Pro His Tyr Tyr Ala Gly His Ser Leu Gly
            2725                2730                2735

Glu Ile Thr Ala Ala His Leu Ala Gly Ile Leu Thr Leu Thr Asp Ala
        2740                2745                2750

Thr Thr Leu Ile Thr Gln Arg Ala Thr Leu Met Gln Thr Met Pro Pro
    2755                2760                2765

Gly Thr Met Thr Thr Leu His Thr Thr Pro His His Ile Thr His His
2770                2775                2780

Leu Thr Ala His Glu Asn Asp Leu Ala Ile Ala Ala Ile Asn Thr Pro
2785                2790                2795                2800

Thr Ser Leu Val Ile Ser Gly Thr Pro His Thr Val Gln His Ile Thr
            2805                2810                2815

Thr Leu Cys Gln Gln Gln Gly Ile Lys Thr Lys Thr Leu Pro Thr Asn
        2820                2825                2830

His Ala Phe His Ser Pro His Thr Asn Pro Ile Leu Asn Gln Leu His
    2835                2840                2845

Gln His Thr Gln Thr Leu Thr Tyr His Pro Pro His Thr Pro Leu Ile
    2850                2855                2860

Thr Ala Asn Thr Pro Pro Asp Gln Leu Leu Thr Pro His Tyr Trp Thr
2865                2870                2875                2880

Gln Gln Ala Arg Asn Thr Val Asp Tyr Ala Thr Thr Thr Gln Thr Leu
            2885                2890                2895

His Gln His Gly Val Thr Thr Tyr Ile Glu Leu Gly Pro Asp Asn Thr
            2900                2905                2910

Leu Thr Thr Leu Thr His His Asn Leu Pro Asn Pro Thr Thr Thr
        2915                2920                2925

Leu Thr Leu Thr His Pro His His Pro Gln Thr His Leu Leu Thr
    2930                2935                2940

Asn Leu Ala Lys Thr Thr Thr Thr Trp His Pro His His Tyr Thr His
2945                2950                2955                2960

His Asp Asn Gln Pro His Thr His Thr His Leu Asp Leu Pro Thr Tyr
            2965                2970                2975
```

```
Pro Phe Gln His His His Tyr Trp Leu Glu Ser Thr Gln Pro Gly Ala
            2980                2985                2990

Gly Asn Val Ser Ala Ala Gly Leu Asp Pro Thr Glu His Pro Leu Leu
            2995                3000                3005

Gly Ala Thr Leu Glu Leu Ala Thr Asp Gly Gly Ala Leu Leu Ala Gly
        3010                3015                3020

Arg Leu Ser Leu Arg Ser His Pro Trp Leu Ala Asp His Ala Val Gly
3025                3030                3035                3040

Gly Thr Val Leu Leu Ser Gly Ala Thr Phe Leu Glu Leu Ala Leu His
            3045                3050                3055

Ala Gly Thr Tyr Val Gly Cys Asp Arg Val Asp Glu Leu Thr Leu His
            3060                3065                3070

Ala Pro Leu Val Val Pro Val Asp Gly Gly Val Ser Val Gln Val Gly
            3075                3080                3085

Val Ala Ala Ala Asp Gly Glu Gly Arg Leu Val Ser Val Tyr Ala
        3090                3095                3100

Arg Gly Gly Ser Ala Cys Gly Gly Gly Gly Ala Ser Gly Gly Val Trp
3105                3110                3115                3120

Thr Cys His Ala Ser Gly Val Leu Val Glu Ala Ala Gly Gly Val
            3125                3130                3135

Val Val Asp Gly Leu Ala Gly Val Trp Pro Pro Arg Gly Ala Val Ala
            3140                3145                3150

Val Asp Val Asp Gly Val Arg Asp Arg Leu Ala Gly Ala Gly Cys Val
            3155                3160                3165

Leu Gly Pro Val Phe Ser Gly Leu Arg Ala Val Trp Arg Asp Gly Gly
            3170                3175                3180

Asp Leu Leu Ala Glu Val Cys Leu Pro Glu Glu Ala Trp Gly Asp Ala
3185                3190                3195                3200

Ala Gly Phe Gly Leu His Pro Ala Leu Leu Asp Gly Val Val Gln Pro
            3205                3210                3215

Leu Ser Val Leu Leu Pro Gly Thr Gly Phe Gly Glu Gly Ala Gly
            3220                3225                3230

Phe Gly Glu Gly Val Arg Val Pro Ala Val Trp Gly Gly Val Ser Leu
            3235                3240                3245

His Arg Ala Gly Val Thr Gly Val Arg Val Arg Val Ser Ala Val Gly
            3250                3255                3260

Arg Gly Gly Gly Arg Glu Ala Val Ser Val Val Gly Asp Glu Ala
3265                3270                3275                3280

Gly Val Pro Val Ala Ser Val Asp Arg Leu Glu Leu Arg Pro Val Asp
            3285                3290                3295

Met Gly Gln Leu Arg Ala Val Ser Val Ser Ala Gly Arg Arg Gly Ser
            3300                3305                3310

Leu Tyr Ala Val Gln Trp Ala Glu Val Gly Pro Val Pro Val Cys Gly
        3315                3320                3325

Gln Ala Trp Ala Trp His Glu Asp Val Gly Glu Ser Gly Gly Gly Pro
3330                3335                3340

Val Pro Gly Val Val Val Leu Arg Cys Pro Asp Ala Gly Ala Gly Gly
3345                3350                3355                3360

Gly Gly Gly Gly Gly Gly Gly Gly Val Gly Glu Val Gly Gly
            3365                3370                3375

Val Leu Gly Val Val Gln Gly Trp Leu Gly Leu Glu Arg Phe Ala Gly
            3380                3385                3390

Ser Arg Leu Val Val Val Thr Arg Gly Ala Val Val Ala Gly Pro Glu
```

-continued

```
          3395                3400                3405
Asp Gly Pro Val Asp Val Val Gly Ala Ser Val Trp Gly Leu Val Arg
        3410                3415                3420
Ser Ala Gln Ala Glu His Pro Asp Arg Phe Val Leu Leu Asp Leu Asp
3425                3430                3435                3440
Thr Asp Thr Gly Thr Asp Leu Asp Thr Gly Ala Gly Ala Gly Trp Gly
                3445                3450                3455
Val Asp Gly Gly Arg Val Ala Ala Val Val Ala Cys Gly Glu Pro Gln
            3460                3465                3470
Leu Ala Val Arg Gly Glu Arg Leu Leu Ala Ala Arg Leu Lys Arg Leu
        3475                3480                3485
Glu Ser Ser Gly Asp Val Pro Ala Gln Arg Ser Gly Asp Thr Arg Ala
        3490                3495                3500
Arg Arg Ser Asp Val Pro Ala Gln Arg Ser Gly Gly Val Pro Ala Arg
3505                3510                3515                3520
Arg Ser Val Asp Val Ser Gly Arg Glu Val Leu Pro Trp Leu Ser Gly
                3525                3530                3535
Gly Ser Val Leu Val Thr Gly Gly Thr Gly Val Leu Gly Ala Ala Val
            3540                3545                3550
Ala Arg His Leu Ala Gly Val Cys Gly Val Arg Asp Leu Leu Leu Val
        3555                3560                3565
Ser Arg Arg Gly Pro Asp Ala Pro Gly Ala Glu Gly Leu Arg Ala Glu
        3570                3575                3580
Leu Ala Ala Leu Gly Ala Glu Val Arg Ile Val Ala Cys Asp Val Gly
3585                3590                3595                3600
Glu Arg Arg Glu Val Val Arg Leu Leu Glu Gly Val Pro Ala Gly Cys
                3605                3610                3615
Pro Leu Thr Gly Val Val His Ala Ala Gly Val Leu Asp Asp Ala Thr
            3620                3625                3630
Ile Ala Ser Leu Thr Pro Glu Arg Leu Gly Thr Val Phe Ala Ala Lys
        3635                3640                3645
Val Asp Ala Ala Leu Leu Leu Asp Glu Leu Thr Arg Gly Met Glu Leu
        3650                3655                3660
Ser Ala Phe Val Leu Phe Ser Ser Ala Ala Gly Ile Leu Gly Ser Ala
3665                3670                3675                3680
Gly Gln Gly Asn Tyr Ala Ala Ala Asn Ala Ala Leu Asp Ala Leu Ala
                3685                3690                3695
Tyr Arg Arg Arg Ala Ala Gly Leu Pro Gly Val Ser Leu Ala Trp Gly
            3700                3705                3710
Leu Trp Glu Glu Ala Ser Gly Met Thr Gly His Leu Ala Gly Thr Asp
        3715                3720                3725
His Arg Arg Ile Ile Arg Ser Gly Leu His Pro Met Ser Thr Pro Asp
        3730                3735                3740
Ala Leu Ala Leu Phe Asp Ala Ala Leu Ala Leu Asp Arg Pro Val Leu
3745                3750                3755                3760
Leu Pro Ala Asp Leu Arg Pro Ala Pro Leu Pro Pro Leu Leu Gln
            3765                3770                3775
Asp Leu Leu Pro Ala Thr Arg Arg Arg Thr Thr Arg Thr Thr Thr Thr
                3780                3785                3790
Gly Gly Ala Asp Asn Gly Ala Gln Leu His Ala Arg Leu Ala Gly Gln
            3795                3800                3805
Thr His Glu Gln Gln His Thr Thr Leu Leu Ala Leu Val Arg Ser His
        3810                3815                3820
```

-continued

```
Ile Ala Thr Val Leu Gly His Thr Thr Pro Asp Thr Ile Pro Pro Asp
3825                3830                3835                3840

Arg Ala Phe Arg Asp Leu Gly Phe Asp Ser Leu Thr Ala Val Glu Leu
            3845                3850                3855

Arg Asn Arg Leu Ser Arg Thr Thr Gly Leu Arg Leu Pro Thr Thr Leu
        3860                3865                3870

Ala Phe Asp His Pro Asn Pro Thr Thr Leu Thr His His Leu His Thr
    3875                3880                3885

Gln Leu Gln Pro Gln Pro Asp Asn Ala Val Ala Pro Val Leu Ala Glu
        3890                3895                3900

Leu Asp Lys Leu Glu Ser Ala Leu Ser Ala Leu Asp Lys Thr Asp Ser
3905                3910                3915                3920

Ala Ser Glu Arg Val Thr Leu Arg Leu Lys Ser Leu Met Leu Arg Trp
            3925                3930                3935

Asn Ala Pro Gln His Pro Thr Ala Glu Ser Ala Asp Asp Asp Glu Lys
        3940                3945                3950

Phe Thr Ser Ala Thr Glu Ala Glu Ile Phe Lys Phe Ile Asp Asn Asp
    3955                3960                3965

Leu Gly Leu Ser
    3970

<210> SEQ ID NO 4
<211> LENGTH: 6239
<212> TYPE: PRT
<213> ORGANISM: Streptomyces avermitilis

<400> SEQUENCE: 4

Met Gln Leu Ala Asn Glu Ala Lys Leu Leu Glu Tyr Leu Lys Arg Val
1               5                   10                  15

Thr Ala Asp Leu Asp Arg Thr Arg Arg Leu Tyr Glu Val Val Glu
            20                  25                  30

Arg Glu Gln Glu Pro Ile Ala Ile Val Gly Met Ala Cys Arg Tyr Pro
        35                  40                  45

Gly Gly Ala Thr Ser Pro Thr Arg Leu Trp His Leu Val Lys Ser Gln
    50                  55                  60

Thr Asp Ala Ile Gly Glu Phe Pro Thr Asp Arg Gly Trp Asn Leu Glu
65                  70                  75                  80

Gln Leu Tyr Asp Pro Asp Pro Asp Arg Ser Gly Thr Ser Tyr Thr Arg
                85                  90                  95

Ser Gly Gly Phe Leu Tyr Asp Ala Gly Asp Phe Asp Ala Ala Phe Phe
            100                 105                 110

Glu Leu Ser Pro Arg Glu Ala Leu Ala Met Asp Pro Gln Gln Arg Leu
        115                 120                 125

Leu Leu Glu Thr Thr Trp Glu Thr Phe Glu Gln Gly Gly Ile Asp Pro
    130                 135                 140

Arg Ser Met Arg Gly Ser Arg Thr Gly Val Phe Val Gly Ile Asn Pro
145                 150                 155                 160

Glu Asp Tyr Thr Thr Gly Tyr Thr His Gln Pro Ser Asn Ala Val Glu
                165                 170                 175

Gly Tyr Leu Leu Thr Gly Ser Ala Ala Ser Ile Ala Ser Gly Arg Ile
            180                 185                 190

Ser Tyr Asn Phe Gly Leu Glu Gly Pro Ala Ile Thr Ile Asp Thr Ala
        195                 200                 205

Cys Ser Ser Ser Leu Val Ala Leu His Leu Ala Cys Gln Ala Leu Arg
```

-continued

```
            210                 215                 220
Ser Gly Glu Cys Thr Met Ala Leu Ala Gly Gly Ala Ser Val Met Ala
225                 230                 235                 240

Thr Pro Phe Val Phe Thr Glu Phe Ser Arg Gln Arg Gly Leu Ala Ala
                245                 250                 255

Asp Gly Arg Cys Lys Ala Phe Ser Ala Ala Ala Asp Gly Thr Gly Trp
                260                 265                 270

Ser Glu Gly Val Gly Met Leu Leu Val Glu Arg Leu Ser Asp Ala Arg
                275                 280                 285

Arg Asn Gly His Arg Val Leu Ala Val Val Arg Gly Ser Ala Val Asn
                290                 295                 300

Gln Asp Gly Ala Ser Asn Gly Leu Thr Ala Pro Asn Gly Arg Ser Gln
305                 310                 315                 320

Val Lys Val Ile Arg Gln Ala Leu Ala Asn Ala His Leu Ser Pro Ala
                325                 330                 335

Asp Val Asp Ala Val Glu Ala His Gly Thr Gly Thr Thr Leu Gly Asp
                340                 345                 350

Pro Ile Glu Ala Gln Ala Leu Val Glu Ala Tyr Gly Gln Asp Arg Pro
                355                 360                 365

Asn Gly Arg Pro Leu Trp Leu Gly Thr Leu Lys Ser Asn Ile Gly His
                370                 375                 380

Ser Met Ala Ala Ala Gly Val Gly Gly Val Ile Lys Met Val Met Ala
385                 390                 395                 400

Leu Arg Asn Gly Leu Leu Pro Arg Thr Leu His Val Asp Glu Pro Ser
                405                 410                 415

Pro His Val Asp Trp Ser Ala Gly Ala Val Gln Leu Leu Thr Glu Thr
                420                 425                 430

Val Pro Trp Pro Gly Gly Glu Gly Arg Leu Arg Arg Ala Gly Val Ser
                435                 440                 445

Ser Phe Gly Val Ser Gly Thr Asn Ala His Val Ile Leu Glu Glu Ala
                450                 455                 460

Pro Ala His Asn Ile Pro Ser Asp Thr Pro Ala Asp Val Pro Gly
465                 470                 475                 480

Glu Ser Ala Ala Asp Glu Asp Ala Gly Ser Gly Asp Glu Ala Ala Ala
                485                 490                 495

Gly Ser Pro Gly Val Trp Pro Trp Leu Val Ser Ala Lys Ser Gln Pro
                500                 505                 510

Ala Leu Arg Ala Gln Ala Gln Ala Leu His Ala His Leu Thr Asp His
                515                 520                 525

Pro Gly Leu Asp Leu Ala Asp Val Gly Tyr Thr Leu Ala His Ala Arg
                530                 535                 540

Ala Val Phe Asp His Arg Ala Thr Leu Ile Ala Ala Asp Arg Asp Thr
545                 550                 555                 560

Phe Leu Gln Ala Leu Gln Ala Leu Ala Ala Gly Glu Pro His Pro Ala
                565                 570                 575

Val Ile His Ser Ser Ala Pro Gly Gly Thr Gly Thr Gly Glu Ala Ala
                580                 585                 590

Gly Lys Thr Ala Phe Ile Cys Ser Gly Gln Gly Thr Gln Arg Pro Gly
                595                 600                 605

Met Ala His Gly Leu Tyr His Thr His Pro Val Phe Ala Ala Ala Leu
                610                 615                 620

Asn Asp Ile Cys Thr His Leu Asp Pro His Leu Asp His Pro Leu Leu
625                 630                 635                 640
```

```
Pro Leu Leu Thr Gln Asp Pro Asn Thr Gln Asp Thr Thr Leu Glu
            645                 650                 655

Glu Ala Ala Ala Leu Leu Gln Gln Thr Arg Tyr Ala Gln Pro Ala Leu
            660                 665                 670

Phe Ala Phe Gln Val Ala Leu His Arg Leu Leu Thr Asp Gly Tyr His
            675                 680                 685

Ile Thr Pro His Tyr Tyr Ala Gly His Ser Leu Gly Glu Ile Thr Ala
            690                 695                 700

Ala His Leu Ala Gly Ile Leu Thr Leu Thr Asp Ala Thr Thr Leu Ile
705                 710                 715                 720

Thr Gln Arg Ala Thr Leu Met Gln Thr Met Pro Pro Gly Thr Met Thr
            725                 730                 735

Thr Leu His Thr Thr Pro His His Ile Thr His His Leu Thr Ala His
            740                 745                 750

Glu Asn Asp Leu Ala Ile Ala Ala Ile Asn Thr Pro Thr Ser Leu Val
            755                 760                 765

Ile Ser Gly Thr Pro His Thr Val Gln His Ile Thr Thr Leu Cys Gln
770                 775                 780

Gln Gln Gly Ile Lys Thr Lys Thr Leu Pro Thr Asn His Ala Phe His
785                 790                 795                 800

Ser Pro His Thr Asn Pro Ile Leu Asn Gln Leu His Gln His Thr Gln
            805                 810                 815

Thr Leu Thr Tyr His Pro Pro His Thr Pro Leu Ile Thr Ala Asn Thr
            820                 825                 830

Pro Pro Asp Gln Leu Leu Thr Pro His Tyr Trp Thr Gln Gln Ala Arg
            835                 840                 845

Asn Thr Val Asp Tyr Ala Thr Thr Gln Thr Leu His Gln His Gly
            850                 855                 860

Val Thr Thr Tyr Ile Glu Leu Gly Pro Asp Asn Thr Leu Thr Thr Leu
865                 870                 875                 880

Thr His Asp Asn Leu Pro Asn Thr Pro Thr Thr Thr Leu Thr Leu Thr
            885                 890                 895

His Pro His His His Pro Gln Thr His Leu Leu Thr Asn Leu Ala Lys
            900                 905                 910

Thr Thr Thr Thr Trp His Pro His Tyr Thr His His Asn Gln
            915                 920                 925

Pro His Thr His Thr His Leu Asp Leu Pro Thr Tyr Pro Phe Gln His
            930                 935                 940

His His Tyr Trp Leu Gln Pro Gly Lys Pro Ser Asp Pro Ser Pro
945                 950                 955                 960

Ser Glu Gly Arg Glu Gln Ala Thr Thr Pro Ser Thr Pro Leu Arg Asp
            965                 970                 975

Val Leu Val Gly Lys Ser Pro Gln Glu Arg Asp Glu Leu Leu Arg
            980                 985                 990

Leu Val Arg Thr His Ala Ala Val Leu Gly His Ala Thr Pro Glu
            995                 1000                1005

Val Ile Val Pro Asn Lys Ala Phe Lys Glu Leu Gly Phe Asp Ser Leu
    1010                1015                1020

Ala Ala Ile Gln Leu Arg Asn Arg Leu Leu Ala Asp Val Asp Leu Pro
1025                1030                1035                1040

Leu Pro Ala Thr Leu Ile Phe Asp Tyr Pro Thr Pro Met Ala Leu Cys
            1045                1050                1055
```

```
Gln Phe Leu Arg Ala Ala Ile Val Gly Ala Asp Thr Gly Thr Thr Thr
            1060                1065                1070
Arg Leu Pro Leu Thr Ala Val Pro Ala Asp Glu Pro Ile Ala Ile Val
        1075                1080                1085
Gly Met Ala Cys Arg Tyr Pro Gly Asp Val Arg Thr Val Asp Asp Leu
    1090                1095                1100
Trp Gln Val Val Ser Gly Gly His Asp Ala Ile Gly Gly Phe Pro Thr
1105                1110                1115                1120
Asn Arg Gly Trp Asp Leu Asp Thr Leu Tyr Asn Pro Asp Pro Asp His
            1125                1130                1135
His Gly Thr Ser Tyr Thr Arg Ser Gly Gly Phe Leu Tyr Asp Ala Gly
        1140                1145                1150
Asn Phe Asp Pro Asp Phe Phe Gly Ile Ser Pro Arg Glu Ala Leu Ala
    1155                1160                1165
Met Asp Pro Gln Gln Arg Leu Leu Leu Glu Thr Ala Trp Glu Ser Ile
1170                1175                1180
Glu His Ala Cys Ile Asn Pro Asp Ser Leu Arg Gly Thr Pro Thr Gly
1185                1190                1195                1200
Val Phe Ala Gly Leu Thr Tyr His Asp Tyr Ala Ala Arg Phe Pro Thr
        1205                1210                1215
Ala Pro Ala Gly Phe Glu Gly Tyr Leu Gly His Gly Ser Ala Gly Ser
    1220                1225                1230
Ile Ala Ser Gly Arg Val Ala Tyr Ala Leu Gly Leu Glu Gly Pro Ala
        1235                1240                1245
Leu Thr Val Asp Thr Ala Cys Ser Ser Ser Leu Val Ala Leu His Leu
    1250                1255                1260
Ala Cys Gln Ala Leu Arg Ser Gly Glu Cys Ser Met Ala Leu Ala Gly
1265                1270                1275                1280
Gly Val Thr Val Met Ser Thr Pro Ala Gly Phe Val Glu Phe Ser Arg
        1285                1290                1295
Gln Arg Gly Leu Ala Val Asp Gly Arg Cys Lys Ala Phe Ser Ala Ala
    1300                1305                1310
Ala Asp Gly Thr Gly Trp Gly Glu Gly Val Gly Met Leu Leu Val Glu
    1315                1320                1325
Arg Leu Ser Asp Ala Arg Arg Leu Gly His Arg Ile Leu Ala Val Val
    1330                1335                1340
Arg Gly Ser Ala Val Asn Gln Asp Gly Ala Ser Asn Gly Leu Thr Ala
1345                1350                1355                1360
Pro Asn Gly Pro Ser Gln Glu Arg Val Ile Arg Leu Ala Leu Ala Asn
            1365                1370                1375
Ala Asp Leu Thr Pro Ala Asp Val Asp Ala Val Glu Ala His Gly Thr
        1380                1385                1390
Gly Thr Thr Leu Gly Asp Pro Ile Glu Ala Gln Ala Leu Leu Ala Thr
        1395                1400                1405
Tyr Gly Gln Asp Arg Pro Gly Asn Glu Pro Leu Trp Leu Gly Ser Met
    1410                1415                1420
Lys Ser Asn Ile Gly His Ala Gln Ala Ala Ala Gly Val Gly Gly Val
1425                1430                1435                1440
Ile Lys Met Val Met Ala Leu Arg Asn Gly Leu Leu Pro Arg Thr Leu
            1445                1450                1455
His Val Asp Glu Pro Ser Pro His Val Asp Trp Ser Ala Gly Ala Val
        1460                1465                1470
Gln Leu Leu Thr Glu Thr Val Pro Trp Pro Gly Gly Glu Gly Arg Leu
```

-continued

```
            1475                1480                1485
Arg Arg Ala Gly Val Ser Ser Phe Gly Val Ser Gly Thr Asn Ala His
    1490                1495                1500
Val Ile Leu Glu Glu Ala Pro Ala His Asn Ile Pro Ser Asp Thr Pro
1505                1510                1515                1520
Ala Asp Asp Ala Pro Gly Glu Ala Ala Asp Asp Val Pro Gly Glu
            1525                1530                1535
Ala Ala Gly Asp Asp Ala Gly Thr Gly Gly Glu Ala Thr Gly Pro Ala
            1540                1545                1550
Ala Gly Ser Pro Gly Val Trp Pro Trp Leu Val Ser Ala Lys Ser Gln
    1555                1560                1565
Pro Ala Leu Arg Ala Gln Ala Gln Ala Leu His Ala His Leu Thr Asp
    1570                1575                1580
His Pro Gly Leu Asp Leu Ala Asp Val Gly Tyr Thr Leu Ala His Ala
1585                1590                1595                1600
Arg Ala Val Phe Asp His Arg Ala Thr Leu Ile Ala Ala Asp Arg Asp
            1605                1610                1615
Thr Phe Leu Gln Ala Leu Gln Ala Leu Ala Ala Gly Glu Pro His Pro
    1620                1625                1630
Ala Val Ile His Ser Ser Ala Pro Gly Gly Thr Gly Thr Gly Glu Ala
            1635                1640                1645
Ala Gly Lys Thr Ala Phe Ile Cys Ser Gly Gln Gly Thr Gln Arg Pro
    1650                1655                1660
Gly Met Ala His Gly Leu Tyr His Thr His Pro Val Phe Ala Ala Ala
1665                1670                1675                1680
Leu Asn Asp Ile Cys Thr His Leu Asp Pro His Leu Asp His Pro Leu
            1685                1690                1695
Leu Pro Leu Leu Thr Gln Asp Pro Asn Thr Gln Asp Thr Thr Thr Leu
            1700                1705                1710
Glu Glu Ala Ala Ala Leu Leu Gln Gln Thr Pro Tyr Ala Gln Pro Ala
    1715                1720                1725
Leu Phe Ala Phe Gln Val Ala Leu His Arg Leu Leu Thr Asp Gly Tyr
    1730                1735                1740
His Ile Thr Pro His Tyr Tyr Ala Gly His Ser Leu Gly Glu Ile Thr
1745                1750                1755                1760
Ala Ala His Leu Ala Gly Ile Leu Thr Leu Thr Asp Ala Thr Thr Leu
            1765                1770                1775
Ile Thr Gln Arg Ala Thr Leu Met Gln Thr Met Pro Pro Gly Thr Met
            1780                1785                1790
Thr Thr Leu His Thr Thr Pro His His Ile Thr His His Leu Thr Ala
            1795                1800                1805
His Glu Asn Asp Leu Ala Ile Ala Ala Ile Asn Thr Pro Thr Ser Leu
    1810                1815                1820
Val Ile Ser Gly Thr Pro His Thr Val Gln His Ile Thr Thr Leu Cys
1825                1830                1835                1840
Gln Gln Gln Gly Ile Lys Thr Lys Thr Leu Pro Thr Lys Asn Ala Phe
            1845                1850                1855
His Ser Pro His Thr Asn Pro Ile Leu Asn Gln Leu His Gln His Thr
            1860                1865                1870
Gln Thr Leu Thr Tyr His Pro Pro His Thr Pro Leu Ile Thr Ala Asn
    1875                1880                1885
Thr Pro Pro Asp Gln Leu Leu Thr Pro His Tyr Trp Thr Gln Gln Ala
    1890                1895                1900
```

-continued

```
Arg Asn Thr Val Asp Tyr Ala Thr Thr Thr Gln Thr Leu His Gln His
1905                1910                1915                1920

Gly Val Thr Thr Tyr Ile Glu Leu Gly Pro Asp Asn Thr Leu Thr Thr
            1925                1930                1935

Leu Thr His His Asn Leu Pro Asn Thr Pro Thr Thr Thr Leu Thr Leu
        1940                1945                1950

Thr His Pro His His Pro Gln Thr His Leu Leu Thr Asn Leu Ala
        1955                1960            1965

Lys Thr Thr Thr Thr Trp His Pro His His Tyr Thr His His Asn
    1970                1975                1980

Gln Pro His Thr His Thr His Leu Asp Leu Pro Thr Tyr Pro Phe Gln
1985                1990                1995                2000

His Gln His Tyr Trp Leu Glu Ser Thr Gln Pro Gly Ala Gly Ser Gly
            2005                2010                2015

Ser Gly Ser Gly Ser Gly Arg Ala Gly Thr Ala Gly Gly Thr Ala Glu
            2020                2025                2030

Val Glu Ser Arg Phe Trp Asp Ala Val Ala Arg Gln Asp Leu Glu Thr
            2035                2040                2045

Val Ala Thr Thr Leu Ala Val Pro Pro Ser Ala Gly Leu Asp Thr Val
    2050                2055                2060

Val Pro Ala Leu Ser Ala Trp His Arg His Gln His Asp Gln Ala Arg
2065                2070                2075                2080

Ile Asn Thr Trp Thr Tyr Gln Glu Thr Trp Lys Pro Leu Thr Leu Pro
            2085                2090                2095

Thr Thr His Gln Pro His Gln Thr Trp Leu Ile Ala Ile Pro Glu Thr
            2100                2105                2110

Gln Thr His His Pro His Ile Thr Asn Ile Leu Thr Asn Leu His His
        2115                2120                2125

His Gly Ile Thr Pro Ile Pro Leu Thr Leu Asn His Thr His Thr Asn
    2130                2135                2140

Pro Gln His Leu His His Thr Arg Gln Gln Ala Gln Asn His Thr Thr
2145                2150                2155                2160

Gly Pro Ile Thr Gly Leu Leu Ser Leu Leu Ala Leu Asp Glu Thr Pro
            2165                2170                2175

His Pro His His Pro His Thr Pro Thr Gly Thr Leu Leu Asn Leu Thr
            2180                2185                2190

Leu Thr Gln Thr His Thr Gln Thr His Pro Pro Thr Pro Leu Trp Tyr
        2195                2200                2205

Ala Thr Thr Asn Ala Thr Thr Thr His Pro Asn Asp Pro Leu Thr His
    2210                2215                2220

Pro Thr Gln Ala Gln Thr Trp Gly Leu Ala Arg Thr Thr Leu Leu Glu
2225                2230                2235                2240

His Pro Thr His Thr Ala Gly Ile Ile Asp Leu Pro Thr Thr Pro Thr
            2245                2250                2255

Pro His Thr Leu His His Leu Thr Gln Thr Leu Thr Gln Pro His His
            2260                2265                2270

Gln Thr Gln Leu Ala Ile Arg Thr Thr Gly Thr His Thr Arg Arg Leu
        2275                2280                2285

Thr Pro Thr Thr Leu Thr Pro Thr His Gln Pro Pro Thr Pro Thr Pro
    2290                2295                2300

His Gly Thr Thr Leu Ile Thr Gly Gly Thr Gly Ala Leu Ala Thr His
2305                2310                2315                2320
```

```
Leu Thr His His Leu Thr Thr His Gln Pro Thr Gln His Leu Leu Leu
            2325                2330                2335

Thr Ser Arg Thr Gly Pro His Thr Pro His Ala Gln His Leu Thr Thr
            2340                2345                2350

Gln Leu Gln Gln Lys Gly Ile His Leu Thr Ile Thr Thr Cys Asp Thr
            2355                2360                2365

Ser Asn Pro Asp Gln Leu Gln Gln Leu Leu Asn Thr Ile Pro Pro Gln
            2370                2375                2380

His Pro Leu Thr Thr Val Ile His Thr Ala Gly Ile Leu Asp Asp Ala
2385                2390                2395                2400

Thr Leu Thr Asn Leu Thr Pro Thr Gln Leu Asn Asn Val Leu Arg Ala
            2405                2410                2415

Lys Ala His Ser Ala His Leu Leu His Gln Leu Thr Gln His Thr Pro
            2420                2425                2430

Leu Asn Ala Phe Val Leu Tyr Ser Ser Ala Ala Ala Thr Phe Gly Ala
            2435                2440                2445

Pro Gly Gln Ala Asn Tyr Ala Ala Ala Asn Ala Tyr Leu Asp Ala Leu
            2450                2455                2460

Ala His His Arg His Thr His His Leu Pro Ala Thr Ser Ile Ala Trp
2465                2470                2475                2480

Gly Thr Trp Gln Gly Asn Gly Leu Ala Thr Gly Gln Val Ser Glu His
            2485                2490                2495

Leu Arg Arg Arg Gly Met Phe Ala Met Pro Pro Glu Leu Ala Val Thr
            2500                2505                2510

Ala Val Asp Gly Ala Ile Ala Ser Gly Arg Pro Ser Leu Leu Val Ala
            2515                2520                2525

Asp Ile Asp Trp Lys Lys Leu Gly Pro Val Leu Ser Ser Lys Ser Ser
            2530                2535                2540

Val Leu Leu Glu Asp Leu Pro Gln Ala Gln Gly Thr Glu Glu Ala Arg
2545                2550                2555                2560

Ser Thr Val Glu Gln Thr Glu Ser Thr Asn Leu Arg Gln Leu Leu Met
            2565                2570                2575

Gly Arg Ser Arg Ser Glu Gln Glu Glu Leu Leu Ser Leu Val Arg
            2580                2585                2590

Ile His Ser Ala Ala Val Leu Gly Arg Asp Asp Ser Glu Ala Ile Pro
            2595                2600                2605

Pro Gly Arg Leu Phe Arg Asp Leu Gly Phe Asp Ser Leu Ala Ala Val
            2610                2615                2620

Glu Leu Arg Asn His Leu Ala Ala Gln Thr Glu Leu Ala Leu Pro Thr
2625                2630                2635                2640

Thr Leu Val Phe Asp Tyr Pro Ser Pro Thr Lys Leu Ala Gln Phe Leu
            2645                2650                2655

Leu Ser Glu Ile Ala Glu Phe Gln Pro Asp Asn Ser Thr Pro Leu Pro
            2660                2665                2670

Arg Pro Arg Ala Glu Leu Asp Glu Pro Ile Ala Ile Val Gly Met Ala
            2675                2680                2685

Cys Arg Phe Pro Gly Gly Val Thr Ser Ala Asp Asp Phe Trp Asp Leu
            2690                2695                2700

Ile Ser Ser Glu Gln Asp Ala Ile Gly Gly Phe Pro Thr Asp Arg Gly
2705                2710                2715                2720

Trp Asp Leu Asp Thr Leu Tyr Asp Pro Asp Pro Asp His Pro Gly Thr
            2725                2730                2735

Cys Tyr Thr Arg Asn Gly Gly Phe Leu Tyr Asp Ala Gly His Phe Asp
```

-continued

```
                 2740                2745                2750
Ala Glu Phe Phe Gly Ile Ser Pro Arg Glu Ala Leu Ala Met Asp Pro
        2755                2760                2765
Gln Gln Arg Leu Leu Leu Glu Thr Ala Trp Glu Thr Ile Glu His Ala
    2770                2775                2780
Gly Ile Asn Pro His Thr Leu His Gly Thr Pro Thr Gly Val Phe Thr
2785                2790                2795                2800
Gly Thr Asn Gly Gln Asp His Ala Ala His Ile Arg Gln Ala Pro Ser
                2805                2810                2815
Gly Thr Glu Gly Phe Val Leu Thr Gly Ala Ala Thr Ser Ile Ala Ser
            2820                2825                2830
Gly Arg Ile Ser Tyr Ile Leu Gly Leu Glu Gly Pro Ala Val Thr Leu
        2835                2840                2845
Asp Thr Ala Cys Ser Ser Ser Leu Val Ala Leu His Leu Ala Cys Gln
    2850                2855                2860
Ser Leu Arg Ser Gly Glu Cys Thr Met Ala Leu Ala Gly Gly Ala Thr
2865                2870                2875                2880
Val Met Thr Thr Pro Ile Thr Phe Thr Glu Phe Ala Arg Gln Arg Gly
                2885                2890                2895
Leu Ala Pro Asp Gly Arg Cys Lys Ala Phe Ser Ala Ala Ala Asp Gly
            2900                2905                2910
Thr Gly Trp Gly Glu Gly Val Gly Met Leu Leu Val Glu Arg Leu Ser
        2915                2920                2925
Asp Ala Arg Arg Asn Gly His Arg Val Leu Ala Val Val Arg Gly Ser
    2930                2935                2940
Ala Val Asn Gln Asp Gly Ala Ser Asn Gly Leu Thr Ala Pro Asn Gly
2945                2950                2955                2960
Pro Ser Gln Gln Arg Val Ile Arg Gln Ala Leu Ala Asn Ala Asp Leu
                2965                2970                2975
Thr Pro Ala Asp Val Asp Ala Val Glu Ala His Gly Thr Gly Thr Thr
            2980                2985                2990
Leu Gly Asp Pro Ile Glu Ala Gln Ala Ile Leu Ala Thr Tyr Gly Gln
        2995                3000                3005
Asp Arg Pro Gly Asn Gly Pro Leu Trp Leu Gly Ser Val Lys Ser Asn
    3010                3015                3020
Val Gly His Thr Gln Ala Ala Ala Gly Val Ala Gly Val Ile Lys Met
3025                3030                3035                3040
Val Met Ala Leu Arg His Arg Thr Leu Pro Pro Thr Leu His Ala Asp
                3045                3050                3055
Glu Pro Ser Pro His Val Asp Trp Ser Ala Gly Ala Val Gln Leu Leu
            3060                3065                3070
Thr Glu Thr Val Pro Trp Pro Gly Gly Glu Gly Arg Pro Arg Arg Ala
        3075                3080                3085
Gly Val Ser Ser Phe Gly Val Ser Gly Thr Asn Ala His Val Ile Leu
    3090                3095                3100
Glu Glu Ala Pro Ala Asp Asp Val Pro Gly Gly Pro Pro Ala Asp Glu
3105                3110                3115                3120
Asp Ala Gly Ser Gly Glu Glu Ala Ala Ala Gly Ser Pro Gly Val Trp
                3125                3130                3135
Pro Trp Leu Val Ser Ala Lys Ser Gln Pro Ala Leu Arg Ala Gln Ala
            3140                3145                3150
Gln Ala Leu His Ala His Leu Thr Asp His Pro Gly Leu Asp Leu Ala
        3155                3160                3165
```

```
Asp Val Gly Tyr Thr Leu Ala His Ala Arg Ala Val Phe Asp His Arg
    3170            3175                3180
Ala Thr Leu Ile Ala Ala Asp Arg Asp Thr Phe Leu Gln Ala Leu Gln
3185            3190                3195                3200
Ala Leu Ala Ala Gly Glu Pro His Pro Ala Val Ile His Ser Ser Ala
            3205                3210                3215
Pro Gly Gly Thr Gly Thr Gly Glu Ala Ala Gly Lys Thr Ala Phe Ile
            3220                3225                3230
Cys Ser Gly Gln Gly Thr Gln Arg Pro Gly Met Ala His Gly Leu Tyr
        3235                3240                3245
His Thr His Pro Val Phe Ala Ala Leu Asn Asp Ile Cys Thr His
    3250            3255                3260
Leu Asp Pro His Leu Asp His Pro Leu Leu Pro Leu Leu Thr Gln Asn
3265            3270                3275                3280
Asp Asn Asp Asn Asp Asn Glu Asp Ala Ala Ala Leu Leu Gln Gln Thr
            3285                3290                3295
Pro Tyr Ala Gln Pro Ala Leu Phe Ala Phe Gln Val Ala Leu His Arg
            3300                3305                3310
Leu Leu Thr Asp Gly Tyr His Ile Thr Pro His Tyr Tyr Ala Gly His
        3315                3320                3325
Ser Leu Gly Glu Ile Thr Ala Ala His Leu Ala Gly Ile Leu Thr Leu
    3330            3335                3340
Thr Asp Ala Thr Thr Leu Ile Thr Gln Arg Ala Thr Leu Met Gln Thr
3345            3350                3355                3360
Met Pro Pro Gly Thr Met Thr Thr Leu His Thr Thr Pro His His Ile
            3365                3370                3375
Thr His His Leu Thr Ala His Glu Asn Asp Leu Ala Ile Ala Ala Ile
        3380                3385                3390
Asn Thr Pro Thr Ser Leu Val Ile Ser Gly Thr Pro His Thr Val Gln
    3395            3400                3405
His Ile Thr Thr Leu Cys Gln Gln Gln Gly Ile Lys Thr Lys Thr Leu
    3410            3415                3420
Pro Thr Asn His Ala Phe His Ser Pro His Thr Asn Pro Ile Leu Asn
3425            3430                3435                3440
Gln Leu His Gln His Thr Gln Thr Leu Thr Tyr His Pro Pro His Thr
            3445                3450                3455
Pro Leu Ile Thr Ala Asn Thr Pro Pro Asp Gln Leu Leu Thr Pro His
            3460                3465                3470
Tyr Trp Thr Gln Gln Ala Arg Asn Thr Val Asp Tyr Ala Thr Thr Thr
        3475                3480                3485
Gln Thr Leu His Gln His Gly Val Thr Thr Tyr Ile Glu Leu Gly Pro
3490            3495                3500
Asp Asn Thr Leu Thr Thr Leu Thr His His Asn Leu Pro Asn Thr Pro
3505            3510                3515                3520
Thr Thr Thr Leu Thr Leu Thr His Pro His His Pro Gln Thr His
            3525                3530                3535
Leu Leu Thr Asn Leu Ala Lys Thr Thr Thr Thr Trp His Pro His His
        3540                3545                3550
Tyr Thr His His His Asn Gln Pro His Thr His Thr His Leu Asp Leu
    3555            3560                3565
Pro Thr Tyr Pro Phe Gln His His His Tyr Trp Leu Glu Leu Pro Ser
    3570            3575                3580
```

-continued

```
Ala Gln Thr Ser Pro Gly Gln Arg Arg Ser Arg Arg Ser Ala Pro Asp
3585                3590                3595                3600

Thr Ala Glu Ser Glu Phe Trp Asp Ala Val Asn Glu Glu Asp Leu Gln
            3605                3610                3615

Ser Leu Ala Glu Thr Leu Asp Ile Asp Ala Ser Ala Leu Asp Thr Val
            3620                3625                3630

Val Pro Ala Leu Ser Ala Trp His Arg His Gln His Asp Gln Ala Arg
            3635                3640                3645

Ile Asn Thr Trp Thr Tyr Gln Glu Thr Trp Lys Pro Leu Thr Leu Pro
    3650                3655                3660

Thr Thr His Gln Pro His Gln Thr Trp Leu Ile Ala Ile Pro Glu Thr
3665                3670                3675                3680

Gln Thr His His Pro His Ile Thr Asn Ile Leu Thr Asn Leu His His
            3685                3690                3695

His Gly Ile Thr Pro Ile Pro Leu Thr Val Asn His Thr His Thr Asn
            3700                3705                3710

Pro Gln His Leu His His Thr Leu His His Thr Arg Gln Gln Ala Gln
            3715                3720                3725

Asn His Thr Thr Gly Pro Ile Thr Gly Leu Leu Ser Leu Leu Ala Leu
    3730                3735                3740

Asp Glu Thr Pro His Pro His His Pro His Thr Pro Thr Gly Thr Leu
3745                3750                3755                3760

Leu Asn Leu Thr Leu Pro Gln Thr His Thr Gln Thr His Pro Pro Thr
            3765                3770                3775

Pro Leu Trp Tyr Ala Thr Thr Asn Ala Thr Thr Thr His Pro Asn Asp
            3780                3785                3790

Pro Leu Thr His Pro Thr Gln Ala Gln Thr Trp Gly Leu Ala Arg Thr
    3795                3800                3805

Thr Leu Leu Glu His Pro Thr His Thr Ala Gly Ile Ile Asp Leu Pro
    3810                3815                3820

Thr Thr Pro Thr Pro His Thr Leu His His Leu Thr Gln Thr Leu Thr
3825                3830                3835                3840

Gln Pro His His Gln Thr Gln Leu Ala Ile Arg Thr Thr Gly Thr His
            3845                3850                3855

Thr Arg Arg Leu Thr Pro Thr Thr Leu Thr Pro Thr His Gln Pro Pro
            3860                3865                3870

Thr Pro Thr Pro His Gly Thr Thr Leu Ile Thr Gly Gly Thr Gly Ala
    3875                3880                3885

Leu Ala Thr His Leu Thr His His Leu Thr Thr His Gln Pro Thr Gln
    3890                3895                3900

His Leu Leu Leu Thr Ser Arg Thr Gly Pro His Thr Pro His Ala Gln
3905                3910                3915                3920

His Leu Thr Thr Gln Leu Gln Gln Lys Gly Ile His Leu Thr Ile Thr
            3925                3930                3935

Thr Cys Asp Thr Ser Asn Pro Asp Gln Leu Gln Gln Leu Leu Asn Thr
            3940                3945                3950

Ile Pro Pro Gln His Pro Leu Thr Thr Val Ile His Thr Ala Gly Val
    3955                3960                3965

Asn Leu Phe Ala Pro Val Ser Glu Thr Asp Ala Glu Ser Phe Ser Ser
    3970                3975                3980

Val Thr Ala Ala Lys Ala Thr Gly Ala Ala Ile Leu His Glu Leu Leu
3985                3990                3995                4000

Leu Asp His Glu Thr Leu Glu His Phe Ile Leu Phe Ser Ser Gly Ala
```

-continued

```
                    4005                4010                4015
Gly Ala Trp Gly Ser Gly Asn Gln Cys Ala Tyr Ser Ala Ala Asn Ala
            4020                4025                4030
Tyr Leu Asp Ala Leu Ala Thr His Arg Gln Thr His Gly Leu Pro Gly
        4035                4040                4045
Ala Ser Ile Ala Trp Gly Pro Trp Ala Gly Lys Gly Met Ser Ala Gly
    4050                4055                4060
Asp Ala Ala His Gly Tyr Leu Glu Lys Arg Gly Ile Leu Pro Met Glu
4065                4070                4075                4080
Pro Arg Met Ala Leu Ala Ala Phe His Arg Ala Arg Ala Gln Arg Pro
                4085                4090                4095
Asn Ser Asn Leu Ile Ile Ala Asp Ile Asp Trp Glu Arg Phe Val Pro
            4100                4105                4110
Ala Phe Thr Ala Arg Arg His Ser Pro Leu Ile Glu Asp Ile Pro Glu
        4115                4120                4125
Val Arg Gln Ala Ala Gln Glu Leu Glu Ala Ala Ala Ser Thr Ala Lys
    4130                4135                4140
Thr Thr Thr Ala Gln Pro Ile Ala Thr Ser Leu Arg Glu Arg Leu Ala
4145                4150                4155                4160
Arg Leu Thr Ser Ser Lys Gln Asn Gln Val Leu Leu Gly Leu Ile Arg
                4165                4170                4175
Thr Gly Ile Cys Thr Val Leu Gly Leu Arg Asn Pro Glu Gly Ile Glu
            4180                4185                4190
Asp Gln Arg Ala Phe Arg Asp Leu Gly Phe Asp Ser Leu Thr Ser Ala
        4195                4200                4205
Gln Phe Ser Lys Glu Leu Ala Lys Glu Thr Gly Leu Pro Leu Pro Pro
    4210                4215                4220
Ser Leu Val Phe Asp Tyr Pro Thr Pro Gln Glu Cys Ala Ala His Leu
4225                4230                4235                4240
Arg Thr Gln Leu Val Asp Leu Asp Asp Glu Glu Asp Ala Ala Leu Ser
                4245                4250                4255
Asn Ala Leu Pro Gln Val Ala His Arg Arg Thr Val Glu Asp Glu Pro
            4260                4265                4270
Ile Ala Ile Ile Gly Met Ala Cys Arg Phe Pro Gly Gly Val Arg Ser
        4275                4280                4285
Ala Asp Asp Leu Trp Glu Leu Leu Ala Ser Gly Lys Asp Ala Ile Gly
    4290                4295                4300
Val Phe Pro Thr Asp Arg Gly Trp Asp Leu Asp Thr Leu Tyr Asp Pro
4305                4310                4315                4320
Asp Pro Asp His Pro Gly Thr Cys Tyr Thr Arg Asn Gly Gly Phe Leu
                4325                4330                4335
Tyr Gly Ala Gly His Phe Asp Ala Glu Phe Phe Gly Ile Ser Pro Arg
            4340                4345                4350
Glu Ala Leu Ala Met Asp Pro Gln Gln Arg Leu Leu Leu Glu Thr Ala
        4355                4360                4365
Trp Glu Thr Ile Glu His Ala Gly Ile Asn Pro His Thr Leu His Gly
    4370                4375                4380
Thr Pro Thr Gly Val Phe Ala Gly Ile Asn Ala Gln Asp His Ala Ala
4385                4390                4395                4400
His Ile Arg Gln Ser Arg Asp Val Glu Thr Ile Glu Gly Tyr Ala Leu
                4405                4410                4415
Thr Gly Ser Ser Gly Ser Val Ala Ser Gly Arg Val Ala Tyr Thr Leu
            4420                4425                4430
```

```
Gly Leu Glu Gly Pro Ala Val Ser Val Asp Thr Ala Cys Ser Ser Ser
        4435                4440                4445

Leu Val Ala Leu His Trp Ala Ala Gln Ala Leu Arg Ala Gly Glu Cys
    4450                4455                4460

Ser Met Ala Leu Ala Gly Gly Val Thr Val Met Ser Ser Pro Gly Thr
4465                4470                4475                4480

Phe Val Glu Phe Ser Arg Gln Arg Gly Leu Ala Ala Asp Gly Arg Cys
            4485                4490                4495

Lys Ala Tyr Ser Ala Ala Ala Asp Gly Thr Gly Trp Ala Glu Gly Val
        4500                4505                4510

Gly Met Leu Leu Val Glu Arg Leu Ser Asp Ala Arg Arg Asn Gly His
    4515                4520                4525

Arg Val Leu Ala Val Val Arg Gly Ser Ala Val Asn Gln Asp Gly Ala
4530                4535                4540

Ser Asn Gly Leu Thr Ala Pro Asn Gly Pro Ser Gln Gln Arg Val Ile
4545                4550                4555                4560

Arg Gln Ala Leu Ala Asn Ala Gly Leu Thr Pro Ala Asp Val Asp Ala
            4565                4570                4575

Val Glu Gly His Gly Thr Gly Thr Thr Leu Gly Asp Pro Ile Glu Ala
        4580                4585                4590

Gln Ala Leu Leu Ala Ala Tyr Gly Gln His Arg Pro His His Arg Pro
    4595                4600                4605

Leu Trp Leu Gly Ser Leu Lys Ser Asn Ile Gly His Ala Gln Ala Ala
    4610                4615                4620

Ala Gly Val Gly Gly Val Ile Lys Met Val Met Ala Leu Arg Asn Gly
4625                4630                4635                4640

Leu Leu Pro Gln Thr Leu His Val Asp Glu Pro Thr Pro Gln Val Asp
            4645                4650                4655

Trp Ser Thr Gly Ala Val Gln Leu Leu Thr Gln Pro Val Pro Trp Pro
        4660                4665                4670

Ala Asp Pro Ala Gly Arg Pro Arg His Ala Gly Val Ser Ser Phe Gly
    4675                4680                4685

Val Ser Gly Thr Asn Ala His Ile Ile Leu Glu Glu Ala Pro Thr Pro
    4690                4695                4700

Gln Asp Ser Asp Thr Asp Asp Glu Pro Pro Ala Asn Ala Pro Ala Leu
4705                4710                4715                4720

Pro His Pro Leu Pro Leu Pro Val Pro Val Ser Ala Arg Ser Glu Ala
            4725                4730                4735

Gly Leu Arg Ala Gln Ala Gln Ala Leu Arg Gln Tyr Val Ala Ala Arg
        4740                4745                4750

Pro Asp Met Ser Pro Ala Asp Ile Gly Ala Gly Leu Ala Arg Gly Arg
    4755                4760                4765

Ala Val Leu Glu His Arg Ala Val Ile Leu Ala Ala Asp Arg Glu Glu
    4770                4775                4780

Leu Ala Gln Ala Leu Thr Ala Leu Ala Ala Gly Glu Pro His Pro His
4785                4790                4795                4800

Ile Thr Thr Gly His Thr Arg Gly Gly Asp Arg Gly Val Val Phe
            4805                4810                4815

Val Phe Pro Gly Gln Gly Gly Gln Trp Ala Gly Met Gly Leu Thr Leu
        4820                4825                4830

Leu Thr Ser Ser Pro Val Phe Ala Glu His Ile Asp Ala Cys Glu Lys
    4835                4840                4845
```

```
Ala Leu Thr Pro Trp Val Pro Trp Ser Leu Thr Asp Ile Leu His Arg
    4850                4855                4860

Asp Pro Asp Asp Pro Ala Trp Gln Gln Ala Asp Val Val Gln Pro Val
4865                4870                4875                4880

Leu Phe Ser Ile Met Val Ser Leu Ala Ala Leu Trp Arg Ser Tyr Gly
        4885                4890                4895

Ile Glu Pro Asp Ala Val Leu Gly His Ser Gln Gly Glu Ile Ala Ala
        4900                4905                4910

Ala His Ile Cys Gly Ala Leu Ser Leu Lys Asp Ala Ala Lys Thr Val
        4915                4920                4925

Ala Leu Arg Ser Arg Ala Leu Ala Ala Val Arg Gly Arg Gly Ala Met
    4930                4935                4940

Ala Ser Leu Pro Leu Pro Ala Gln Asp Val Gln Gln Leu Ile Ser Glu
4945                4950                4955                4960

Arg Trp Glu Gly Gln Leu Trp Val Ala Ala Leu Asn Gly Pro His Ser
        4965                4970                4975

Thr Thr Val Ser Gly Asp Thr Lys Ala Val Asp Glu Val Leu Ala His
        4980                4985                4990

Cys Thr Asp Thr Gly Leu Arg Ala Lys Arg Ile Pro Val Asp Tyr Ala
    4995                5000                5005

Ser His Cys Pro His Val Gln Pro Leu His Asp Glu Leu Leu His Leu
    5010                5015                5020

Leu Gly Asp Ile Thr Pro Gln Pro Ser Thr Val Pro Phe Phe Ser Thr
5025                5030                5035                5040

Val Glu Gly Thr Trp Leu Asp Thr Thr Thr Leu Asp Ala Ala Tyr Trp
        5045                5050                5055

Tyr Arg Asn Leu His Gln Pro Val Arg Phe Ser His Ala Ile Gln Thr
        5060                5065                5070

Leu Thr Asp Asp Gly His Arg Ala Phe Ile Glu Ile Ser Pro His Pro
    5075                5080                5085

Thr Leu Val Pro Ala Ile Glu Asp Thr Thr Glu Asn Thr Thr Glu Asn
    5090                5095                5100

Ile Thr Ala Thr Gly Ser Leu Arg Arg Gly Asp Asn Asp Thr His Arg
5105                5110                5115                5120

Phe Leu Thr Ala Leu Ala His Thr His Thr Thr Gly Ile Gly Thr Pro
        5125                5130                5135

Thr Thr Trp His His His Tyr Thr Gln Thr His Pro His Pro Asn Pro
        5140                5145                5150

His Thr His Leu Asp Leu Pro Thr Tyr Pro Phe Gln His Gln His Tyr
    5155                5160                5165

Trp Leu Gln Pro Pro Thr Thr Thr Thr Asp Leu Thr Thr Thr Gly Leu
    5170                5175                5180

Thr Pro Thr His His Pro Leu Leu Thr Ala Thr Leu Thr Leu Ala Asp
5185                5190                5195                5200

Asn Asn Thr Gln Leu Leu Thr Gly Arg Leu Ser Leu Arg Thr His Pro
        5205                5210                5215

Trp Leu Thr Asp His Thr Val Ala Gly Met Val Leu Leu Pro Gly Thr
        5220                5225                5230

Ala Leu Leu Glu Leu Ala Leu Gln Ala Gly Glu Arg Val Asp Cys Pro
    5235                5240                5245

Arg Val Glu Glu Leu Thr Leu His Ala Pro Leu Val Ile Pro His Thr
    5250                5255                5260

Glu Asp Val Thr Leu Gln Val Thr Val Arg Ala Ala Asp Glu Ser Gly
```

-continued

```
         5265                5270                5275                5280
His Arg Ala Leu Ala Ile His Ser Tyr Ser Gly Thr Ala Ser Ser Ala
             5285                5290                5295

Asp Arg Glu Trp Thr Arg His Ala Thr Gly Leu Leu Thr His His Ala
         5300                5305                5310

Asp Thr Asp His Arg Ala Asp Thr His Thr Asp Ala Cys Leu Gly Gly
         5315                5320                5325

Ser Trp Pro Pro Pro Gly Ala Gln Pro Ile Glu Leu Gly Asp Val Tyr
         5330                5335                5340

Gly Arg Met Ala Ala Asp Ser Asp Ile Ala Tyr Gly Pro Val Phe Gln
5345                5350                5355                5360

Gly Leu His Ala Ala Trp Arg Phe Gly Asp Asp Val Leu Ala Glu Val
             5365                5370                5375

Arg Leu Pro Glu Glu Ala Leu Arg Asp Ala Pro Ala Ala Phe Gly
             5380                5385                5390

Val His Pro Ala Leu Leu Asp Ala Ala Leu His Ala Thr Ala Leu Thr
             5395                5400                5405

Pro Gln Asn Gly Asp Gly Ser Thr Glu Asn Val Ala Gln Glu Ser Met
         5410                5415                5420

Pro Asp Arg Ala Ala His Gln Ala Arg Leu Pro Phe Ser Trp Ser Gly
5425                5430                5435                5440

Val Ser Leu His Thr Ala Gly Ser Ser Val Leu Arg Val Arg Leu Ser
             5445                5450                5455

Arg Ser Pro Gln His Gly Asn Ala Val Ala Leu Thr Ala Ala Asp Glu
             5460                5465                5470

Asp Gly Arg Pro Val Val Thr Ile Glu Ser Leu Ala Leu Arg Pro Val
             5475                5480                5485

Ser Thr Glu Glu Leu Arg Ala Ala Ala Asp Arg Thr Pro Glu His Glu
             5490                5495                5500

Ser Leu Phe Arg Leu Asp Trp Val Ser Val Pro Val Pro Ala Asn Ala
5505                5510                5515                5520

Pro Ser Pro Thr Ala Asp Arg Pro Trp Ala Val Ile Gly Ala Gly Leu
             5525                5530                5535

Pro His Leu Pro Gly Leu Thr Glu His Glu His Val Thr Ala Tyr Asp
             5540                5545                5550

Glu Pro Ala Asp Leu Leu Leu Ala Leu Asp Arg Gly Ala Pro Pro Pro
             5555                5560                5565

Gly Val Leu Val Val Gly Gly Val Ala His Thr Glu Ala Arg Glu Tyr
             5570                5575                5580

Ser Ala Glu Ala Pro Gly Glu Arg Gly Thr Glu Ala Cys Glu Ala Arg
5585                5590                5595                5600

Pro Asp Val Val His Val Gly Val Val His Thr Ala Ala Val His Ala
             5605                5610                5615

Ala Ala Ala Gln Met Leu Ala Arg Leu Gln Ala Trp Leu Gly Asp Glu
             5620                5625                5630

Arg Leu Ala Asp Ser Arg Leu Leu Val Leu Thr Cys Gly Ala Val Ala
             5635                5640                5645

Arg Ala Ser Gly Asp Asp Ala Thr Asp Leu Pro Gly Ala Ala Val Trp
             5650                5655                5660

Gly Leu Val Arg Ser Ala Gln Ser Glu His Pro Asp Arg Ile Thr Leu
5665                5670                5675                5680

Leu Asp Phe Glu Arg Gly Thr Glu Ala Glu Pro Gly Gln Leu Ala Thr
             5685                5690                5695
```

-continued

```
Ala Leu Asn Cys Gly Glu Arg Gln Leu Ala Val Arg Pro Gly Gly Leu
        5700                5705                5710
Phe Thr Pro Arg Leu Val Arg Ala Pro Arg Val Ala Asp Ala Val Pro
        5715                5720                5725
Ala Val Pro Ala Val Ala Val Pro Ser Ala Gly His Ala Ala Val Pro
5730                5735                5740
Ala Ala Gly Pro Phe Leu Pro Gly Gly Thr Val Leu Ile Thr Gly Gly
5745                5750                5755                5760
Thr Gly Val Leu Gly Arg Leu Val Ala Arg His Leu Val Glu Ala His
        5765                5770                5775
Gly Val Arg His Leu Leu Ala Gly Arg Arg Gly Pro Asp Ala Glu
        5780                5785                5790
Gly Ala Pro Glu Leu Arg Ala Glu Leu Gly Gly Leu Gly Ala Thr Val
        5795                5800                5805
Glu Val Val Ala Cys Asp Ala Ala Asp Arg Gln Gln Leu Ala Asp Leu
        5810                5815                5820
Leu Thr Arg Ile Pro Asp Asp Arg Pro Leu Thr Gly Val Val His Ser
5825                5830                5835                5840
Ala Gly Ile Leu Asp Asp Gly Val Ile Thr Ser Leu Ser Pro Glu Arg
        5845                5850                5855
Leu Gly Ala Val Leu Arg Ala Lys Ala Asp Ala Ala Leu Leu Leu Asp
        5860                5865                5870
Glu Leu Thr Arg Gly Ala Glu Leu Ser Ala Phe Val Met Phe Ser Ser
        5875                5880                5885
Ala Ser Ala Val Val Gly Ser Pro Gly Gln Gly Asn Tyr Ala Ala Ala
        5890                5895                5900
Asn Ala Val Leu Asp Phe Leu Ala His Arg Arg Arg Ala Glu Gly Leu
5905                5910                5915                5920
Pro Ala Val Ser Leu Ala Trp Gly Leu Trp Glu Glu Gly Thr Gly Met
        5925                5930                5935
Thr Gly His Leu Asp Val Asp Asp His Ala Arg Ile Ser Arg Ala Gly
        5940                5945                5950
Met Arg Pro Leu Pro Thr Ala Glu Ala Leu Ala Leu Phe Asp Ala Ala
        5955                5960                5965
Leu Ala Asp Gly Glu Pro Phe Leu Met Pro Ala Arg Leu Asp Leu Thr
        5970                5975                5980
Ala Val Arg Ser Gly Ala Ala Ser Ala Pro Val Pro Pro Leu Leu Gln
5985                5990                5995                6000
Gly Leu Leu Gln Leu Pro Arg Ser Arg Ser Ala Ala Ala Pro Gly
        6005                6010                6015
His Gly Ala Pro Ala Ala Asp Glu Ala Ala Ala Trp Arg Glu Arg Leu
        6020                6025                6030
Ala Arg Gln Ser Ala Gly Glu Arg Arg Gln Ala Leu Leu Arg Leu Val
        6035                6040                6045
Arg Ser His Val Ala Ala Val Leu Gly His Ser Gly Ala Asp Gly Ile
        6050                6055                6060
Asp Ala Ser Arg Ala Phe Arg Glu Leu Gly Phe Asp Ser Leu Thr Ala
6065                6070                6075                6080
Val Glu Leu Arg Asn Arg Leu Thr Ala Ala Thr Gly Leu Arg Leu Arg
        6085                6090                6095
Ala Thr Leu Ala Phe Asp Phe Pro Thr Pro Ala Ala Leu Ala Glu His
        6100                6105                6110
```

-continued

```
Leu Gly Glu Arg Leu Leu Pro Asp Gln Glu Ala Thr Gly Glu Gln Ala
        6115                6120                6125

Gly Asp Gln Leu Ser Gly Gly Ser Glu Glu Asp Val Arg Ser Leu Leu
    6130                6135                6140

Thr Ser Ile Pro Ile Gly Arg Leu Arg Asp Ala Gly Leu Leu Gly Pro
6145                6150                6155                6160

Leu Leu Thr Leu Ala Asp Thr Gly Arg Gly Ala Ser Gly Ala Ala Ala
        6165                6170                6175

Gly Pro Glu Asp Ala Pro Pro Ser Gly Gln Asp Thr Pro Ala Pro Val
            6180                6185                6190

Ser Ile Asp Glu Met Asp Ile Asp Asp Leu Met Asp Leu Ala His Gly
        6195                6200                6205

His Gly Thr Ala Pro Ala Arg Glu Pro Ala Asp Ala Glu Asp Ser Ser
    6210                6215                6220

Ser Ser Arg Asn Arg Thr His His Thr His Glu Gly Glu Thr Ala
6225                6230                6235

<210> SEQ ID NO 5
<211> LENGTH: 4881
<212> TYPE: PRT
<213> ORGANISM: Streptomyces avermitilis

<400> SEQUENCE: 5

Met Ala Asn Glu Glu Lys Leu Arg Asp Tyr Leu Lys Arg Val Thr Ala
1               5                   10                  15

Asp Leu Leu Asn Val Arg Arg Leu Gln Gln Ile Glu Ser Gly Glu
            20                  25                  30

Gln Glu Pro Ile Ala Ile Val Gly Met Ala Cys Arg Phe Pro Gly Gly
        35                  40                  45

Val Glu Ser Ala Glu Asp Phe Trp Glu Leu Ile Ala Ser Gly Arg Asp
    50                  55                  60

Ala Val Gly Glu Phe Pro Val Asp Arg Gly Trp Asp Val Glu Ala Phe
65                  70                  75                  80

Tyr Asp Pro Glu Pro Gly Arg Ala Gly Ser Ser Tyr Thr Arg Arg Gly
                85                  90                  95

Gly Phe Leu Glu Gly Ala Ala Glu Phe Asp Ala Gly Phe Phe Gly Ile
            100                 105                 110

Ser Pro Arg Glu Ala Leu Ala Met Asp Pro Gln Gln Arg Leu Met Leu
        115                 120                 125

Glu Val Ser Trp Glu Ala Leu Glu Arg Ala Gly Ile Asp Pro Ala Thr
    130                 135                 140

Leu Arg Gly Ser Arg Thr Gly Val Phe Ala Gly Leu Met Ser Gln Asp
145                 150                 155                 160

Tyr Ala Thr Arg Leu Leu Ser Val Pro Asp Asp Leu Ala Gly Tyr Leu
                165                 170                 175

Gly Asn Gly Asn Ala Gly Ser Ile Leu Ser Gly Arg Val Ala Tyr Thr
            180                 185                 190

Phe Gly Phe Glu Gly Pro Ala Val Thr Val Asp Thr Ala Cys Ser Ser
        195                 200                 205

Ser Leu Val Ala Leu His Leu Ala Cys Gln Ser Leu Arg Thr Gly Glu
    210                 215                 220

Ser Ser Phe Ala Leu Ala Gly Gly Val Thr Val Met Ser Thr Pro Gly
225                 230                 235                 240

Met Phe Val Glu Phe Ser Arg Gln Arg Gly Leu Ser Pro Asp Gly Arg
                245                 250                 255
```

-continued

```
Cys Lys Ala Tyr Ala Ser Ala Ala Asp Gly Thr Gly Met Ser Glu Gly
            260                 265                 270
Val Gly Ile Leu Leu Glu Arg Leu Ser Glu Ala Glu Arg Arg Gly
        275                 280                 285
His Arg Val Leu Ala Val Val Arg Gly Ser Ala Val Asn Gln Asp Gly
        290                 295                 300
Ala Ser Asn Gly Leu Thr Ala Pro Asn Gly Pro Ser Gln Gln Arg Val
305                 310                 315                 320
Ile Arg Gln Ala Leu Ala Cys Ala Gly Leu Ser Val Ala Asp Val Asp
                325                 330                 335
Val Val Glu Gly His Gly Thr Gly Thr Thr Leu Gly Asp Pro Ile Glu
            340                 345                 350
Ala Gln Ala Leu Leu Ala Thr Tyr Gly Gln Arg Ala Gly Asp Thr Pro
        355                 360                 365
Val Trp Leu Gly Ser Val Lys Ser Asn Ile Gly His Ala Gln Ala Ala
        370                 375                 380
Ala Gly Val Ala Gly Val Ile Lys Met Val Met Ala Leu Arg Ala Gly
385                 390                 395                 400
Val Leu Pro Arg Thr Leu His Val Asp Glu Pro Ser Ser Gln Val Asp
                405                 410                 415
Trp Ser Ser Gly Ser Val Arg Val Leu Ala Asp Glu Val Glu Trp Pro
            420                 425                 430
Gly Val Glu Gly Arg Leu Arg Arg Ala Gly Val Ser Ala Phe Gly Val
        435                 440                 445
Ser Gly Thr Asn Ala His Val Ile Leu Glu Glu Ala Ser Gly Gly Ala
        450                 455                 460
Gly Gly Gly Ala Gly Arg Leu Gln Glu Leu Gly Pro Gly Val Val Ser
465                 470                 475                 480
Gly Ser Gly Val Val Pro Trp Val Val Ser Ala Arg Ser Glu Leu Ala
                485                 490                 495
Leu Arg Gly Gln Ala Arg Arg Leu Arg Gly Val Val Ala Val Gly Gly
            500                 505                 510
Gly Ala Asp Gly Val Gly Val Ser Pro Ala Gly Val Gly Arg Ala Leu
        515                 520                 525
Val Ser Glu Arg Ser Val Phe Glu His Arg Ala Val Val Ala Glu
        530                 535                 540
Asp Arg Asp Glu Phe Leu His Ala Leu Asp Ala Leu Ala Gly Gly Arg
545                 550                 555                 560
Pro Val Pro Gly Val Val Glu Gly Arg Thr Thr Ser Gly Glu Leu Ala
                565                 570                 575
Val Leu Phe Ala Gly Gln Gly Thr Gln Arg Ala Gly Met Gly Arg Glu
            580                 585                 590
Leu Tyr Glu Ala Tyr Pro Val Phe Ala Gln Ala Ile Asp Glu Ile Cys
        595                 600                 605
Ala Glu Ala Asp Thr Ala Arg Thr Asp Pro Gly Ala Pro Gly Leu Arg
610                 615                 620
Asp Val Leu Phe Ala Pro Gln Asp Ser Pro Glu Gly Arg Leu Ile Glu
625                 630                 635                 640
Asp Thr Gly Phe Ala Gln Pro Ala Leu Phe Ala Phe Glu Val Ala Leu
                645                 650                 655
Phe Arg Leu Leu Glu Thr Trp Gly Leu Thr Pro Asp Tyr Val Leu Gly
            660                 665                 670
```

-continued

```
His Ser Val Gly Glu Leu Ala Ala His Ala Gly Met Leu Cys
        675                 680                 685
Leu Ala Asp Ala Val Ala Leu Val Val Ala Arg Gly Arg Leu Met Gln
        690                 695                 700
Gly Leu Pro Ser Gly Gly Ala Met Val Ala Ile Glu Ala Ser Glu Asp
705                 710                 715                 720
Glu Ile Leu Pro Leu Pro Asp Glu Tyr Ala Ser Arg Val Ala His Ala
                    725                 730                 735
Ala Val Asn Gly Pro Arg Ser Ile Val Leu Ser Gly Asp Glu Asp Ala
                740                 745                 750
Val Leu Asp Leu Ala Gln Gln Trp Ala Ala Arg Gly Arg Arg Thr Arg
        755                 760                 765
Arg Leu Arg Thr Ser His Ala Phe His Ser Pro His Met Asp Ala Met
        770                 775                 780
Leu Gly Asp Phe Arg Arg Ala Ala Glu Gln Val Thr Phe Ser Ala Pro
785                 790                 795                 800
Arg Ile Pro Val Val Ser Asn Val Thr Gly Ala Pro Leu Pro Ala Glu
                    805                 810                 815
Thr Met Cys Thr Pro Asp Tyr Trp Val Glu His Ala Arg Ser Thr Val
                820                 825                 830
Arg Phe Ala Asp Gly Ile Ser Trp Leu Gln Glu Gln Gly Val Thr Thr
        835                 840                 845
Cys Leu Glu Ile Gly Pro Asp Gly Thr Leu Ser Ala Leu Ala Gln Asp
        850                 855                 860
Ser Leu Ser Ala Pro Ala Arg Ala Ile Pro Ala Leu Arg Pro Asp Gln
865                 870                 875                 880
Pro Glu Ala Arg Ser Val Met Thr Ala Leu Ala Glu Leu Phe Val Ala
                    885                 890                 895
Gly Thr Ala Val Glu Trp Ala Gly Val Phe Glu Gly Thr Ala Arg Glu
                900                 905                 910
Val Gly Asp Gly Cys Gly Val Glu Leu Pro Thr Tyr Ala Phe Glu Arg
        915                 920                 925
Glu Arg Phe Trp Leu Asp Val Glu Glu Gly Ser Ala Gly Gly Ser Gly
        930                 935                 940
Val Ser Gly Met Trp Gly Gly Pro Leu Trp Glu Ala Val Glu Cys Gly
945                 950                 955                 960
Asp Ala Gly Val Val Ala Ser Leu Leu Gly Val Asp Glu Gly Ala Ser
                    965                 970                 975
Leu Gly Ala Val Val Ser Ala Leu Gly Glu Trp Gly Arg Val Arg His
                980                 985                 990
Glu Arg Glu Val Val Asp Gly Trp Arg Tyr Arg Glu Val Trp Arg Pro
        995                 1000                1005
Val Ser Gly Gly Gly Val Gly Gly Leu Ser Gly Ala Trp Leu Val Val
        1010                1015                1020
Ser Glu Gly Glu Ala Gly Pro Val Asp Val Val Ala Glu Gly Leu Glu
1025                1030                1035                1040
Arg Cys Gly Ala Arg Val Val Arg Val Glu Val Glu Ala Gly Cys Val
                    1045                1050                1055
Ser Arg Glu Val Leu Ala Gly His Leu Arg Glu Ala Val Asp Gly Glu
                1060                1065                1070
Ala Val Gly Gly Val Val Ser Leu Val Gly Trp Gly Ser Gly Val Val
        1075                1080                1085
Gln Ala Gly Val Ala Ser Val Gly Leu Val Gln Ala Leu Gly Asp Val
```

-continued

```
                1090                1095                1100
Gly Val Gly Ala Arg Leu Trp Cys Val Thr Gly Gly Ala Val Ser Val
1105                1110                1115                1120
Gly Gly Arg Asp Ala Val Trp Gly Pro Ala Ser Gly Val Val Trp Gly
                1125                1130                1135
Leu Gly Arg Val Val Gly Ala Glu Ala Pro Asp Arg Trp Gly Gly Leu
            1140                1145                1150
Val Asp Val Pro Glu Leu Val Asp Glu Arg Val Val Asp Gly Leu Val
        1155                1160                1165
Gly Val Leu Ala Gly Val Gly Gly Gly Glu Ser Glu Phe Ala Val
    1170                1175                1180
Arg Ser Ser Gly Ala Phe Val Arg Arg Leu Val Arg Ala Pro Leu Glu
1185                1190                1195                1200
Glu Ala Val Ala Glu Arg Glu Trp Arg Pro Arg Gly Thr Val Leu Val
                1205                1210                1215
Thr Gly Gly Thr Gly Glu Leu Gly Ala His Val Ala Arg Trp Met Ala
            1220                1225                1230
Arg Arg Gly Ala Glu His Leu Leu Leu Val Ser Arg Arg Gly Glu Ser
        1235                1240                1245
Ala Gln Gly Val Glu Glu Leu Arg Ala Asp Leu Met Gly Leu Gly Ala
    1250                1255                1260
Arg Val Ser Val Val Ala Cys Asp Ala Ala Asp Arg Glu Ala Leu Ala
1265                1270                1275                1280
Glu Val Leu Arg Ser Ala Val Pro Ala Glu Cys Pro Leu Gly Val Val
                1285                1290                1295
Val His Ala Ala Gly Val Val Asp Asp Gly Val Leu Glu Gly Leu Ser
            1300                1305                1310
Ser Glu Arg Val Thr Gly Val Leu Arg Ala Lys Ala Leu Ala Ala Trp
        1315                1320                1325
Asn Leu His Glu Leu Thr Arg Gly Ala Asp Leu Ser Gly Phe Val Val
    1330                1335                1340
Phe Ser Ser Ala Ala Ala Thr Phe Gly Pro Ala Gly Gln Gly Ser Tyr
1345                1350                1355                1360
Ala Ala Ala Asn Ala Tyr Val Glu Ala Ile Val Arg His Arg Arg Gly
                1365                1370                1375
Glu Gly Leu Pro Gly Leu Ala Val Ala Trp Gly Pro Trp Ala Gly Gly
            1380                1385                1390
Gly Met Ala Glu Gly Ala Val Gly Gln Met Arg Arg Arg Gly Leu Ala
        1395                1400                1405
Ala Met Thr Pro Glu Thr Ala Leu Val Ala Leu Gly Gln Ala Leu Asp
    1410                1415                1420
His Asp Glu Thr Cys Val Thr Val Ala Asp Ile Asp Trp Asp Arg Phe
1425                1430                1435                1440
Thr Ala Asn Ser Leu Pro Gly Ser Arg Leu Ser Pro Leu Ile Ser Asp
                1445                1450                1455
Ile Pro Glu Ala Arg Leu Ala Arg Glu Thr Thr Gly Leu Asp Thr Ala
            1460                1465                1470
Thr Ala Ser Pro Asp Ser Phe Ser Ala Arg Leu Lys Ala Met Asp Thr
        1475                1480                1485
Ala Glu Gln Glu Arg Ala Leu Leu Asp Leu Val Arg Thr Tyr Ala Ala
    1490                1495                1500
Thr Val Leu Gly His Ser Thr Pro Thr Ala Val Arg Pro Glu Arg Ala
1505                1510                1515                1520
```

```
Phe Arg Asp Leu Gly Phe Val Ser Val Ser Ala Val Glu Leu Arg Asn
            1525                1530                1535

Arg Leu Asn Ala Val Thr Gly Leu Leu Leu Pro Thr Thr Leu Ile Phe
        1540                1545                1550

Asp Tyr Pro Thr Pro Ser Ala Leu Ala Gly Tyr Leu Lys Glu Gln Leu
    1555                1560                1565

Glu Glu Gly Ala Gly Gly Gln Arg Asp Ile Ala Pro Pro Val Pro Ala
1570                1575                1580

Ser Arg Val Asp Val Asp Glu Pro Ile Ala Ile Val Gly Met Ala Cys
1585                1590                1595                1600

Arg Phe Pro Gly Gly Val Glu Ser Ala Glu Asp Leu Trp Glu Leu Val
            1605                1610                1615

Ala Ser Gly Arg Asp Ala Val Gly Glu Phe Pro Val Asp Arg Gly Trp
        1620                1625                1630

Asp Val Glu Ala Phe Tyr Asp Pro Glu Pro Gly Arg Ala Gly Ser Ser
    1635                1640                1645

Tyr Thr Arg Arg Gly Gly Phe Leu Glu Gly Ala Ala Glu Phe Asp Ala
1650                1655                1660

Gly Phe Phe Gly Ile Ser Pro Arg Glu Ala Leu Ala Met Asp Pro Gln
1665                1670                1675                1680

Gln Arg Leu Met Leu Glu Val Ser Trp Glu Ala Leu Glu Arg Ala Gly
            1685                1690                1695

Ile Asp Pro Ala Thr Leu Arg Gly Ser Thr Thr Gly Val Phe Ala Gly
        1700                1705                1710

Met Cys Ser Gln Asp Tyr Ala Asp Leu Val Arg Arg Ala Thr Glu Asp
    1715                1720                1725

Leu Glu Gly Tyr Ala Met Thr Gly Leu Ser Ser Ser Val Thr Ser Gly
    1730                1735                1740

Arg Val Ala Tyr Thr Leu Gly Leu Glu Gly Pro Ala Val Thr Val Asp
1745                1750                1755                1760

Thr Ala Cys Ser Ser Ser Leu Val Ala Leu His Leu Ala Cys Gln Ala
            1765                1770                1775

Leu Arg Ser Gly Glu Cys Ser Leu Ala Leu Ala Gly Gly Val Thr Val
        1780                1785                1790

Met Ser Thr Pro Gly Ala Phe Val Glu Phe Ser Arg Gln Arg Gly Leu
    1795                1800                1805

Ser Pro Asp Gly Arg Cys Lys Ala Tyr Gly Ser Gly Ala Asp Gly Val
    1810                1815                1820

Gly Trp Ala Glu Gly Val Gly Val Leu Leu Val Glu Arg Leu Ser Glu
1825                1830                1835                1840

Ala Glu Arg Arg Gly His Arg Val Leu Ala Val Val Arg Gly Ser Ala
            1845                1850                1855

Val Asn Gln Asp Gly Ala Ser Asn Gly Leu Thr Ala Pro Asn Gly Pro
        1860                1865                1870

Ser Gln Gln Arg Val Ile Arg Gln Ala Leu Ala Cys Ala Gly Leu Ser
    1875                1880                1885

Val Ala Asp Val Asp Val Val Glu Gly His Gly Thr Gly Thr Thr Leu
    1890                1895                1900

Gly Asp Pro Ile Glu Ala Gln Ala Leu Leu Ala Thr Tyr Gly Gln Gly
1905                1910                1915                1920

Arg Ser Gly Glu Arg Pro Val Trp Leu Gly Ser Val Lys Ser Asn Ile
            1925                1930                1935
```

-continued

```
Gly His Ala Gln Ala Ala Ala Gly Val Ala Gly Val Ile Lys Met Val
            1940                1945                1950

Met Ala Leu Arg Ala Gly Val Leu Pro Arg Thr Leu His Val Asp Glu
            1955                1960                1965

Pro Ser Ser Gln Val Asp Trp Ser Ser Gly Ser Val Arg Val Leu Ala
            1970                1975                1980

Asp Glu Val Glu Trp Pro Gly Val Glu Gly Arg Leu Arg Arg Ala Gly
1985                1990                1995                2000

Val Ser Ala Phe Gly Val Ser Gly Thr Asn Ala His Val Ile Leu Glu
            2005                2010                2015

Glu Ala Ser Gly Gly Ala Asp Gly Gly Ala Gly Arg Leu Gln Glu Leu
            2020                2025                2030

Gly Pro Gly Val Val Ser Gly Ser Gly Val Val Pro Trp Val Val Ser
            2035                2040                2045

Ala Arg Ser Glu Leu Ala Leu Arg Gly Gln Ala Arg Arg Leu Arg Gly
            2050                2055                2060

Val Val Ala Val Gly Gly Gly Ala Asp Gly Val Gly Val Ser Pro Ala
2065                2070                2075                2080

Gly Val Gly Arg Ala Leu Val Ser Glu Arg Ser Val Phe Glu His Arg
            2085                2090                2095

Ala Val Val Val Ala Glu Asp Arg Asp Glu Phe Leu His Ala Leu Asp
            2100                2105                2110

Ala Leu Ala Glu Gly Ala Pro Thr Ala Gly Val Val Gln Gly Val Ala
            2115                2120                2125

Gly Pro Ala Ala Asp Gly Lys Ile Ala Met Leu Phe Gly Gly Gln Gly
            2130                2135                2140

Thr His Trp Glu Gly Met Ala Gln Glu Leu Leu Gly Ser Ser Pro Val
2145                2150                2155                2160

Phe Ala Gln Gln Met Ser Asp Cys Ala Gln Ala Leu Glu Pro Tyr Leu
            2165                2170                2175

Asp Trp Ser Leu Leu Asp Val Leu Arg Gly Ala Pro Asp Ala Pro Pro
            2180                2185                2190

Leu Gln Arg Val Asp Val Val Gln Pro Val Leu Phe Ala Val Met Val
            2195                2200                2205

Ser Leu Ala Ala Leu Trp Arg Ser Tyr Gly Val His Pro Asp Ala Val
            2210                2215                2220

Ala Gly His Ser Gln Gly Glu Ile Ala Ala Ala Tyr Val Ala Gly Ala
2225                2230                2235                2240

Leu Ser Leu Asp Asp Ala Ala Arg Val Thr Ala Leu Arg Ser Gln Ala
            2245                2250                2255

Leu Ala Ala Leu Ala Gly Gln Gly Ala Met Ala Ser Val Gly Leu Pro
            2260                2265                2270

Val Glu Lys Leu Glu Pro Arg Leu Ala Thr Trp Gly Asp Arg Leu Val
            2275                2280                2285

Ile Ala Ala Val Asn Gly Ala Arg Ser Ala Val Val Ser Gly Glu Pro
            2290                2295                2300

Glu Ala Val Asp Ala Leu Val Glu Glu Leu Ser His Glu Asp Val Pro
2305                2310                2315                2320

Ala Arg Arg Leu Met Val Asp Trp Ala Ser His Ser Pro Gln Val Glu
            2325                2330                2335

Ala Ile Gln Gly Arg Leu Leu Glu Leu Leu Ala Pro Ile Arg Ala Arg
            2340                2345                2350

Thr Gly Asp Val Pro Phe Tyr Ser Thr Val Thr Gly Glu Arg Ile Asp
```

-continued

```
                2355                2360                2365
Gly Thr Glu Leu Asp Ala Asp Tyr Trp Tyr Arg Asn Leu Arg Gln Val
    2370                2375                2380

Val Arg Phe Arg Asp Ala Thr Gln Ala Leu Val Arg Ala Gly His Thr
2385                2390                2395                2400

Val Phe Ile Glu Ala Cys Pro His Pro Ala Val Ala Gly Val Gln
            2405                2410                2415

Glu Thr Leu Asp Glu Met Gly Asp Leu Asp Ser Leu Val Val Gly Ser
        2420                2425                2430

Leu Arg Arg Gly Glu Gly Gly Leu Arg Arg Phe Leu Met Ser Val Ala
    2435                2440                2445

Glu Leu Phe Val Gly Gly Val Ala Val Glu Trp Ser Gly Val Phe Gly
    2450                2455                2460

Ser Val Gly Arg Gly Val Ala Gly Gly Cys Gly Val Glu Leu Pro Thr
2465                2470                2475                2480

Tyr Ala Phe Glu Arg Glu Arg Phe Trp Leu Asp Val Glu Gly Ala Pro
            2485                2490                2495

Arg Gly Ser Gly Val Ser Gly Gln Trp Gly Gly Gln Leu Ser Glu Ala
        2500                2505                2510

Val Asp Thr Val Arg Gly Gly Met Leu Arg Asp Cys Leu Ala Gly Leu
    2515                2520                2525

Asp Pro Ala Ala Gln Ala Glu Thr Val Leu Asp Leu Val Leu Thr His
    2530                2535                2540

Ala Ala Ala Val Leu Gly His Gly Thr Ala Asp Ala Val Val Pro Glu
2545                2550                2555                2560

Arg Ala Phe Arg Asp Leu Gly Phe Asp Ser Leu Thr Ala Val Glu Leu
            2565                2570                2575

Arg Asn Arg Leu Asn Thr Ala Thr Gly Leu Arg Phe Pro Arg Thr Leu
        2580                2585                2590

Val Phe Asp His Pro Arg Pro Val Ala Leu Ala Ala His Ile His Glu
    2595                2600                2605

Gln Leu Ser Gly Gly Ser Pro Thr Thr Gly Thr Ala Leu Ala Leu Ala
    2610                2615                2620

Leu Arg Ala Pro Ala Pro Arg Val Asp Val Asp Glu Pro Ile Ala Ile
2625                2630                2635                2640

Val Gly Met Ala Cys Arg Phe Pro Gly Gly Val Glu Ser Ala Glu Asp
            2645                2650                2655

Phe Trp Glu Leu Ile Ala Ser Gly Arg Asp Ala Val Gly Glu Phe Pro
        2660                2665                2670

Val Asp Arg Gly Trp Asp Val Glu Ala Phe Tyr Asp Pro Glu Pro Gly
    2675                2680                2685

Arg Ala Gly Thr Ser Tyr Thr Arg Cys Gly Gly Phe Leu Gln Gly Ala
    2690                2695                2700

Ala Glu Phe Asp Ala Gly Phe Phe Gly Ile Ser Pro Arg Glu Ala Leu
2705                2710                2715                2720

Ala Met Asp Pro Gln Gln Arg Leu Met Leu Glu Val Ser Trp Glu Ala
            2725                2730                2735

Leu Glu Arg Ala Gly Ile Asp Pro Ala Thr Leu His Gly Ser Thr Thr
        2740                2745                2750

Gly Val Phe Ala Gly Val Ser Gln Gln Asp Tyr Ala Glu Leu Leu Arg
    2755                2760                2765

Arg Gly Thr Gln Asp His Glu Gly Tyr Ala Leu Thr Gly Val Ser Asn
    2770                2775                2780
```

-continued

```
Ser Val Val Ser Gly Arg Leu Ser Tyr Thr Phe Gly Phe Glu Gly Pro
2785            2790            2795            2800

Ala Val Thr Val Asp Thr Ala Cys Ser Ser Ser Leu Val Ala Leu His
        2805            2810            2815

Leu Ala Cys Gln Ala Leu Arg Ser Gly Glu Cys Ser Leu Ala Leu Ala
        2820            2825            2830

Gly Gly Val Thr Val Met Ser Thr Pro Gly Ala Phe Val Glu Phe Ser
        2835            2840            2845

Arg Gln Arg Gly Leu Ser Pro Asp Gly Arg Cys Lys Ala Tyr Gly Ser
        2850            2855            2860

Gly Ala Asp Gly Val Gly Trp Ala Glu Gly Val Gly Val Leu Leu Val
2865            2870            2875            2880

Glu Arg Leu Ser Glu Ala Glu Arg Arg Gly His Arg Val Leu Ala Val
            2885            2890            2895

Val Arg Gly Ser Ala Val Asn Gln Asp Gly Ala Ser Asn Gly Leu Thr
        2900            2905            2910

Ala Pro Asn Gly Pro Ser Gln Gln Arg Val Ile Arg Gln Ala Leu Ala
        2915            2920            2925

Cys Ala Gly Leu Ser Val Ala Asp Val Asp Val Val Glu Gly His Gly
    2930            2935            2940

Thr Gly Thr Thr Leu Gly Asp Pro Ile Glu Ala Gln Ala Leu Leu Ala
2945            2950            2955            2960

Thr Tyr Gly Gln Gly Arg Ser Gly Glu Arg Pro Val Trp Leu Gly Ser
        2965            2970            2975

Val Lys Ser Asn Ile Gly His Ala Gln Ala Ala Ala Gly Val Ala Gly
        2980            2985            2990

Val Ile Lys Met Val Met Ala Leu Asn His Glu Leu Leu Pro Thr Ser
        2995            3000            3005

Leu His Ile Asp Glu Pro Ser Pro His Ile Asp Trp Ser Ser Gly Gly
    3010            3015            3020

Val Arg Leu Leu Thr Glu Pro Val Pro Trp Gln Gln Asn Gly Arg Pro
3025            3030            3035            3040

Arg Arg Ala Gly Val Ser Ala Phe Gly Val Ser Gly Thr Asn Ala His
        3045            3050            3055

Val Ile Ile Glu Gln Ala Pro Val Glu Ala His Val Ile Ser Glu Pro
            3060            3065            3070

Val Pro Ala Glu Ala His Val Ile Val Glu Gln Ala Pro Val Glu Ala
        3075            3080            3085

Pro His Val Val Asp Ala Thr Gly Pro Ala Asp Leu Thr Glu Pro Gln
        3090            3095            3100

Glu Glu Ala Ala Glu Pro Glu Cys Val Ala Asp Ala Val Thr Glu Met
3105            3110            3115            3120

Ser Ala Glu Pro Glu Cys Val Ala Asp Ala Met Ser Glu Met Ser Ala
            3125            3130            3135

Glu Cys Val Ala Glu Ala Val Ser Asp Lys Ser Ala Glu Pro Glu Cys
        3140            3145            3150

Val Ala Asp Ala Met Ser Asp Lys Pro Ala Leu Leu Pro Ile Pro Trp
        3155            3160            3165

Leu Leu Ser Ala Lys Ser Glu Arg Ala Leu Arg Gly Gln Ala Arg Arg
        3170            3175            3180

Leu Arg Gln Phe Ala Ala Arg Ala Ser Asp Ala Arg Pro Ala Asp Val
        3185            3190            3195            3200
```

-continued

Ala His Ala Leu Ala Ala Gln Arg Ser Val Phe Asp His Arg Ala Val
        3205                3210                3215

Val Val Ala Glu Asp Arg Asp Gly Phe Leu Gln Ala Leu Asp Ala Leu
        3220                3225                3230

Ala Glu Gly Arg Ser Ala Asp Gly Leu Ile Glu Gly Ser Val Gly Pro
        3235                3240                3245

Arg Gly Gly His Ser Gly Arg Arg Gly Lys Thr Ala Met Leu Phe
        3250                3255                3260

Ala Gly Gln Gly Thr Gln Arg Val Gly Met Gly Arg Gln Leu Tyr Ala
3265                3270                3275                3280

Ala His Pro Ala Tyr Ala Asp Ala Leu Asp Gln Val Leu Ala Glu Leu
        3285                3290                3295

Asp Gly His Leu Asp Gln Pro Leu Arg Pro Leu Ile His Ala Ser Ala
        3300                3305                3310

Asp Leu Ala Asp Val Ala Asp Ala Ala Asp Val Leu Asp Arg Thr Arg
        3315                3320                3325

Tyr Ala Gln Pro Ala Leu Phe Ala Val Gln Val Ala Leu Phe Arg His
    3330                3335                3340

Leu Glu Arg Leu Gly Val Arg Ala Asp Phe Val Ala Gly His Ser Ile
3345                3350                3355                3360

Gly Glu Leu Ala Ala Ala His Val Ala Gly Val Leu Pro Leu Ala Ala
        3365                3370                3375

Ala Cys Arg Leu Val Ala Ala Arg Gly Arg Leu Met Glu Gln Leu Ala
        3380                3385                3390

Pro Gly Gly Ala Met Val Ala Val Arg Ala Ser Glu Ala Glu Ala Arg
        3395                3400                3405

Gln Ala Leu Asp Gly Arg Glu Ala Arg Val Ser Val Ala Ala Val Asn
3410                3415                3420

Gly Pro Ala Ser Val Val Phe Ser Gly Ala Glu Asp Glu Val Gly Asn
3425                3430                3435                3440

Met Ala Asp Trp Phe Ala Glu Arg Gly Arg Arg Val Lys Arg Leu Arg
        3445                3450                3455

Thr Gly His Ala Phe His Ser Pro Leu Met Asp Pro Met Leu Glu Glu
        3460                3465                3470

Phe Gln Gln Val Ala Ala Ser Leu Thr Tyr Ser Glu Pro Ala Ile Pro
    3475                3480                3485

Met Val Ser Thr Leu Thr Gly Asp Ile Val Ala Ala Gly Glu Leu Ser
        3490                3495                3500

Asp Pro Glu Tyr Trp Val Arg Gln Val Arg Arg Thr Val Arg Phe Gly
3505                3510                3515                3520

Asp Ala Ile Ser Arg Leu His Thr Asp Gly Val Arg Thr Phe Met Glu
        3525                3530                3535

Leu Gly Pro Asp Gly Thr Leu Ser Ala Leu Ala Glu Glu Cys Leu Glu
        3540                3545                3550

Ala Thr Ala Asp Ser His Pro Ala Asp Asp Thr Gly Thr Pro Gln
        3555                3560                3565

Glu Asn Leu Leu Ile Pro Leu Leu Arg Pro Asp Ser Pro Glu Pro Gly
    3570                3575                3580

Thr Leu Leu Thr Gly Leu Ala Arg Leu His Thr His Gly Ala Ala Ala
3585                3590                3595                3600

Val Asn Trp Pro Ala Ala Leu Pro Glu Arg Asp Arg Ala Arg His Leu
        3605                3610                3615

Asp Leu Pro Thr Tyr Ala Phe Asp His His Arg Tyr Trp Val Asp Thr

-continued

```
              3620            3625            3630
Ser Ala Gly His Pro Asp Leu Ser Ala Ala Gly Leu Gly Thr Ala
        3635            3640            3645
Gly His Pro Leu Leu Gly Ser Ala Val Ala Leu Ala Glu Ser Gln Glu
        3650            3655            3660
Leu Leu Phe Thr Gly Arg Leu Ser Leu Arg Thr His Pro Trp Leu Ala
3665            3670            3675            3680
Asp His Ala Ile Phe Gly Thr Val Leu Leu Pro Gly Thr Ala Ile Leu
        3685            3690            3695
Glu Leu Ala Val Arg Ala Gly Asp Glu Val Asp Cys Gly Thr Val Glu
        3700            3705            3710
Glu Leu Thr Leu Arg Thr Pro Leu Val Leu Pro Glu Gln Gly Ser Val
        3715            3720            3725
Ile Leu Gln Leu Ser Val Gly Ala Pro Gln Gly Pro Gln Thr Pro Glu
        3730            3735            3740
Glu Pro Glu Arg Arg Thr Phe Ala Leu Tyr Ala Arg Glu Asp Asp Gly
3745            3750            3755            3760
Leu Ser Ser Ser Ala Ala Ala Thr Gly Thr Glu Trp Thr Cys His
        3765            3770            3775
Ala Thr Gly Val Leu Thr Gly Thr Ala Arg Pro Ala Glu Glu His Thr
        3780            3785            3790
Gln Glu Pro Trp Pro Ala Asp Ala Ala Pro Val Asp Leu Asp Gly
        3795            3800            3805
Trp Tyr Glu Gln Leu Ala Gly Ala Gly Leu Gly Tyr Gly Pro Val Phe
        3810            3815            3820
Gln Gly Leu Arg Glu Val Trp Arg Arg Gly Asp Glu Val Phe Ala Val
3825            3830            3835            3840
Val Thr Leu Pro Glu Ser Thr Glu Gly Gln Ala Ala Asp Ala Ala Arg
        3845            3850            3855
Tyr Ala Leu His Pro Ala Leu Leu Asp Ala Ala Leu His Pro Val Val
        3860            3865            3870
Leu Arg His Glu Gly Asp Ala Ala Ala Asp Gly His Gly Trp Leu Pro
        3875            3880            3885
Phe Ser Trp Thr Gly Val Thr Val Ala Ala Ser Gly Ala Ser Thr Leu
        3890            3895            3900
His Val Arg Leu Thr Val Arg Thr Asp Glu Asp Ala Val Gly Leu Leu
3905            3910            3915            3920
Ala Thr Asp Ala Ser Gly Arg Ile Val Ile Ser Ala Gly Ser Leu Ala
        3925            3930            3935
Phe Arg Pro Val Ser Ala Glu Gln Leu Gln Ala Ala Arg Thr Gly Tyr
        3940            3945            3950
His Asp His Leu Phe Arg Ile Glu Trp Arg Pro Leu His Leu Pro Thr
        3955            3960            3965
Thr Pro Ala Arg Thr Ala Asp Trp Ala Leu Ile Gly Pro Gly Ala Arg
        3970            3975            3980
Arg Thr Ala Ala Val Leu Glu Arg Asn Gly Ala Ser Trp Gln Ala Tyr
3985            3990            3995            4000
Pro Asp Pro Ala Ala Leu Ala Glu Ala Leu Ala Ala Gly Ala Pro Ala
        4005            4010            4015
Pro Gly Met Val Val Ile Ser Cys Glu Pro Asp Gly Ala Ser Ala Pro
        4020            4025            4030
Thr Asp Ser Ala Leu Thr Asp Ser Ala Leu Thr Asp Ser Ala Pro Ala
        4035            4040            4045
```

```
Gly Ser Ala Pro Ala Asp Ser Thr Ala Leu Ala Asp Ala Thr Arg Gln
    4050                4055                4060
Ala Thr Thr Arg Val Leu Ala Leu Leu Gln Glu Trp Val Ala Asp Glu
4065                4070                4075                4080
Arg Leu Ala Ala Cys Arg Leu Ala Leu Leu Thr His Gly Ser Val Thr
            4085                4090                4095
Ala Thr Pro Asp Glu Pro Val Ser Asp Leu Ala His Ala Ala Val Trp
        4100                4105                4110
Gly Leu Val Arg Ser Val Gln Thr Glu Asn Pro Asp Arg Phe Leu Leu
    4115                4120                4125
Ala Asp Thr Asp Asp Thr Asp Ala Ser Arg Asn Ala Leu Pro Leu Leu
    4130                4135                4140
Ala Gly Glu Pro Gln Ile Ala Leu Arg Asn Gly Ala Val Arg Ile Pro
4145                4150                4155                4160
Arg Met Thr Arg Val Pro Val Arg Gln Pro Gln Pro Ser Thr Thr Asp
            4165                4170                4175
Ala Asp Trp Asp Pro Glu Ala Thr Val Leu Ile Thr Gly Gly Thr Gly
        4180                4185                4190
Val Leu Gly Arg Leu Val Ala Arg His Leu Ala Thr Ala His Gly Val
    4195                4200                4205
Arg His Leu Leu Leu Ala Thr Arg Arg Gly Thr Ala Ala Asp Gly Ala
    4210                4215                4220
Ala Asp Leu Val Ala Glu Leu Ala Gly Leu Gly Ala Glu Ala Thr Val
4225                4230                4235                4240
Ala Ala Cys Asp Ile Gly Asp Arg Ala Ala Val Ala Ala Leu Leu Asp
            4245                4250                4255
Gln Val Pro Ala Gln His Pro Leu Lys Ala Val Ile His Thr Ala Gly
        4260                4265                4270
Val Val Asp Asp Gly Ile Leu Thr Ser Leu Thr Pro Glu Arg Met Glu
    4275                4280                4285
Ala Val Leu His Ala Lys Ala Phe Gly Ala Ala His Leu His Asp Leu
    4290                4295                4300
Thr Arg Asp Ala Gly Leu Thr Thr Phe Thr Val Phe Ser Ser Ala Ala
4305                4310                4315                4320
Ala Ser Phe Gly Ser Pro Gly Gln Gly Asn Tyr Thr Ala Ala Asn Ala
            4325                4330                4335
Phe Leu Asp Ala Leu Met Gln His Arg His Thr Gln Ala Leu Pro Gly
        4340                4345                4350
Arg Ser Leu Ala Trp Gly Leu Trp Gly Glu Ala Asp Gly Met Thr Arg
    4355                4360                4365
Asn Leu Ala Gly Thr Asp Phe Ala Arg Met Ala Arg Gly Gly Leu Leu
    4370                4375                4380
Pro Leu Ser Asn Ala Gln Gly Leu Ala Leu Leu Asp Thr Ala Asp Arg
4385                4390                4395                4400
Leu Gly Pro Phe Gly Asp Gly Leu Leu Leu Ala Thr Arg Leu Asp Ala
            4405                4410                4415
Ala Thr Leu His Ala Gln Ala Thr Ala Gly Ala Leu Pro Arg Ile Leu
        4420                4425                4430
His Gly Leu Ile Arg Ile Pro Ala Arg Arg Ser Ala Asp His Gly Ile
    4435                4440                4445
Ala Thr Asp Thr Pro Ala Thr Leu Arg Glu Arg Leu Ala Gly Leu Thr
    4450                4455                4460
```

-continued

```
Ile Pro Ala Gln Arg Thr Gly Leu Leu Glu Leu Val Arg Thr His
4465                4470                4475                4480

Ala Ala Ala Val Leu Gly His Pro Thr Ser Ala Val Thr Ala Ala Asp
                4485                4490                4495

Gly Ala Leu Pro Asp Asp Leu Val Pro Ala Asp Thr Glu Phe Arg Asp
            4500                4505                4510

Leu Gly Phe Asp Ser Leu Thr Ala Val Glu Leu Arg Asn Arg Ile Asn
        4515                4520                4525

Ala Val Thr Gly Leu Arg Leu Pro Ala Thr Leu Ile Phe Asp Gln Pro
    4530                4535                4540

Ser Pro Ala Ala Leu Ala Asp His Leu Ala Thr Arg Leu Thr Ala Glu
4545                4550                4555                4560

Ala Gly Thr Pro Asp Glu Pro Ala Pro Ala Ala Ala Ala Ala Gly Ala
                4565                4570                4575

Gly Ser Ala Gly Ser Ala Glu Thr Gly Gln Gln Arg Ser Thr Gly Ser
            4580                4585                4590

Glu Lys Gln Gln Thr Arg Gly Gly Thr Ser Thr Glu Thr Val Glu Ser
        4595                4600                4605

Leu Phe Trp Ile Gly His Asp Thr Arg Arg Ile Glu Glu Ser Met Ala
    4610                4615                4620

Leu Leu Ser Ala Ala Ser Phe Phe Arg Pro Ala Phe Thr Asp Pro Ser
4625                4630                4635                4640

Asp Ile Pro Glu Pro Thr Phe Val Arg Leu Ala Gln Gly Glu Ala Arg
                4645                4650                4655

Ala Gln Gly Glu Ala Leu Ala Arg Gly Glu Thr Arg Pro Ala Leu Ile
            4660                4665                4670

Cys Leu Pro Thr Val Ala Ala Val Ser Ser Val Tyr Gln Tyr Ser Arg
        4675                4680                4685

Phe Ala Ala Gly Leu Asn Gly His Arg Asp Val Trp Tyr Val Pro Ala
    4690                4695                4700

Pro Gly Phe Leu Glu Gly Glu Pro Leu Pro Ser Gly Ile Gly Ala Val
4705                4710                4715                4720

Thr Arg Met Phe Ala Asp Ala Ile Val Arg Phe Thr Asp Gly Ala Pro
                4725                4730                4735

Phe Ala Leu Ala Gly His Ser Ala Gly Gly Trp Phe Val Tyr Ala Val
            4740                4745                4750

Thr Ser His Leu Glu Arg Leu Gly Val Arg Pro Glu Ala Val Val Thr
        4755                4760                4765

Met Asp Ala Tyr Leu Pro Asp Asp Gly Ile Ala Pro Val Ala Ser Ala
    4770                4775                4780

Leu Thr Ser Glu Ile Phe Asp Arg Val Thr Gln Phe Val Asp Val Asp
4785                4790                4795                4800

Tyr Thr Arg Leu Val Ala Met Gly Gly Tyr Phe Arg Ile Phe Ser Gly
                4805                4810                4815

Trp Ser Pro Pro Asp Ile Thr Thr Pro Ala Leu Phe Leu Arg Gly Arg
            4820                4825                4830

Asp Gly Glu Gln Met Pro Pro Pro Trp Gly Val Pro His Thr Val Leu
        4835                4840                4845

Asp Ile Gln Gly Asn His Phe Thr Met Leu Glu Gln Phe Ala Asp Ser
    4850                4855                4860

Thr Ala Arg His Val Asp Glu Trp Leu Thr Glu Ile Ala Ser Val Arg
4865                4870                4875                4880

Arg
```

<210> SEQ ID NO 6
<211> LENGTH: 5532
<212> TYPE: PRT
<213> ORGANISM: Streptomyces avermitilis

<400> SEQUENCE: 6

```
Met Asp Thr Ser Ser Glu Lys Leu Val Asp Ala Leu Arg Ala Ser Leu
 1               5                  10                  15

Lys Ala Asn Gln Thr Leu Arg Ala Arg Asn Glu Gln Leu Ala Ala Ala
            20                  25                  30

Met Glu Ala Ser Ser Glu Pro Ile Ala Ile Val Gly Met Ala Cys Arg
        35                  40                  45

Phe Pro Gly Gly Val Cys Ser Pro Glu Glu Leu Trp Glu Leu Val Ala
    50                  55                  60

Ser Gly Gly Asp Ala Ile Gly Glu Phe Pro Ala Gly Arg Gly Trp Asp
65                  70                  75                  80

Leu Glu Gly Leu Phe Asp Ser Asp Pro Asp Arg Ser Gly Thr Ser Tyr
                85                  90                  95

Ala Arg Tyr Gly Gly Phe Leu Tyr Glu Ala Gly Glu Phe Asp Ala Asp
            100                 105                 110

Phe Phe Gly Ile Ser Pro Arg Glu Ala Leu Ala Met Asp Pro Gln Gln
        115                 120                 125

Arg Leu Leu Leu Glu Thr Ser Trp Glu Ala Phe Glu Arg Ala Gly Ile
    130                 135                 140

Asp Pro Leu Ser Met Arg Gly Ser Arg Thr Gly Val Phe Ala Gly Val
145                 150                 155                 160

Met Tyr His Asp Tyr Gly Ser Arg Leu Gly Thr Ile Pro Glu Gly Phe
                165                 170                 175

Glu Gly Tyr Ile Gly Asn Gly Ser Gly Gly Ala Val Ala Ser Gly Arg
            180                 185                 190

Val Ala Tyr Thr Leu Gly Leu Glu Gly Pro Ala Val Ser Val Asp Thr
        195                 200                 205

Ala Cys Ser Ser Ser Leu Val Ala Leu His Leu Ala Cys Gln Ser Leu
    210                 215                 220

Arg Ser Gly Glu Cys Thr Leu Ala Leu Ala Gly Gly Val Thr Val Met
225                 230                 235                 240

Ser Thr Pro His Leu Phe Val Glu Phe Ser Arg Gln Arg Gly Leu Ser
                245                 250                 255

Val Asp Gly Arg Cys Lys Ser Phe Ala Gly Ala Asp Gly Thr Gly
            260                 265                 270

Met Gly Glu Gly Val Gly Met Leu Leu Val Glu Arg Leu Ser Asp Ala
        275                 280                 285

Val Arg Leu Gly His Arg Val Leu Ala Val Leu Arg Gly Ser Ala Val
    290                 295                 300

Asn Gln Asp Gly Ala Ser Asn Gly Leu Thr Ala Pro Asn Gly Pro Ala
305                 310                 315                 320

Gln Glu Arg Val Ile Arg Gln Ala Leu Ala Asn Ala Gly Leu Ser Val
                325                 330                 335

Ala Asp Val Asp Val Val Glu Gly His Gly Thr Gly Thr Thr Leu Gly
            340                 345                 350

Asp Pro Ile Glu Ala Gln Ala Leu Leu Ala Thr Tyr Gly Gln Arg Ala
        355                 360                 365

Gly Asn Arg Pro Leu Trp Leu Gly Ser Val Lys Ser Asn Ile Gly His
```

-continued

```
                370                 375                 380
Ala Gln Ala Ala Ala Gly Val Gly Gly Val Ile Lys Met Val Met Ala
385                 390                 395                 400

Leu Arg Glu Gly Val Leu Pro Arg Thr Leu His Val Asp Glu Pro Ser
                405                 410                 415

Pro Gln Val Asp Trp Ser Ala Gly Ala Val Arg Leu Leu Thr Glu Ala
                420                 425                 430

Val Pro Trp Pro Gly Asp Ala Ala Gly Arg Leu Arg Ala Gly Val
                435                 440                 445

Ser Ser Phe Gly Val Ser Gly Thr Asn Ala His Val Ile Leu Glu Glu
                450                 455                 460

Ala Pro Ala Ala Gly Gly Cys Val Ala Gly Gly Val Leu Glu Gly
465                 470                 475                 480

Ala Pro Gly Leu Ala Ile Ser Val Ala Glu Ser Val Ala Pro Val
                485                 490                 495

Ala Val Ser Ala Pro Val Ala Glu Ser Val Pro Val Pro Val
                500                 505                 510

Pro Val Pro Val Pro Val Ser Ala Arg Ser Glu Ala Gly Leu Arg Ala
                515                 520                 525

Gln Ala Glu Ala Leu Arg Gln Tyr Val Ala Val Arg Pro Asp Val Ser
530                 535                 540

Leu Ala Asp Val Gly Ala Gly Leu Ala Cys Gly Arg Ala Val Leu Glu
545                 550                 555                 560

His Arg Ala Val Val Leu Ala Ala Asp Arg Glu Glu Leu Val Gln Gly
                565                 570                 575

Leu Gly Ala Leu Ala Ala Gly Glu Pro Asp Arg Arg Val Thr Thr Gly
                580                 585                 590

His Ala Pro Gly Gly Asp Arg Gly Gly Val Val Phe Val Phe Pro Gly
                595                 600                 605

Gln Gly Gly Gln Trp Ala Gly Met Gly Val Arg Leu Leu Ala Ser Ser
                610                 615                 620

Pro Val Phe Ala Arg Arg Met Gln Ala Cys Glu Glu Ala Leu Ala Pro
625                 630                 635                 640

Trp Val Asp Trp Ser Val Val Asp Ile Leu Arg Arg Asp Ala Gly Asp
                645                 650                 655

Ala Val Trp Glu Arg Ala Asp Val Val Gln Pro Val Leu Phe Ser Val
                660                 665                 670

Met Val Ser Leu Ala Ala Leu Trp Arg Ser Tyr Gly Ile Glu Pro Asp
                675                 680                 685

Ala Val Leu Gly His Ser Gln Gly Glu Ile Ala Ala His Val Cys
                690                 695                 700

Gly Ala Leu Ser Leu Lys Asp Ala Ala Lys Thr Val Ala Leu Arg Ser
705                 710                 715                 720

Arg Ala Leu Ala Ala Val Arg Gly Arg Gly Gly Met Ala Ser Val Pro
                725                 730                 735

Leu Pro Ala Gln Glu Val Glu Gln Leu Ile Gly Glu Arg Trp Ala Gly
                740                 745                 750

Arg Leu Trp Val Ala Ala Val Asn Gly Pro Arg Ser Thr Ala Val Ser
                755                 760                 765

Gly Asp Ala Glu Ala Val Asp Glu Val Leu Ala Tyr Cys Ala Gly Thr
                770                 775                 780

Gly Val Arg Ala Arg Arg Ile Pro Val Asp Tyr Ala Ser His Cys Pro
785                 790                 795                 800
```

-continued

```
His Val Gln Pro Leu Arg Glu Glu Leu Leu Glu Leu Leu Gly Asp Ile
            805                 810                 815
Ser Pro Gln Pro Ser Gly Val Pro Phe Phe Ser Thr Val Glu Gly Thr
            820                 825                 830
Trp Leu Asp Thr Thr Thr Leu Asp Ala Ala Tyr Trp Tyr Arg Asn Leu
            835                 840                 845
His Gln Pro Val Arg Phe Ser Asp Ala Val Gln Ala Leu Ala Asp Asp
            850                 855                 860
Gly His Arg Val Phe Val Glu Val Ser Pro His Pro Thr Leu Val Pro
865                 870                 875                 880
Ala Ile Glu Asp Thr Thr Glu Asp Thr Ala Glu Asp Val Thr Ala Ile
            885                 890                 895
Gly Ser Leu Arg Arg Gly Asp Asn Asp Thr Arg Arg Phe Leu Thr Ala
            900                 905                 910
Leu Ala His Thr His Thr Thr Gly Ile Gly Thr Pro Thr Thr Trp His
            915                 920                 925
His His Tyr Thr His His His Thr His Pro His Asn His His Leu Asp
            930                 935                 940
Leu Pro Thr Tyr Pro Phe Gln Arg Gln His Tyr Trp Leu Asp Ala Pro
945                 950                 955                 960
Thr Gly Ala Gly Asp Val Ala Ala Ala Gly Leu Glu Pro Ala Glu His
            965                 970                 975
Pro Leu Leu Ala Ala Thr Val Gln Leu Ala Asp Thr Asp Gly Cys Leu
            980                 985                 990
Leu Thr Gly Arg Leu Ser Leu Arg Ser His Pro Trp Leu Gly Asp Tyr
            995                 1000                1005
Glu Val Gly Gly Ala Val Leu Leu Ser Gly Ser Ala Phe Val Glu Leu
            1010                1015                1020
Ala Val Gln Val Gly Glu Arg Val Gly Cys Thr Arg Ile Glu Gln Leu
1025                1030                1035                1040
Thr Val His Ala Pro Leu Val Val Pro Val Gly Gly Gly Val Ser Val
            1045                1050                1055
Gln Val Gly Val Ala Ala Ala Asp Gly Glu Gly Arg Arg Leu Val Ser
            1060                1065                1070
Val Tyr Ala Arg Gly Gly Ser Ala Cys Gly Gly Gly Ala Ser Gly
            1075                1080                1085
Gly Val Trp Thr Cys His Ala Ser Gly Val Leu Val Glu Ala Ala Ala
            1090                1095                1100
Gly Gly Gly Val Val Asp Gly Leu Ala Gly Val Trp Pro Pro Arg
1105                1110                1115                1120
Gly Ala Val Ala Val Asp Val Asp Gly Val Arg Asp Arg Leu Ala Gly
            1125                1130                1135
Ala Gly Cys Val Leu Gly Pro Val Phe Ser Gly Leu Arg Ala Val Trp
            1140                1145                1150
Arg Asp Gly Gly Asp Leu Leu Ala Glu Val Cys Leu Pro Glu Glu Ala
            1155                1160                1165
Trp Gly Asp Ala Ala Gly Phe Gly Leu His Pro Ala Leu Leu Asp Gly
            1170                1175                1180
Val Val Gln Pro Leu Ser Val Leu Leu Pro Gly Gly Thr Gly Phe Gly
1185                1190                1195                1200
Glu Gly Ala Gly Phe Gly Glu Gly Val Arg Val Pro Ala Val Trp Gly
            1205                1210                1215
```

```
Gly Val Ser Leu His Arg Ala Gly Val Thr Gly Val Arg Val Arg Val
        1220                1225                1230

Trp Ala Val Gly Arg Gly Gly Arg Glu Ala Val Ser Val Val Val
        1235                1240                1245

Gly Asp Glu Ala Gly Val Pro Val Ala Ser Val Asp Arg Leu Glu Leu
    1250                1255                1260

Arg Pro Val Asp Met Gly Gln Leu Arg Ala Val Ser Val Ser Ala Gly
1265                1270                1275                1280

Arg Arg Gly Ser Leu Tyr Ala Val Gln Trp Ala Glu Val Gly Pro Val
                1285                1290                1295

Pro Val Cys Gly Gln Ala Trp Ala Trp His Glu Asp Val Gly Glu Ser
            1300                1305                1310

Gly Gly Gly Pro Val Pro Gly Val Val Leu Arg Cys Pro Asp Ala
        1315                1320                1325

Gly Ala Gly Gly Gly Gly Gly Gly Val Gly Glu Val Val Gly Gly
        1330                1335                1340

Val Leu Gly Val Val Gln Gly Trp Leu Gly Leu Glu Arg Phe Ala Gly
1345                1350                1355                1360

Ser Arg Leu Val Val Val Thr Arg Gly Ala Val Val Ala Gly Gln Glu
            1365                1370                1375

Asp Gly Pro Val Asp Val Val Gly Ala Ala Val Trp Gly Leu Val Arg
        1380                1385                1390

Ser Ala Gln Ala Glu His Pro Asp Arg Phe Val Leu Leu Asp Leu Asp
        1395                1400                1405

Thr Asp Thr Asp Thr Gly Thr Asp Leu Asp Thr Gly Ala Gly Ala Gly
    1410                1415                1420

Ala Gly Ala Gly Trp Gly Val Asp Gly Gly His Val Ala Ala Val Val
1425                1430                1435                1440

Ala Cys Gly Glu Pro Gln Leu Ala Val Arg Gly Glu Arg Val Leu Ala
            1445                1450                1455

Ala Arg Leu Thr Arg Leu Glu Ser Ser Val Asp Val Pro Ala Gln Arg
        1460                1465                1470

Ser Gly Asp Val Ala Gly Arg Glu Val Leu Pro Trp Leu Ser Gly Gly
    1475                1480                1485

Ser Val Leu Val Thr Gly Gly Thr Gly Val Leu Gly Ala Ala Val Ala
    1490                1495                1500

Arg His Leu Ala Gly Val Cys Gly Val Arg Asp Leu Leu Leu Val Ser
1505                1510                1515                1520

Arg Arg Gly Pro Asp Ala Pro Gly Ala Glu Gly Leu Arg Ala Glu Leu
            1525                1530                1535

Ala Ala Leu Gly Ala Glu Val Arg Ile Val Ala Cys Asp Val Gly Glu
        1540                1545                1550

Arg Arg Glu Val Val Arg Leu Leu Glu Gly Val Pro Ala Gly Cys Pro
    1555                1560                1565

Leu Thr Gly Val Val His Ala Ala Gly Val Leu Asp Asp Ala Thr Ile
    1570                1575                1580

Ala Ser Leu Thr Pro Glu Arg Leu Gly Thr Val Phe Ala Ala Lys Val
1585                1590                1595                1600

Asp Ala Ala Leu Leu Leu Asp Glu Leu Thr Arg Gly Met Glu Leu Ser
                1605                1610                1615

Ala Phe Val Leu Phe Ser Ser Ala Ala Gly Ile Leu Gly Ser Ala Gly
        1620                1625                1630

Gln Gly Asn Tyr Ala Ala Ala Asn Ala Ala Leu Asp Ala Leu Ala Tyr
```

-continued

```
              1635                1640                1645
Arg Arg Arg Ala Ala Gly Leu Pro Gly Val Ser Leu Ala Trp Gly Leu
    1650                1655                1660
Trp Glu Glu Ala Ser Gly Met Thr Gly His Leu Ala Gly Thr Asp His
1665                1670                1675                1680
Arg Arg Ile Ile Arg Ser Gly Leu His Pro Met Ser Thr Pro Asp Ala
                1685                1690                1695
Leu Ala Leu Phe Asp Ala Ala Leu Ala Leu Asp Arg Pro Val Leu Leu
        1700                1705                1710
Pro Ala Asp Leu Arg Pro Ala Pro Leu Pro Pro Leu Leu Gln Asp
    1715                1720                1725
Leu Leu Pro Ala Thr Arg Arg Thr Thr Arg Thr Thr Thr Gly
    1730                1735                1740
Gly Ala Asp Asn Gly Ala Gln Leu His Ala Arg Leu Ala Gly Gln Thr
1745                1750                1755                1760
His Glu Gln Gln His Thr Thr Leu Leu Ala Leu Val Arg Ser His Ile
                1765                1770                1775
Ala Thr Val Leu Gly His Thr Thr Pro Asp Thr Ile Pro Pro Asp Arg
        1780                1785                1790
Ala Phe Arg Asp Leu Gly Phe Asp Ser Leu Thr Ala Val Glu Leu Arg
    1795                1800                1805
Asn Arg Leu Ser Arg Thr Thr Gly Leu Arg Leu Pro Thr Thr Leu Ala
    1810                1815                1820
Phe Asp His Pro Asn Pro Thr Thr Leu Thr His His Leu His Thr Gln
1825                1830                1835                1840
Leu Leu Gly Ser Asp Ser Thr Ala Ser Ile Pro Ala Pro Arg Ala Ala
                1845                1850                1855
Ala Val Pro Ala Asp Gln Asp Glu Pro Val Ala Ile Ile Gly Met Ala
        1860                1865                1870
Cys Arg Tyr Pro Gly Gly Val Thr Ser Ala Glu Glu Leu Trp Glu Leu
    1875                1880                1885
Leu Ala Ser Gly Arg Asp Thr Val Gly Glu Phe Pro Thr Asp Arg Gly
    1890                1895                1900
Trp Asp Leu Glu Ala Leu Phe Asp Pro Glu Pro Gly Arg Pro Gly Thr
1905                1910                1915                1920
Ser Tyr Thr Arg Cys Gly Ser Phe Leu Tyr Asp Ala Gly Glu Phe Asp
                1925                1930                1935
Ala Gly Phe Phe Gly Ile Ser Pro Arg Glu Ala Leu Ala Met Asp Pro
        1940                1945                1950
Gln Gln Arg Leu Leu Leu Glu Ala Ser Trp Glu Ala Met Glu Gln Ala
    1955                1960                1965
Gly Ile Asp Pro Thr Thr Val Arg Gly Ser Gln Thr Gly Val Phe Ala
    1970                1975                1980
Gly Leu Ile Pro Gln Ala Tyr Gly Pro Arg Leu His Glu Asn Ala Ala
1985                1990                1995                2000
Ala Asp Thr Glu Gly Tyr Val Leu Thr Gly Thr Ser Gly Ser Val Ala
                2005                2010                2015
Ser Gly Arg Ile Ser Tyr Thr Phe Gly Phe Glu Gly Pro Ala Val Ser
        2020                2025                2030
Val Asp Thr Ala Cys Ser Ser Ser Leu Val Ala Leu His Leu Ala Cys
    2035                2040                2045
Gln Ala Leu Arg Ala Gly Glu Cys Ser Met Ala Leu Ala Gly Gly Val
    2050                2055                2060
```

-continued

```
Thr Val Met Ser Ser Pro Gly Ala Phe Val Glu Phe Ser Arg Gln Arg
2065                2070                2075                2080

Gly Leu Ala Ala Asp Gly His Cys Lys Ala Phe Ser Ala Ala Ala Asp
            2085                2090                2095

Gly Thr Gly Trp Gly Glu Gly Val Gly Met Leu Leu Val Glu Arg Leu
            2100                2105                2110

Ser Asp Ala Arg Arg Asn Gly His Arg Val Leu Ala Val Val Arg Gly
            2115                2120                2125

Ser Ala Val Asn Gln Asp Gly Ala Ser Asn Gly Leu Thr Ala Pro Asn
            2130                2135                2140

Gly Pro Ser Gln Gln Arg Val Ile Arg Gln Ala Leu Ala Asn Ala Gly
2145                2150                2155                2160

Leu Ser Ala Gly Asp Val Asp Ala Val Glu Ala His Gly Thr Gly Thr
            2165                2170                2175

Thr Leu Gly Asp Pro Ile Glu Ala Gln Ala Leu Leu Ala Thr Tyr Gly
            2180                2185                2190

Gln Asp Arg Ala Gly Glu Gly Pro Leu Trp Leu Gly Ser Val Lys Ser
            2195                2200                2205

Asn Val Gly His Thr Gln Ala Ala Ala Gly Val Ala Gly Val Ile Lys
2210                2215                2220

Met Val Met Ala Leu Arg Asn Gly Leu Leu Pro Arg Thr Leu His Val
2225                2230                2235                2240

Asp Glu Pro Ser Pro His Val Asp Trp Ser Ala Gly Ala Val Gln Leu
            2245                2250                2255

Leu Thr Glu Thr Val Pro Trp Pro Gly Gly Glu Gly Arg Leu Arg Arg
            2260                2265                2270

Ala Gly Val Ser Ser Phe Gly Val Ser Gly Thr Asn Ala His Val Ile
            2275                2280                2285

Leu Glu Glu Ala Pro Ala His Asn Ile Pro Ser Asp Thr Pro Ala Asp
            2290                2295                2300

Asp Val Pro Gly Gly Pro Pro Ala Gly Glu Asp Ala Gly Ser Gly Glu
2305                2310                2315                2320

Glu Ala Ala Ala Gly Ser Pro Gly Val Trp Pro Trp Leu Val Ser Ala
            2325                2330                2335

Lys Ser Gln Pro Ala Leu Arg Ala Gln Ala Leu His Ala His
            2340                2345                2350

Leu Thr Asp His Pro Gly Leu Asp Leu Ala Asp Val Gly Tyr Thr Leu
            2355                2360                2365

Ala His Ala Arg Ala Val Phe Asp His Arg Ala Thr Leu Ile Ala Ala
            2370                2375                2380

Asp Arg Asp Thr Phe Leu Gln Ala Leu Gln Ala Leu Ala Ala Gly Glu
2385                2390                2395                2400

Pro His Pro Ala Val Ile His Ser Ser Ala Pro Gly Gly Thr Gly Thr
            2405                2410                2415

Gly Glu Ala Ala Gly Lys Thr Ala Phe Ile Cys Ser Gly Gln Gly Thr
            2420                2425                2430

Gln Arg Pro Gly Met Ala His Gly Leu Tyr His Thr His Pro Val Phe
            2435                2440                2445

Ala Ala Ala Leu Asn Asp Ile Cys Thr His Leu Asp Pro His Leu Asp
            2450                2455                2460

His Pro Leu Leu Pro Leu Leu Thr Gln Asp Pro Asn Thr Gln Asp Thr
2465                2470                2475                2480
```

-continued

```
Thr Thr Leu Glu Glu Ala Ala Ala Leu Leu Gln Gln Thr Pro Tyr Ala
            2485                2490                2495

Gln Pro Ala Leu Phe Ala Phe Gln Val Ala Leu His Arg Leu Leu Thr
        2500                2505                2510

Asp Gly Tyr His Ile Thr Pro His Tyr Ala Gly His Ser Leu Gly
    2515                2520                2525

Glu Ile Thr Ala Ala His Leu Ala Gly Ile Leu Thr Leu Thr Asp Ala
    2530                2535                2540

Thr Thr Leu Ile Thr Gln Arg Ala Thr Leu Met Gln Thr Met Pro Pro
2545                2550                2555                2560

Gly Thr Met Thr Thr Leu His Thr Thr Pro His Ile Thr His His
            2565                2570                2575

Ile Thr Ala His Glu Asn Asp Leu Ala Ile Ala Ala Ile Asn Thr Pro
            2580                2585                2590

Thr Ser Leu Val Ile Ser Gly Thr Pro His Thr Val Gln His Ile Thr
        2595                2600                2605

Thr Leu Cys Gln Gln Gln Gly Ile Lys Thr Lys Thr Leu Pro Thr Asn
    2610                2615                2620

His Ala Phe His Ser Pro His Thr Asn Pro Ile Leu Asn Gln Leu His
2625                2630                2635                2640

Gln His Thr Gln Thr Leu Thr Tyr His Pro Pro His Thr Pro Leu Ile
            2645                2650                2655

Thr Ala Asn Thr Pro Pro Asp Gln Leu Leu Thr Pro His Tyr Trp Thr
        2660                2665                2670

Gln Gln Ala Arg Asn Thr Val Asp Ile Ala Thr Thr Thr Gln Thr Leu
    2675                2680                2685

His Gln His Gly Val Thr Thr Tyr Ile Glu Leu Gly Pro Asp Asn Thr
    2690                2695                2700

Leu Thr Thr Leu Thr His His Asn Leu Pro Asn Thr Pro Thr Thr Thr
2705                2710                2715                2720

Leu Thr Leu Thr His Pro His His Pro Gln Thr His Leu Leu Thr
            2725                2730                2735

Asn Leu Ala Lys Thr Thr Thr Thr Trp His Pro His His Tyr Thr His
            2740                2745                2750

His His Asn Gln Pro His Thr His Thr His Leu Asp Leu Pro Thr Tyr
        2755                2760                2765

Pro Phe Gln His His His Tyr Trp Leu Glu Ser Thr Gln Pro Gly Ala
    2770                2775                2780

Gly Asn Val Ser Ala Ala Gly Leu Asp Pro Thr Glu His Pro Leu Leu
2785                2790                2795                2800

Gly Ala Thr Leu Glu Leu Ala Glu Gly Asp Gly Cys Leu Leu Thr Gly
            2805                2810                2815

Arg Leu Ser Leu Arg Thr His Pro Trp Leu Ala Gly His Ala Val Gly
            2820                2825                2830

Gly Val Val Leu Leu Pro Gly Thr Ala Phe Ala Glu Leu Ala Leu His
        2835                2840                2845

Ala Gly Glu Ser Val Gly Cys Asp His Val Asp Glu Leu Thr Leu His
    2850                2855                2860

Thr Pro Leu Val Ile Pro Glu Val Gly Asp Val Thr Leu Gln Val Ala
2865                2870                2875                2880

Ile Ala Ala Pro Asp Glu Ser Gly Arg Arg Met Met Thr Ile His Ser
            2885                2890                2895

Arg Gly Glu Gly Gly Ser Gly Gly Ala Asp Ala Ser Ala Ser Ala Trp
```

-continued

```
                  2900                2905                2910

Thr Arg His Ala Ala Gly Val Leu Ser Pro Ala Lys Asp Asp Thr
        2915                2920                2925

Ala Ser Tyr Glu Leu Leu Ala Gly Pro Trp Pro Val Gly Ala Thr
        2930                2935                2940

Pro Val Asp Leu Asn Thr Ala Tyr Asp Gln Met Ala Asp Ala Gly Phe
2945                2950                2955                2960

Ala Tyr Gly Leu Ala Phe Gln Gly Leu Arg Ala Ala Trp Arg Tyr Gly
            2965                2970                2975

Asp Asp Ile Leu Val Glu Ala Arg Leu Pro Glu Glu Val Ser Gly Asp
            2980                2985                2990

Ala Ala Ala Tyr Gly Leu His Pro Ala Leu Leu Asp Ala Ala Leu Gln
        2995                3000                3005

Gly Thr Gly Leu Leu Ser Val Ala Gly Pro Gly Thr Pro Val Val Pro
        3010                3015                3020

His Val Trp Asn Gly Leu Arg Phe Arg Thr His Gly Ala Val Ser Val
3025                3030                3035                3040

Arg Ala Cys Leu Ser Thr Leu Gly Ala Thr Gly Ala Ala Val Cys Val
                3045                3050                3055

Arg Ile Thr Asp Asp Thr Gly Val Pro Val Ala Ser Val Asp Arg Leu
            3060                3065                3070

Glu Leu Arg Pro Val Asp Met Gly Gln Leu Arg Ala Val Ser Val Ser
        3075                3080                3085

Ala Gly Arg Arg Gly Ser Leu Tyr Ala Val Gln Trp Ala Glu Val Gly
        3090                3095                3100

Pro Val Pro Val Cys Gly Gln Ala Trp Ala Trp His Glu Asp Val Gly
3105                3110                3115                3120

Glu Ser Gly Gly Gly Pro Val Pro Gly Val Val Leu Arg Cys Pro
                3125                3130                3135

Asp Ala Gly Ala Asp Gly Gly Gly Gly Gly Val Gly Glu Val Val
                3140                3145                3150

Gly Gly Val Leu Gly Val Val Gln Gly Trp Leu Gly Leu Glu Arg Phe
        3155                3160                3165

Ala Gly Ser Arg Leu Val Val Val Thr Arg Gly Ala Val Val Ala Gly
        3170                3175                3180

Pro Glu Asp Gly Pro Val Asp Val Val Gly Ala Ala Val Trp Gly Leu
3185                3190                3195                3200

Val Arg Ser Ala Gln Ala Glu His Pro Asp Arg Phe Val Leu Leu Asp
            3205                3210                3215

Leu Asp Thr Asp Leu Asp Ser Gly Ala Asp Ala Asp Ala Gly Asn Glu
            3220                3225                3230

Ala Gly Met Gly Ser Gly Leu Asp Gly Gly Arg Val Ala Ala Val Val
        3235                3240                3245

Ala Cys Gly Glu Pro Gln Leu Ala Val Arg Gly Glu Arg Val Leu Ala
        3250                3255                3260

Ala Arg Leu Thr Arg Leu Glu Ser Pro Val Asp Val Ser Gly Arg Glu
3265                3270                3275                3280

Val Leu Pro Trp Leu Ser Gly Gly Ser Val Leu Val Thr Gly Gly Thr
                3285                3290                3295

Gly Val Leu Gly Ala Ala Val Ala Arg His Leu Ala Gly Val Cys Gly
            3300                3305                3310

Val Arg Asp Leu Leu Leu Val Ser Arg Arg Gly Pro Asp Ala Pro Gly
        3315                3320                3325
```

-continued

```
Ala Glu Gly Leu Arg Ala Glu Leu Ala Ala Leu Gly Ala Glu Val Arg
    3330            3335                3340
Ile Val Ala Cys Asp Val Gly Glu Arg Arg Glu Val Val Arg Leu Leu
3345            3350                3355                3360
Glu Gly Val Pro Ala Gly Cys Pro Leu Thr Gly Val Val His Ala Ala
            3365                3370                3375
Gly Val Leu Asp Asp Ala Thr Ile Ala Ser Leu Thr Pro Glu Arg Leu
        3380                3385                3390
Gly Thr Val Phe Ala Ala Lys Val Asp Ala Ala Leu Leu Leu Asp Glu
        3395                3400                3405
Leu Thr Arg Gly Met Glu Leu Ser Ala Phe Val Leu Phe Ser Ser Ala
    3410                3415                3420
Ala Gly Ile Leu Gly Ser Ala Gly Gln Gly Asn Tyr Ala Ala Ala Asn
3425            3430                3435                3440
Ala Ala Leu Asp Ala Leu Ala Tyr Arg Arg Ala Ala Gly Leu Pro
            3445                3450                3455
Gly Val Ser Leu Ala Trp Gly Leu Trp Glu Glu Ala Ser Gly Met Thr
            3460                3465                3470
Gly His Leu Ala Gly Thr Asp His Arg Arg Ile Ile Arg Ser Gly Leu
        3475                3480                3485
His Pro Met Ser Thr Pro Asp Ala Leu Ala Leu Phe Asp Ala Ala Leu
    3490                3495                3500
Ala Leu Asp Arg Pro Val Leu Leu Pro Ala Asp Leu Arg Pro Ala Pro
3505            3510                3515                3520
Pro Leu Pro Pro Leu Leu Gln Asp Leu Leu Pro Ala Thr Arg Arg Arg
            3525                3530                3535
Thr Thr Arg Thr Thr Thr Thr Gly Gly Ala Asp Asn Gly Ala Gln Leu
        3540                3545                3550
His Ala Arg Leu Ala Gly Gln Thr His Glu Gln Gln His Thr Thr Leu
    3555                3560                3565
Leu Ala Leu Val Arg Ser His Ile Ala Thr Val Leu Gly His Asn Ala
    3570                3575                3580
Pro Glu Met Ile Pro Val Asp Ser Ala Phe Arg Asp Leu Gly Phe Asp
3585            3590                3595                3600
Ser Leu Thr Ala Val Glu Leu Arg Asn Arg Leu Gly Glu Ala Thr Gly
            3605                3610                3615
Leu Arg Leu Pro Thr Ser Leu Val Phe Asp Gln Pro Asn Ala Ala Thr
        3620                3625                3630
Leu Ala Arg His Leu Arg Arg Glu Leu Met Gly Asp Ala Glu Gly
        3635                3640                3645
Glu Thr Pro Ser Gln Val Ala Leu His Gln Val Ala Ala Asp Glu Pro
    3650                3655                3660
Ile Ala Ile Val Gly Met Ala Cys Arg Phe Pro Gly Gly Val Cys Ser
3665            3670                3675                3680
Pro Glu Glu Leu Trp Glu Leu Val Ala Ser Gly Gly Asp Ala Ile Gly
            3685                3690                3695
Glu Phe Pro Ala Gly Arg Gly Trp Asp Leu Glu Gly Leu Phe Asp Ser
        3700                3705                3710
Asp Pro Asp Arg Ser Gly Thr Ser Tyr Ala Arg Tyr Gly Gly Phe Leu
        3715                3720                3725
Tyr Glu Ala Gly Glu Phe Asp Ala Asp Phe Phe Gly Ile Ser Pro Arg
    3730                3735                3740
```

-continued

```
Glu Ala Leu Ala Met Asp Pro Gln Gln Arg Leu Leu Glu Thr Ser
3745                3750                3755                3760

Trp Glu Ala Phe Glu Arg Ala Gly Ile Asp Pro Leu Ser Met Arg Gly
                3765                3770                3775

Ser Arg Thr Gly Val Phe Ala Gly Val Met Tyr His Asp Tyr Ala Ala
            3780                3785                3790

Arg Leu His His Val Pro Glu Gly Phe Glu Gly Leu Ile Ala Asn Gly
        3795                3800                3805

Ser Ala Gly Ser Val Ala Thr Gly Arg Val Ala Tyr Ser Phe Gly Leu
    3810                3815                3820

Glu Gly Pro Ala Val Thr Val Asp Thr Ala Cys Ser Ser Ser Leu Val
3825                3830                3835                3840

Ala Leu His Trp Ala Ala Gln Ala Leu Arg Ala Gly Glu Cys Ser Met
                3845                3850                3855

Ala Leu Ala Gly Gly Val Thr Val Met Ser Ser Pro Gly Thr Phe Val
            3860                3865                3870

Glu Phe Ser Arg Gln Arg Gly Leu Ala Ala Asp Gly Arg Cys Lys Ala
        3875                3880                3885

Tyr Ser Ala Ala Ala Asp Gly Thr Gly Trp Ala Glu Gly Val Gly Met
    3890                3895                3900

Leu Leu Val Glu Arg Leu Ser Asp Ala Arg Arg Asn Gly His Arg Val
3905                3910                3915                3920

Leu Ala Val Val Arg Gly Ser Ala Val Asn Gln Asp Gly Ala Ser Asn
                3925                3930                3935

Gly Leu Thr Ala Pro Asn Gly Pro Ser Gln Gln Arg Val Ile Arg Gln
            3940                3945                3950

Ala Leu Ala Asn Ala Gly Leu Thr Pro Ala Asp Val Asp Ala Val Glu
        3955                3960                3965

Gly His Gly Thr Gly Thr Thr Leu Gly Asp Pro Ile Glu Ala Gln Ala
    3970                3975                3980

Leu Leu Ala Ala Tyr Gly Gln His Arg Pro His His Arg Pro Leu Trp
3985                3990                3995                4000

Leu Gly Ser Leu Lys Ser Asn Ile Gly His Ala Gln Ala Ala Ala Gly
                4005                4010                4015

Val Gly Gly Val Ile Lys Met Val Met Ala Leu Arg Asn Gly Leu Leu
            4020                4025                4030

Pro Gln Thr Leu His Val Asp Glu Pro Thr Pro Gln Val Asp Trp Ser
        4035                4040                4045

Thr Gly Ala Val Gln Leu Leu Thr Gln Pro Val Pro Trp Pro Ala Asp
    4050                4055                4060

Pro Ala Gly Arg Pro Arg His Ala Gly Val Ser Ser Phe Gly Val Ser
4065                4070                4075                4080

Gly Thr Asn Ala His Val Ile Leu Glu Glu Ala Pro Ala Ala Ala Gly
                4085                4090                4095

Gly Ala Ala Gly Gly Gly Val Ser Val Gly Ala Pro Asn Pro Ala Leu
            4100                4105                4110

Pro Val Ala Glu Ser Glu Pro Val Pro Val Pro Val Pro Val Ser Ala
        4115                4120                4125

Arg Ser Glu Ala Gly Leu Arg Ala Gln Ala Gln Ala Leu Arg Gln Tyr
    4130                4135                4140

Val Ala Ala Arg Pro Asp Met Ser Pro Ala Asp Ile Gly Ala Gly Leu
4145                4150                4155                4160

Ala Arg Gly Arg Ala Val Leu Glu His Arg Ala Val Ile Leu Ala Ala
```

-continued

```
                4165                4170                4175
Asp Arg Glu Glu Leu Ala Gln Ala Leu Thr Ala Leu Ala Ala Gly Glu
            4180                4185                4190
Pro His Pro His Ile Thr Thr Gly His Thr Arg Gly Ser Asp Arg Gly
        4195                4200                4205
Gly Val Val Phe Val Phe Pro Gly Gln Gly Gly Gln Trp Ala Gly Met
    4210                4215                4220
Gly Leu Thr Leu Leu Thr Ser Ser Pro Val Phe Ala Glu His Ile Asp
4225                4230                4235                4240
Ala Cys Glu Lys Ala Leu Thr Pro Trp Val Pro Trp Ser Leu Thr Asp
            4245                4250                4255
Ile Leu His Arg Asp Pro Asp Pro Ala Trp Gln Gln Ala Asp Val
        4260                4265                4270
Val Gln Pro Val Leu Phe Ser Ile Met Val Ser Leu Ala Ala Leu Trp
    4275                4280                4285
Arg Ser Tyr Gly Ile Glu Pro Asp Ala Val Leu Gly His Ser Gln Gly
        4290                4295                4300
Glu Ile Ala Ala Ala His Ile Cys Gly Ala Leu Ser Leu Lys Asp Ala
4305                4310                4315                4320
Ala Lys Thr Val Ala Leu Arg Ser Gln Ala Leu Ala Ala Val Arg Gly
            4325                4330                4335
Arg Gly Ala Met Val Ser Leu Pro Leu Pro Ala Gln Asp Val Gln Gln
        4340                4345                4350
Leu Ile Ser Glu Arg Trp Glu Gly Gln Leu Trp Val Ala Ala Leu Asn
        4355                4360                4365
Gly Pro His Ser Thr Thr Val Ser Gly Asp Thr Thr Ala Val Glu Glu
    4370                4375                4380
Leu Leu Thr His Cys Ala Asp Thr Gly Leu Arg Ala Lys Arg Ile Pro
4385                4390                4395                4400
Val Asp Tyr Ala Ser His Cys Pro His Val Gln Pro Leu His Asp Glu
            4405                4410                4415
Leu Leu His Leu Leu Gly Asp Ile Thr Pro Gln Pro Ser Thr Met Pro
        4420                4425                4430
Phe Phe Ser Thr Val Val Gly His Leu Val Trp Tyr Thr Thr Thr Leu
    4435                4440                4445
Asp Ala Ala Tyr Trp Tyr Arg Asn Leu His Gln Pro Val Arg Phe Ser
4450                4455                4460
His Ala Ile Gln Thr Leu Thr Asp Asp Gly His Arg Pro Phe Ile Glu
4465                4470                4475                4480
Ile Ser Pro His Pro Thr Leu Val Pro Ala Ile Glu Asp Thr Thr Glu
            4485                4490                4495
Asn Thr Thr Glu Asn Ile Thr Ala Thr Gly Ser Leu Arg Arg Gly Asp
        4500                4505                4510
Asn Asp Thr His Arg Phe Leu Thr Ala Leu Ala His Thr His Thr Thr
        4515                4520                4525
Gly Ile Arg Thr Pro Thr Thr Trp His His Tyr Thr Gln Thr His
    4530                4535                4540
Pro His Pro His Asn His His Leu Asp Leu Pro Thr Tyr Pro Phe Gln
4545                4550                4555                4560
His Gln His Tyr Trp Leu Gln Pro Pro Thr Thr Thr Asp Leu Thr
            4565                4570                4575
Thr Thr Gly Leu Thr Pro Thr His His Pro Leu Leu Thr Ala Thr Leu
        4580                4585                4590
```

```
Thr Leu Ala Asn Asn Asn Thr Gln Leu Leu Thr Gly Arg Leu Ser Leu
    4595                4600                4605

Arg Thr His Pro Trp Leu Thr Asp His Thr Val Val Gly Thr Thr Leu
    4610                4615                4620

Val Pro Gly Thr Ala Leu Leu Glu Leu Ala Leu Gln Ala Thr Thr Thr
4625                4630                4635                4640

Asp His Leu Glu Glu Leu Ala Leu His Thr Pro Leu Val Ile Pro Arg
            4645                4650                4655

Glu Gly Ala Val Asp Val Gln Val His Ile Asn Pro Pro Asp Asp Thr
            4660                4665                4670

Asp Thr Arg Ser Leu Thr Ile Tyr Ser Arg Ser Glu Asn Ala Pro Ala
        4675                4680                4685

Ala Ala Pro Trp Arg His His Ala Thr Ala Val Leu Gly Thr Lys Thr
        4690                4695                4700

Ser Arg Ile Glu Thr Gly Arg Ser His Asp Asp Leu Ser Met Trp Pro
4705                4710                4715                4720

Pro Ala Gly Ala Val Arg Cys Ala Asp Glu Glu Leu Ala Ala Leu Tyr
            4725                4730                4735

Gly Asp Tyr Glu Ala Asn Gly Phe Val Tyr Gly Pro Ala Phe Arg Gly
            4740                4745                4750

Leu Thr Ala Ala Trp Arg Leu Gly Asp Glu Val Phe Ala Glu Val Arg
        4755                4760                4765

Leu Pro Glu Gln Val His Gly Glu Ala Ser Ala Tyr Asn Leu His Pro
        4770                4775                4780

Ala Leu Leu Asp Ala Ala Leu His Ala Ala Phe Ala Pro Ser Gly
4785                4790                4795                4800

Ser Leu Pro Gln Gly Ser Val Pro Phe Ser Phe Thr Gly Val Thr Leu
            4805                4810                4815

His Ala Ala Asn Ala Ser Ser Leu Arg Val Arg Leu Ser Pro Ala Asp
            4820                4825                4830

Pro Asn Ser Gly His Ala Ala Val Ser Val Leu Val Thr Asp Asp Thr
        4835                4840                4845

Gly Thr Pro Val Ala Ser Val Glu Ala Leu Ala Val Arg Pro Leu Ala
        4850                4855                4860

Ala Asp Glu Leu Arg Ala Ala Glu Arg Ala Val Gln Arg Ala Glu Leu
4865                4870                4875                4880

Phe Asp Met Lys Trp Val Glu Val Pro Ser Asp Val Leu Val Ser Gly
            4885                4890                4895

Gly Ala Ser Val Val Val Leu Asp Gly Ala Asp Asp Leu Val Gly Leu
            4900                4905                4910

Ala Ala Glu Glu Asp Gly Val Pro Gly Val Val Leu Arg Cys Pro
        4915                4920                4925

Asp Ala Gly Ala Asp Gly Gly Gly Gly Gly Val Gly Glu Val
        4930                4935                4940

Val Gly Gly Val Leu Gly Val Val Gln Gly Trp Leu Gly Leu Glu Arg
4945                4950                4955                4960

Phe Ala Gly Ser Arg Leu Val Val Val Thr Arg Gly Ala Val Ala
            4965                4970                4975

Gly Pro Glu Asp Gly Pro Val Asp Gly Pro Val Asp Val Val Gly Ala
            4980                4985                4990

Ala Val Trp Gly Leu Val Arg Ser Ala Gln Ala Glu His Pro Asp Arg
        4995                5000                5005
```

-continued

```
Phe Val Leu Leu Asp Leu Asp Thr Asp Leu Asp Ser Gly Ala Asp Arg
    5010                5015                5020

Asp Ala Gly Asn Glu Ala Gly Met Gly Ser Gly Leu Asp Gly Gly Arg
5025                5030                5035                5040

Val Ala Ala Val Val Ala Cys Gly Glu Pro Gln Leu Ala Val Arg Gly
            5045                5050                5055

Glu Arg Val Leu Ala Ala Arg Leu Thr Arg Leu Glu Ser Pro Val Asp
        5060                5065                5070

Val Ser Gly Arg Glu Val Leu Pro Trp Leu Ser Gly Gly Ser Val Leu
    5075                5080                5085

Val Thr Gly Gly Thr Gly Val Leu Gly Ala Ala Val Ala Arg His Leu
 5090                5095                5100

Ala Gly Val Cys Gly Val Arg Asp Leu Leu Leu Val Ser Arg Arg Gly
5105                5110                5115                5120

Pro Asp Ala Pro Gly Ala Glu Gly Leu Arg Ala Glu Leu Ala Ala Leu
        5125                5130                5135

Gly Ala Glu Val Arg Ile Val Ala Cys Asp Val Gly Glu Arg Arg Glu
            5140                5145                5150

Val Val Arg Leu Leu Glu Gly Val Pro Ala Gly Cys Pro Leu Thr Gly
    5155                5160                5165

Val Val His Ala Ala Gly Val Leu Asp Asp Ala Thr Ile Ala Ser Leu
    5170                5175                5180

Thr Pro Glu Arg Leu Gly Thr Val Phe Ala Ala Lys Val Asp Ala Ala
5185                5190                5195                5200

Leu Leu Leu Asp Glu Leu Thr Arg Gly Met Glu Leu Ser Ala Phe Val
            5205                5210                5215

Leu Phe Ser Ser Ala Ala Gly Ile Leu Gly Ser Ala Gly Gln Gly Asn
        5220                5225                5230

Tyr Ala Ala Asn Ala Ala Leu Asp Ala Leu Ala Tyr Arg Arg Arg
    5235                5240                5245

Ala Ala Gly Leu Pro Gly Val Ser Leu Ala Trp Gly Leu Trp Glu Glu
 5250                5255                5260

Ala Ser Gly Met Thr Gly His Leu Ala Gly Thr Asp His Arg Arg Ile
5265                5270                5275                5280

Ile Arg Ser Gly Leu His Pro Met Ser Thr Pro Asp Ala Leu Ala Leu
        5285                5290                5295

Phe Asp Ala Ala Leu Ala Leu Asp Arg Pro Val Leu Leu Pro Ala Asp
            5300                5305                5310

Leu Arg Pro Ala Pro Pro Leu Pro Pro Leu Leu Gln Asp Leu Leu Pro
        5315                5320                5325

Ala Thr Arg Arg Arg Thr Thr Arg Thr Thr Thr Gly Gly Ala Asp
    5330                5335                5340

Asn Gly Ala Gln Leu His Gly Arg Leu Ala Gly Gln Thr His Glu Gln
5345                5350                5355                5360

Gln His Thr Thr Leu Leu Ala Leu Val Arg Ser His Ile Ala Thr Val
            5365                5370                5375

Leu Gly His Thr Thr Pro Asp Thr Ile Pro Pro Asp Arg Ala Phe Arg
        5380                5385                5390

Asp Leu Gly Phe Asp Ser Leu Thr Ala Val Glu Leu Arg Asn Arg Leu
    5395                5400                5405

Ser His Thr Thr Gly Leu Arg Leu Pro Thr Thr Leu Ala Phe Asp His
    5410                5415                5420

Pro Asn Pro Thr Thr Leu Thr His His Leu His Thr Gln Leu Val Ser
```

```
                    5425            5430            5435            5440
Lys Gly Leu Thr Ala Ala Ala Glu Pro Asp Ala Ala Thr Thr Pro Pro
                5445            5450            5455

Gly Leu Pro Ser Leu Leu Ser Glu Leu Glu Arg Leu Glu Ala Val Val
            5460            5465            5470

Leu Ser Ser Thr Thr Ser Ser Ala Ala Pro Leu Asp Asp Gly Ala Arg
        5475            5480            5485

Thr Arg Leu Ala Ser Arg Leu His Ser Leu Ala Gln Lys Leu Asn Gly
    5490            5495            5500

Asp Asp Thr Ala Pro Asp Leu Ala Glu Thr Ser Asp Glu Glu Met Phe
5505            5510            5515            5520

Ala Leu Ile Asp Arg Glu Val Gly Phe Glu Ser Gln
            5525            5530

<210> SEQ ID NO 7
<211> LENGTH: 438
<212> TYPE: DNA
<213> ORGANISM: Streptomyces avermitilis
<220> FEATURE:
<221> NAME/KEY: CDS
<222> LOCATION: (1)..(438)

<400> SEQUENCE: 7 tac tgg ctc gaa agc aca cag ccc ggt gcc ggc aac gtg tca gca gcc    48
Tyr Trp Leu Glu Ser Thr Gln Pro Gly Ala Gly Asn Val Ser Ala Ala
 1               5                  10                  15 gga ctc gac ccc acc gaa cac ccc cta ctc ggc gcc aca ttg gaa ctg    96
Gly Leu Asp Pro Thr Glu His Pro Leu Leu Gly Ala Thr Leu Glu Leu
             20                  25                  30 gcg act gac ggt gga gcg ctt ctt gca ggg cgc ttg tct ttg agg tcg   144
Ala Thr Asp Gly Gly Ala Leu Leu Ala Gly Arg Leu Ser Leu Arg Ser
         35                  40                  45 cat ccg tgg ctg gct gac tac gag gtc ggc ggc acg gtg ctg ctg tcg   192
His Pro Trp Leu Ala Asp Tyr Glu Val Gly Gly Thr Val Leu Leu Ser
     50                  55                  60 ggc gcc acc ttc ctc gaa ctc gcc ctt cat gcg ggc aca tac gtg ggc   240
Gly Ala Thr Phe Leu Glu Leu Ala Leu His Ala Gly Thr Tyr Val Gly
 65                  70                  75                  80 tgc gac cga gtg gat gag ctg acg ctg cat gcg ccg ctg gtg gtt cct   288
Cys Asp Arg Val Asp Glu Leu Thr Leu His Ala Pro Leu Val Val Pro
                 85                  90                  95 gtg gat ggg ggt gtg agt gtg cag gtt ggg gtt gcg gct gcg gat ggg   336
Val Asp Gly Gly Val Ser Val Gln Val Gly Val Ala Ala Ala Asp Gly
            100                 105                 110 gag ggg cgg cgt ttg gtg agt gtg tat gcg cgg ggt ggg agt gct tgt   384
Glu Gly Arg Arg Leu Val Ser Val Tyr Ala Arg Gly Gly Ser Ala Cys
        115                 120                 125 ggt ggg ggt ggt gcg tcg ggt ggg gtg tgg acg tgt cat gcc tcg ggg   432
Gly Gly Gly Gly Ala Ser Gly Gly Val Trp Thr Cys His Ala Ser Gly
    130                 135                 140 gtg ctg                                                            438
Val Leu
145

<210> SEQ ID NO 8
<211> LENGTH: 146
<212> TYPE: PRT
<213> ORGANISM: Streptomyces avermitilis

<400> SEQUENCE: 8
```

```
Tyr Trp Leu Glu Ser Thr Gln Pro Gly Ala Gly Asn Val Ser Ala Ala
 1               5                  10                  15

Gly Leu Asp Pro Thr Glu His Pro Leu Leu Gly Ala Thr Leu Glu Leu
             20                  25                  30

Ala Thr Asp Gly Gly Ala Leu Leu Ala Gly Arg Leu Ser Leu Arg Ser
         35                  40                  45

His Pro Trp Leu Ala Asp Tyr Glu Val Gly Thr Val Leu Leu Ser
 50                  55                      60

Gly Ala Thr Phe Leu Glu Leu Ala Leu His Ala Gly Thr Tyr Val Gly
 65                  70                  75                  80

Cys Asp Arg Val Asp Glu Leu Thr Leu His Ala Pro Leu Val Val Pro
                 85                  90                  95

Val Asp Gly Gly Val Ser Val Gln Val Gly Val Ala Ala Asp Gly
             100                 105                 110

Glu Gly Arg Arg Leu Val Ser Val Tyr Ala Arg Gly Gly Ser Ala Cys
             115                 120                 125

Gly Gly Gly Ala Ser Gly Gly Val Trp Thr Cys His Ala Ser Gly
 130                 135                 140

Val Leu
145

<210> SEQ ID NO 9
<211> LENGTH: 30
<212> TYPE: DNA
<213> ORGANISM: Artificial Sequence
<220> FEATURE:
<223> OTHER INFORMATION: Primer from the sequence between 9098 and 9127
      of SEQ ID NO:1

<400> SEQUENCE: 9
ggctggctga ctacgaggtc ggcggcacgg                                        30

<210> SEQ ID NO 10
<211> LENGTH: 30
<212> TYPE: DNA
<213> ORGANISM: Artificial Sequence
<220> FEATURE:
<223> OTHER INFORMATION: Antisense primer from the sequence between
      9193 and 9222 of SEQ ID NO:1

<400> SEQUENCE: 10
cggcgcatgc agcgtcagct catccactcg                                        30

<210> SEQ ID NO 11
<211> LENGTH: 30
<212> TYPE: DNA
<213> ORGANISM: Artificial Sequence
<220> FEATURE:
<223> OTHER INFORMATION: Antisense primer from the sequence between
      9098 and 9127 of SEQ ID NO:1

<400> SEQUENCE: 11
ccgtgccgcc gacctcgtag tcagccagcc                                        30

<210> SEQ ID NO 12
<211> LENGTH: 30
<212> TYPE: DNA
<213> ORGANISM: Artificial Sequence
<220> FEATURE:
<223> OTHER INFORMATION: Primer from the sequence between 8948 and
      8977 of SEQ ID NO:1

<400> SEQUENCE: 12
```

```
actggctcga aagcacacag cccggtgccg                                        30
```

```
<210> SEQ ID NO 13
<211> LENGTH: 10
<212> TYPE: PRT
<213> ORGANISM: Streptomyces avermitilis
<220> FEATURE:
<221> NAME/KEY: SITE
<222> LOCATION: 2, 3, 4, 6, 7, 8, 9
<223> OTHER INFORMATION: Xaa denotes an unspecified amino acid

<400> SEQUENCE: 13

His Xaa Xaa Xaa Gly Xaa Xaa Xaa Xaa Pro
  1               5                  10

<210> SEQ ID NO 14
<211> LENGTH: 10
<212> TYPE: PRT
<213> ORGANISM: Streptomyces avermitilis
<220> FEATURE:
<221> NAME/KEY: SITE
<222> LOCATION: 2, 3, 4, 6, 7, 8, 9
<223> OTHER INFORMATION: Xaa denotes an unspecified amino acid

<400> SEQUENCE: 14

His Xaa Xaa Xaa Gly Xaa Xaa Xaa Xaa Ser
  1               5                  10

<210> SEQ ID NO 15
<211> LENGTH: 10
<212> TYPE: PRT
<213> ORGANISM: Streptomyces avermitilis
<220> FEATURE:
<221> NAME/KEY: SITE
<222> LOCATION: 2, 3, 4, 6, 7, 8, 9
<223> OTHER INFORMATION: Xaa denotes an unspecified amino acid

<400> SEQUENCE: 15

Tyr Xaa Xaa Xaa Gly Xaa Xaa Xaa Xaa Ser
  1               5                  10

<210> SEQ ID NO 16
<211> LENGTH: 10
<212> TYPE: PRT
<213> ORGANISM: Streptomyces avermitilis

<400> SEQUENCE: 16

His Ala Val Gly Gly Thr Val Leu Leu Ser
  1               5                  10
```

AVERMECTIN AGLYCON SYNTHASE GENES

This is a national stage application under 35 U.S.C. 371 of PCT/JP00/01041, filed on Feb. 23, 2000, now abandoned.

TECHNICAL FIELD

The present invention relates to DNAs encoding multifunctional enzyme involved in the biosynthesis of an avermectin compound which is a polyketide; polypeptides encoded by the DNAs; vectors containing the DNAs; host cells transformed with the DNAs or the vectors; and a process for producing avermectin.

BACKGROUND ART

A polyketide is a group of compounds containing a number of natural substances which vary in their structures and functions. Polyketides are known to include compounds having a variety of bioactivities such as antibacterial agents, antimyotic agents, antiparasitic agents, anti-insect agents, antitumor agents, and immunosuppressant agents, and aromatic compounds which are produced by bacteria, fungi and plants.

The above-mentioned various polyketide compounds are synthesized by the same biosynthetic mechanism which is very similar to the biosynthesis of fatty acids. That is, a polyketide compound is biosynthesized by the steps of continuous condensation of lower fatty acids including acetic acids and propionic acids, and subsequent reactions such as reduction of ketone, dehydration and enoyl reduction of each carbonyl group at β position of the extended acyl group which is similar to fatty acid synthesis. These various repetitive synthetic processes of many polyketide compounds are carried out a macromolecule, multifunctional enzyme complex, which has specific active sites (domains) required for each catalytic activity. A general reaction manner of polyketide biosynthesis is outlined, for example in Ann. Rev. Gen., 24, 37 (1990), and Ann. Rev. Microbiol., 47, 875 (1993).

It has been shown that a DNA sequence encoding polyketide synthase usually encodes all the required activities for the synthesis of a polyketide backbone. The DNA sequence encoding polyketide synthase is composed of modules, that is, repeating units involving condensation steps and modification steps following condensation. Each catalytic activity is involved in specificity to a specific carboxylic acid component of each condensation step, or in a different site which specifies a modification function following a specific condensation step to be achieved. For example, International Publication WO93/13663 describes the constitution of a gene encoding polyketide synthase of *Saccharopolyspora erythaea*. This gene consists of 6 modules, each of which is responsible for one condensation step. That is, a correct sequence of acyl side chain elongation and modification of an elongating chain are determined by genetic information present in each module.

Regarding the biosynthetic mechanism of avermectin aglycon, it has been reported that like other polyketide compounds, synthesis units of avermectin aglycon are lower fatty acids, such as acetic acid and propionic acid as its components [J. Antibiot., 39, 541–549 (1986)], and as in *Saccharopolyspora erythaea*, polyketide synthase consisting of modules is present in avermectin-producing bacteria [Gene, 115, 119–125 (1992), Ann. New York Acad. of Sci., 721, 123–132 (1994)].

Japanese Published Unexamined Patent Application No. 15391/91 describes a DNA fragment involved in avermectin biosynthesis, but shows no nucleotide sequence of the DNA fragment. This publication merely assumes the presence of polyketide synthase, which is involved in the synthesis of avermectin aglycon and the presence of partial modules. Therefore, the entire structure of polyketide synthase of avermectin cannot be predicted.

Similarly, MacNeil et al have reported a domain structure of partial modules [Ann. New York Acad. of Sci., 721, 123–132 (1994)]. However, they have not revealed the nucleotide sequence that should be evidence for polyketide synthase of avermectin.

Alteration of polyketide synthase would be a very useful breeding technique upon breeding of bacterial strains which can be used for a novel process for producing a novel avermectin useful as veterinary drugs and agricultural chemicals, and can produce a more effective avermectin derivative. Steps required to carry out such alteration include determination of the entire nucleotide sequence of a gene encoding polyketide synthase, accurate determination of a domain structure of each module based on the sequence, and introduction of a desired mutation. However, as described above, it was very difficult to carry out such improved-breeding, since the polyketide synthase gene of avermectin aglycon had not been specified and the nucleotide sequence of the gene was unknown.

The present inventors have studied approaches for producing a component different from that produced by the wild type strain by engineering DNA involved in polyketide synthesis with various methods. To apply this methodology, first we had to isolate a DNA molecule involved in the biosynthesis of a polyketide compound.

Hence, an object of the present invention is to provide a DNA encoding a multifunctional enzyme involved in biosynthesis of avermectin aglycon, and a process for producing avermectin aglycon, altered avermectin aglycon, avermectin, and altered avermectin using the DNA.

DISCLOSURE OF THE INVENTION

The present inventors made an intensive investigation to attain the object. As a result, the inventors have succeeded in isolating DNAs encoding a multifunctional enzyme involved in biosynthesis of avermectin aglycon. The present invention has been completed on the basis of this result.

The present invention relates to the following (1) to (43).

(1) A DNA encoding avermectin aglycon synthase (hereinafter, also referred to as an avermectin aglycon synthase gene).

In an embodiment of the present invention, the DNA is derived from a wild-type avermectin-producing strain or a mutant strain thereof, such as one belonging to the genus *Streptomyces*, specifically *Streptomyces avermitilis*.

(2) A DNA comprising a nucleotide sequence selected from the group consisting of nucleotide Nos. 1–11916 and 11971–30688 of SEQ ID NO: 1, and nucleotide Nos. 1–14643 and 14824–31419 of SEQ ID NO: 2; or a DNA which hybridizes with this DNA under stringent conditions and which encodes a polypeptide having avermectin aglycon synthase activity.

The above term "a DNA which hybridizes with this DNA under stringent conditions" refers to a DNA which is obtained by colony hybridization, plaque hybridization or Southern hybridization or the like using the DNA having a nucleotide sequence of SEQ ID NO. 1 or 2. For example, such a DNA can be identified by carrying out hybridization at 65° C. in the presence of 0.7 to 1.0 mol/l sodium chloride using a filter on which DNAs derived from colonies or plaques have been immobilized, followed by washing the filter at 65° C., using 0.1 to 2-fold concentrated SSC solution (1-fold concentrated SSC solution consists of 150 mmol/l sodium chloride, 15 mmol/l sodium citrate).

Hybridization can be carried out according to a method described in experimental protocols, such as Molecular Cloning, A Laboratory Manual, Second Edition, Cold Spring Harbor Laboratory Press, 1989 (hereinafter abbreviated as Molecular Cloning $2^{nd}$ Edition), Current Protocols in Molecular Biology, John Wiley & Sons, 1987–1997 (hereinafter abbreviated as Current Protocols in Molecular Biology), DNA Cloning 1; Core Techniques, A Practical Approach, Second Edition, Oxford University, 1995. Specific examples of the DNA which can be hybridized include a DNA having at least homology of 80% or more, preferably 95% or more with a nucleotide sequence selected from the group consisting of nucleotide Nos. 1–11916 and 11971–30688 of SEQ ID NO: 1, and nucleotide Nos. 1–14643 and 14824–31419 of SEQ ID NO: 2.

The following term "a DNA which hybridizes with this DNA (or said DNA) under stringent conditions" can also be defined in the same manner as described above.

(3) The DNA according to the above (1) or (2) wherein the DNA comprises DNAs encoding avermectin aglycon synthase domains.

(4) The DNA according to the above (3) wherein the DNA encoding avermectin aglycon synthase domains is selected from the group consisting of:

a DNA encoding a polypeptide having acyltransferase activity and acyl carrier protein activity;

a DNA encoding a polypeptide having β-ketoacyl-ACP synthase activity, acyltransferase activity, β-ketoacyl-ACP reductase activity and acyl carrier protein activity;

a DNA encoding a polypeptide having β-ketoacyl-ACP synthase activity, acyltransferase activity, dehydratase activity, β-ketoacyl-ACP reductase activity and acyl carrier protein activity;

a DNA encoding a polypeptide having β-ketoacyl-ACP synthase activity, acyltransferase activity, and acyl carrier protein activity; and a DNA encoding a polypeptide having β-ketoacyl-ACP synthase activity, acyltransferase activity, dehydratase activity, β-ketoacyl-ACP reductase activity, acyl carrier protein activity, and thioesterase activity.

(5) The DNA according to the above (4) wherein the DNA encoding a polypeptide having acyltransferase activity and acyl carrier protein activity is a DNA comprising the nucleotide sequence of nucleotide Nos. 85–1353 of SEQ ID NO: 1; or a DNA which hybridizes with this DNA under stringent conditions and which encodes a polypeptide having acyltransferase activity and acyl carrier protein activity.

(6) The DNA according to the above (4) wherein the DNA encoding a polypeptide having β-ketoacyl-ACP synthase activity, acyltransferase activity, β-ketoacyl-ACP reductase activity, and acyl carrier protein activity is:

a DNA comprising the nucleotide sequence selected from the group consisting of nucleotide Nos. 1441–6180, 15217–19938 and 20008–24690 of SEQ ID NO: 1, and nucleotide Nos. 100–4692 and 14935–20334 of SEQ ID NO: 2; or a DNA which hybridizes with this DNA under stringent conditions and which encodes a polypeptide having β-ketoacyl-ACP synthase activity, acyltransferase activity, β-ketoacyl-ACP reductase activity, and acyl carrier protein activity.

(7) The DNA according to the above (4) wherein the DNA encoding a polypeptide having β-ketoacyl-ACP synthase activity, acyltransferase activity, dehydratase activity, β-ketoacyl-ACP reductase activity, and acyl carrier protein activity is:

a DNA comprising the nucleotide sequence selected from the group consisting of nucleotide Nos. 6256–11658 and 24781–30309 of SEQ ID NO: 1, and nucleotide Nos. 20413–25734 and 25810–31125 of SEQ ID NO: 2; or a DNA which hybridizes with this DNA under stringent conditions and which encodes polypeptides having β-ketoacyl-ACP synthase activity, acyltransferase activity, dehydratase activity, β-ketoacyl-ACP reductase activity, and acyl carrier protein activity.

(8) The DNA according to the above (4) wherein the DNA encoding a polypeptide having β-ketoacyl-ACP synthase activity, acyltransferase activity, and acyl carrier protein activity is:

a DNA comprising the nucleotide sequence of nucleotide No. 12076–15147 of SEQ ID NO: 1, or nucleotide No. 4771–7818 of SEQ ID NO: 2;

or a DNA which hybridizes with this DNA under stringent conditions and which encodes a polypeptide having β-ketoacyl-ACP synthase activity, acyltransferase activity, and acyl carrier protein activity.

(9) The DNA according to the above (4) wherein the DNA encoding a polypeptide having β-ketoacyl-ACP synthase activity, acyltransferase activity, dehydratase activity, β-ketoacyl-ACP reductase activity, acyl carrier protein activity, and thioesterase activity is:

a DNA comprising the nucleotide sequence of nucleotide Nos. 7906–14619 of SEQ ID NO: 2; or a DNA which hybridizes with this DNA under stringent conditions and which encodes a polypeptide having β-ketoacyl-ACP synthase activity, acyltransferase activity, dehydratase activity, β-ketoacyl-ACP reductase activity, acyl carrier protein activity, and thioesterase activity.

(10) The DNA according to the above (4) wherein the DNA encoding a polypeptide having acyltransferase activity is:

a DNA comprising the nucleotide sequence selected from the group consisting of nucleotide Nos. 85–1032, 7906–8829, 13756–14694, 16917–17862, 21658–22584, and 26413–27336 of SEQ ID NO: 1, and nucleotide Nos. 1648–2673, 6322–7344, 9676–10773, 16543–17565, 21991–23019 and 27367–28392 of SEQ ID NO: 2; or a DNA which hybridizes with this DNA under stringent conditions and which encodes a polypeptide having acyltransferase activity.

(11) The DNA according to the above (4) wherein the DNA encoding a polypeptide having acyl carrier protein activity is:

a DNA comprising the nucleotide sequence selected from the group consisting of nucleotide Nos. 1096–1353, 5935–6180, 11413–11658, 14902–15147, 19693–19938, 24445–24690 and 30064–30309 of SEQ ID NO: 1, and nucleotide Nos. 4447–4692, 7573–7818, 13378–13659, 20089–20334, 25489–25734 and 30880–31125 of SEQ ID NO: 2; or a DNA which hybridizes with this DNA under stringent conditions and which encodes a polypeptide having acyl carrier protein activity.

(12) The DNA according to the above (4) wherein the DNA encoding a polypeptide having β-ketoacyl-ACP synthase activity is:

a DNA comprising the nucleotide sequence selected from the group consisting of nucleotide Nos. 1441–2742, 6256–7545, 12076–13368, 15217–16506, 20008–21297 and 24781–26079 of SEQ ID NO: 1, and nucleotide Nos. 100–1383, 4771–6060, 7906–9258, 14935–16224, 20413–21705 and 25810–27102 of SEQ ID NO: 2; or a DNA which hybridizes with this DNA under stringent conditions and which encodes a polypeptide having β-ketoacyl-ACP synthase activity.

(13) The DNA according to the above (4) wherein the DNA encoding a polypeptide having β-ketoacyl-ACP reductase activity is:

a DNA comprising the nucleotide sequence selected from the group consisting of nucleotide Nos. 5143–5676, 10609–11142, 18886–19419, 23602–24138 and 29227–29760 of SEQ ID NO: 1, and nucleotide Nos. 3634–4188, 12547–13104, 19285–19842, 24685–25242 and 30076–30633 of SEQ ID NO: 2; or a DNA which hybridizes with this DNA under stringent conditions and which encodes a polypeptide having β-ketoacyl-ACP reductase activity.

(14) The DNA according to the above (4) wherein the DNA encoding a polypeptide having dehydratase activity is:

a DNA comprising the nucleotide sequence selected from the group consisting of nucleotide Nos. 8947–9384 and 27475–27894 of SEQ ID NO: 1, and nucleotide Nos. 10885–11289, 23149–23529 and 28516–28878 of SEQ ID NO: 2; or a DNA which hybridizes with this DNA under stringent conditions and which encodes a polypeptide having dehydratase activity.

(15) The DNA according to the above (4) wherein the DNA encoding a polypeptide having thioesterase activity is:

a DNA having the nucleotide sequence of nucleotide No. 13879–14619 of SEQ ID NO: 2; or a DNA which hybridizes with this DNA under stringent conditions and which encodes a polypeptide having thioesterase activity.

(16) The DNA according to the above (3) or (4) wherein the DNA encoding an avermectin aglycon synthase domain is a mutated DNA encoding a polypeptide having enhanced or diminished activity of the domain.

(17) The DNA according to the above (16) wherein the DNA encoding a polypeptide having diminished activity of avermectin aglycon synthase domain is the DNA comprising a nucleotide sequence of SEQ ID NO: 7.

(18) A DNA encoding an avermectin aglycon synthase domain which comprises a nucleotide sequence selected from the group consisting of nucleotide Nos. 85–1032, 1096–1353, 1441–2742, 3148–4068, 5143–5676, 5935–6180, 6256–7545, 7906–8829, 8947–9384, 10609–11142, 11413–11658, 12076–13368, 13756–14694, 14902–15147, 15217–16506, 16917–17862, 18886–19419, 19693–19938, 20008–21297, 21658–22584, 23602–24138, 24445–24690, 24781–26079, 26413–27336, 27475–27894, 29227–29760 and 30064–30309 of SEQ ID NO: 1, and nucleotide Nos. 100–1383, 1648–2673, 3634–4188, 4447–4692, 4771–6060, 6322–7344, 7573–7818, 7906–9258, 9676–10773, 10885–11289, 12547–13104, 13378–13659, 13879–14619, 14935–16224, 16543–17565, 17689–18066, 19285–19842, 20089–20334, 20413–21705, 21991–23019, 23149–23529, 24685–25242, 25489–25734, 25810–27102, 27367–28392, 28516–28878, 30076–30633, and 30880–31125 of SEQ ID NO: 2; or a DNA which hybridizes with this DNA under stringent conditions and which encodes a polypeptide having avermectin aglycon synthase domain activity.

(19) A DNA comprising the nucleotide sequence of nucleotide No. 85–1353 of SEQ ID NO: 1; or a DNA which hybridizes with this DNA under stringent conditions and which encodes a polypeptide having acyltransferase activity and acyl carrier protein activity.

(20) A DNA comprising the nucleotide sequence selected from the group consisting of nucleotide Nos. 1441–6180, 15217–19938 and 20008–24690 of SEQ ID NO: 1, and nucleotide Nos. 100–4692 of SEQ ID NO: 2; or a DNA which hybridizes with this DNA under stringent conditions and which encodes a polypeptide having β-ketoacyl-ACP synthase activity, acyltransferase activity, β-ketoacyl-ACP reductase activity and acyl carrier protein activity.

(21) A DNA comprising the nucleotide sequence selected from the group consisting of nucleotide Nos. 6256–11658 and 24781–30309 of SEQ ID NO: 1, and nucleotide Nos. 14935–20334, 20413–25734 and 25810–31125 of SEQ ID NO: 2; or a DNA which hybridizes with this DNA under stringent conditions and which encodes a polypeptide having β-ketoacyl-ACP synthase activity, acyltransferase activity, dehydratase activity, β-ketoacyl-ACP reductase activity and acyl carrier protein activity.

(22) A DNA comprising the nucleotide sequence of nucleotide No. 12076–15147 of SEQ ID NO: 1, or the nucleotide sequence of nucleotide No. 4771–7818 of SEQ ID NO: 2; or a DNA which hybridizes with this DNA under stringent conditions and which encodes a polypeptide having β-ketoacyl-ACP synthase activity, acyltransferase activity, and acyl carrier protein activity.

(23) A DNA comprising the nucleotide sequence of nucleotide No. 7906–14619 of SEQ ID NO: 2; or a DNA which hybridizes with this DNA under stringent conditions and which encodes a polypeptide having β-ketoacyl-ACP synthase activity, acyltransferase activity, dehydratase activity, β-ketoacyl-ACP reductase activity, acyl carrier protein activity, and thioesterase activity.

(24) A DNA comprising the nucleotide sequence selected from the group consisting of nucleotide Nos. 85–1032, 7906–8829, 13756–14694, 16917–17862, 21658–22584 and 26413–27336 of SEQ ID NO: 1, and nucleotide Nos. 1648–2673, 6322–7344, 9676–10773, 16543–17565, 21991–23019 and 27367–28392 of SEQ ID NO: 2; or a DNA which hybridizes with this DNA under stringent conditions and which encodes a polypeptide having acyltransferase activity.

(25) A DNA comprising the nucleotide sequence selected from the group consisting of nucleotide Nos. 1096–1353, 5935–6180, 11413–11658, 14902–15147, 19693–19938, 24445–24690, and 30064–30309 of SEQ ID NO: 1, and nucleotide Nos. 4447–4692, 7573–7818, 13378–13659, 20089–20334, 25489–25734 and 30880–31125 of SEQ ID NO: 2; or a DNA which hybridizes with this DNA under stringent conditions and which encodes a polypeptide having acyl carrier protein activity.

(26) A DNA comprising the nucleotide sequence selected from the group consisting of nucleotide Nos. 1441–2742, 6256–7545, 12076–13368, 15217–16506, 20008–21297 and 24781–26079 of SEQ ID NO: 1, and nucleotide Nos.

100–1383, 4771–6060, 7906–9258, 14935–16224, 20413–21705, and 25810–27102 of SEQ ID NO: 2; or a DNA which hybridizes with this DNA under stringent conditions and which encodes a polypeptide having β-ketoacyl-ACP synthase activity.

(27) A DNA comprising the nucleotide sequence selected from the group consisting of nucleotide Nos. 5143–5676, 10609–11142, 18886–19419, 23602–24138, and 29227–29760 of SEQ ID NO: 1, and nucleotide Nos. 3634–4188, 12547–13104, 19285–19842, 24685–25242 and 30076–30633 of SEQ ID NO: 2; or a DNA which hybridizes with this DNA under stringent conditions and which encodes a polypeptide having β ketoacyl ACP reductase activity.

(28) A DNA comprising the nucleotide sequence selected from the group consisting of nucleotide Nos. 8947–9384 and 27475–27894 of SEQ ID NO: 1, and nucleotide Nos. 10885–11289, 17689–18066, 23149–23529 and 28516–28878 of SEQ ID NO: 2; or a DNA which hybridizes with this DNA under stringent conditions and which encodes a polypeptide having dehydratase activity.

(29) A DNA comprising the nucleotide sequence of nucleotide Nos. 13879–14619 of SEQ ID NO: 2; or a DNA which hybridizes with this DNA under stringent conditions and which encodes a polypeptide having thioesterase activity.

(30) A DNA comprising the nucleotide sequence shown in SEQ ID NO: 7.

(31) A polypeptide encoded by the DNA according to any one of the above (1) to (29).

(32) A polypeptide comprising the amino acid sequence according to any one of SEQ ID NOS: 3 to 6; or a polypeptide comprising an amino acid sequence wherein one or more amino acids are deleted, replaced or added in the amino acid sequence according to any one of SEQ ID NOS: 3 to 6, and having avermectin aglycon synthase activity.

The above "polypeptide comprising an amino acid sequence wherein one or more amino acids are deleted, replaced or added, and having avermectin aglycon synthase activity" can be prepared according to site-directed mutagenesis as described in Molecular Cloning, 2$^{nd}$ Edition, Current Protocols in Molecular Biology, Nucleic Acids Research, 10, 6487 (1982), Proc. Natl. Acad. Sci., USA, 79, 6409 (1982), Gene, 34, 315 (1985), Nucleic Acids Research, 13, 4431 (1985), Proc. Natl. Acad. Sci USA, 82, 488 (1985) and the like. The number of amino acids which are deleted, replaced or added is not specifically limited, but is a number of amino acids which can be deleted, replaced, or added by known methods, such as the above site-directed mutagenesis, and within the range from 1 to several tens of amino acids, preferably 1 to 20, more preferably 1 to 10, and even more preferably 1 to 5 amino acids.

(33) A polypeptide comprising the amino acid sequence selected from the group consisting of amino acid Nos. 29–344, 366–451, 481–914, 1050–1356, 1715–1892, 1979–2060, 2086–2515, 2983–3128, 3537–3714 and 3805–3886 of SEQ ID NO: 3, amino acid Nos. 36–466, 596–908, 978–1059, 1083–1512, 1653–1964, 2306–2483, 2575–2656, 2680–3109, 3230–3538, 3878–4056, 4159–4240, 4271–4703, 4815–5122, 5168–5307, 5753–5930 and 6032–6113 of SEQ ID NO: 4, amino acid Nos. 34–461, 550–891,1212–1396, 1483–1564, 1591–2020, 2108–2448, 2525–2606, 2636–3086, 3226–3591, 3629–3763, 4183–4363, 4460–4553 and 4627–4873 of SEQ ID NO: 5, amino acid Nos. 38–467, 574–914, 956–1081, 1488–1673, 1756–1837, 1864–2294, 2390–2732, 2776–2902, 3288–3473, 3556–3637, 3663–4093, 4182–4523, 4565–4685, 5085–5270 and 5353–5434 of SEQ ID NO: 6; or a polypeptide comprising an amino acid sequence wherein one or more amino acids are deleted, replaced or added in the amino acid sequence selected above, and having avermectin aglycon synthase domain activity.

The above "polypeptide comprising an amino acid sequence wherein one or more amino acids are deleted, replaced or added in the amino acid sequence selected above, and having avermectin aglycon synthase domain activity" can be obtained according to the method described in the above (32).

(34) A recombinant vector comprising the DNA according to any one of the above (1) to (30).

(35) A transformant which is obtained by introducing the DNA according to any one of the above (1) to (30) or the recombinant vector of the above (34) into a host cell.

(36) The transformant according to the above (35) wherein the host cell is an avermectin-producing bacterial strain.

(37) The transformant according to the above (35) or (36) wherein the host cell is *Streptomyces avermitilis* K2038 (FERM BP-2775).

(38) A process for producing avermectin aglycon synthase or an avermectin aglycon synthase domain polypeptide comprising:

culturing the transformant according to any one of the above (35) to (37) in a medium to form and accumulate the enzyme or the domain polypeptide in the culture, and recovering the enzyme or the domain polypeptide from the culture.

(39) A process for producing avermectin aglycon or an altered avermectin aglycon comprising:

culturing the transformant according to any one of the above (35) to (37) in a medium to form and accumulate the avermectin aglycon or the altered avermectin aglycon in the culture, and recovering the avermectin aglycon or the altered avermectin aglycon from the culture.

(40) A process for producing avermectin or altered avermectin comprising:

culturing the transformant according to any one of the above (35) to (37) in a medium to form and accumulate avermectin aglycon or altered avermectin aglycon in the culture, glycosylating the avermectin aglycon or altered avermectin glycon, and recovering avermectin or altered avermectin.

(41) The method according to the above (40) wherein altered avermectin is an avermectin which has been altered from avermectin B1a to avermectin B2a.

(42) An altered avermectin obtainable by the process according to the above (40).

(43) An oligonucleotide having a sequence corresponding to 5 to 60 continuous nucleotides in the nucleotide sequence of the DNA according to the above (1) or (2); or an oligonucleotide having a sequence complementary to the oligonucleotide.

BRIEF DESCRIPTION OF THE DRAWINGS

FIG. 1 is a restriction enzyme map showing BamHI, BglII, ClaI, EcoRI, KpnI, MluI, PstI, StuI and XhoI sites of avermectin aglycon synthase genes, aveAI and aveAII, of

*Streptomyces avermitilis*. Each arrow indicates the predicted transcriptional direction of each gene.

Figure 2A:
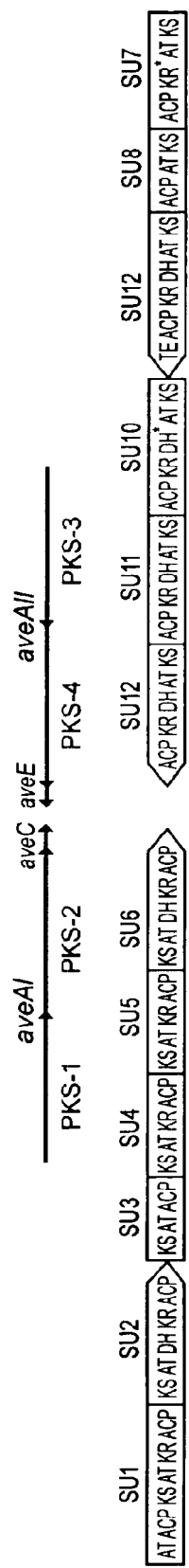
Figure 2B:
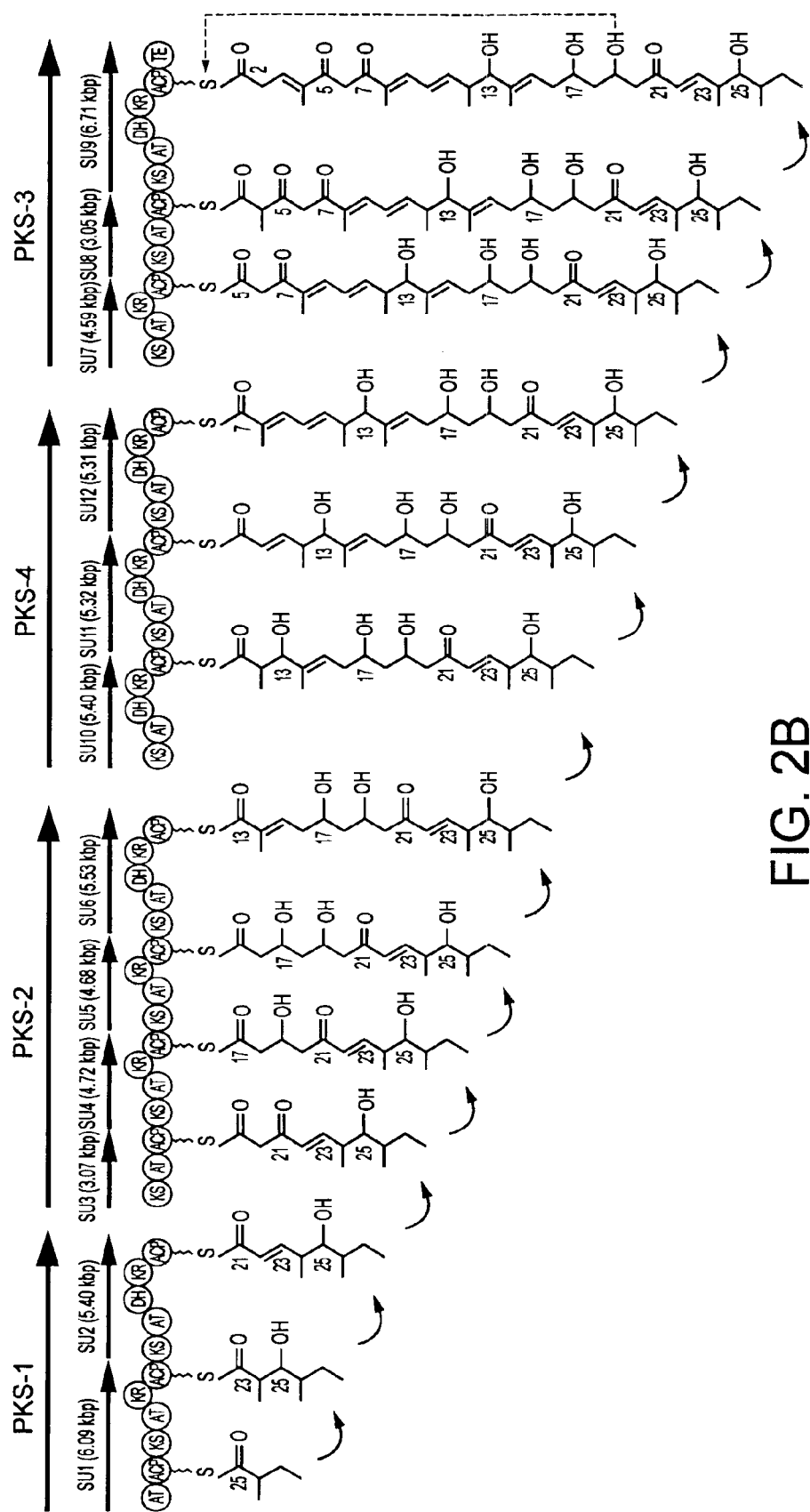
Figure 2C:
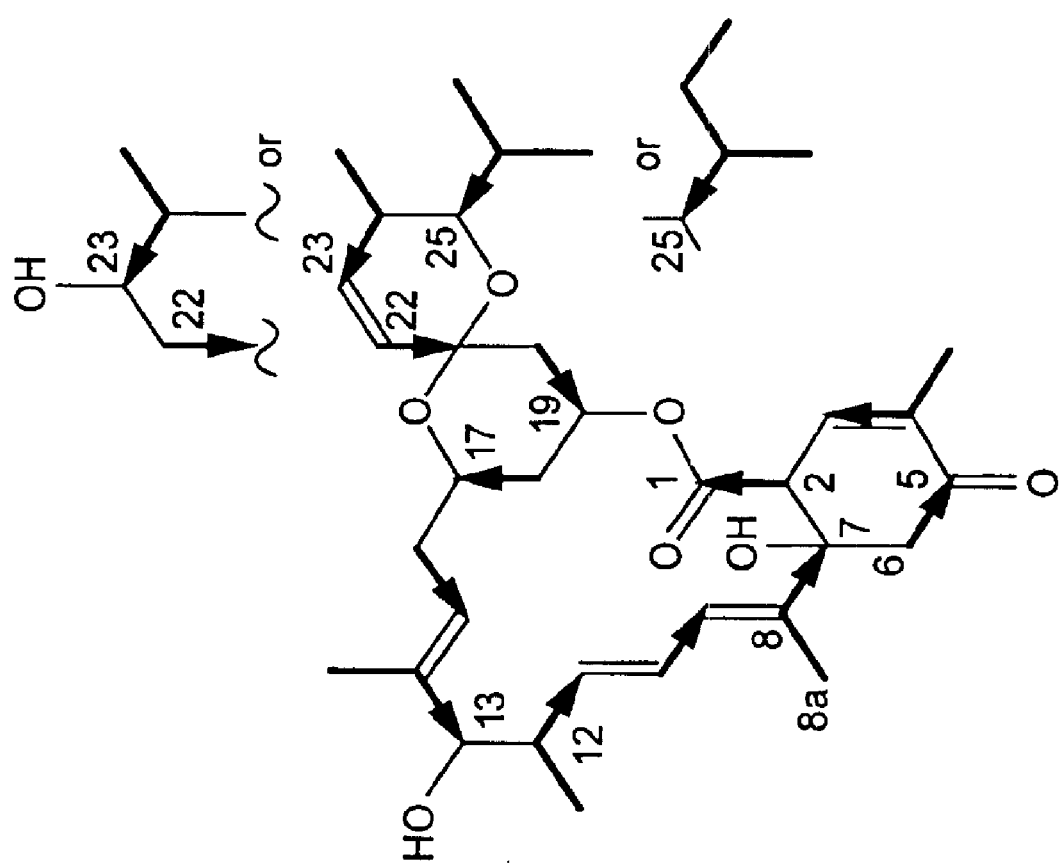

FIG. 2 shows (FIG. 2A) the chromosomal positions of avermectin aglycon synthase genes and the domain sequences of synthase units, (FIG. 2B) the estimated steps of synthesizing avermectin aglycon, and (FIG. 2C) the structure of 6,8a-seco-6,8a-deoxy-5-oxoAvermectin aglycon synthesized with polyketide synthases, which are the gene products of avermectin aglycon synthase genes aveAI and aveAII, and the positions of lower fatty acid which are incorporated into the skeleton of the compound. In this figure, SU indicates synthase unit, ACP indicates acyl carrier protein, AT indicates an acyltransferase, DH indicates dehydratase, DH* indicates a dehydratase-like domain which is estimated to be inactive, KR indicates β-ketoacyl-ACP reductase, KR* indicates a β-ketoacyl-ACP reductase-like domain which is estimated to be active but is not reflected in the polyketide synthetic reaction, KS indicates β-ketoacyl-ACP synthase, and TE indicates thioesterase.

DETAILED DESCRIPTION OF THE INVENTION

The present invention will be described in detail below.

The present invention relates to DNA sequences of genes encoding avermectin aglycon synthase, and a process for producing avermectin aglycon, a basic constitutional unit of avermectin. According to the present invention, it becomes possible to produce a novel avermectin-associated compound or a specific component of avermectins by modification of the DNA to make a change to the type and number of carboxylic acids to be taken in, modification reaction after condensation, or any combination thereof.

1. Preparation of the DNA of the Present Invention

A DNA encoding avermectin aglycon synthase (an avermectin aglycon synthase gene) can be isolated from bacteria belonging to the genus *Streptomyces*, e.g. *Streptomyces avermitilis*.

Examples of a method for isolating an avermectin aglycon synthase gene include the method described in Japanese Published Unexamined Patent Application No. 15391/91, colony hybridization described in *Molecular Cloning*, Second Edition, etc.

Specific examples include a method which comprises: ligating the partially digested chromosomal DNA of *Streptomyces avermitilis* with appropriate restriction enzyme such as Sau3AI, to a cosmid vector capable of replicating in *E. coli* cleaved at a unique restriction enzyme site, e.g. the vector digested with BamHI; transforming *E. coli* with the obtained recombinant DNA; and selecting a transformant having the avermectin aglycon synthase gene from the obtained transformant by colony hybridization.

Examples of DNAs obtained by the above method include DNAs having the nucleotide sequences shown in SEQ ID NOS: 1 and 2.

The DNA having the nucleotide sequence of SEQ ID NO: 1 or 2 was found by chance to be a DNA fragment encoding a portion of polyketide synthase, when a gene encoding avermectin B5-O-methyl transferase (aveD) was isolated (*Gene*, 206, 175–180 (1998)), and was obtained by the above method.

Modules, domains and ORFs, which are relevant to the avermectin aglycon synthase genes of the present invention, can be determined by comparing similarity with the sequences of 3 types of polyketide synthase domains of erythromycin (*Nature*, 348, 176–178 (1990), *Science*, 252, 675–679 (1991), or *Eur. J. Biochem.*, 204, 39–49 (1992)).

Figure 1:
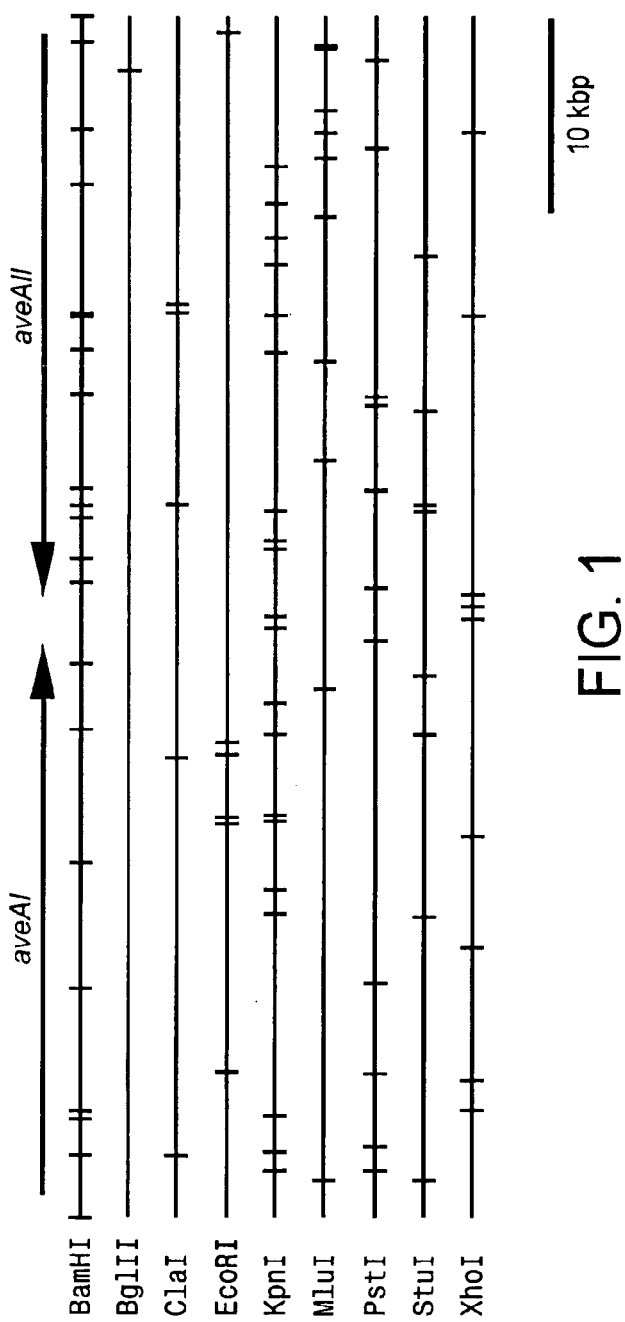

FIG. 1 shows a restriction map of the avermectin aglycon synthase gene regions (aveAI and aveAII) of genomic DNA (~65 kbp) of *Streptomyces avermitilis* together with predicted transcription units (arrow).

Polyketide compounds are natural organic compounds having a variety of structures and functions, and the common characteristics of these compounds are that their synthesis is carried out with a multifunctional enzyme called polyketide synthase.

One polyketide synthase has substrate specificity, and catalyzes the extention of a lower fatty acid constitutional unit (which is used in the form of CoA ester of dicarboxylic acid in reactions other than intial reaction), i.e., condensation to make a polyketide carbon chain, and has a catalytic activity and a controlling activity which modify a β-carbonyl group generated from such a reaction.

The condensation reaction, which is a basic reaction in the synthesis of polyketide, needs various catalytic activities including an acyl carrier protein (ACP) activity, a β-ketoacyl-ACP synthase (KS) activity and an acyltransferase (AT) activity.

In many cases, β-carbonyl groups generated by the condensation reaction are modified. However, depending on a module, some β-carbonyl groups may not be modified and may be used for the next condensation reaction.

Catalytic activities associated with the modification of β-carbonyl group after the condensation reaction include a β-ketoacyl-ACP reductase (KR) activity, a dehydratase (DH) activity and an enoyl reductase (ER) activity. The biosynthesis of a polyketide chain is terminated by cleaving out the polyketide chain from polyketide synthase by action of thioesterase (TE) activity.

All or several of these modification activities act in each condensation process, thereby determining the structure of a final product.

The avermectin aglycon synthase genes (aveAI and aveAII) of *Streptomyces avermitilis* are characterized in that the genes have several open reading frames each of which comprises one or more repeating units called a module, just as with other known polyketide biosynthetic genes. A module is defined as a gene fragment which encodes activities for a one-time synthesis, i.e., a one-time condensation reaction, and the subsequent various modification reactions of the β-carbonyl group. Each module encodes ACP, KS and AT associated with the condensation reaction in polyketide synthesis, and all or several of KR, DH and ER associated with the modification reaction of the β-carbonyl group. Furthermore, there is also a module which does not have any domain for a modification reaction. A polypeptide encoding such a module is referred to as synthase unit (SU).

FIG. 2 shows a biosynthetic pathway of 6,8a-seco-6,8a-deoxy-5-oxo-avermectin aglycon synthesized with avermectin aglycon synthases of *Streptomyces avermitilis*.

It is clear that PKS-1 is associated with initiation reaction, since an initiation module (SUs), differing from other modules, has acyltransferase (AT) activity on the N-terminal side. It is clear that PKS-3 is associated with the final reaction of polyketide, since module 9 (SU9) has a thioesterase (TE) domain.

The determined DNA sequences comprising avermectin aglycon synthase genes derived from *Streptomyces avermitilis* are shown in SEQ ID NOS: 1 and 2. The DNA of the present invention comprises open reading frames (ORFs) encoding respective multifunctional enzymes, and these ORFs are ORFs corresponding to nucleotide Nos. 11 to 11916 and nucleotide Nos. 211971 to 30688 of SEQ ID NO: 1 and nucleotide Nos. 31 to 14643 and nucleotide Nos. 414824 to 31419 of SEQ ID NO: 2. The amino acid sequences of various peptides encoded by these sequences are shown in SEQ ID NOS: 3, 4, 5 and 6.

Each of the above DNAs comprises a module encoding a synthesis unit having all catalytic activities necessary for a one-time carbon chain extension reaction. These modules are represented as the following nucleotides in SEQ ID NOS: 1 and 2. That is to say, the modules are represented in SEQ ID NO: 1 as,
Initiation Module: 85 to 1353,
Module 1: 1441 to 6180,
Module 2: 6256 to 11658,
Module. 3: 12076 to 15147,
Module 4: 15217 to 19938,
Module 5: 20008 to 24690,
Module 6: 24781 to 30309, and,
are represented in SEQ ID NO: 2 as,
Module 7: 100 to 4692,
Module 8: 4771 to 7818,
Module 9: 7906 to 14619,
Module 10: 14935 to 20334,
Module 11: 20413 to 25734,
Module 12: 25810 to 31125.

The amino acid sequences of various synthase units (SU) encoded by these modules are represented as the following amino acids. That is to say, the sequences are represented in SEQ ID NO: 3 as,
Initiation SU: 29 to 451,
SU1: 481 to 2060,
SU2: 2086 to 3886;
in SEQ ID NO: 4 as,
SU3: 36 to 1059,
SU4: 1083 to 2656,
SU5: 2680 to 4240,
SU6: 4271 to 6113;
in SEQ ID NO: 5 as,
SU7: 34 to 1564,
SU8: 1591 to 2606,
SU9: 2636 to 4873; and,
in SEQ ID NO: 6 as,
SU10: 38 to 1837,
SU11: 1864 to 3637,
SU12: 3663 to 5434.

DNAs encoding Avermectin aglycon synthase domains (submodules) are represented as the following nucleotides. That is to say, the DNAs are represented in SEQ ID NO: 1 as,
in Initiation Module,
ATs: 85 to 1032,
ACPs: 1096 to 1353;
in Module 1,
KS1: 1441 to 2742,
AT1: 3148 to 4068,
KR1: 5143 to 5676,
ACP1: 5935 to 6180;
in Module 2,
KS2: 6256 to 7545,
AT2: 7906 to 8829,
DH2: 8947 to 9384,
KR2: 10609 to 11142,
ACP2: 11413 to 11658;
in Module 3,
KS3: 12076 to 13368,
AT3: 13756 to 14694,
ACP3: 14902 to 15147;
in Module 4,
KS4: 15217 to 16506,
AT4: 16917 to 17862,
KR4: 18886 to 19419,
ACP4: 19693 to 19938;
in Module 5,
KS5: 20008 to 21297,
AT5: 21658 to 22584,
KR5: 23602 to 24138,
ACP5: 24445 to 24690;
in Module 6,
KS6: 24781 to 26079,
AT6: 26413 to 27336,
DH6: 27475 to 27894,
KR6: 29227 to 29760,
ACP6: 30064 to 30309; and,
are also represented in SEQ ID NO: 2 as,
in Module 7,
KS7: 100 to 1383,
AT7: 1648 to 2673,
KR7: 3634 to 4188,
ACP7: 4447 to 4692;
in Module 8,
KS8: 4771 to 6060,
AT8: 6322 to 7344,
ACP8: 7573 to 7818;
in Module 9,
KS9: 7906 to 9258,
AT9: 9676 to 10773,
DH9: 10885 to 11289,
KR9: 12547 to 13104,
ACP9: 13378 to 13659,
TE9: 13879 to 14619;
in Module 10,
KS10: 14935 to 16224,
AT10: 16543 to 17565,
DH10: 17689 to 18066,
KR10: 19285 to 19842,
ACP10: 20089 to 20334;
in Module 11,
KS11: 20413 to 21705
AT11: 21991 to 23019,
DH11: 23149 to 23529,
KR11: 24685 to 25242,
ACP11: 25489 to 25734;
in Module 12,
KS12: 25810 to 27102,
AT12: 27367 to 28392,
DH12: 28516 to 28878,
KR12: 30076 to 30633,
ACP12: 30880 to 31125.

The deduced amino acid sequences of various domains encoded by these submodules are represented as:
in SEQ ID NO: 3,
ATs: 29 to 344,
ACPs: 366 to 451,
KS1: 481 to 914,
AT1: 1050 to 1356,
KR1: 1715 to 1892,
ACP1: 1979 to 2060,
KS2: 2086 to 2515,
DH2: 2983 to 3128,
KR2: 3537 to 3714,
ACP2: 3805 to 3886;
in SEQ NO: 4,
KS3: 36 to 466,
AT3: 596 to 908,
ACP3: 978 to 1059,
KS4: 1083 to 1512,
AT4: 1653 to 1964,
KR4: 2306 to 2483,
ACP4: 2575 to 2656, KS5: 2680 to 3109,
AT5: 3230 to 3538,
KR5: 3878 to 4056,
ACP5: 4159 to 4240,
KS6: 4271 to 4703,
AT6: 4815 to 5122,
DH6: 5168 to 5307,
KR6: 5753 to 5930,
ACP6: 6032 to 6113;
in SEQ ID NO: 5,
KS7: 34 to 461,
AT7: 550 to 891,
KR7: 1212 to 1396,
ACP7: 1483 to 1564,
KS8: 1591 to 2020,
AT8: 2108 to 2448,
ACP8: 2525 to 2606,
KS9: 2636 to 3086,
AT9: 3226 to 3591,
DH9: 3629 to 3763,
KR9: 4183 to 4363,
ACP9: 4460 to 4553,
TE9: 4627 to 4873; and,
in SEQ ID NO: 6,
KS10: 38 to 467,
AT10: 574 to 914,
DH10: 956 to 1081,
KR10: 1488 to 1673,
ACP10: 1756 to 1837,
KS11: 1864 to 2294,
AT11: 2390 to 2732,
DH11: 2776 to 2902,
KR11: 3288 to 3473,
ACP11: 3556 to 3637,
KS12: 3663 to 4093,
AT12: 4182 to 4523,
DH12: 4565 to 4685,
KR12: 5085 to 5270,
ACP12: 5353 to 5434.

From a comparison of sequence information regarding the known polyketide synthase genes, it was found that a similarity of sequences exists between domains having identical functions. By using such similarity, it becomes possible to predict the domain of a novel polyketide synthase gene.

In other words, based on the above module, domain and ORF information obtained from DNAs having nucleotide sequences of SEQ ID NO: 1 and 2 derived from *Strepromyces avermitilis*, modules, domains and ORFs, which are relevant to the Avermectin aglycon synthase genes derived from other bacteria capable of producing avermectin, can be determined.

Using a DNA having the nucleotide sequence of SEQ ID NO: 1 or 2, an avermectin aglycon synthase gene can be obtained by the following method.

A DNA having the nucleotide sequence of SEQ ID NO: 1 or 2 is digested with appropriate restriction enzymes, the DNA fragment was separated and recovered by the method described in *Molecular Cloning*, Second Edition, and an oligonucleotide consisting of the DNA fragment is used as a probe or primer.

As a probe, the DNA fragment labeled with digoxigenin etc. is preferably used. The DIG labeling & detection kit, which can be purchased from Roche Diagnostic Corp., can be used for labeling with digoxigenin.

A library is prepared from bacteria producing avermectin by genome cloning or cDNA cloning described in *Molecular Cloning*, Second Edition etc.

A clone (or a colony) which is to be cross-hybridized with the probe obtained above is selected from the library, then a plasmid is extracted from the clone by the method described in *Molecular Cloning*, Second Edition, and finally an avermectin aglycon synthase gene can be obtained from the plasmid. In addition, DNAs (i.e. submodules) and modules which encode an avermectin aglycon synthase gene domain can be obtained by the same method.

Otherwise, an avermectin aglycon synthase gene, a submodule and a module can also be obtained by direct PCR amplification, using the above library and primers prepared as above.

In a case where the only partial DNA fragment encoding an avermectin aglycon synthase exists in the plasmid extracted as above, according to standard techniques, a restriction map of the plasmid is prepared by digesting the extracted plasmid with appropriate restriction enzymes such as BamHI.

A restriction enzyme map of a DNA comprising the DNA encoding the entire avermectin polyketide synthase can be prepared by finding restriction enzyme fragments which commonly exist in several clones and binding up the cloned fragments at overlapping portions, so that the DNA encoding avermectin polyketide synthase can be obtained.

The nucleotide sequence of a DNA encoding avermectin polyketide synthase can be determined by commonly applied nucleotide sequencing analysis, e.g. the dideoxy method (*Proc. Natl. Acad. Sci.* USA, 74, 5463 (1977)), or by the analysis with a DNA sequencing analyzer such as 373A DNA sequencer (Perkin Elmer Corp.).

Specifically, a DNA sequence can be determined by directly using double-stranded plasmid DNA as a template for a cycle sequence reaction, wherein oligonucleotide primers specific for various sequences are used. Alternatively, a DNA sequence can also be determined by: cleaving a DNA fragment into its small fragments; introducing the resulting fragments into bacteria phage M13 at random; preparing an overlapping library, which comprises DNA fragments deleted successively from the termini thereof, using a library or plasmid vector comprising partially overlapping fragments; and subjecting each recombinant DNA fragment to the DNA sequencing using oligonucleotide primers specific to the vector sequence. The fluorescently labeled reactant obtained by the cycle sequence reaction can be analyzed with a DNA sequencer (e.g. Model 4000L, LiCor).

Moreover, based on the nucleotide sequence of the determined DNA, a desired DNA can also be prepared by the chemical synthesis, using a DNA synthesizer (Model 8905, Perceptive BioSystems) etc.

The obtained nucleotide sequence data can be arranged, edited and analyzed using existing software, for example, Genetyx™ (Software Development).

Using the DNAs and DNA fragments of the present invention obtained by the above method, oligonucleotides such as an antisense oligonucleotide and a sense oligonucleotide, which have a portion of the DNA sequence of the present invention, or oligonucleotides comprising an RNA can be prepared according to standard techniques. Alternatively, based on the DNA sequence information obtained as above, these oligonucleotides can also be synthesized with the above-mentioned DNA synthesizer.

Examples of the thus obtained oligonucleotides include a DNA having a sequence corresponding to 5 to 60 continuous nucleotides in the nucleotide sequence of the DNA obtained by the above-mentioned method, or a DNA having a sequence complementary to this DNA. Furthermore, the oligonucleotides of the present invention also include an RNA having a sequence complementary to these DNAs.

Examples of the thus obtained oligonucleotides include a DNA having a sequence corresponding to 5 to 60 continuous nucleotides in the nucleotide sequence of SEQ ID NO: 1 or 2, or a DNA having a sequence complementary to this DNA. Where the oligonucletides are used as sense and antisense primers, from among the above oligonucleotides, it is preferable to apply oligonucleotides wherein melting temperature (Tm) and the number of bases do not significantly differ between both oligonucleotides.

Examples of the thus obtained oligonucleotides include ones having the nucleotide sequences shown in SEQ ID NOS: 9 to 14.

Moreover, the derivatives of these oligonucleotides (hereinafter, also referred to as oligonucleotide derivatives) can also be used as the oligonucleotides of the present invention.

Examples of the oligonucleotide derivatives include: an oligonucleotide derivative obtained by conversion of a phosphodiester phosphate bond into a phosphorothioate bond in the above-described oligonucleotide; an oligonucleotide derivative obtained by conversion of a phosphodiester bond into a N3'-P5' phosphoamidate bond in the above-described oligonucleotide; an oligonucleotide derivative obtained by conversion of a ribose and a phosphodiester phosphate bond into a peptide nucleic acid bond in the above-described oligonucleotide; an oligonucleotide derivative obtained by substitution of uracil by C-5 propynyl uracil in the above-described oligonucleotide; an oligonucleotide derivative obtained by substitution of uracil by C-5 thiazole uracil in the above-described oligonucleotide; an oligonucleotide derivative obtained by substitution of cytosine by C-5 propynyl cytosine in the above-described oligonucleotide; an oligonucleotide derivative obtained by substitution of cytosine by phenoxazine-modified cytosine in the above-described oligonucleotide; an oligonucleotide derivative obtained by substitution of ribose by 2'-O-propyl ribose in the above-described oligonucleotide; and an oligonucleotide derivative obtained by substitution of ribose by 2'-methoxyethoxy ribose in the above-described oligonucleotide etc. (*Cell Engineering* (*Saibo Kogaku*) 16, 1463 (1997)).

2. Preparation of the Polypeptide of the Present Invention

The polypeptide of the present invention can be produced by using a method described in Molecular Cloning, Second Edition or Current Protocols in Molecular Biology. For example, it can be produced by expressing the DNA of the present invention obtained as described in the above Section 1 in a host cell, according to the following procedure.

Based on the DNA of the present invention, a DNA fragment of an appropriate length containing a region encoding the polypeptide of the present invention can be prepared, if necessary. Further, DNA useful for improving the production efficiency of the polypeptide can be prepared by replacing a nucleotide in the nucleotide sequence of the region encoding the polypeptide so as to make a codon most suitable for expression in a host cell.

The DNA fragment is inserted at a site downstream of a promoter in an appropriate expression vector to construct a recombinant vector.

The recombinant vector is introduced into a host cell suitable for the expression vector, whereby a transformant producing the polypeptide of the present invention can be obtained.

As a host cell, any bacterial cells, yeast cells, animal cells, insect cells, plant cells etc, that are capable of expressing the desired gene can be used.

As an expression vector, it is possible to use any vector that can autonomously replicate in the above host cells or can be integrated into chromosomes thereof and that contains a promoter at a position appropriate for the transcription of the DNA of the present invention.

When a prokaryote (e.g., a bacterial cell) is used as a host cell, a preferred expression vector for the polypeptide of the present invention may be a recombinant DNA construct that is autonomously replicative in prokaryotes and that comprises a promoter, a ribosome-binding sequence, the DNA of the present invention and a terminator. The vector may further comprise a gene regulating the promoter.

Examples of expression vectors include pBTrp2, pBTac1, pBTac2 (each of which is manufactured by Boehringer Mannheim), pKK233-2 (manufactured by Pharmacia), pGEX (manufactured by Pharmacia), pSE280 (manufactured by Invitrogen), pGEMEX-1 (manufactured by Promega), pQE-8 (manufactured by QIAGEN), pQE-9 (manufactured by QIAGEN), pQE-70 (manufactured by QIAGEN), pQE-60 (manufactured by QIAGEN), pET-3 (manufactured by Novagen), pET-11a (manufactured by Novagen), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci., USA, 82, 4306 (1985)], pBluescript II SK+ (manufactured by Stratagene), pBluescript II SK(-) (manufactured by Stratagene), pTrS30 [prepared from *E. coli* JM109/pTrS30 (FERM BP-5407)], pTrS32 [prepared from *E. coli* JM109/pTrS32 (FERM BP-5408)], pUC19 [Gene, 33, 103 (1985)], pSTV28 (manufactured by Takara Shuzo Co., Ltd.), pUC118 (manufactured by Takara Shuzo Co., Ltd.), pPA1 (Japanese Published Unexamined Patent Application No. 233798/88), pKC30 (Rosenberg et al., 1983, in "Methods in Enzymology," Vol. 101, pp. 123–138, Academic Press, San Diego), pKK223-3 (manufactured by Pharmacia), pDR540 (manufactured by Pharmacia), pRIT2T (manufactured by Pharmacia), and ptrc99a [Gene, 69, 301 (1988)].

As a promoter, any promoter capable of expressing in host cells, such as *E. coli,* can be used, including promoters derived from *E. coli* or a phage such as trp promoter (Ptrp), lac promoter (Plac), $P_L$ promoter, $P_R$ promoter and $P_{SE}$ promoter, SPO1 promoter, SPO2 promoter, and penP promoter. An artificially designed, modified promoter may also be used, including a promoter obtained by binding two Ptrp promoters in tandem (Ptrp×2), tac promoter, lac T7 promoter, and let I promoter.

It is preferable to use a plasmid having an appropriate distance (e.g., 6–18 bases) between Shine-Dalgarno sequence (i.e., ribosome-binding sequence) and an initiation codon.

A terminator is not necessarily required for expression of the recombinant DNA construct of the present invention, but it is desirably located immediately downstream of a structural gene.

A prokaryote includes a microorganism belonging to *Escherichia, Serratia, Bacillus, Brevibacterium, Corynebacterium, Microbacterium, Pseudomonas,* and the like. Specific examples include *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum* ATCC14068, *Brevibacterium saccharolyticum* ATCC14066, *Corynebacterium glutamicum* ATCC13032, *Corynebacterium glutamicum*

ATCC14067, *Corynebacterium glutamicum* ATCC13869, *Corynebacterium acetoacidophilum* ATCC13870, *Microbacterium ammoniaphilum* ATCC15354, and *Pseudomonas* sp. D-0110.

Introduction of the recombinant DNA can be carried out by any method for introducing DNA into these host cells: for example, the calcium ion method [Proc. Natl. Acad. Sci. USA, 69, 2110 (1972)], the protoplast method (Japanese Published Unexamined Patent Application No. 248394/88) and electroporation [Nucleic Acids Research., 16, 6127 (1988)].

When a yeast cell is used as a host cell, an expression vector which can be used includes YEp13 (ATCC37115), YEp24 (ATCC37051), YCp50 (ATCC37419), pHS19, pHS15, pG-1, pXT1 (manufactured by Stratagene), pSG5 (manufactured by Stragtagene), pSVK3 (manufactured by Pharmacia), pBPV, pMSG (manufactured by Pharmacia), and pSVL SV40 (manufactured by Pharmacia).

As a promoter, any promoter capable of expressing in yeast cells may be used, including PHO5 promoter, PGK promoter, GAP promoter, ADH promoter, GPD promoter, AOX1 promoter, gal 1 promoter, gal 10 promoter, heat shock polypeptide promoter, MF α 1 promoter, and CUP 1 promoter.

Examples of the host cell include yeast strains belonging to the genus *Saccharomyces, Schizosaccharomyces, Kluyveromyces, Trichosporon, Schwanniomyces, Pichia* and the like. Specific examples include *Saccharomyces cerevisiae, Schizosaccharomyces pombe, Kluyveromyces lactis, Trichosporon pullulans, Schwanniomyces alluvius,* or *Pichia pastoris.*

Introduction of the recombinant DNA can be carried out by any method for introducing DNA into yeast cells: for example, electroporation [Methods in Enzymol., 194, 182 (1990)], the spheroplast method [Proc. Natl. Acad. Sci. USA, 81, 4889 (1984)], the lithium acetate method [J. Bacteriol., 153, 163 (1983)] and the method described in Proc. Natl. Acad. Sci. USA, 75, 1929 (1978).

When an animal cell is used as a host cell, an expression vector which can be used includes pcDNAI, pcDM8 (commercially available from Funakoshi), pAGE107 (Japanese Published Unexamined Patent Application No. 22979/91), pAS3-3 (Japanese Published Unexamined Patent Application No. 227075/90), pCDM8 [Nature, 329, 840 (1987)], pcDNAI/Amp (manufactured by Invitrogen), pREP4 (manufactured by Invitrogen), pAGE103 [J. Biochem, 101, 1307 (1987)], pAGE210, pAMo, and pAMoA.

As a promoter, any promoter capable of expressing in animal cells can be used, including a promoter for immediate early (IE) gene of Cytomegalovirus (CMV), SV40 early promoter or metallothionein promoter, retroviral promoter, heat shock promoter, and SRα promoter. An enhancer for IE gene of Human CMV may also be used together with such a promoter.

Host cells include mouse myeloma cells, rat myeloma cells, mouse hybridoma cells, human Namalwa or Namalwa KJM-1 cells, human fetal kidney cells, human leukemia cells, African green monkey kidney cells, chinese hamster CHO cells, or HBT5637 (Japanese Published Unexamined Patent Application No. 299/88).

Specific examples include SP2/O, NSO and the like for mouse myeloma cells, YB2/O and the like for at myeloma cells, HEK293 (ATCC: CRL-1573), and the like for human fetal kidney cells, BALL-1 and the like for human leukemia cells, and COS-1, COS-7 and the like for African green monkey kidney cells.

Introduction of the recombinant DNA can be carried out by any method for introducing DNA into animal cells: for example, electroporation [Cytotechnology, 3, 133 (1990)], the calcium phosphate method (Japanese Published Unexamined Patent Application No. 227075/90), the lipofection method [Prc. Natl. Acad. Sci. USA, 84, 7413 (1987)] and the method described in Virology, 52, 456 (1973).

When an insect cell is used as a host cell, a polypeptide can be expressed by a method described in Baculovirus Expression Vectors, A Laboratory Manual, W. H. Freeman and Company, New York (1992); Current Protocols in Molecular Biology; Molecular Biology, A Laboratory Manual; or Bio/Technology, 6, 47 (1988).

More specifically, a recombinant gene transfer vector and a baculovirus may be co-introduced into insect cells to obtain a recombinant virus in the supernatant from the cultured insect cells. Thereafter, insect cells may further be infected with the resulting recombinant virus to express the polypeptide.

Examples of the gene transfer vector used in the above procedure includes pVL1392, pVL1393, pBlueBacIII (commercially available from Invitrogen, respectively) and the like.

Examples of the baculovirus include *Autographa californica* nuclear polyhedrosis virus, which infects *Noctuidae* insects, and the like.

Examples of insect cells include *Spodoptera frugiperda* ovarian cells, *Trichoplusia ni* ovarian cells, cultured cells derived from silk worm ovary, and the like.

Specific examples are Sf9 and Sf21 (Baculovirus Expression Vectors, A Laboratory Manual) for *Spodoptera frugiperda* ovarian cells, High 5 and BTI-TN-5B 1-4 (manufactured by Invitrogen) for *Trichoplusia ni* ovarian cells, *Bombyx mori* N4 for cultured cells derived from silk worm ovary, and the like.

Co-introduction of the recombinant gene transfer vector and the baculovirus into insect cells for recombinant virus production can be carried out by the calcium phosphate method (Japanese Published Unexamined Patent Application No. 227075/90) or the lipofection method [Proc. Natl. Acad. Sci. USA, 84, 7413 (1987)].

When a plant cell is used as a host cell, examples of an expression vector include Ti plasmid, tobacco mosaic virus vector, and the like.

As a promoter, any promoter capable of expressing in plant cells can be used, including cauliflower mosaic virus (CaMV) 35S promoter, rice actin 1 promoter, and the like.

Host cells include plant cells such as tobacco, potato, tomato, carrot, soy bean, *Brassica,* alfalfa, rice, wheat, barley, and the like.

Introduction of the recombinant vector can be carried out by any method for introducing DNA into plant cells: for example, the *Agrobacterium* method (Japanese Published Unexamined Patent Application No. 140885/84, Japanese Published Unexamined Patent Application No. 70080/85, WO94/00977), electroporation (Japanese Published Unexamined Patent Application No. 251887/85), and the particle gun method (Japanese Patent No. 2606856, Japanese Patent No. 2517813).

The gene can be either expressed directly, or expressed as a secreted polypeptide or a fusion polypeptide according to the method as described in Molecular Cloning, Second Edition. Expression in yeast, animal, insect or plant cells can provide a polypeptide with sugar or sugar chain attached thereto.

The polypeptide of the present invention can be produced by culturing the thus obtained transformant in a medium to produce and accumulate the polypeptide of the present invention in the culture, and recovering the polypeptide from the culture.

The transformant of the present invention can be cultured in a medium according to a conventional method used for culturing host cells.

A medium for culturing a transformant derived from a prokaryote host (e.g., *E. coli*) or a eukaryote host (e.g., yeast) may be a natural or synthetic medium insofar as the medium contains a carbon source, a nitrogen source, an inorganic salt etc., which can be assimilated by the organism, and enables the efficient culture of the transformant.

Any carbon source assimilated by the organisms can be used as a carbon source. Illustrative examples include carbohydrates such as glucose, fructose, sucrose, molasses containing them, starch or starch hydrolysate; organic acids such as acetic acid, propionic acid; alcohols such as ethanol, propanol, and the like.

Examples of the nitrogen source which can be used include ammonium salts of various inorganic or organic acids, such as ammonia, ammonium chloride, ammonium sulfate, ammonium acetate, and ammonium phosphate; other nitrogen-containing compounds; and peptone, meat extracts, yeast extracts, corn steep liquor, casein hydrolysate, soy bean meal, soy bean meal hydrolysate, various fermented cells and hydrolysates thereof and the like.

Inorganic salts which can be used include potassium dihydrogen phosphate, dipotassium hydrogen phosphate, magnesium phosphate, magnesium sulfate, sodium chloride, ferrous sulfate, manganese sulfate, copper sulfate, calcium carbonate, and the like.

Culture is carried out under aerobic conditions by shaking culture, submerged spinner culture under aeration, and the like. The culture temperature is preferably from 15 to 40° C., and culturing time is usually from 5 hours to 7 days. During the culture, pH is maintained at 3.0 to 9.0. The pH can be adjusted using an inorganic or organic acid, an alkaline solution, urea, calcium carbonate, ammonia and the like.

Also, if necessary, antibiotics such as ampicillin and tetracycline can be added to a medium during the culturing.

In a case where a microorganism is transformed with an expression vector containing an inducible promoter, the transformant can be cultured in a medium supplemented with an inducer, if necessary. For example, when an expression vector containing lac promoter is used for transformation, the transformant may be cultured in a medium supplemented with isopropyl-β-D-thiogalactopyranoside or the like; when an expression vector containing trp promoter is used for transformation, the transformant can be cultured in a medium supplemented with indole acrylic acid or the like.

A medium for culturing a transformant obtained using an animal cell as the host includes generally-used media such as RPMI 1640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)] as well as other media to which fetal calf serum or the like has been added to the above media and the like.

Culturing is generally carried out at pH 6 to 8, at a temperature of 25 to 40° C. for a period of 1 to 7 days in the presence of 5% $CO_2$.

Also, if necessary, antibiotics such as kanamycin, penicillin and streptomycin may be added to a medium during the culturing.

A medium for culturing a transformant obtained using an insect cell as the host includes generally-used media such as TNM-FH medium (manufactured by PharMingen), Sf-900 II SFM medium (manufactured by Life Technologies), ExCell 400 and ExCell 405 [both being products of JRH Biosciences], Grace's Insect Medium [Nature, 195, 788 (1962)] or the like.

Culturing is generally carried out at pH 6 to 7, at a temperature of 25 to 30° C. for a period of 1 to 5 days.

Also, if necessary, antibiotics such as gentamycin can be added to a medium during the culture.

The transformant obtained using a plant cell as the host can be cultured as a cell or can be allowed to differentiate into plant cell or organ before culture. Examples of the medium for culturing the transformant include a generally used medium such as Murashige and Skoog (MS) medium, White medium, or any one of these media further supplemented with a plant hormone such as auxin or cytokinin.

Culturing is carried out usually at pH 5 to 9, at a temperature of 20 to 40° C. for a period of 3 to 60 days.

Also, if necessary, antibiotics such as kanamycin and hygromycin can be added to a medium during the culturing.

As described above, the polypeptide of the present invention can be produced by culturing a microorganism-, animal cell-, or plant cell-derived transformant carrying a recombinant vector in which a DNA encoding the polypeptide of the present invention has been inserted according to a general manner to produce and accumulate the polypeptide, and then recovering the polypeptide from the culture.

A method for producing the polypeptide of the present invention includes intracellular production in host cells, extracellular secretion by host cells or production on outer membranes of host cells, and the method can be selected depending on the type of host cells to be used and/or the structure of polypeptide to be produced.

If the polypeptide of the present invention is produced in host cells or on outer membranes of host cells, the polypeptide can be efficiently secreted to extracellularly from the host cells by using the method of Paulson et al. [J. Biol. Chem., 264, 17619 (1989)], the method of Lowe et al. [Proc. Natl. Acad. Sci., USA, 86, 8227 (1989), Genes Develop., 4, 1288 (1990)] or methods as described in Japanese Published Unexamined Patent Application No. 336963/93 and PCT WO94/23021.

More specifically, the polypeptide of the present invention can be efficiently secreted from host cells by expressing it in a form with signal peptide using genetic recombination techniques, the signal peptide being added upstream of a portion containing the active site of the polypeptide of the present invention.

Furthermore, the amount of the production can be increased using a gene amplification system using a dihydrofolate reductase gene or the like according to the method described in Japanese Published Unexamined Patent Application No. 227075/90.

Further, animal or plant cells introduced with a gene may be re-differentiated to create an animal individual carrying a transgene (transgenic non-human animal) or a plant individual carrying a transgene (transgenic plant), which may be used for producing the polypeptide of the present invention.

When the transformant is an animal or plant individual, the polypeptide may be obtained by feeding or cultivating the individual in a general manner to produce and accumulate the polypeptide, and then recovering the polypeptide from the animal or plant individual.

The methods for producing the polypeptide of the present invention using an animal individual include a method using an animal obtained by introducing a gene in accordance with known manners as described in American Journal of Clinical Nutrition, 63, 639S (1996); American Journal of Clinical Nutrition, 63, 627S (1996); and Bio/Technology, 9, 830 (1991).

In the case of an animal individual, for example, the polypeptide of the present invention may be obtained by feeding a transgenic non-human animal introduced with a DNA insert encoding the polypeptide of the present invention to produce and accumulate therein the polypeptide, and then recovering the polypeptide from the animal. The polypeptide can be produced and accumulated in the animal's milk (Japanese Published Unexamined Patent Application No. 309192/88), egg, and the like. As a promoter used for this purpose, any promoter can be used so long as it can be expressed in the animal, for example, mammary gland cell-specific promoters such as an a-casein promoter, a β-casein promoter, a β-lactoglobulin promoter and a whey acidic protein promoter being preferred.

The methods for producing the polypeptide of the present invention using a plant individual include a method cultivating a transgenic plant obtained by introducing a gen encoding the polypeptide of the present invention to produce and accumulate therein the polypeptide in a known manner as described in Tissue Culture (Soshiki Baiyo), 20 (1994); Tissue Culture, 21 (1995); and Trends in Biotechnology, 15, 45 (1997), and then the polypeptide can be recovered from the plant.

For isolation and purification of the polypeptide produced by the transformant of the present invention, conventional methods for the isolation and purification of enzymes can be used.

For example, if the polypeptide of the present invention is expressed in a soluble form in cells, after completion of culturing, the cells are recovered by centrifugation, and suspended in an aqueous buffer and then disrupted with ultrasonic disrupter, French Press, Manton-Gaulin homogenizer, Dynomill or the like, to obtain a cell-free extract.

From the supernatant obtained by centrifuging the cell-free extract, a purified product can be obtained by the general method used for isolating and purifying an enzyme, for example, solvent extraction, salting-out using ammonium sulfate or the like, desalting, precipitation using an organic solvent, anion exchange chromatography using a resin, such as diethylaminoethyl (DEAE)-Sepharose, DIAION HPA-75 (manufactured by Mitsubishi Chemical) or the like, cation exchange chromatography using a resin, such as S-Sepharose FF (manufactured by Pharmacia) or the like, hydrophobic chromatography using a resin, such as butyl sepharose, phenyl sepharose or the like, gel filtration using a molecular sieve, affinity chromatography, chromatofocusing, or electrophoresis, such as isoelectronic focusing or the like, alone or in combination thereof.

When the protein is expressed as an inclusion body in the host cells, the cells are collected in the same manner, disrupted and centrifuged to recover the inclusion body of the protein as the precipitate fraction. Next, the inclusion body of the protein is solubilized with a protein-denaturing agent.

The solubilized protein solution is diluted with or dialyzed against a solution containing no protein-denaturing agent or such a dilute solution containing the protein-denaturing agent at a lower concentration that denaturation of the protein is not caused. Thus, the normal tertiary structure of the protein is reconstituted. After the procedure, a purified product of the protein can be obtained by a purification and isolation method similar to the above.

When the protein of the present invention or its glycosylated-derivative is secreted out of cells, the protein or its derivative can be collected from the culture supernatant.

Namely, the culture supernatant is obtained by treating the culture in a similar manner to the above-mentioned centrifugation or the like. Then, a purified product can be obtained from the supernatant using a purification and isolation method similar to the above.

Examples of the thus obtained protein include a protein comprising the amino acid sequence represented by SEQ ID NOS:3, 4, 5 and 6.

Furthermore a fusion protein of the protein of the present invention and other protein may be produced, and purified by affinity chromatography using a substance having affinity to the fusion protein. For example, the protein of the present invention may be produced as a fusion protein with protein A according to the method of Lowe et al. (*Proc. Natl. Acad. Sci. USA*, 86: 8227 (1989); *Genes Develop.*, 4: 1288 (1990)), or the method described in Japanese Published Unexamined Patent Application No. 336963/93 or WO 94/23021, and purified by affinity chromatography using immunoglobulin G.

Moreover, the protein of the present invention may be produced as a fusion protein with Flag peptide, and the fusion protein can be purified by affinity chromatography using an anti-Flag antibody (*Proc. Natl. Acad. Sci., USA*, 86: 8227 (1989), *Genes Develop.*, 4: 1288 (1990)). Further purification can be carried out by affinity chromatography using the antibody against the protein per se.

Also, based on the information of the thus obtained protein, the protein of the present invention can be produced by the chemical synthesis method, such as Fmoc (fluorenylmethyloxycarbonyl) method, tBoc (t-butyloxycarbonyl) method, or the like. It can also be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

3. Production of Avermectin Aglycon or Avermectin

Avermectin aglycon can be produced by culturing the transformant prepared in the above Section 2, which carries the avermectin aglycon synthase gene or a module or submodule thereof, in a medium to produce and accumulate avermectin aglycon in the culture, and then recovering avermectin aglycon from the culture.

When a host used for preparation of a transformant can produce avermectin, avermectin aglycon or avermectin can be efficiently produced in any one of the transformants obtained by introducing the avermectin aglycon synthase gene or a module or submodule thereof into the host. The transformant thus obtained can produce avermectin aglycon or avermectin with higher efficiency than that of the host.

When a host used for preparation of a transformant cannot produce avermectin, the avermectin aglycon synthase gene may be introduced into the host to obtain a transformant capable of producing avermectin aglycon.

In the production of avermectin or avermectin aglycon, the above transformant can be cultured according to a culture procedure as described in the above Section 2.

A known avermectin is a macrocyclic lactone having a 16-membered ring with two sugar residues attached thereto via glycosidic linkage. Avermectin aglycon can be converted into avermectin in a manner well known in the art, for example, by glycosylating avermectin aglycon as described in J. Bacteriol., 175, 2552–2563 (1993).

4. Production of Modified Avermectin Aglycon or Avermectin

Avermectin aglycon is formed through extension of lower-fatty acid units (used in the form of CoA ester of dicarboxylic acid in reactions other than the initial reaction) by avermectin aglycon synthase, i.e., condensation to give a polyketide carbon chain, and modification of β-carbonyl groups generated during the condensation.

As described above, the avermectin aglycon synthase gene is composed of modules, each module comprising DNA encoding avermectin aglycon synthase domains (submodule).

A submodule encodes ACP, KS and AT involved in condensation during polyketide synthesis, as well as KR, DH or ER involved in modification of β-carbonyl groups.

Accordingly, the carbon chain length of the aglycon part and the type of functional group on β-carbon in the condensation process can be altered by modifying a submodule, based on nucleotide sequence information of the Avermectin aglycon synthase gene determined in the above Section 1.

Further, selective inactivation of a submodule can result in production of a predictable novel avermectin or a particular component thereof alone.

By way of example, a strain producing avermectin B1a and B2a, *Streptomyces avermitilis* K2038, can be converted into a strain producing only avermectin B2a by replacing or converting a submodule DH2 region of the avermectin aglycon synthase gene by or into its inactivated form without dehydratase activity.

The submodule DH2 region can be replaced by or converted into its inactivated form, for example, by homologous recombination on submodule DH2 of the above strain to give the nucleotide sequence shown in SEQ ID NO: 7 in a general manner as described in Molecular Cloning, Second Edition.

The strain thus obtained, which becomes capable of producing a modified (or altered) avermectin aglycon, can be used to produce and obtain the modified avermectin aglycon or modified avermectin according to the general process for producing avermectin.

BEST MODES FOR CARRYING OUT THE INVENTION

The following examples are provided for illustrative purposes only, and are not intended to limit the scope of the invention clearly defined above.

Example 1

Determination of the Nucleotide Sequence of the Avermectin Aglycon Synthase Gene of *Streptomyces avermitilis*

A nucleotide sequence of the DNA encoding avermectin aglycon synthase derived from *Streptomyces avermitilis* K2033 (U.S. Pat. No. 5,206,155, FERM BP-2773) was determined as follows.

Continuous or overlapping DNA fragments within the avermectin aglycon synthase gene were subcloned from plasmids containing a fragment of the avermectin aglycon synthase genes (aveAI and aveAII) co-isolated with a gene encoding avermectin B5-O-transmethylase (aveD; Gene, 206, 175–180 (1998)). Nucleotide sequences of the inserted DNA fragments in these subclones were then determined.

More specifically, the entire nucleotide sequences of aveAI and aveAII were determined by subcloning BamHI-treated fragments of 3.4 kbp, 2.0 kbp, 0.5 kbp, 6.8 kbp, 7.0 kbp, 7.8 kbp, 3.7 kbp, 4.8 kbp, 1.3 kbp, 2.4 kbp, 0.7 kbp, 1.0 kbp, 5.4 kbp, 2.5 kbp, 1.9 kbp, 0.1 kbp, 7.0 kbp, 3.1 kbp, 4.7 kbp and 1.3 kbp found in the BamHI-restriction map of aveAI and aveAII shown in FIG. 1; treating the inserted DNA fragments in these subclones with exonuclease III and S1 nuclease to prepare a series of deletion fragments; and then carrying out a cycle-sequencing reaction using fluorescently-labeled primers to determine a nucleotide sequence of each deletion fragment. The genes aveAI and aveAII had the nucleotide sequences shown in SEQ ID NO: 1 and SEQ ID NO: 2, respectively.

Example 2

Production of Avermectin B2a Alone by Nucleotide Modification of Dehydratase Domain in Module 2

*Streptomyces avermitilis* K2038 (FERM BP-2775) produces avermectin B1a and B2a.

The information of avermectin aglycon synthase genes (SEQ ID NOs:1 and 2) derived from the avermectin-producing strain, which were obtained and sequenced in Example 1, indicated that avermectin was biosynthesized through the biosynthetic pathway shown in FIGS. 2A–2C.

Avermectin B1a differs from avermectin B2a only in that avermectin B1a has a double bond between 22- and 23-positions in its aglycon part, while avermectin B2a has a single bond between 22- and 23-positions and a hydroxyl group at 23-position in its aglycon part.

The biosynthetic pathway for avermectin found above indicated that avermectin aglycon synthase domain DH of SU2 (DH2) is responsible for the formation of a double bond between 22- and 23-positions in the aglycon part of avermectin B1a and that avermectin aglycon synthase domain DH of SU10 (DH10) has no dehydratase activity.

Based on the idea that a strain producing only avermectin B2a could be obtained by converting DH2 into a domain without dehydratase activity like DH10, DH2 without dehydratase activity was prepared as follows.

The Avermectin aglycon synthase genes obtained in Example 1 had six DH domains: DH2, DH6, DH9, DH10, DH11 and DH12. Comparisons of nucleotide sequences of these domains showed that DH10 clearly differed from other DH domains in a consensus sequence common to dehydratase.

More specifically, amino acid sequences of DH2, DH6, DH9, DH11 and DH12, which were directly involved in the avermectin aglycon formation, were shown to include a consensus sequence of HXaaXaaXaaGXaaXaaXaaXaaP (SEQ ID NO: 13) or HXaaXaaXaaGXaaXaaXaaXaaS (SEQ ID NO: 14), wherein H, G, P, S and Xaa represent histidine, glycine, proline, serine and any amino acid, respectively; whereas the corresponding sequence of DH10 was YXaaXaaXaaGXaaXaaXaaXaaS (SEQ ID NO: 15), wherein Y represents tyrosine, and Xaa, G and S are as defined above.

Thus, replacement of an N-terminal H (His) by Y (Tyr) was thought to provide dehydratase without its activity.

A DNA was constructed, which had a nucleotide sequence encoding the sequence for replacement of the N-terminal amino acid sequence -His-Ala- in the consensus sequence of DH2 [-His-Ala-Val-Gly-Gly-Thr-Val-Leu-Leu-Ser- (SEQ ID NO: 16), amino acids 3037–3046 in SEQ ID NO: 3] by the corresponding sequence of DH10: -Tyr-Glu- (amino acids 1008–1017 in SEQ ID NO: 6). That is, the DNA sequence of DH2 domain: 5'-CAT GCC-3' (nucleotides 9109–9114 in SEQ ID NO: 1) was replaced by the sequence: 5'-TAC GAG-3' as follows.

A DNA fragment of the aveAI region containing DH2 domain was digested with restriction enzyme SmaI, and the 2327 bp SmaI fragment corresponding to nucleotides 7869–10196 in SEQ ID NO: 1 was cloned into the SmaI site of vector plasmid pUC19.

Taq DNA polymerase buffer, dATP, dGTP, dCTP, dTTp and Taq DNA polymerase were added to the resulting recombinant plasmid, which was then divided into two aliquots.

To one of these two aliquots, a primer having the nucleotide sequence shown in SEQ ID NO: 9 (corresponding to nucleotides 9098–9127 in SEQ ID NO: 1) and an antisense primer having the nucleotide sequence shown in SEQ ID NO: 10 (corresponding to an antisense of nucleotides 9193–9222 in SEQ ID NO: 1) were added.

To the other aliquot, an antisense primer having the nucleotide sequence shown in SEQ ID NO: 11 (corresponding to an antisense of nucleotides 9098–9127 in SEQ ID NO: 1) and a primer having the nucleotide sequence shown in SEQ ID NO: 12 (corresponding to nucleotides 8948–8977 in SEQ ID NO: 1) were added.

After the addition, each aliquot was treated at 96° C., for 5 minutes, and the reaction was repeated for 5 to 10 cycles under the following conditions: at 98° C. for 15 seconds and 68° C. for 30 seconds per cycle.

After the reaction, exonuclease I and alkaline phosphatase were added to each aliquot, incubated at 37° C. for 15 minutes, and then treated at 80° C. for 10 minutes to inactivate both the enzymes.

After the inactivation of both the enzymes, Taq DNA polymerase buffer, dATP, dGTP, dCTP, dTTp, a primer having the nucleotide sequence of SEQ ID NO: 12 (corresponding to nucleotides 8948–8977 in SEQ ID NO: 1), an antisense primer having the nucleotide sequence of SEQ ID NO: 10 (corresponding to an antisense of nucleotides 9193–9222 in SEQ ID NO: 1) and Taq DNA polymerase were added to each reaction solution. Each reaction solution was then treated at 96° C. for 5 minutes, and the reaction was repeated for 25 cycles under the following conditions: at 98° C. for 15 seconds and 68° C. for 30 seconds per cycle.

After the reaction, exonuclease I and alkaline phosphatase were added to each reaction solution, incubated at 37° C. for 15 minutes, and then treated at 80° C. for 10 minutes to inactivate the enzymes.

After the inactivation of the enzymes, restriction enzymes XcmI and BsaAI were added to each reaction solution to obtain a XcmI-BsaAI treated DNA fragment.

Restriction enzymes XcmI and BsaAI were added to the recombinant plasmid prepared above, which carried the inserted 2327 bp SmaI fragment, to obtain a XcmI-BsaAI treated vector fragment. The XcmI-BsaAI treated vector fragment, T4 DNA ligase buffer, ATP and T4 DNA ligase were added to the XcmI-BsaAI treated DNA fragment, and then incubated overnight at 22° C., to ligate these fragments together, thereby obtaining a plasmid carrying the inserted XcmI-BsaAI treated DNA fragment.

After the transformation of E. coli cells with the plasmid, the recombinant plasmids were extracted from individual colonies, and each DNA fragment inserted into the vector was then confirmed for its nucleotide sequence, thereby selecting a clone carrying a fragment introduced with the intended nucleotide replacement.

The inserted DNA fragment was taken from the selected clone, and then carried out recombination with DH2 region on the chromosome of Strepromyces avermitilis K2038 by homologous recombination according to a method as described in Japanese Published Examined Patent Application No. 344605/92.

The resulting recombinant Strepromyces avermitilis K2210 was cultured under the conditions for general avermectin production, and then the resulting cells were extracted with methanol.

The resulting extract was analyzed using two procedures presented below.

(1) Procedure using thin-layer chromatography on silica gel
    Chromatography condition:  silica gel, Merck Silica Gel plate F254 (Merck Corp.)
    Development solution:  n-hexane/iso-propyl alcohol = 85/15
    Detection:  UV
(2) Procedure using high performance liquid chromatography
    Chromatography condition:  column, ODS-Hypersil-3 (Elmer Corp.)
    Mobile phase:  acetonitrile/methanol/water = 60/14/26
    Flow rate:  0.6 ml/min
    Detection:  246 nm
    Temperature:  room temperature In both analytical procedures, only the same peak as that of avermectin B2a was observed. Further, the culture extract was purified by chromatographies on Sephadex LH-20 and silica gel to give the purified product. The purified product was analyzed by NMR and mass spectrometry, indicating that the above recombinant strain produced only avermectin B2a.

Namely, avermectin B2a alone could be produced and obtained according to the method as described above.

INDUSTRIAL APPLICABILITY

The present invention can provide the DNAs encoding a multifunctional enzyme involved in the biosynthesis of avermectin compound useful as a pharmaceutical agent, a veterinary agent and a agricultural chemical; polypeptides encoded by the DNAs; vectors comprising the DNAs; a host cell transformed with the DNA or vector; and a process for producing avermectin or modified avermectin.

Sequence Listing Free Text

SEQ ID NO: 9 represents a primer based on the sequence between nucleotides 9098 and 9127 in SEQ ID NO: 1

SEQ ID NO: 10 represents an antisense primer based on the sequence between nucleotides 9193 and 9222 in SEQ ID NO: 1

SEQ ID NO: 11 represents an antisense primer based on the sequence between nucleotides 9098 and 9127 in SEQ ID NO: 1

SEQ ID NO: 12 represents a primer based on the sequence between nucleotides 8948 and 8977 in SEQ ID NO: 1

The scope of the present invention will be defined by the appended claims, and it will be appreciated that other numerous variations and modifications may be made without departing from the spirit or scope of the invention. The above examples are therefore to be construed in all respects as illustrative and not restrictive. Further, equivalents of the claims will also fall within the scope of the present invention.

All of patents, patent applications and other publications cited in this specification and the contents as disclosed in the specification and/or drawings of Japanese Patent Application No. 046961/99, which is a priority document of the present application, are incorporated herein by reference in their entirety.

What is claimed is:

1. An isolated DNA consisting of a nucleotide sequence of nucleotide Nos. 1–11916 of SEQ ID NO:1.

2. A DNA encoding a polypeptide comprising an amino acid sequence wherein His residue at position 3037 is substituted by an amino acid other than His, and Ala residue at position 3038 is substituted by an amino acid other than Ala in the amino acid sequence of SEQ ID NO:3.

3. A recombinant vector comprising the DNA according to claim 1 or 2.

4. A host cell obtainable by introducing the DNA according to claim 1 or 2.

5. The host cell according to claim 4 wherein the DNA is introduced into an avermectin-producing bacterial strain.

6. The host cell according to claim 4 wherein the DNA is introduced into *Streptomyces avermitilis* K2038 (FERM BP-2775).

7. A process for producing the polypeptide of SEQ ID NO: 3 comprising: culturing a cell transformed with a DNA encoding the amino acid sequence of SEQ ID NO: 3, said cell expressing the polypeptide in a medium; and recovering the polypeptide from the medium.

8. The DNA according to claim 2 wherein the amino acid other than His is Tyr, and the amino acid other than Ala is Glu.

9. The DNA according to claim 8 wherein the DNA comprises a nucleotide sequence 5'-CATGCC-3' of nucleotide Nos. 9109–9114 of SEQ ID NO:1 is replaced by a nucleotide sequence 5'-TACGAG-3'.

10. An isolated polypeptide comprising an amino acid sequence of SEQ ID NO:3.

11. A polypeptide comprising an amino acid sequence wherein His residue at position 3037 is substituted by an amino acid other than His and Ala residue at position 3038 is substituted by an amino acid other than Ala in the amino acid sequence of SEQ ID NO:3.

12. The polypeptide according to claim 11 wherein the amino acid other than His is Tyr and the amino acid other than Ala is Glu.

* * * * *